(12) United States Patent
Kishi et al.

(10) Patent No.: US 11,407,762 B2
(45) Date of Patent: Aug. 9, 2022

(54) MACROCYCLIC COMPOUNDS AND USES THEREOF

(71) Applicants: President and Fellows of Harvard College, Cambridge, MA (US); Eisai R&D Management Co., LTD., Tokyo (JP)

(72) Inventors: Yoshito Kishi, Cambridge, MA (US); Kazunobu Kira, Tsukuba (JP); Ken Ito, Tsukuba (JP)

(73) Assignees: President and Fellows of Harvard College, Cambridge, MA (US); Eisai R&D Management Co., LTD., Tokyo (JP)

( * ) Notice: Subject to any disclaimer, the term of this patent is extended or adjusted under 35 U.S.C. 154(b) by 3 days.

(21) Appl. No.: 16/764,245

(22) PCT Filed: Nov. 15, 2018

(86) PCT No.: PCT/US2018/061250
§ 371 (c)(1),
(2) Date: May 14, 2020

(87) PCT Pub. No.: WO2019/099646
PCT Pub. Date: May 23, 2019

(65) Prior Publication Data
US 2020/0325152 A1    Oct. 15, 2020

Related U.S. Application Data

(60) Provisional application No. 62/765,310, filed on Aug. 20, 2018, provisional application No. 62/586,416, filed on Nov. 15, 2017.

(51) Int. Cl.
C07D 493/22    (2006.01)
A61P 35/04    (2006.01)

(52) U.S. Cl.
CPC ............ C07D 493/22 (2013.01); A61P 35/04 (2018.01)

(58) Field of Classification Search
CPC ................................ C07D 493/22; A61P 35/04
See application file for complete search history.

(56) References Cited

U.S. PATENT DOCUMENTS

| | | | |
|---|---|---|---|
| 5,338,865 A | 8/1994 | Kishi et al. | |
| 5,436,238 A | 7/1995 | Kishi et al. | |
| 5,519,050 A * | 5/1996 | Pettit .................... | C07D 493/22 514/450 |
| 5,786,492 A | 7/1998 | Gravalos et al. | |
| 6,214,865 B1 | 4/2001 | Littlefield et al. | |
| 6,469,182 B1 | 10/2002 | Littlefield et al. | |
| 6,653,341 B1 | 11/2003 | Littlefield et al. | |
| 7,470,720 B2 | 12/2008 | Littlefield et al. | |
| 7,982,060 B2 | 7/2011 | Austad et al. | |
| 8,093,410 B2 | 1/2012 | Chase et al. | |
| 8,097,648 B2 | 1/2012 | Littlefield et al. | |
| 8,203,010 B2 | 6/2012 | Endo et al. | |
| 8,350,067 B2 | 1/2013 | Endo et al. | |
| 8,445,701 B2 | 5/2013 | Austad et al. | |

(Continued)

FOREIGN PATENT DOCUMENTS

| | | |
|---|---|---|
| CO | 2018008667 A2 | 8/2018 |
| CO | 2019009000 A2 | 1/2020 |

(Continued)

OTHER PUBLICATIONS

US 9,029,573 B2, 05/2015, Hu (withdrawn)
Renouf, Invest NEw Drugs, vol. 30, 1203-1207, 2012. (Year: 2012).*
International Search Report and Written Opinion for PCT/US2020/043501, dated Dec. 3, 2020.

(Continued)

*Primary Examiner* — D Margaret M Seaman
(74) *Attorney, Agent, or Firm* — Wolf, Greenfield & Sacks, P.C.

(57) ABSTRACT

The present invention provides novel compounds (e.g., compounds of Formulae (I), (II), (III), (IV)) having tumor vascular remodeling effect and/or anti-CAF (Cancer Associated Fibroblasts) activity, or pharmaceutically acceptable salts thereof, optionally in a pharmaceutically acceptable carrier, and a medical uses thereof.

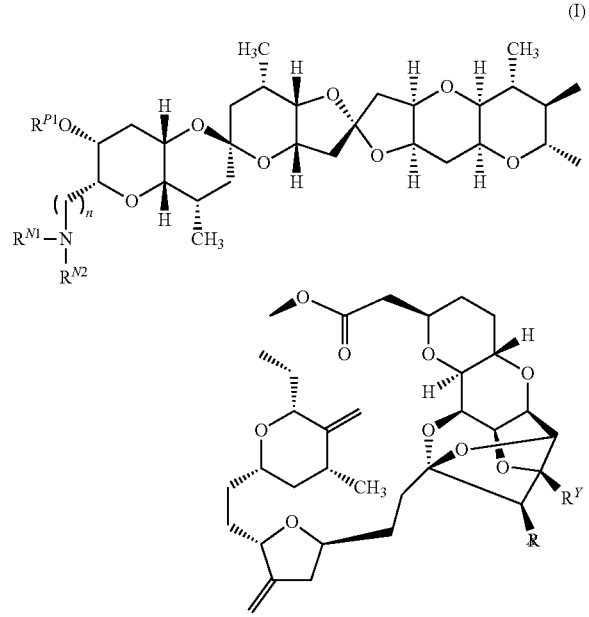

50 Claims, 30 Drawing Sheets

(56) References Cited

U.S. PATENT DOCUMENTS

| | | | |
|---|---|---|---|
| 8,598,373 B2 | 12/2013 | Hu | |
| 8,618,313 B2 | 12/2013 | Benayoud et al. | |
| 8,884,031 B2 | 11/2014 | Chase et al. | |
| RE45,324 E | 1/2015 | Austad et al. | |
| 8,927,597 B2 | 1/2015 | Endo et al. | |
| 8,975,422 B2 | 3/2015 | Fang et al. | |
| 8,987,479 B2 | 3/2015 | Chase et al. | |
| 9,206,194 B2 | 12/2015 | Hu | |
| 9,278,979 B2 * | 3/2016 | Souza | C07D 493/22 |
| 9,303,039 B2 | 4/2016 | Zhang et al. | |
| 9,303,050 B2 | 4/2016 | Benayoud et al. | |
| 9,382,262 B2 | 7/2016 | Endo et al. | |
| 9,469,651 B2 | 10/2016 | Hu | |
| 9,938,288 B1 | 4/2018 | Kishi et al. | |
| 10,344,038 B2 | 7/2019 | Kishi et al. | |
| 10,556,910 B2 | 2/2020 | Kishi et al. | |
| 10,633,392 B2 | 4/2020 | Kishi et al. | |
| 10,844,073 B2 | 11/2020 | Lee et al. | |
| 10,954,249 B2 | 3/2021 | Kishi et al. | |
| 11,155,562 B2 | 10/2021 | Kishi et al. | |
| 11,220,513 B2 | 1/2022 | Kishi et al. | |
| 2004/0198806 A1 | 10/2004 | Eisai et al. | |
| 2006/0104984 A1 | 5/2006 | Littlefield et al. | |
| 2006/0154312 A1 | 7/2006 | Agoulnik et al. | |
| 2007/0244187 A1 | 10/2007 | Austad et al. | |
| 2009/0198074 A1 | 8/2009 | Chase et al. | |
| 2009/0203771 A1 | 8/2009 | Inanaga et al. | |
| 2010/0254996 A1 | 10/2010 | Brantley-Sieders et al. | |
| 2011/0054194 A1 | 3/2011 | Hu et al. | |
| 2011/0184190 A1 | 7/2011 | Endo et al. | |
| 2013/0336974 A1 | 12/2013 | Collier et al. | |
| 2014/0198806 A1 | 7/2014 | Pani et al. | |
| 2016/0090391 A1 | 3/2016 | Souza et al. | |
| 2017/0137437 A1 | 5/2017 | Kishi et al. | |
| 2018/0155361 A1 | 6/2018 | Lee et al. | |
| 2018/0230164 A1 | 8/2018 | Kishi et al. | |
| 2020/0002352 A1 | 1/2020 | Lee et al. | |
| 2020/0148698 A1 | 3/2020 | Kishi et al. | |
| 2020/0165183 A1 | 5/2020 | Kishi et al. | |
| 2020/0223863 A1 | 7/2020 | Kishi et al. | |
| 2021/0009605 A1 | 1/2021 | Kishi et al. | |
| 2021/0230177 A1 | 7/2021 | Kishi et al. | |
| 2021/0261566 A1 | 8/2021 | Kishi et al. | |

FOREIGN PATENT DOCUMENTS

| | | | |
|---|---|---|---|
| JP | S6-1191687 A | 8/1986 | |
| JP | 6-122687 | 5/1994 | |
| JP | 6-279450 | 10/1994 | |
| JP | 6-279451 A | 10/1994 | |
| JP | H07-504664 A | 5/1995 | |
| JP | H08-208600 A | 8/1996 | |
| JP | 2001-305734 A | 11/2001 | |
| JP | 2003-261447 A | 9/2003 | |
| RU | 2517167 C2 | 5/2014 | |
| WO | WO 1993/017690 A1 | 9/1993 | |
| WO | WO 1999/065894 A1 | 12/1999 | |
| WO | WO 2005/118565 A1 | 12/2005 | |
| WO | WO 2006/076100 A2 | 7/2006 | |
| WO | WO 2007/139149 A1 | 12/2007 | |
| WO | WO 2009/046308 A1 | 4/2009 | |
| WO | WO 2009/064029 A1 | 5/2009 | |
| WO | WO 2009/124237 A1 | 10/2009 | |
| WO | WO 2011/094339 A1 | 8/2011 | |
| WO | WO 2012/147900 A1 | 11/2012 | |
| WO | WO 2013/086634 A1 | 6/2013 | |
| WO | WO 2013/097042 A1 | 7/2013 | |
| WO | WO 2013/142999 A1 | 10/2013 | |
| WO | WO 2015/000070 A1 | 1/2015 | |
| WO | WO 2015/066729 A1 | 5/2015 | |
| WO | WO 2015/085193 A1 | 6/2015 | |
| WO | WO 2016/003975 A1 | 1/2016 | |
| WO | WO 2016/038624 A1 | 3/2016 | |
| WO | WO 2016/176560 A1 | 11/2016 | |
| WO | WO 2016/179607 A1 | 11/2016 | |
| WO | WO 2017/151979 A1 | 9/2017 | |
| WO | WO 2018/149552 A1 | 8/2018 | |
| WO | WO 2018/187331 A1 | 10/2018 | |
| WO | WO 2019/009956 A1 | 1/2019 | |
| WO | WO 2019/010363 A1 | 1/2019 | |

OTHER PUBLICATIONS

Bockus et al. Form and Function in Cyclic Peptide Natural Products: A Pharmacokinetic Perspective. Curr Top Med Chem. 2013;13(7):821-36. doi: 10.2174/1568026611313070005.

Dybdal-Hargreaves et al. Eribulin Mesylate: Mechanism of Action of a Unique Microtubule-Targeting Agent. Clin Cancer Res. Jun. 1, 2015;21(11):2445-52. doi: 10.1158/1078-0432.CCR-14-3252. Epub Apr. 2, 2015.

Horita et al. Synthetic Studies of Halichondrin B, an Antitumor Polyether Macrolide Isolated from a Marine Sponge. 7. Synthesis of Two C27—C36 Units via Construction of the F Ring and Completely Stereoselective C-Glycosylation Using Mixed Lewis Acids. Chemical & Pharmaceutical Bulletin. 1997; 45(10): 1558-1572. doi:10.1248/cpb.45.1558.

Jackson et al. The Halichondrins and E7389. Chem Rev. Jul. 2009;109(7):3044-79. doi: 10.1021/cr900016w.

Mori et al. Pd(OH)2/C (Pearlman's catalyst): a highly active catalyst for Fukuyama, Sonogashira, and Suzuki coupling reactions. J Org Chem. Feb. 21, 2003;68(4):1571-4. doi: 10.1021/jo0265277.

Mori et al. A novel procedure for the synthesis of multifunctional ketones through the Fukuyama coupling reaction employing dialkylzincs. Tetrahedron Letters. Sep. 20, 2004; 45(39):7343-45.

Mori et al. Synthesis of Multi-Functionalized Ketones Through The Fukuyama Coupling Reaction Catalyzed by Pearlman's Catalyst: Preparation of Ethyl 6-Oxotridecanoate (Tridecanoic Acid, 6-Oxo-, Ethyl Ester).Organic Syntheses. 2007;84: 285-294.

Movassaghi et al. Enantioselective total synthesis of (−)-acylfulvene and (−)-irofulven. Angew Chem Int Ed Engl. Sep. 4, 2006;45(35):5859-63. doi: 10.1002/anie.200602011.

Swami et al. Eribulin in Cancer Treatment. Mar Drugs. Aug. 7, 2015;13(8):5016-58. doi: 10.3390/md13085016.

Ueda et al. Total synthesis of (+)-haplophytine. Angew Chem Int Ed Engl. 2009;48(41):7600-3. doi: 10.1002/anie.200902192.

Umehara et al. Further Studies on Ni/Zr-mediated One-pot Ketone Synthesis: Use of a 1-6 Mixture of NiI- and NiII-catalysts Greatly Improves the Molar Ratio of Coupling Partners. Chem Lett. 2019;48:947-950.

Extended European Search Report for EP 15814059.0, dated Nov. 24, 2017.

International Search Report and Written Opinion for PCT/US2015/038439, dated Sep. 29, 2015.

International Preliminary Report on Patentability for PCT/US2015/038439, dated Jan. 12, 2017.

International Search Report and Written Opinion for PCT/US2016/030064, dated Aug. 8, 2016.

International Preliminary Report on Patentability for PCT/US2016/030064, dated Nov. 9, 2017.

International Search Report and Written Opinion for PCT/US2018/025887, dated Jun. 21, 2018.

International Preliminary Report on Patentability for Application No. PCT/US2018/025887 dated Oct. 17, 2019.

Invitation to Pay Additional Fees for PCT/US2018/041005, dated Sep. 14, 2018.

International Preliminary Report on Patentability for PCT/US2018/041005, dated Jan. 16, 2020.

Invitation to Pay Additional Fees for PCT/US2018/061250, dated Feb. 26, 2019.

International Search Report and Written Opinion for PCT/US2018/061250, dated Apr. 16, 2019.

International Preliminary Report on Patentability for PCT/US2018/061250, dated May 28, 2020.

International Search Report and Written Opinion for PCT/US2018/031765, dated Jul. 2, 2018.

International Preliminary Report on Patentability for PCT/US2018/031765, dated Jan. 16, 2020.

(56) References Cited

OTHER PUBLICATIONS

[No Author Listed] American Chemical Society. STN Database. Apr. 11, 2014. RN # 1583253-64-8.

[No Author Listed] Application for Product Designation Under the SAKIGAKE Designation System. Generic name E7130. Eisai Co., Ltd. Nov. 22, 2017.

[No Author Listed] Evidentiary Document for Applicability of E7130 to Designation Requirements. Eisai Co., Ltd. Nov. 22, 2017.

[No Author Listed] Overview Relating to the Suitability for Designation Requirements Under the SAKIGAKE Designation System. Generic name E7130. Eisai Co., Ltd.

Aicher et al., Synthetic studies towards halichondrins. Tetrahedron Lett. 1987;28(30):3463-66.

Aicher et al., Synthetic Studies towards Halichondrins: Synthesis of the C.27-C.38 Segment. Tetrahedron Lett. 1992;33(12):1549-52.

Aicher et al., Total synthesis of halichondrin B and norhalichondrin B. J. Am. Chem. Soc., 1992, 114(8), pp. 3162-3164.

Araki et al., A Convenient Method for the Preparation of Ketones by the Reaction of Grignard Reagents with Carboxylic Acid Derivatives. Chem. Soc. Jpn. 1974;47:1777-80.

Austed et al., Commercial Manufacture of Halaven®: Chemoselective Transformations En Route to Structurally Complex Macrocyclic Ketones. Synlett 2013; 24(3): 333-337. doi: 10.1055/s-0032-1318026.

Berge et al., Pharmaceutical Salts. J. Pharmaceutical Sciences 1977;66(1):1-19.

Bringans, Studies on natural product derivatives: HIV therapies incorporating marine natural products. Dissertation. University of Canterbury, 2001.

Britovsek et al., Synthesis of iron(ii), manganese(ii) cobalt(ii) and ruthenium(ii) complexes containing tridentate nitrogenligands and their application in the catalytic oxidation of alkanes. Dalton Trans. 2005, 945-55.

Buchwald et al., Synthesis, structure, and reactions of (1-ethoxyethyl)zirconocene chloride, a stable acyclic secondary zirconocene alkyl. Organometallics. 1988;7(11):2324-2328.

Buszek et al., Synthetic Studies Towards Halichondrins: Synthesis of the Left Half of Halichondrins. Tetrahedron Lett. 1992;33:1553.

Cardellicchio et al., A highly efficient synthetic route to ketones through sequential coupling reactions of grignard reagents with s-phenyl carbonochloridothioate in the presence of nickel or iron catalysts. Tetrahedron Lett. 1985;26(30):3595-98.

Chen et al., Attempts to Improve the Overall Stereoselectivity of the Ireland-Claisen Rearrangement. Org. Lett. Jan. 15, 2009; 11(2):409-12.

Chen et al., Ni(II)/Cr(II)-mediated coupling reaction: an asymmetric process. J. Org. Chem., 1995, 60 (17), pp. 5386-5387.

Choi et al., Asymmetric Ni(II)/Cr(II)-Mediated Coupling Reaction: Catalytic Process. Org. Lett., 2002, 4 (25), pp. 4435-4438. doi: 10.1021/o102698lx.

Choi et al., Synthetic studies on the marine natural product halichondrins. Pure Appl. Chem., 2003, vol. 75, No. 1, pp. 1-17.

Corey et al., Synthesis of 1,n-Dicarbonyl Derivates Using Carbanions from 1,3-Dithianes. Angew. Chem. Int. Ed. 1965;4(12):1077-78.

Dieter, Reaction of acyl chlorides with organometallic reagents: A banquet table of metals for ketone synthesis. Tetrahedron. 1999;55:4177-4236.

Dong et al., New syntheses of E7389 C14—C35 and halichondrin C14—C38 building blocks: reductive cyclization and oxy-Michael cyclization approaches. J Am Chem Soc. Nov. 4, 2009;131(43):15642-6. doi: 10.1021/ja9058487.

Eliel et al., Conformational analysis. 42. Monosubstituted tetrahydropyrans. J. Am. Chem. Soc. 1982; 104(13):3635-43.

Fang et al., Synthetic Studies Towards Halichondrins: Synthesis of the Left Halves of Norhalichondrins and Homohalichondrins. Tetrahedron Lett. 1992;33(12):1557-60.

Fiandanese et al., One-step synthesis of ketones from carylic acids and grignard reagents in the presence of a nickel(II)-phosphine catalyst. Tetrahedron Lett. 1983;24:3677.

Fleming et al., Grignard Reagents: Alkoxide-Directed Iodine-Magnesium Exchange at sp3 Centers. Org. Lett. 2007; 9(22):4507-09.

Fukuyama et al., Application of a Rotor-Stator High-Shear System for Cr/Mn-Mediated Reactions in Eribulin Mesylate Synthesis. Org. Process Res. Dev., 2016, 20 (1), pp. 100-104. doi: 10.1021/acs.oprd.5b00383.

Fukuyama et al., Application of Continuous Flow for DIBAL-H Reduction and n-BuLi Mediated Coupling Reaction in the Synthesis of Eribulin Mesylate. Org. Process Res. Dev., 2016, 20 (2), pp. 503-509. doi: 10.1021/acs.oprd.5b00353.

Gerlach et al., Bildung von Estern und Lactonen durch Silberionen-Katalyse. Helv. Chim. Acta. 1974; 57(8): 2661-63.

Gould et al., Salt selection for basic drugs. International Journal of Pharmaceutics Nov. 1986;33(1-3):201-217. https://doi.org/10.1016/0378-5173(86)90055-4.

Guo et al., Toolbox approach to the search for effective ligands for catalytic asymmetric Cr-mediated coupling reactions. J Am Chem Soc. Oct. 28, 2009;131(42):15387-93. doi: 10.1021/ja905843e.

Hayashi et al., Diarylprolinol in an Asymmetric, Direct Cross-Aldol Reaction with Alkynyl Aldehydes. ChemCatChem. 2013; 5:2082-84.

Hayashi et al., A diarylprolinol in an asymmetric, catalytic, and direct crossed-aldol reaction of acetaldehyde. Angew Chem Int Ed Engl. 2008;47(11):2082-4. doi: 10.1002/anie.200704870.

Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.

Hirata et al., Halichondrins—antitumor polyether macrolides from a marine sponge. Pure Appl. Chem., 1986, vol. 58, No. 5, pp. 701-710.

Hoveyda et al., The remarkable metal-catalysed olefin metathesis reaction. Nature. 2007;450:243-51.

Jackson et al., A total synthesis of norhalichondrin B. Angew Chem Int Ed Engl. 2009;48(13):2346-50. doi: 10.1002/anie.200806111.

Johannes et al., Biomimetic macrocycle-forming Diels-Alder reaction of an iminium dienophile: synthetic studies directed toward gymnodimine. Org Lett. Sep. 1, 2005;7(18):3997-4000. doi: 10.1021/ol051553n.

Jung et al., Synthesis of 1,4-, 2,4-, and 3,4-dimethylphenanthrenes: a novel deoxygenation of arene 1,4-endoxides with trimethylsilyl iodide. J. Org. Chem. 1989; 54:5667-75.

Kaburagi et al., Effective procedure for selective ammonolysis of monosubstituted oxiranes: application to E7389 synthesis. Tetrahedron Lett. 2007;48(51):8967-71.

Kaburagi, Operationally Simple and Efficient Workup Procedure for TBAF-Mediated Desilylation: Application to Halichondrin Synthesis. Org. Lett. 2007; 9(4):723-26.

Katsuki et al., The first practical method for asymmetric epoxidation. J. Am. Chem. Soc. 1980, 102(18) 5974-76.

Kim et al., Copper ion promoted esterification of (S)-2-pyridyl thioates and 2-pyridyl esters. Efficient methods for the preparation of hindered esters. J. Org. Chem. 1984;49(10):1712-16.

Kim et al., New syntheses of E7389 C14—C35 and halichondrin C14—C38 building blocks: double-inversion approach. J Am Chem Soc. Nov. 4, 2009;131(43):15636-41. doi: 10.1021/ja9058475.

Kobayashi et al., Complete Stereochemistry of Tetrafibricin. Org. Lett. 2003; 5(1):93-96.

Knochel et al., Modern Organocopper Chemistry. 2002. Wiley-VCH, Eds.

Kress et al., Investigations of the intramolecular Ni(II)/Cr(II)-mediated coupling reaction: Application to the taxane ring system. Tetrahedron Letters 1993;34(38);6003-6.

Kumar et al., Fe/Cu-Mediated One-Pot Ketone Synthesis. Org Lett. May 19, 2017;19(10):2766-2769. doi: 10.1021/acs.orglett.7b01128. Epub May 10, 2017.

Lee et al., Extension of Pd-Mediated One-Pot Ketone Synthesis to Macrocyclization: Application to a New Convergent Synthesis of Eribulinv. J. Am. Chem. Soc. 2016;138(50):16248-51.

Lewis et al., Highly stereoselective approaches to alpha and beta-C-glycopyranosides. J. Am. Chem. Soc. 1982;104(18):4976-78.

(56) References Cited

OTHER PUBLICATIONS

Li et al., Stereocontrolled Synthesis of α-Amino-α'-alkoxy Ketones by a Copper-Catalyzed Cross-Coupling of Peptidic Thiol Esters and α-Alkoxyalkylstannanes. Org. Lett. 2011;13(14):3682-85.

Li et al., Unified Synthesis of C1—C19 Building Blocks of Halichondrins via Selective Activation/Coupling of Polyhalogenated Nucleophiles in (Ni)/Cr-Mediated Reactions. J Am Chem Soc. May 20, 2015;137(19):6226-31. doi: 10.1021/jacs.5b03499. Epub May 11, 2015.

Liebeskind et al., Thiol Ester-Boronic Acid Coupling. A Mechanistically Unprecedented and General Ketone Synthesis. J. Am. Chem. Soc. 2000;122(45):11260-61.

Lill, Studies on New Zealand marine natural products. Dissertation. University of Canterbury, 1999.

Lipschutz, Applications of Higher-Order Mixed Organocuprates to Organic Synthesis. Synthesis. 1987:325-41.

Liu et al., Catalytic enantioselective Cr-mediated propargylation: application to halichondrin synthesis. Org Lett. Oct. 15, 2009;11(20):4520-3. doi: 10.1021/ol9016595.

Liu et al., Dramatic improvement in catalyst loadings and molar ratios of coupling partners for Ni/Cr-mediated coupling reactions: heterobimetallic catalysts. J Am Chem Soc. Nov. 25, 2009;131(46):16678-80. doi: 10.1021/ja9079308.

Liu et al., Synthesis of Alcohols from m-Fluorophenylsulfones and Dialkylboranes: Application to the C14—C35 Building Block of E7389. Org. Lett., 2012, 14 (9), pp. 2262-2265. doi: 10.1021/ol300672q.

Loots et al., Nickel-catalyzed conjugate addition of zirconium alkenyls to .alpha.,.beta.-unsaturated ketones. J. Am. Chem. Soc. 1977;99(24):8045-46.

Lu et al., Alkyl-Alkyl Suzuki Cross-Coupling of Unactivated Secondary Alkyl Chlorides. C. Angew. Chem. Int. Ed. 2010;49(37):6676-78.

Masashi et al., A Convenient Method for the Preparation of Ketones by the Reaction of Grignard Reagents with Carboxylic Acid Derivatives. Chem. Soc. Jpn. 1974;47:1777-80.

McGee et al., Synthesis and Isolation of Organogold Complexes through a Controlled 1,2-Silyl Migration. Chem. Eur. J. 2015;21(27): 9662-9665.

Miyajima et al., Electric-field-responsive handle for large-area orientation of discotic liquid-crystalline molecules in millimeter-thick films. Angew. Chem., Int. Ed. 2011;50(34): 7865-7869.

Nahm et al., N-methoxy-n-methylamides as effective acylating agents. Tetrahedron Lett. 1981;22(39):3815-18.

Namba et al., New catalytic cycle for couplings of aldehydes with organochromium reagents. Org Lett. Dec. 23, 2004;6(26):5031-3.

Narayan et al., Novel second generation analogs of eribulin. Part I: Compounds containing a lipophilic C32 side chain overcome P-glycoprotein susceptibility. Bioorg Med Chem Lett, Mar. 15, 2011;21(6):1630-3.

Narayan et al., Novel second generation analogs of eribulin. Part II: Orally available and active against resistant tumors in vivo. Bioorg Med Chem Lett, Mar. 15, 2011;21(6):1634-8.

Narayan et al., Novel second generation analogs of eribulin. Part III: Blood-brain barrier permeability and in vivo activity in a brain tumor model. Bioorg Med Chem Lett, Mar. 15, 2011;21(6):1639-43.

Negishi et al., Palladium-catalyzed acylation of organozincs and other organometallics as a convenient route to ketones. Tetrahedron Lett. 1983;24(47): 5181-4.

Negri et al., A total synthesis of polyether antibiotic (−)-A23187 (calcimycin). Tetrahedron Lett. 1987; 28(10):1063-66.

Normant, Organocopper(I) Compounds and Organocuprates in Synthesis. Synthesis. 1972; 1972(2):63-80.

Onaka et al., A Convenient Method For The Direct Preparation Of Ketones From 2-(6-(2-Methoxyethyl)Pyridyl)Carboxylates And Alkyl Iodides By Use Of Zinc Dust And A Catalytic Amount Of Nickel Dichloride. Chem. Lett. 1981;10(4):531-34.

Ortega et al., Potential clinical applications of halichondrins in breast cancer and other neoplasms. Breast Cancer (Dove Med Press). Feb. 8, 2012;4:9-19. doi: 10.2147/BCTT.S12423.

Ruscoe et al., Copper-Catalyzed Double Additions and Radical Cyclization Cascades in the Re-Engineering of the Antibacterial Pleuromutilin. J. Chem. Eur. J. 2016; 22:116-119.

Schrock, Multiple Metal-Carbon Bonds for Catalytic Metathesis Reactions. Adv. Synth Catal. 2007;349: 41-53.

Scriven et al., Azides: their preparation and synthetic uses. Chem Rev. 1988;88(2):297-368.

Seebach, Methods of Reactivity Umpolung. Angew. Chem. Int. Ed. 1979;18(4):239-58.

Seebach et al., Generation and synthetic applications of 2-lithio-1,3-dithianes. J. Org. Chem. 1975;40(2): 231-37.

Seletsky et al., Structurally simplified macrolactone analogues of halichondrin B. Bioorg Med Chem Lett, Nov. 15, 2004;14(22):5547-50.

Serrano et al., Nickel-Catalyzed Reductive Amidation of Unactivated Alkyl Bromides. Angew. Chem. Int. Ed. 2016;55(37):11207-11.

Shan et al., Concise and Highly Stereoselective Synthesis of the C20—C26 Building Block of Halichondrins and Eribulin. Org. Lett., 2012, 14 (2), pp. 660-663. doi: 10.1021/ol203373d.

Sharpless et al., High stereo- and regioselectivities in the transition metal catalyzed epoxidations of olefinic alcohols by tert-butyl hydroperoxide. J. Am. Chem. Soc. 1973;95(18):6136-37.

Shiina, An Adventurous Synthetic Journey with MNBA from Its Reaction Chemistry to the Total Synthesis of Natural Products. Bull Chem. Soc. Jpn. 2014; 87(2):196-233.

Shiina et al., A novel and efficient macrolactonization of ω-hydroxycarboxylic acids using 2-methyl-6-nitrobenzoic anhydride (MNBA). Tetrahedron Lett. Oct. 14, 2002;43(42):7535-39.

Shiina et al., A Novel Method for the Preparation of Macrolides from ω-Hydroxycarboxylic Acids. Chem. Lett. 1994;23(4):677-80.

Smith III et al., Evolution of Dithiane-Based Strategies for the Construction of Architecturally Complex Natural Products. Acc. Chem. Rev. 2004; 37(6): 365-77.

Stamos et al., Ni(II)/Cr(II)-Mediated Coupling Reaction: Beneficial Effects of 4-tert-Butylpyridine as an Additive and Development of New and Improved Workup Procedures. Tetrahedron Lett. 1997;38(36):6355-8.

Stamos et al., Synthetic studies on halichondrins: A practical synthesis of the C.1 C.13 segment. Tetrahedron Letters Nov. 25, 1996;37(48):8643-8646.

Takai et al., A practical transformation of aldehydes into (E)-iodoalkenes with geminal dichromium reagents. Synlett. 1999;8:1268-70.

Takai et al., Simple and selective method for aldehydes (RCHO)→(E)-haloalkenes (RCH:CHX) conversion by means of a haloform-chromous chloride system. J. Am. Chem. Soc. 1986;108(23):7408-10.

Takaya et al., Investigation of Organoiron Catalysis in Kumada-Tamao-Corriu-Type Cross-Coupling Reaction Assisted by Solution-Phase X-ray Absorption Spectroscopy. Bull. Chem. Soc. Jpn. 2015;88(3): 410-418.

Takuji et al., Kumada-Tamao-Corriu Coupling of Alkyl Halides Catalyzed by an Iron-Bisphosphine Complex. Chem. Lett. 2011, 40(9):1030-32.

Thornton et al., π-Nucleophile Traps for Metallonitrene/Alkyne Cascade Reactions: A Versatile Process for the Synthesis of α-Aminocyclopropanes and β-Aminostyrenes. J. Am. Chem. Soc. 2009;131(7): 2434-2435.

Trnka et al., The Development of L2X2RuCHR Olefin Metathesis Catalysts: An Organometallic Success Story. Acc. Chem. Res. 2001;34(1):18-29.

Turhanen et al., A powerful tool for acid catalyzed organic addition and substitution reactions. RSC Adv. 2015; 5:26218-26222.

Ueda et al., Total synthesis of halichondrin A, the missing member in the halichondrin class of natural products. J Am Chem Soc. Apr. 2, 2014;136(13):5171-6. doi: 10.1021/ja5013307. Epub Mar. 19, 2014.

Uemura et al., Norhalichondrin A: an antitumor polyether macrolide from a marine sponge. J. Am. Chem. Soc., 1985, 107 (16), pp. 4796-4798. doi: 10.1021/ja00302a042.

Uemura, Exploratory research on bioactive natural products with a focus on biological phenomena. Proc Jpn Acad Ser B Phys Biol Sci. 2010;86(3):190-201.

(56) References Cited

OTHER PUBLICATIONS

Velder et al., Modular Synthesis of Chiral Phosphine-Phosphite-Ligands from Phenolic Precursors: A New Approach to Bidentate Chelate Ligands Exploiting a P O to P C Migration Rearrangement. Adv Synth Catal. 2008; 350(9):1309-15.

Wan et al., Asymmetric Ni(II)/Cr(II)-mediated coupling reaction: stoichiometric process. Org Lett. Dec. 12, 2002;4(25):4431-4.

Wang et al., Structure-activity relationships of Halichondrin B analogues: modifications at C.30-C.38. Bioorg Med Chem Lett, May 15, 2000;10(10):1029-32.

Weix et al., Nickel-Catalyzed Cross-Electrophile Coupling with Organic Reductants in Non-Amide Solvents. Chem. Eur. J. 2016; 22(33):11564-11567.

Williams et al., Competitive oxidation processes in the reaction between (dicyclopentadienyl)zirconium bis(phosphine) complexes and alkyl halides. J. Am. Chem. Soc. 1980; 102(10):3660-62.

Williams et al., Direct observation of metal-centered radicals in an oxidative-addition reaction. J. Am. Chem. Soc. 1982; 104(4):1122-24.

Wipf et al., Transmetalation reactions of alkylzirconocenes: copper-catalyzed conjugate addition to enones. J. Org. Chem. 1991;56(23): 6494-96.

Wittenberg et al., Ketone synthesis under neutral conditions. Cu(I) diphenylphosphinate-mediated, palladium-catalyzed coupling of thiol esters and organostannanes. Org Lett. Aug. 21, 2003;5(17):3033-5. doi: 10.1021/ol034962x.

Wu et al., Ketone Formation via Mild Nickel-Catalyzed Reductive Coupling of Alkyl Halides with Aryl Acid Chlorides. Org. Lett. 2012; 14(12):3044-47.

Xie et al., Synthesis of the C20—C26 Building Block of Halichondrins via a Regiospecific and Stereoselective SN2' Reaction. Org. Lett., 2002;4(25):4427-1429.DOI: 10.1021/ol026982p.

Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.

Yamamoto et al., Total synthesis of halichondrin C. J Am Chem Soc. Jan. 18, 2012;134(2):893-6. doi: 10.1021/ja2108307. Epub Dec. 23, 2011.

Yan et al., Selective Activation/Coupling of Polyhalogenated Nucleophiles in Ni/Cr-Mediated Reactions: Synthesis of C1—C19 Building Block of Halichondrin Bs. J. Am. Chem. Soc., 2015, 137 (19), pp. 6219-6225.

Yoneda et al., Asymmetric Synthesis of Spiroketals with Aminothiourea Catalysts. Angew Chem Int Ed Engl. Dec. 14, 2015;54(51):15497-500. doi: 10.1002/anie.201508405.

Yus et al., The role of 1,3-dithianes in natural product synthesis. Tetrahedron. Aug. 11, 2003; 59(33):6147-6212.

Zhang et al., Alcohols as Latent Coupling Fragments for Metallaphotoredox Catalysis: sp3-sp2 Cross-Coupling of Oxalates with Aryl Halides. J. Am. Chem. Soc. 2016; 138(42):13862-65.

Zhang et al., A Unique Catalyst Effects the Rapid Room-Temperature Cross-Coupling of Organozinc Reagents with Carboxylic Acid Fluorides, Chlorides, Anhydrides, and Thioesters. J. Am. Chem. Soc. 2004; 126(49):15964-65.

Zheng et al., Macrocyclic ketone analogues of halichondrin B. Bioorg Med Chem Lett. Nov. 15, 2004;14(22):5551-4.

Zhao et al., Ni-Catalyzed Reductive Coupling of Alkyl Acids with Unactivated Tertiary Alkyl and Glycosyl Halides. J. Am. Chem. Soc. 2014;136(50):17645-51.

U.S. Appl. No. 17/167,480, filed Feb. 4, 2021, Kishi et al.

PCT/US2020/043501, Dec. 3, 2020, International Search Report and Written Opinion.

International Search Report and Written Opinion for PCT/US2018/041005, dated Nov. 19, 2018.

Durnov et al., Pediatric Oncology. Moscow Medicine. 2002; 139.

Kaburagi et al., Gram-Scale Synthesis of a Halichondrin-Class Anticancer Drug Candidate E7130. Abstract. Japanese language. 2021. 5 pages.

Kaburagi et al., Gram-Scale Synthesis of a Halichondrin-Class Anticancer Drug Candidate E7130. Abstract. English language. 2021. 2 pages.

Kaburagi, A landmark in drug discovery based on complex natural product synthesis. Abstract. 2021. 1 page.

Kira, Gram-scale synthesis of a structurally complex drug candidate E7130. Abstract. 2021. 1 page.

Kümmerer, Pharmaceuticals in the environment. Annu Rev Environ Resour. 2010;35:57-75.

Melzig et al., Preparation of Polyfunctional Zinc Organometallics Using an Fe- or Co-Catalyzed Cl/Zn-Exchange. Org Lett. 2011; 13(12): 3174-3177.

No Author Listed, Presentation material for The 63rd Symposium on the Chemistry of Natural Products. Sep. 15-17, 2021. 26 pages.

No Author Listed, Small Medical Encyclopedia. Soviet Medicine. 1996; 5: 90-96.

Ogawa et al., Total synthesis of resolvin E1. Tetrahedron Letters. Nov. 4, 2009; 50(44): 6079-82.

Sabitha et al., Synthesis of the C45—C53 tetrahydropyran domain of norhalichondrins and the C14—C22 tetrahydrofuran domain of the halichondrin family. RSC Advances. 2012; 2: 10157-10159.

\* cited by examiner

| Compound | *in vitro* cell growth inhibition IC₅₀ (nM) | | | | | F-gp susceptibility |
|---|---|---|---|---|---|---|
| | Esophageal cancer | | | Uterine sarcoma | | |
| | OE21 | OE33 | TE-8 | MES-SA | MES-SA/Dx5-Rx1 | |
| Compound (I) | 0.061 | 0.29 | 0.095 | 0.070 | 8.7 | 123 |

Phospho-Smad2/3, Acetyl-α-Tubulin
Phospho-Smad2 (Ser465/467)/Smad3 (Ser423/425)

MACROCYCLIC COMPOUNDS AND USES THEREOF

RELATED APPLICATIONS

This application is a national stage filing under 35 U.S.C. § 371 of International PCT Application, PCT/US2018/061250, filed Nov. 15, 2018, which claims priority under 35 U.S.C. § 119(e) to U.S. Provisional Patent Applications, U.S. Ser. No. 62/586,416, filed Nov. 15, 2017; and U.S. Ser. No. 62/765,310, filed Aug. 20, 2018; the entire contents of each of which is incorporated herein by reference.

TECHNICAL FIELD

The present invention provides novel macrocyclic compounds having tumor vascular remodeling effects and anti-CAF (Cancer Associated Fibroblast) activity. The compounds can be used for, e.g., treating cancer or inhibiting tumor growth in a subject.

BACKGROUND

Halichondrins, such as Halichondrin B, are anticancer agents originally isolated from the marine sponge *Halichondria okadai* (See, e.g., D. Uemura et al. "Norhalichondrin A: An Antitumor Polyether Macrolide from a Marine Sponge" J. Am. Chem. Soc., 107, 4796 (1985)), and subsequently found in *Axinella* sp., *Phakellia carteri*, and *Lissodendoryx* sp. A total synthesis of Halichondrin B was published in 1992 (See, e.g., Y. Kishi et al. "Total Synthesis of Halichondrin B and Norhalichondrin B" J. Am. Chem. Soc., 114, 3162 (1992)). Halichondrin B has demonstrated in vitro inhibition of tubulin polymerization, microtubule assembly, beta 5-tubulin crosslinking, GTP and vinblastine binding to tubulin, and tubulin-dependent GTP hydrolysis, and has shown in vitro and in vivo anti-cancer properties (See, e.g., Y. Hirata et al. "Halichondrins-antitumor polyether macrolides from a marine sponge" Pure Appl. Chem., 58, 701 (1986); Fodstad et al. "Comparative antitumor activities of halichondrins and vinblastine against human tumor xenografts" J. of Experimental Therapeutics & Oncology 1996; 1: 119, 125).

Eribulin mesylate (Halaven™), which was developed based on Halichondrin B (See, e.g., International Publication No. WO 1999/065894, published Dec. 23, 1999; International Publication No. WO 2005/118565, published Dec. 15, 2005; and W. Zheng et al. "Macrocyclic ketone analogues of halichondrin B" Bioorganic & Medicinal Chemistry Letters 14, 5551-5554 (2004)), is currently in clinical use in many countries for the treatment of, e.g., metastatic breast cancer and advanced liposarcoma.

Additional patent publications describing Halichondrins include U.S. Pat. No. 5,436,238 to Kishi, et al., issued Jul. 25, 1995; U.S. Pat. No. 5,338,865 to Kishi, et al., issued Aug. 16, 1994; and WO 2016/003975 filed by Kishi, et al., all of which are assigned to the President and Fellows of Harvard College.

See also, e.g., U.S. Pat. Nos. 5,786,492; 8,598,373; 9,206,194; 9,469,651; WO/2009/124237A1; WO/1993/017690A1; WO/2012/147900A1; U.S. Pat. Nos. 7,982,060; 8,618,313; 9,303,050; 8,093,410; 8,350,067; 8,975,422; 8,987,479; 8,203,010; 8,445,701; 8,884,031; U.S. Pat. No. RE45,324; U.S. Pat. Nos. 8,927,597; 9,382,262; 9,303,039; WO/2009/046308A1; WO/2006/076100A3; WO/2006/076100A2; WO/2015/085193A1; WO/2016/176560A1; U.S. Pat. Nos. 9,278,979; 9,029,573; WO/2011/094339A1; WO/2016/179607A1; WO/2009/064029A1; WO/2013/142999A1; WO/2015/066729A1; WO/2016/038624A1; and WO/2015/000070A1.

Cancer associated fibroblasts (CAFs), which are widely found in a variety of solid tumors, are stromal cells. It is well known that CAFs play an important role in angiogenesis, invasion, and metastasis. There is a close correlation between the amount of CAFs and clinical prognosis in, for example, invasive breast cancer (See, e.g., M. Yamashita et al. "Role of stromal myofibroblasts in invasive breast cancer: stromal expression of alpha-smooth muscle actin correlates with worse clinical outcome" Breast Cancer 19, 170, 2012) and esophageal adenocarcinoma (See, e.g., T. J. Underwood et al. "Cancer-associated fibroblasts predict poor outcome and promote periostin-dependent invasion in esophageal adenocarcinoma" Journal of Pathol., 235, 466, 2015). It has also been reported that CAFs correlate to resistance in a variety of tumors, such as, for example, breast cancer (See, e.g., P. Farmer et al. "A stroma-related gene signature predicts resistance to neoadjuvant chemotherapy in breast cancer" Nature Medicine, 15(1), 68, 2009), and head and neck cancer (See, e.g., S. Schmitz et al. "Cetuximab promotes epithelial to mesenchymal transition and cancer associated fibroblasts in patients with head and neck cancer" Oncotarget, 6 (33), 34288, 2015; Y. Matsuoka et al. "The tumor stromal features are associated with resistance to 5-FU-based chemoradiotherapy and a poor prognosis in patients with oral squamous cell carcinoma" APMIS 123(3), 205, 2015).

It has thus been observed that tumor vascular remodeling effects and anti-CAF activity result in the improvement of the cancer microenvironment, which assists tumor treatment. Blood vessels are essential for the growth of tumors. Reconstructed blood vessels in tumors can deliver anti-cancer agents to the tumors, in addition to alleviating hypoxia. It is reported that eribulin-induced remodeling of abnormal tumor vasculature leads to a more functional microenvironment that may reduce the aggressiveness of tumors due to the elimination of inner tumor hypoxia. Because abnormal tumor microenvironments enhance both drug resistance and metastasis, the apparent ability of eribulin to reverse these aggressive characteristics may contribute to its clinical benefits (See, e.g., Y. Funahashi et al. "Eribulin mesylate reduces tumor microenvironment abnormality by vascular remodeling in preclinical human breast cancer models" Cancer Sci. 105 (2014), 1334-1342). Anti-cancer drugs having tumor vascular remodeling effects and anti-CAF activities have not been reported as of today.

Despite the progress made, additional compounds are needed to progress research and medical care of patients with tumors and cancer.

SUMMARY OF THE INVENTION

Halichondrins, as well as analogs and derivatives thereof, are useful therapeutic agents. Examples of halichondrins, analogs, and derivatives thereof, as well as methods of using the same, and methods of synthesizing the same, can be found in, e.g., U.S. Publication No. 2017/0137437, published May 18, 2017; International Publication No. WO 2016/003975, published Jan. 7, 2016; U.S. Publication No. 2018/0230164, published Aug. 16, 2018; International Publication No. WO 2016/176560, published Nov. 3, 2016; U.S. Publication No. 2018/0155361, published Jun. 7, 2018; and U.S. Pat. No. 9,938,288, issued Apr. 10, 2018; the entire contents of each of which is incorporated herein by reference.

The present invention relates to macrocyclic compounds (e.g., compounds of Formulae (I), (II), (III), and (IV)), and pharmaceutically acceptable salts thereof, and isotopically labeled derivatives thereof, and pharmaceutical compositions thereof. In certain embodiments, the compounds have tumor vascular remodeling effects and anti-CAF activity.

The invention also provides methods of using the compounds provided herein, e.g., for treating a proliferative disease in a subject. In certain embodiments, the invention includes methods of using compounds provided herein for treating a subject with cancer, methods for reversibly or irreversibly inhibiting mitosis in a cell, and methods for inhibiting tumor growth in vitro, in vivo, or in a subject. In another aspect, the present invention provides kits comprising a compound provided herein, or a pharmaceutically acceptable salt thereof, or a pharmaceutical composition thereof.

In one aspect, the present invention provides compounds of Formula (I):

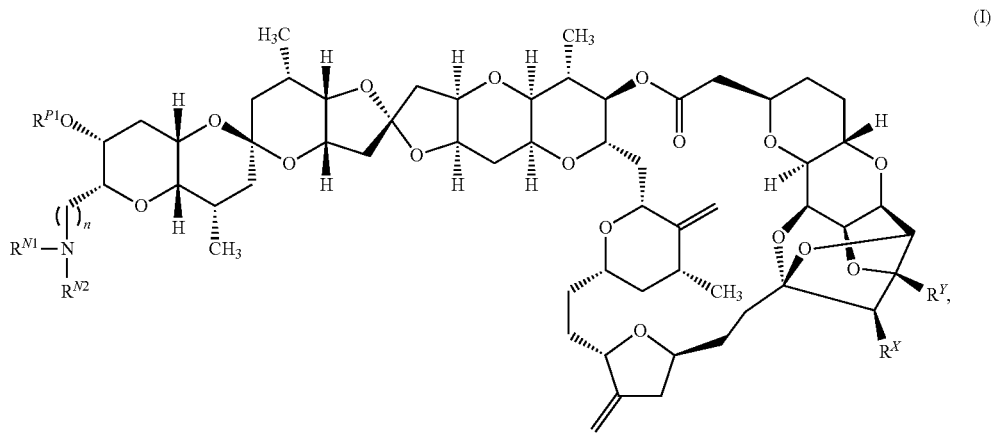

(I)

and pharmaceutically acceptable salts and isotopically labeled derivatives thereof, wherein:

$R^{N1}$ and $R^{N2}$ are independently hydrogen, optionally substituted alkyl, optionally substituted acyl, or a nitrogen protecting group, optionally wherein $R^{N1}$ and $R^{N2}$ are joined together with the intervening atoms to form optionally substituted heterocyclyl or optionally substituted heteroaryl;

$R^{P1}$ is hydrogen, optionally substituted alkyl, optionally substituted acyl, or an oxygen protecting group;

$R^X$ is hydrogen or $-OR^{Xa}$;

$R^Y$ is hydrogen or $-OR^{Ya}$;

$R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl; and n is 1 or 2.

In certain embodiments, the compound of formula (I) is not the following:

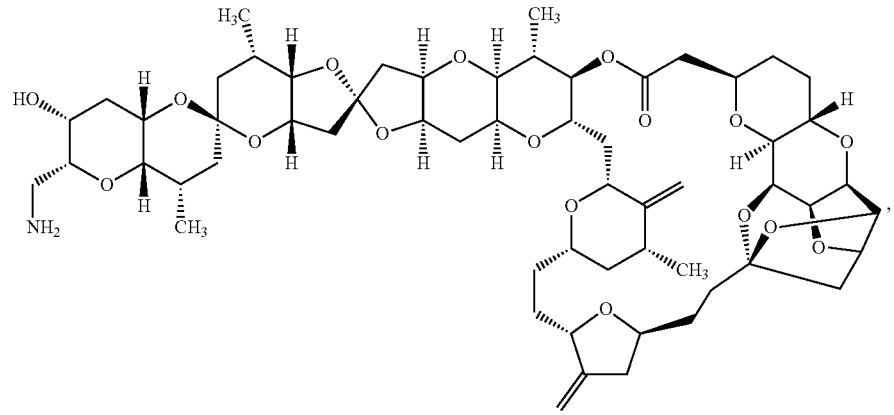 [SMILES: C=C1C[C@@H]2CC[C@@]34CC5O[C@H]6[C@@H](O3)[C@H]3O[C@H](CC[C@@H]3O[C@H]6C5O4)CC(=O)O[C@@H]3[C@@H](C)[C@@H]4O[C@@H]5C[C@]6(C[C@@H]7O[C@]8(C[C@H](C)[C@@H]9O[C@H](CN)[C@H](O)C[C@@H]9O8)C[C@H](C)[C@@H]7O6)O[C@@H]5C[C@@H]4O[C@H]3C[C@H]3O[C@@H](CC[C@@H]1O2)C[C@@H](C)C3=C]

or a pharmaceutically acceptable salt or isotopically labeled derivative thereof.

In another aspect, the present invention provides compounds of Formula (II):

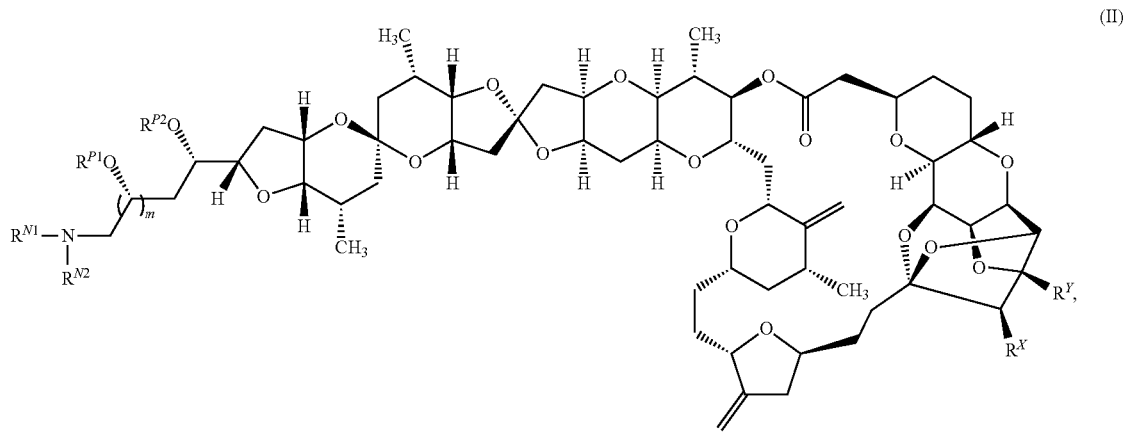

and pharmaceutically acceptable salts and isotopically labeled derivatives thereof, wherein:

$R^{N1}$ and $R^{N2}$ are independently hydrogen, optionally substituted alkyl, optionally substituted acyl, or a nitrogen protecting group, optionally wherein $R^{N1}$ and $R^{N2}$ are joined together with the intervening atoms to form optionally substituted heterocyclyl or optionally substituted heteroaryl;

$R^{P1}$ and $R^{P2}$ are independently hydrogen, optionally substituted alkyl, optionally substituted acyl, or an oxygen protecting group;

$R^X$ is hydrogen or —$OR^{Xa}$;

$R^Y$ is hydrogen or —$OR^{Ya}$;

$R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl; and m is 0 or 1.

In another aspect, the present invention provides compounds of Formula (III):

and pharmaceutically acceptable salts and isotopically labeled derivatives thereof, wherein:

$R^O$ is hydrogen, optionally substituted alkyl, optionally substituted acyl, or an oxygen protecting group;

$R^{P1}$ is hydrogen, optionally substituted alkyl, optionally substituted acyl, or an oxygen protecting group;

$R^X$ is hydrogen or —$OR^{Xa}$;

$R^Y$ is hydrogen or —$OR^{Ya}$;

$R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl; and n is 1 or 2.

In certain embodiments, the compound of Formula (III) is not the following:

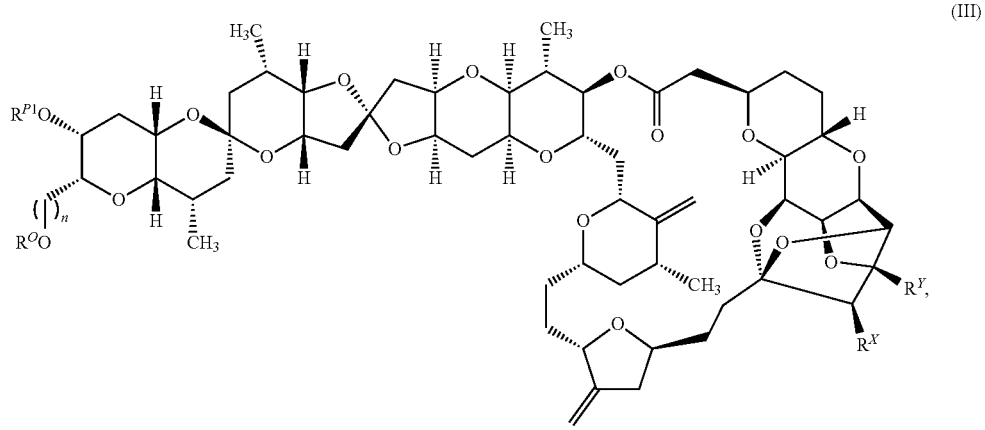

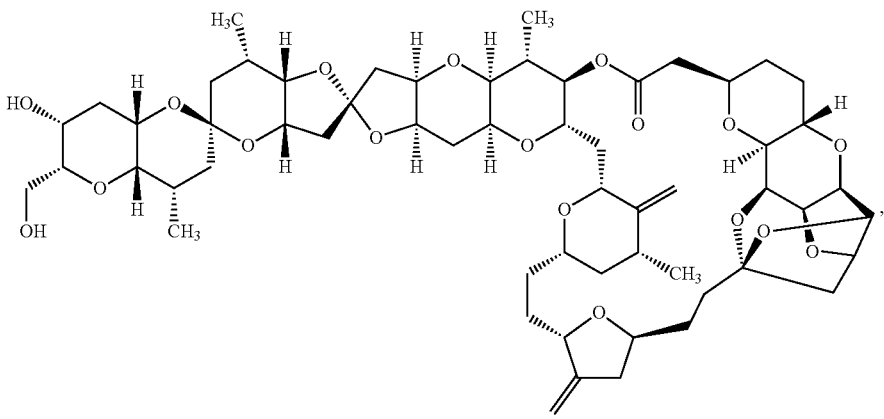 [SMILES: C=C1C[C@@H]2CC[C@@]34CC5O[C@H]6[C@@H](O3)[C@H]3O[C@H](CC[C@@H]3O[C@H]6C5O4)CC(=O)O[C@@H]3[C@@H](C)[C@@H]4O[C@@H]5C[C@]6(C[C@@H]7O[C@]8(C[C@H](C)[C@@H]9O[C@H](CO)[C@H](O)C[C@@H]9O8)C[C@H](C)[C@@H]7O6)O[C@@H]5C[C@@H]4O[C@H]3C[C@H]3O[C@@H](CC[C@@H]1O2)C[C@@H](C)C3=C]

or a pharmaceutically acceptable salt or isotopically labeled derivative thereof.

In yet another aspect, the present invention provides compounds of Formula (IV):

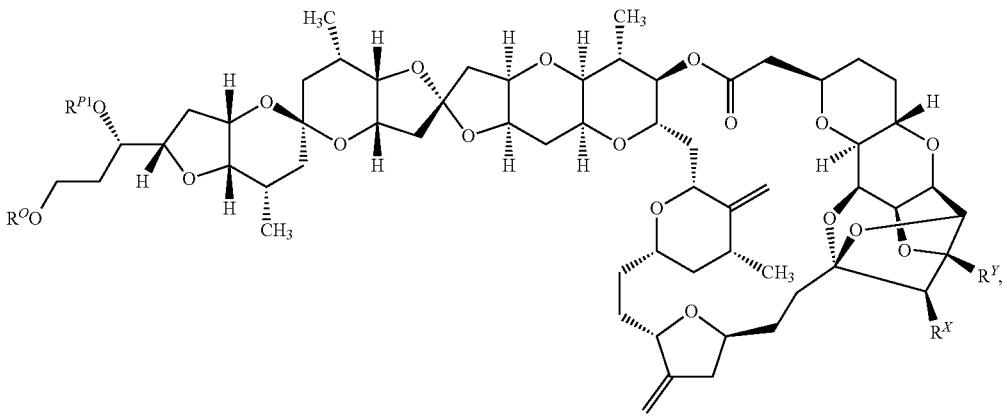

(IV)

and pharmaceutically acceptable salts and isotopically labeled derivatives thereof, wherein:
$R^O$ is hydrogen, optionally substituted alkyl, optionally substituted acyl, or an oxygen protecting group;
$R^{P1}$ is hydrogen, optionally substituted alkyl, optionally substituted acyl, or an oxygen protecting group;
$R^X$ is hydrogen or —$OR^{Xa}$;
$R^Y$ is hydrogen or —$OR^{Ya}$;
$R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl.

In one aspect, the invention features a compound which is Compound (1):

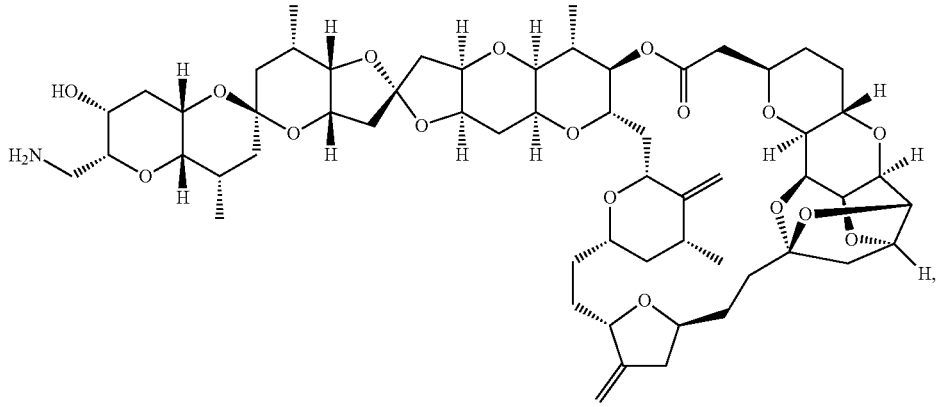

Compound (1)

and pharmaceutically acceptable salts thereof; and isotopically labeled derivatives thereof. In certain embodiments, Compound (1) is excluded from the invention. In certain embodiments, Compound (1) and all pharmaceutically acceptable salts thereof and isotopically labeled derivatives thereof are excluded from the invention.

In another aspect, the invention provides pharmaceutical compositions comprising a compound provided herein, or a pharmaceutically acceptable salt or isotopically labeled derivative thereof. The pharmaceutical compositions may comprise one or more pharmaceutically acceptable excipients or carriers. The pharmaceutical compositions may further comprise one or more additional therapeutic agents in combination, alternation, or other kind of synchronized therapy, to achieve the desired goal of treatment.

The invention also features methods of making compounds provided herein, or intermediates thereto. The synthetic intermediates are also provided herein as part of the invention.

It has been discovered that compounds provided herein have an advantageous effect on tumor vascular remodeling and has anti-CAF activity, as demonstrated in the Figures and Examples. Accordingly, the compounds provided herein have potential use in the treatment of proliferative diseases. In certain embodiments, the compounds can be used to treat cancer (e.g., squamous cell carcinoma of the head and neck (SCCHN), breast cancer, esophageal cancer, uterine cancer, ovarian cancer, colorectal cancer, endometrial cancer, gastric cancer, lung cancer, small bowel cancer, bladder cancer, sweat gland cancer, sarcomas, rare cancers).

In another aspect, the present invention provides methods for treating cancer or inhibiting tumor growth in a subject with a compound provided herein, or a pharmaceutically acceptable salt, or isotopically labeled derivative thereof. In certain embodiments, the present invention provides methods for inhibiting any tumor growth or cancer that will respond to a compound with tumor vascular remodeling effects and/or anti-CAF activity, in a subject, typically a human, with a compound provided herein, or a pharmaceutically acceptable salt, or isotopically labeled derivative thereof.

A compound provided herein, or a pharmaceutically acceptable salt, or isotopically labeled derivative thereof, or a composition thereof, may be administered in combination with any other active agent that provides beneficial results for the patient. In one embodiment, a compound provided herein is used in combination, alternation, or other synchronized therapy with an immunotherapy. In certain embodiments, the immunotherapy is an anti-EGFR (epidermal growth factor receptor) antibody, an anti-HER2 (human epidermal growth factor receptor) antibody, an anti-PD-1 antibody, or an anti-PD-L1 antibody, as described in more detail below.

For example, a method is provided to treat squamous cell carcinoma of the head and neck (SCCHN) in a subject, typically a human, in need thereof comprising administering to the subject an effective amount of a compound provided herein, or a pharmaceutically acceptable salt, or isotopically labeled derivative thereof, or a composition thereof, in combination with an anti-EGFR (epidermal growth factor receptor) mAb therapy. In certain embodiments, the anti-EGFR (epidermal growth factor receptor) mAb is cetuximab.

As another example, a method to treat breast cancer in a subject, typically a human, in need thereof comprising administering to said subject an effective amount of a compound provided herein, or a pharmaceutically acceptable salt, or isotopically labeled derivative thereof, or a composition thereof, in combination with an HER2 (human epidermal growth factor receptor) mAb therapy. In certain embodiments, the HER2 (human epidermal growth factor receptor) mAb is trastuzumab. In other embodiments, the compound may be used to treat breast cancer in combination with traditional chemotherapy, such as adriamycin, cyclophosphamide, taxol, etc., or an anti-estrogen such as a selective estrogen modulator (SERM), a selective estrogen degrader (SERD), a partial or total estrogen inhibitor (such as fulvestrant) or a CDK 4/6 inhibitor such as palbociclib (Pfizer).

Another aspect of the present invention provides a compound of Formula (I), (II), (III), or (IV), or a pharmaceutically acceptable salt, or isotopically labeled derivative thereof, which may be in the form of a hydrate, solvate, polymorph, stereoisomer, or a composition thereof, in a kit, which may be a dosage form package. The kits described herein may include a single dose or multiple doses of the compound or pharmaceutical composition thereof. A kit of the invention may include instructions for using the provided therapeutic dosage forms (e.g., instructions for using the compound or pharmaceutical composition included in the kit).

The present invention thus includes at least the following features:

(i) A compound of Formula (I), (II), (III), or (IV), or a pharmaceutically acceptable salt or isotopically labeled derivative thereof, which may be optionally be in the form of a hydrate, solvate, stereoisomer, or polymorph;

(ii) A method for treatment that includes administering an effective amount to a subject such as a human of a compound provided herein, or a pharmaceutically acceptable salt or isotopically labeled derivative, which may be optionally be in the form of a hydrate, solvate, stereoisomer, or polymorph, to treat a proliferative disease. In certain embodiments, the proliferative disease is cancer. In certain embodiment, the cancer is head and neck cancer (e.g., squamous cell carcinoma of the head and neck (SCCHN), adenoid cystic carcinoma), breast cancer, esophageal cancer (e.g., esophageal adenocarcinoma), uterine cancer (e.g., uterine sarcoma), ovarian cancer, colorectal cancer, or sarcoma (e.g., synovial sarcoma, angiosarcoma, soft tissue sarcoma, fibrosarcoma, uterine sarcoma, intimal sarcoma). In certain embodiments, the cancer is bladder cancer (e.g., urothelial carcinoma), gastric cancer, small bowel cancer (e.g., small bowel adenocarcinoma), endometrial cancer, lung cancer (e.g., non-small cell lung cancer), or sweat gland cancer (e.g., sweat gland carcinoma). In certain embodiments, the cancer is a rare cancer;

(iii) A method for treatment that includes administering an effective amount to a subject such as a human of a compound provided herein, or a pharmaceutically acceptable salt or isotopically labeled derivative thereof, which may be optionally be in the form of a hydrate, solvate, stereoisomer, or polymorph, for use in treating a medical disorder that responds to vascular remodeling effects and/or anti-CAF activity (e.g., a proliferative disease such as cancer or a tumor);

(iv) A compound of Formula (I), (II), (III), or (IV), or a pharmaceutically acceptable salt or isotopically labeled derivative, which may be optionally be in the form of a hydrate, solvate, stereoisomer, or polymorph, for use to treat a proliferative disease. In certain embodiments, the proliferative disease is cancer. In certain embodiments, the cancer is squamous cell carcinoma of the head and neck (SCCHN), breast cancer, esophageal cancer, uterine cancer, ovarian cancer, colorectal cancer, endometrial cancer, or a sarcoma;

(v) A compound of Formula (I), (II), (III), or (IV), or a pharmaceutically acceptable salt or isotopically labeled derivative thereof, which may be optionally be in the form of a hydrate, solvate, stereoisomer, or polymorph, for use in treating a medical disorder that responds to vascular remodeling effects and/or anti-CAF activity (e.g., a proliferative disease such as a cancer or tumor);

(vi) A deuterated derivative of a compound of Formula (I), (II), (III), or (IV), or a pharmaceutically acceptable salt thereof;

(vii) A process for manufacturing a medicament intended for the therapeutic use for treating or preventing a disorder such as a proliferative disease (e.g., cancer or tumor) that responds to vascular remodeling effects and/or anti-CAF activity, characterized in that a compound provided herein, or a pharmaceutically acceptable salt or isotopically labeled derivative thereof, which may be optionally be in the form of a hydrate, solvate, stereoisomer, or polymorph described above, or an embodiment of the active compound, is used in the manufacture;

(viii) A compound of Formula (I), (II), (III), or (IV), or a pharmaceutically acceptable salt or isotopically labeled derivative thereof, in substantially pure form (e.g., at least 90 or 95%);

(ix) A pharmaceutically acceptable composition of a compound provided herein, or a pharmaceutically acceptable salt or isotopically labeled derivative thereof, which may be optionally be in the form of a hydrate, solvate, stereoisomer, or polymorph, in a pharmaceutically acceptable carrier or excipient;

(x) A pharmaceutically acceptable dosage form of a compound provided herein, or a pharmaceutically acceptable salt or isotopically labeled derivative thereof, which may be optionally be in the form of a hydrate, solvate, stereoisomer, or polymorph, optionally in a pharmaceutically acceptable carrier or excipient;

(xi) A compound of Formula (I), (II), (III), or (IV), or a pharmaceutically acceptable salt or isotopically labeled derivative thereof, to treat a disorder described herein (e.g., proliferative disease) whereby it acts through a mechanism other than vascular remodeling effects and/or anti-CAF activity of action; and (xii) Methods for the manufacture of the compounds described herein, and intermediates in the synthesis.

BRIEF DESCRIPTION OF THE DRAWINGS

The accompanying drawings, which are incorporated in and constitute a part of this specification, illustrate several embodiments of the invention and together with the description, provide non-limiting examples of the invention.

FIG. 6A. Nude mice were implanted with luciferase-transduced HSC-2 ($1\times10^6$ cells/spot) in tongue. The amount of luciferase-transduced HSC-2 was analyzed using In Vivo Imaging System (IVIS). Data show the bioluminescence levels in tongue in each mouse. FIG. 6B. Representative bioluminescence image of 16 mice. CDDP, CTX, CDDP+CTX were used for as comparators, which are currently used in treatment of SCCHN cancer patient treatment. CDDP=cisplatin, CTX=cetuximab.

FIG. 7A. Nude mice were implanted with luciferase-transduced HSC-2 ($1\times10^6$ cells/spot) in tongue. Data show the survival curve until Day 100 after treatment of drugs (n=16). *P<0.0001 versus Compound (1) or CTX alone (Log-rank (Mantel-Cox) test). FIG. 7B. The amount of luciferase-transduced HSC-2 was analyzed using In Vivo Imaging System (IVIS). Bioluminescence images of 10 survived mice of Compound (1)+CTX combination group on Day 100. RBW=relative body weight. CDDP=cisplatin, CTX=cetuximab.

FIG. 8A. Nude mice were subcutaneously implanted with luciferase-transduced FaDu ($5\times10^6$ cells/spot) in the right thighs. Thirteen days after the inoculation, mice were randomly assigned (n=6), and intravenously injected with Compound (1) at 90 μg/kg on Day 1 and Day 8 with or without RT of 18 Gy on Day 4 and Day 11. The amount of luciferase-transduced FaDu was analyzed using In Vivo Imaging System (IVIS). Data show the mean relative bioluminescence level to Day 1 and SEM (n=6). SEM=standard error of the mean. * P<0.05 versus non-treated on Day 29 (unpaired t-test). FIG. 8B. Representative bioluminescence images of 6 mice each group on Day 29. RT=radiation therapy.

FIG. 19A. BJ cells (normal human lung fibroblasts) were co-cultured with FaDu cells for three days in the absence (vehicle) or presence of A83-01, a potent selective TGF-β-R inhibitor, and the expression of α-SMA was analysed by immunofluorescence staining (red color). Samples were also stained with anti-pan-human cytokeratin (green color) for cancer cell staining and DAPI (blue color) for nuclear staining. FIGS. 19B-19F. BJ cells were treated with Compound (1) (0.15 nmol/L in immunofluorescence staining data and indicated concentrations in western blot analysis data) and TGF-β for 2 days. FIGS. 19B-19E. Samples were stained with the indicated antibody (red color) and DAPI (blue color) for nuclear staining. FIG. 19F Western blot images and quantification of the images. The graph shows ratios of the results of treatment groups to the non-treated group. FIGS. 19G and 19F BJ cells were pretreated with defactinib (1 μmol/L) and TGF-β for 2 days. The lens magnification used was ×4 (FIGS. 19A, 19B, 19C, 19G, and 19H) or ×40 (FIGS. 19D and 19E).

DEFINITIONS

Chemical Definitions

Figure 1:
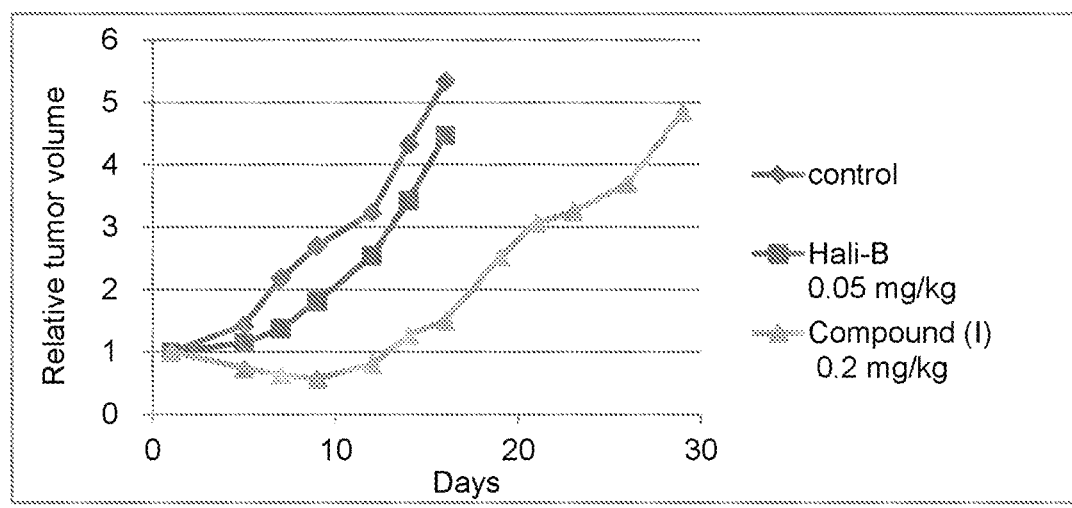
FIG. 1 shows antitumor effects of Compound (1) in FaDu subcutaneous xenograft model (head and neck cancer) in mice as monotherapy as described in Pharmacological Test Example 4.
Figure 2:
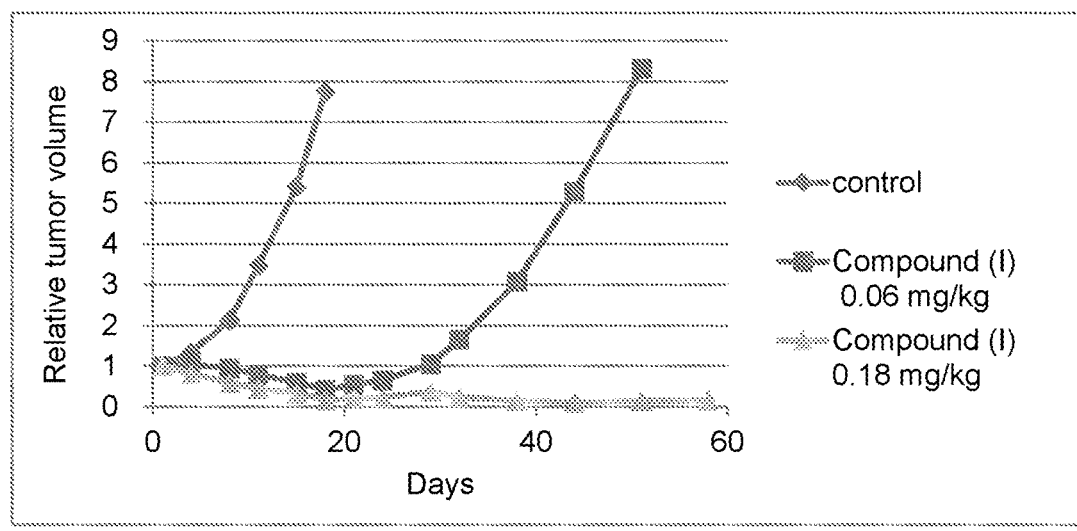
FIG. 2 shows antitumor activity of Compound (1) against OSC-19 subcutaneous xenograft model (head and neck cancer) in mice as monotherapy as described in Pharmacological Test Example 5.
Figure 3:
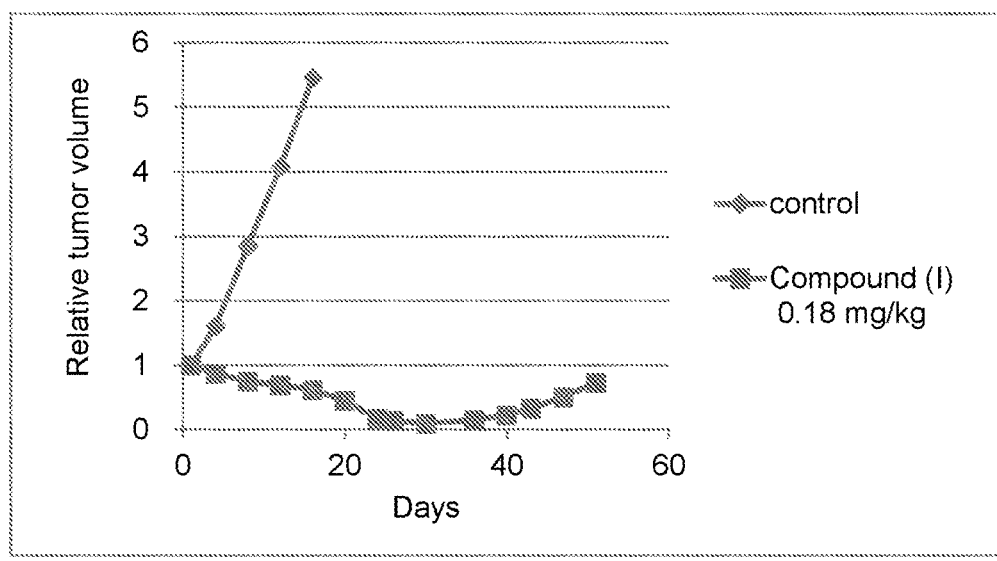
FIG. 3 shows antitumor activity of Compound (1) against HCC-1806 subcutaneous xenograft (breast cancer) model in mice as monotherapy as described in Pharmacological Test Example 6.
Figure 4:
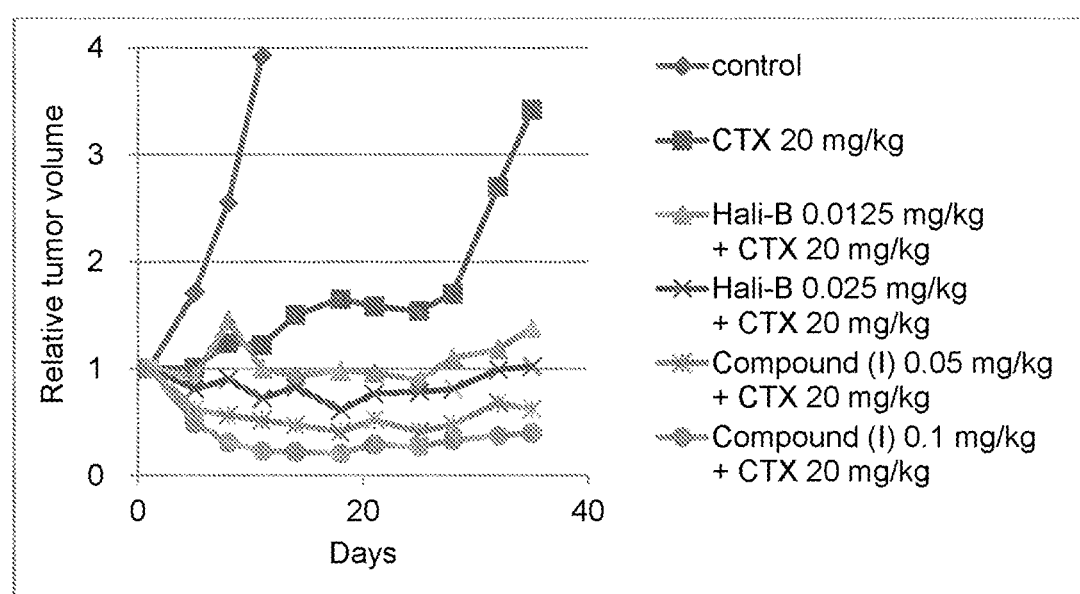
FIG. 4 shows antitumor effects of Compound (1) in FaDu subcutaneous xenograft model in combination with cetuximab in mice as described in Pharmacological Test Example 7.
Figure 5:
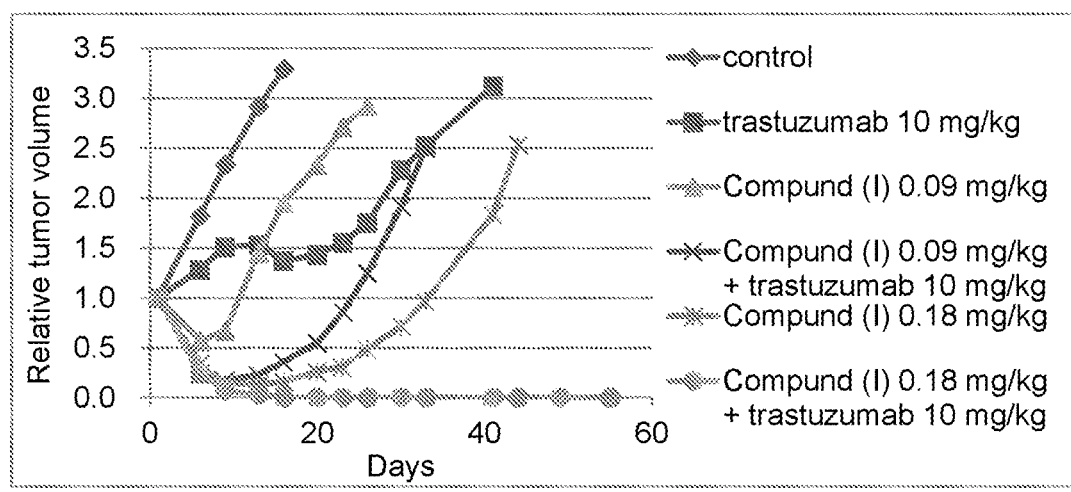
FIG. 5 shows antitumor activity of Compound (1) in KPL-4 subcutaneous xenograft model (breast cancer) in combination with trastuzumab in mice as described in Pharmacological Test Example 8.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, iso-propyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted iso-propyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted iso-butyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

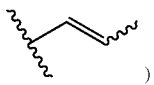
)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_3$0.8 carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{cc}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$—, —C(=S)N(R$^{cc}$)$_2$, —C(=O) SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, substituents include: halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, 5-10 membered heteroaryl; or two geminal hydrogens can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$)$_2$)$_2$, wherein $X^-$, $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC(=O)N($R^{bb}$)$_2$, —NHC(=N$R^{bb}$)N($R^{bb}$)$_2$, —NHSO$_2R^{aa}$, —NHP(=O)(O$R^{cc}$)$_2$, and —NHP(=O)(N($R^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2R^{aa}$, —N$R^{bb}$P(=O)(O$R^{cc}$)$_2$, and —N$R^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

The term "sulfonyl" refers to a group selected from —SO$_2$N($R^{bb}$)$_2$, —SO$_2R^{aa}$, and —SO$_2$O$R^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, —C(=S)O($R^{X1}$), —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (e.g., —C(=O)$R^{aa}$), carboxylic acids (e.g., —CO$_2$H), aldehydes (—CHO), esters (e.g., —CO$_2R^{aa}$, —C(=O)S$R^{aa}$, —C(=S)S$R^{aa}$), amides (e.g., —C(=O)N($R^{bb}$)$_2$, —C(=O)N$R^{bb}$SO$_2R^{aa}$, —C(=S)N($R^{bb}$)$_2$), and imines (e.g., —C(=N$R^{bb}$)$R^{aa}$, —C(=N$R^{bb}$)O$R^{aa}$, —C(=N$R^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{aa}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl- 2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5—(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

Other Definitions

As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Compounds described herein are also provided, and can be administered, as a free base.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms. Treatment may also be continued after symptoms have resolved, for example, to delay or prevent recurrence.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. Alternatively, in a separate method or use, the invention may be used, where indicated and effective, as a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for treating in any disease or condition described.

As used herein, "inhibition", "inhibiting", "inhibit" and "inhibitor", and the like, refer to the ability of a compound to reduce, slow, halt, or prevent the activity of a biological process (e.g., tumor growth). In certain embodiments, the inhibition is about 45% to 50%. In certain embodiments, the inhibition is about 5%, 10%, 15%, 20%, 25%, 30%, 35%, 40%, 45%, 50%, 55%, 60%, 65%, 70%, 75%, 80%, 85%, 90%, 95%, 99.9%, or 100%.

Detailed Description of Certain Embodiments

The present invention is described in detail below with reference to embodiments and the like of the present invention. The invention provides compounds (e.g., compounds of Formulae (I), (II), (III), and (IV)), and pharmaceutically acceptable salts or isotopically labeled derivatives thereof, and pharmaceutical compositions thereof. The invention also provides methods of treating proliferative diseases (e.g., inhibiting tumor growth and/or treating cancer) in a subject comprising administering an effective amount to the subject of a compound or composition provided herein. The compound or composition may be administered as a monotherapy or in combination with another therapy, as described herein. In yet another aspect, the present invention provides methods of preparing compounds of Formulae (I), (II), (III), and (IV), and synthetic intermediates useful to that end.

In one aspect, the present invention provides compounds of Formula (I):

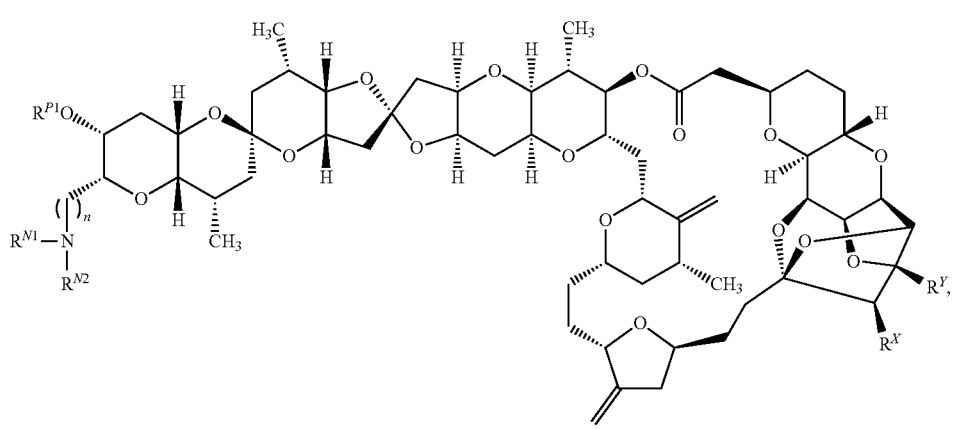

(I)

and pharmaceutically acceptable salts and isotopically labeled derivatives thereof, wherein:

$R^{N1}$ and $R^{N2}$ are independently hydrogen, optionally substituted alkyl, optionally substituted acyl, or a nitrogen protecting group, optionally wherein $R^{N1}$ and $R^{N2}$ are joined together with the intervening atoms to form optionally substituted heterocyclyl or optionally substituted heteroaryl;

$R^{P1}$ is hydrogen, optionally substituted alkyl, optionally substituted acyl, or an oxygen protecting group;

$R^X$ is hydrogen or —$OR^{Xa}$;

$R^Y$ is hydrogen or —$OR^{Ya}$;

$R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl; and n is 1 or 2.

In certain embodiments, the compound of formula (I) is Compound (1):

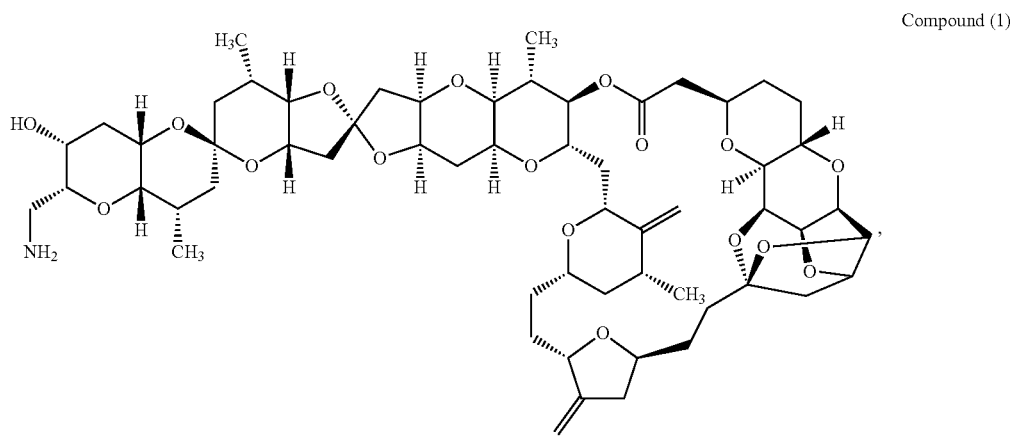 [SMILES: C=C1C[C@@H]2CC[C@@]34CC5O[C@H]6[C@@H](O3)[C@H]3O[C@H](CC[C@@H]3O[C@H]6C5O4)CC(=O)O[C@@H]3[C@@H](C)[C@@H]4O[C@@H]5C[C@]6(C[C@@H]7O[C@]8(C[C@H](C)[C@@H]9O[C@H](CN)[C@H](O)C[C@@H]9O8)C[C@H](C)[C@@H]7O6)O[C@@H]5C[C@@H]4O[C@H]3C[C@H]3O[C@@H](CC[C@@H]1O2)C[C@@H](C)C3=C]

Compound (1)

or a pharmaceutically acceptable salt or isotopically labeled derivative thereof. In certain embodiments, the compound of Formula (I) is not Compound (1), or a pharmaceutically acceptable salt or isotopically labeled derivative thereof. In certain embodiments, Compound (1) and all pharmaceutically acceptable salts and isotopically labeled derivatives thereof are excluded from the invention.

In certain embodiments, the compound of Formula (I) is of one of the following formulae:

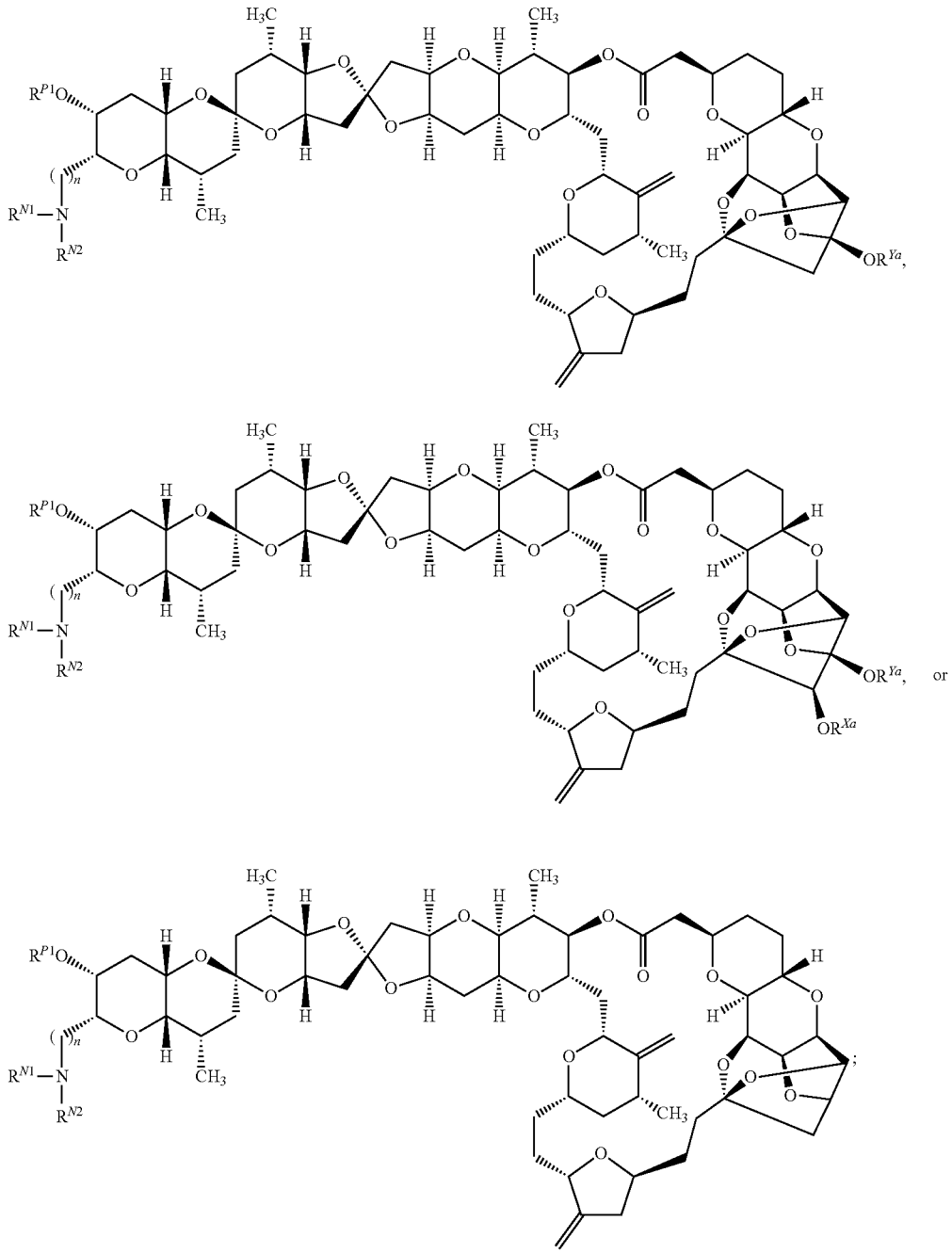

or a pharmaceutically acceptable salt or isotopically labeled derivative thereof.

In certain embodiments, the compound of Formula (I) is of one of the following formulae:

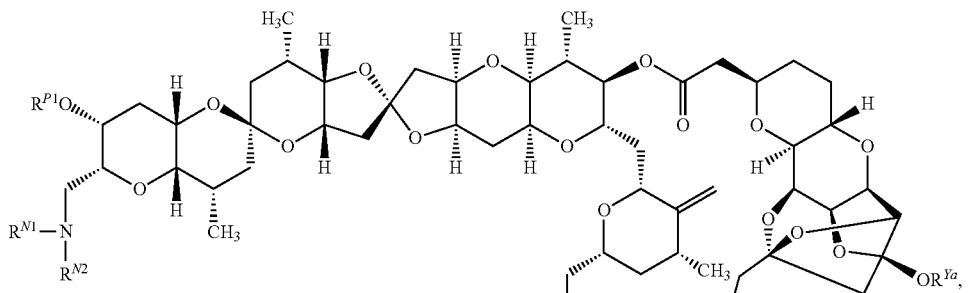
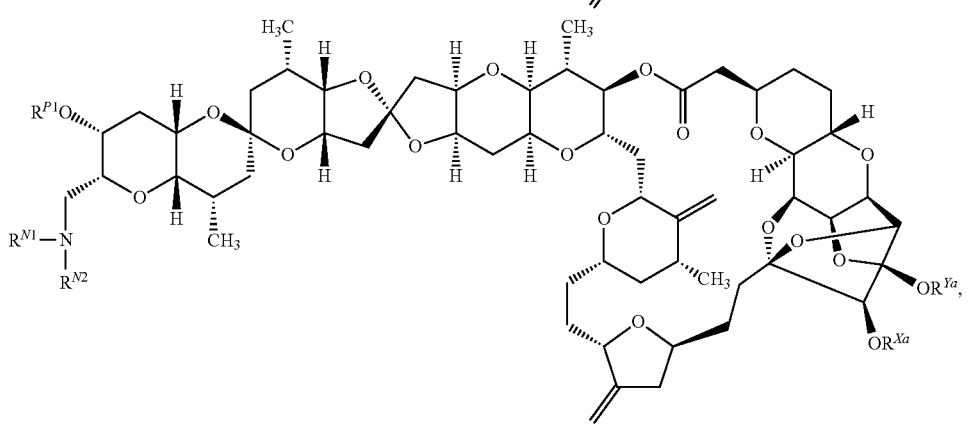
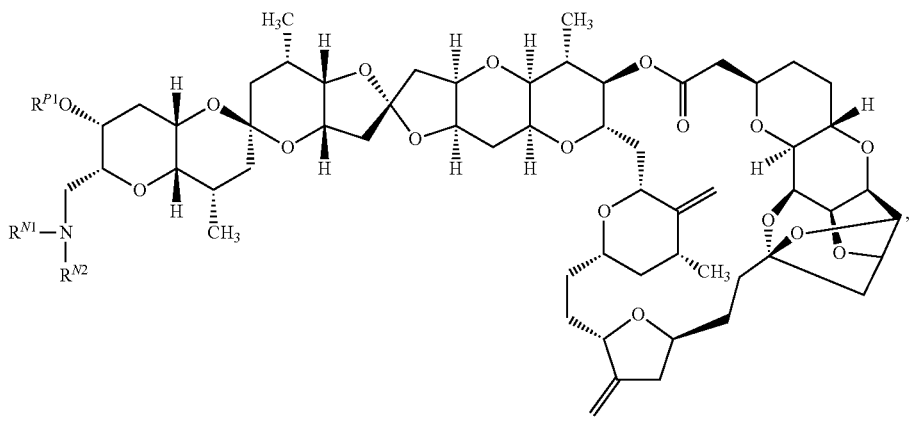
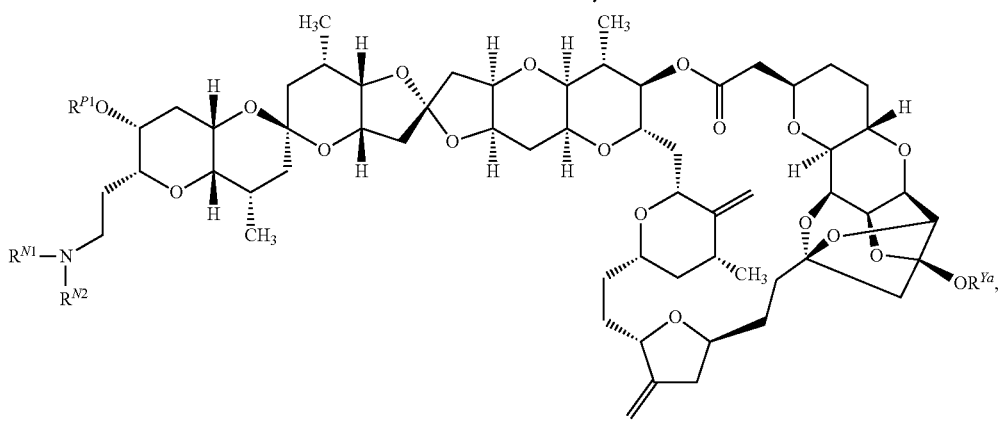

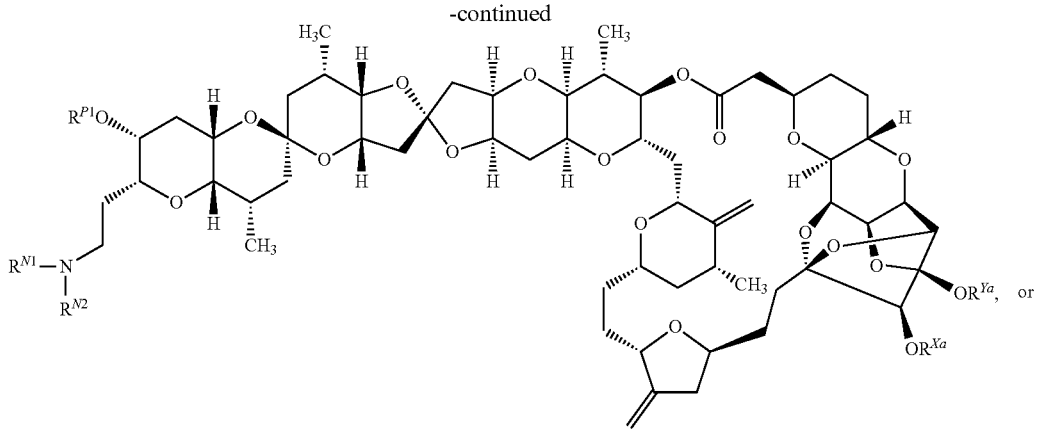
or a pharmaceutically acceptable salt or isotopically labeled derivative thereof.
In certain embodiments, the compound of Formula (I) is selected from the group consisting of:
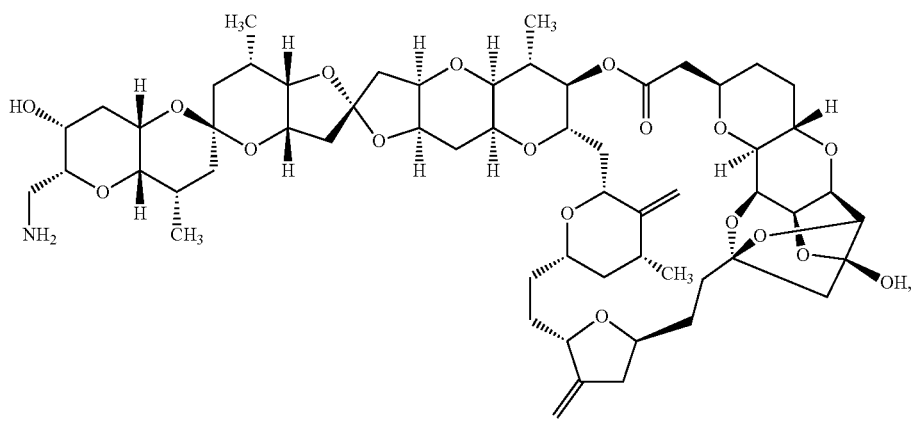

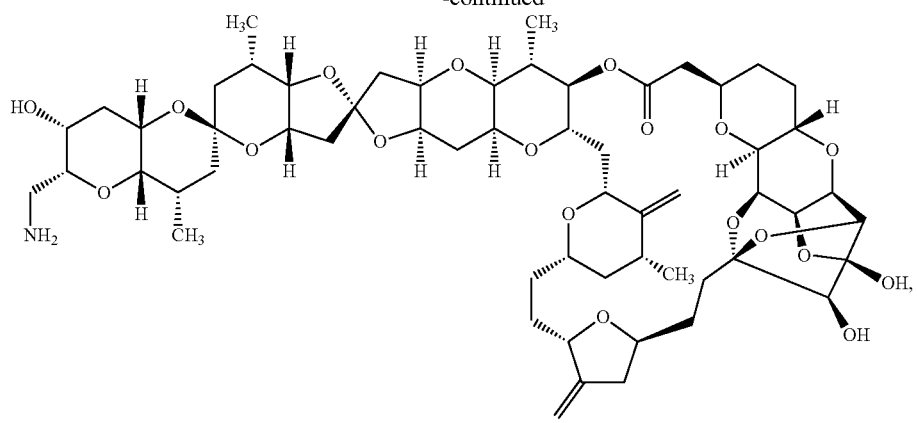
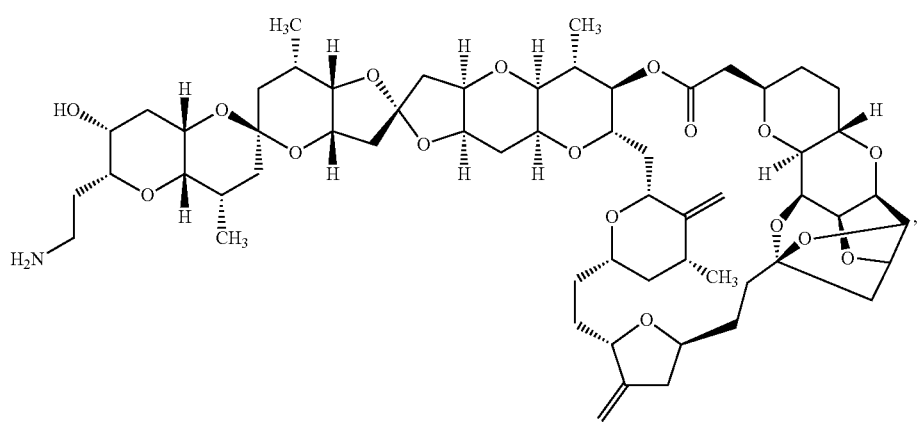
(G-4)
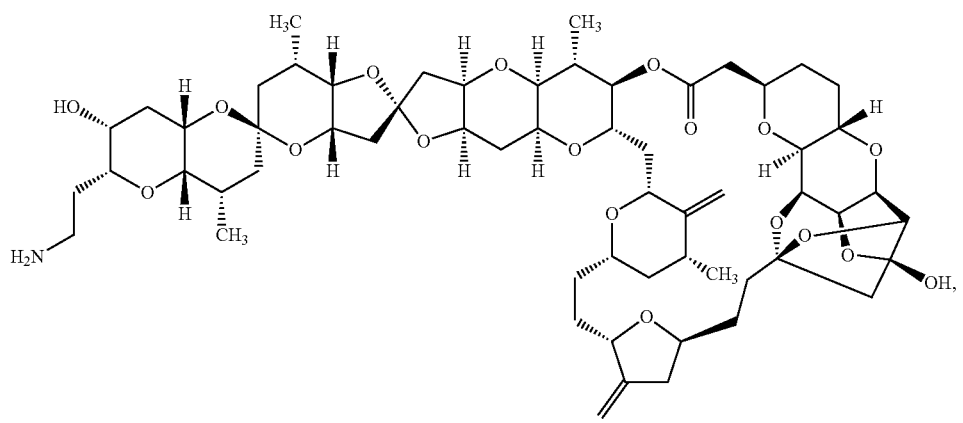
(H-2)
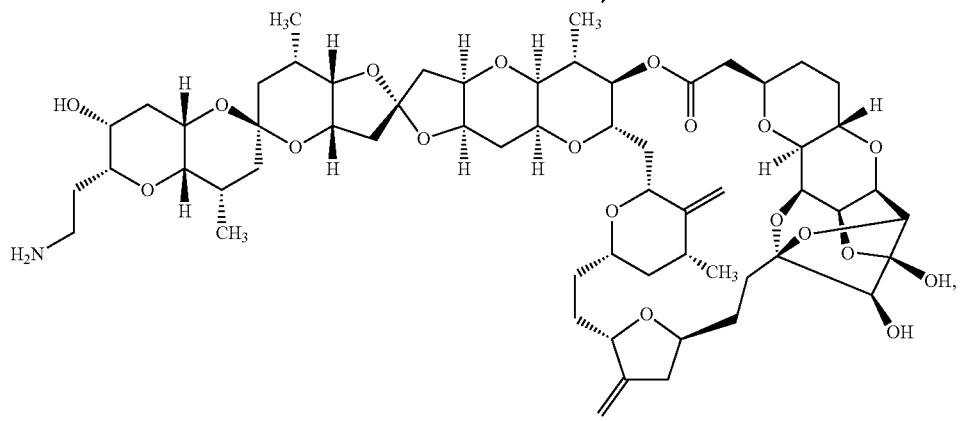

and pharmaceutically acceptable salts and isotopically labeled derivatives thereof.

In another aspect, the present invention provides compounds of Formula (II):

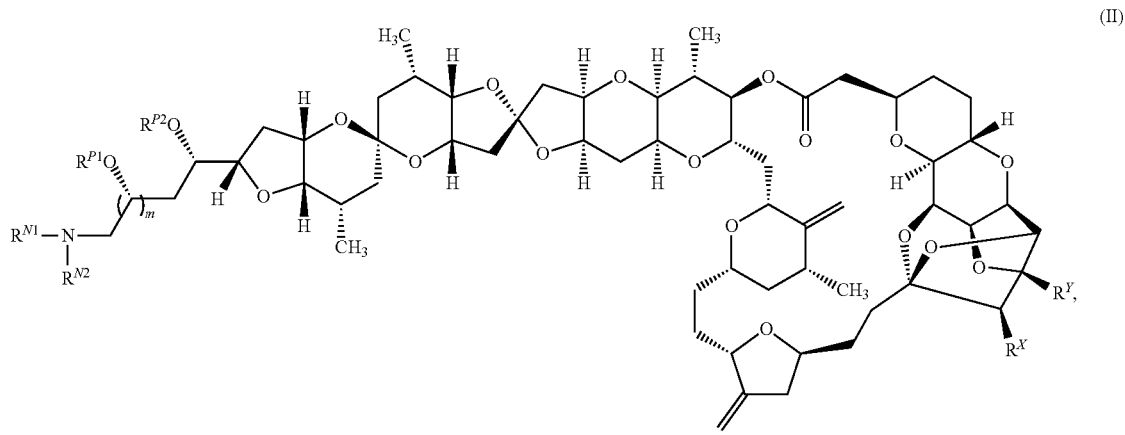

(II)

and pharmaceutically acceptable salts and isotopically labeled derivatives thereof, wherein:

$R^{N1}$ and $R^{N2}$ are independently hydrogen, optionally substituted alkyl, optionally substituted acyl, or a nitrogen protecting group, optionally wherein $R^{N1}$ and $R^{N2}$ are joined together with the intervening atoms to form optionally substituted heterocyclyl or optionally substituted heteroaryl;

$R^{P1}$ and $R^{P2}$ are independently hydrogen, optionally substituted alkyl, optionally substituted acyl, or an oxygen protecting group;

$R^X$ is hydrogen or —$OR^{Xa}$;

$R^Y$ is hydrogen or —$OR^{Ya}$;

$R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl; and m is 0 or 1.

In certain embodiments, the compound of Formula (II) is of one of the following formulae:

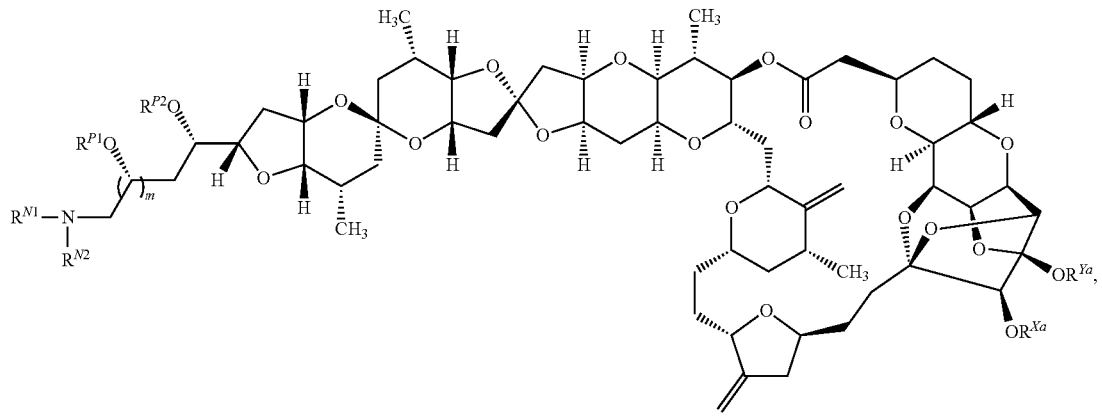

-continued
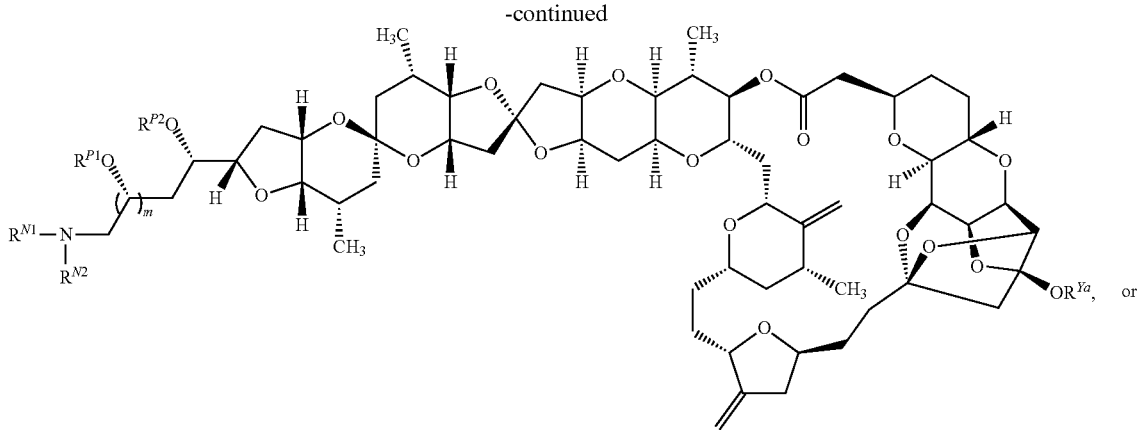
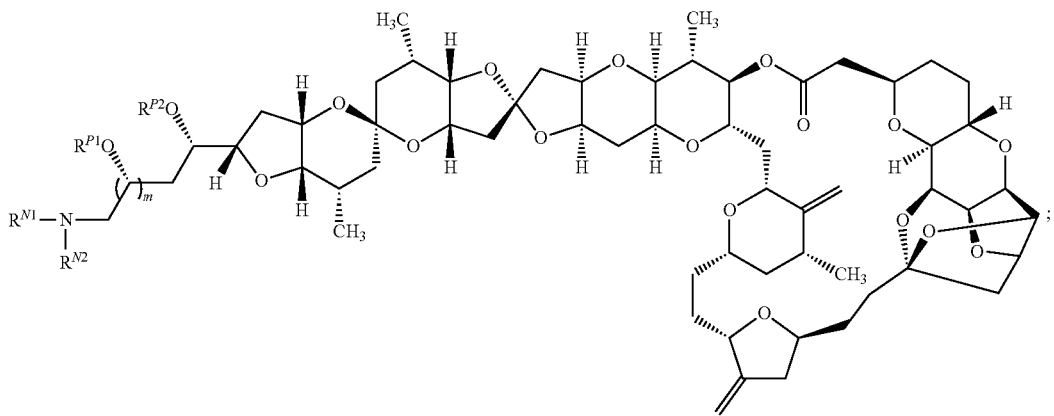
or a pharmaceutically acceptable salt or isotopically labeled derivative thereof.
In certain embodiments, the compound of Formula (II) is of one of the following formulae:
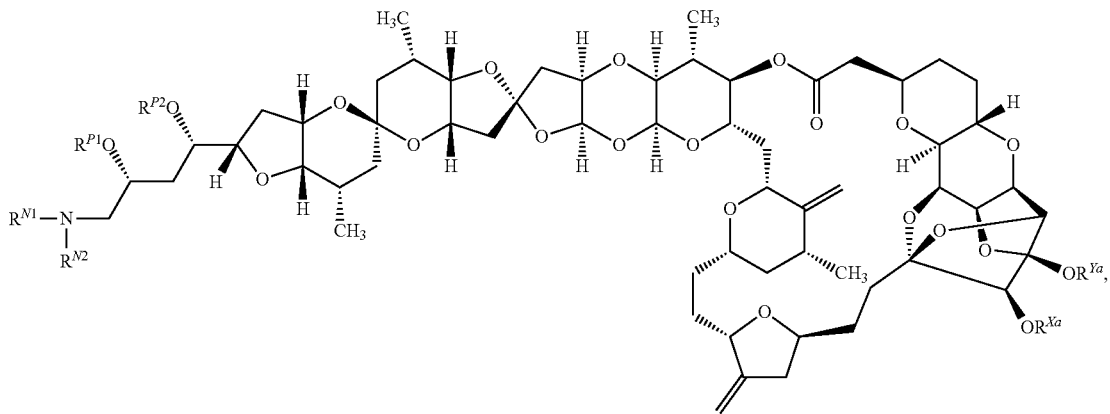

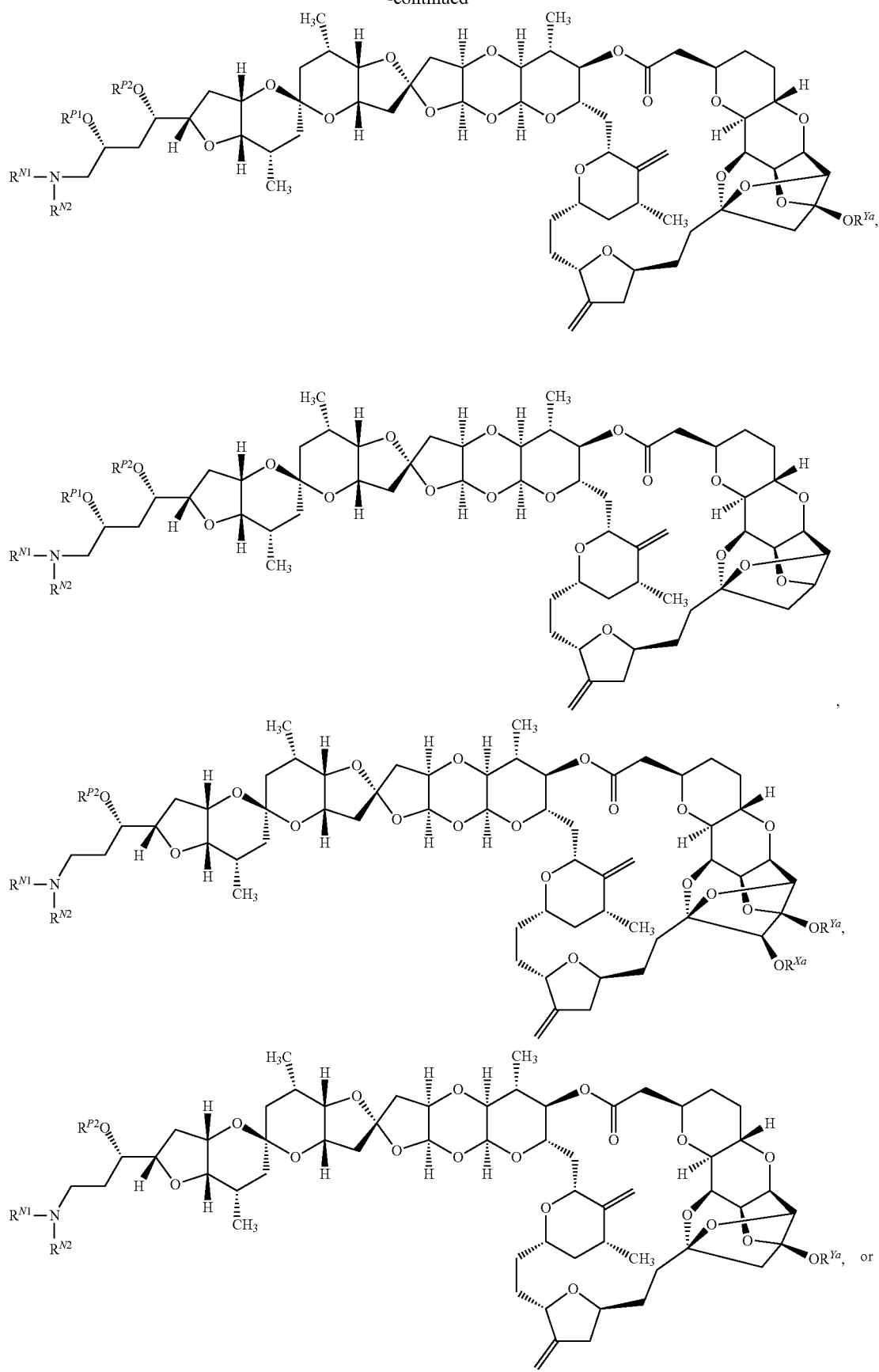

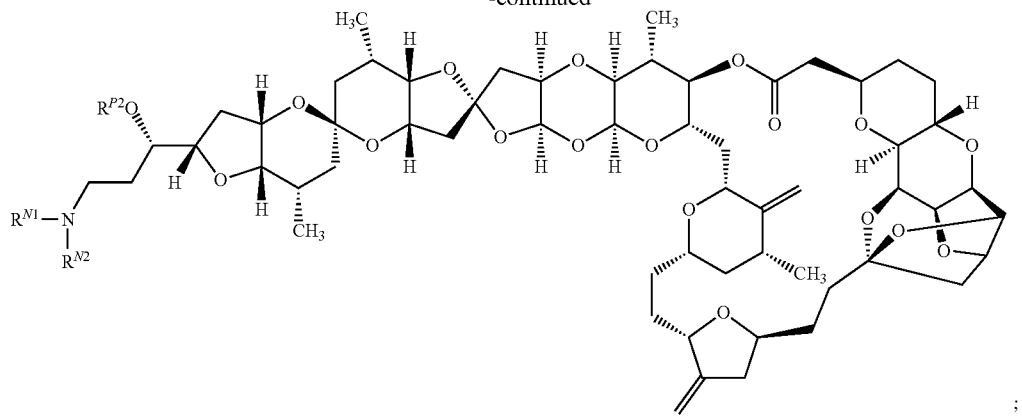
or a pharmaceutically acceptable salt or isotopically labeled derivative thereof.
In certain embodiments, the compound of Formula (II) is selected from the group consisting of:
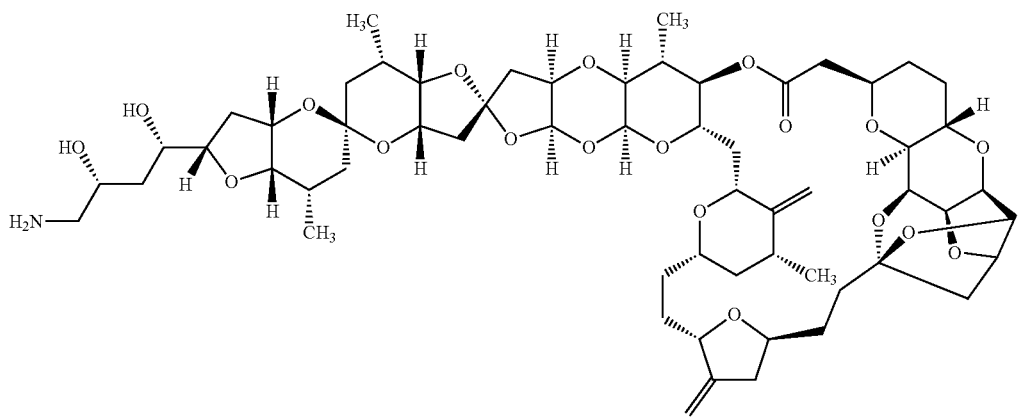
(K-2)
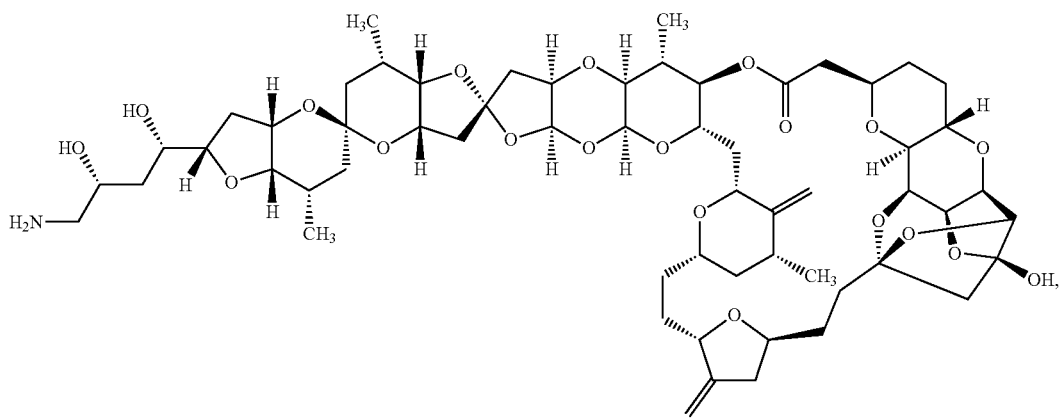
(L-6)

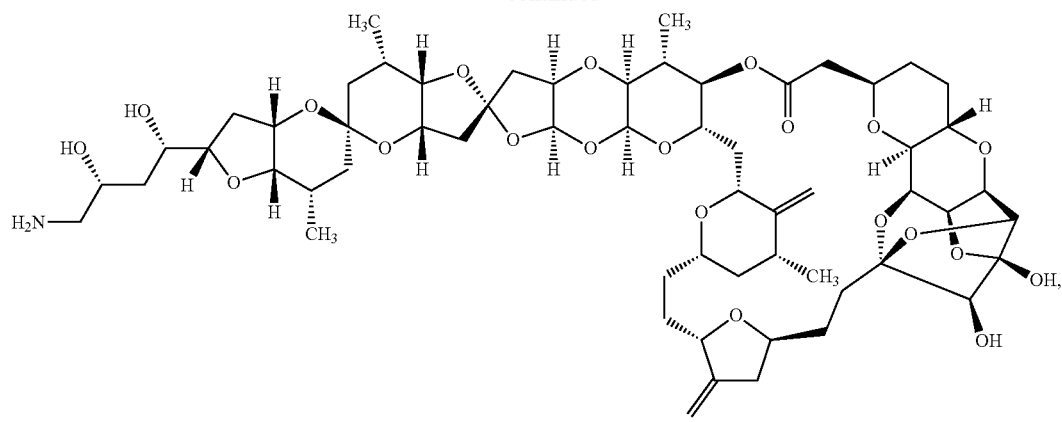
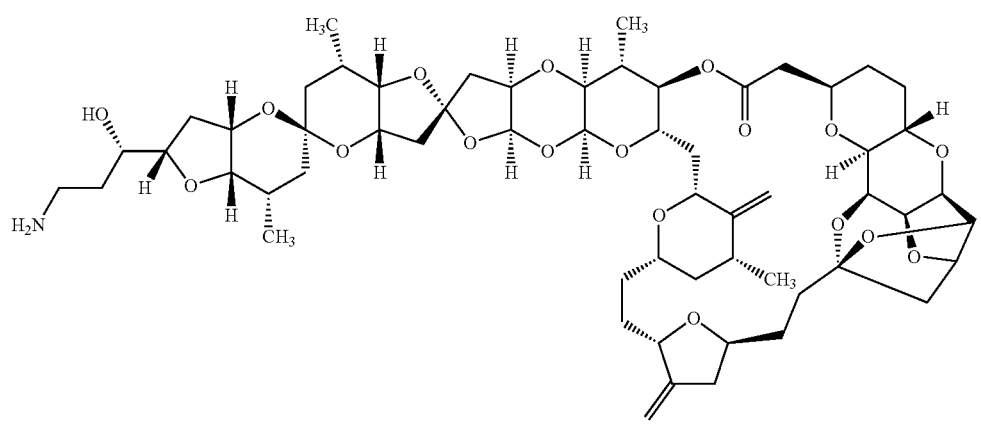
(N-1)
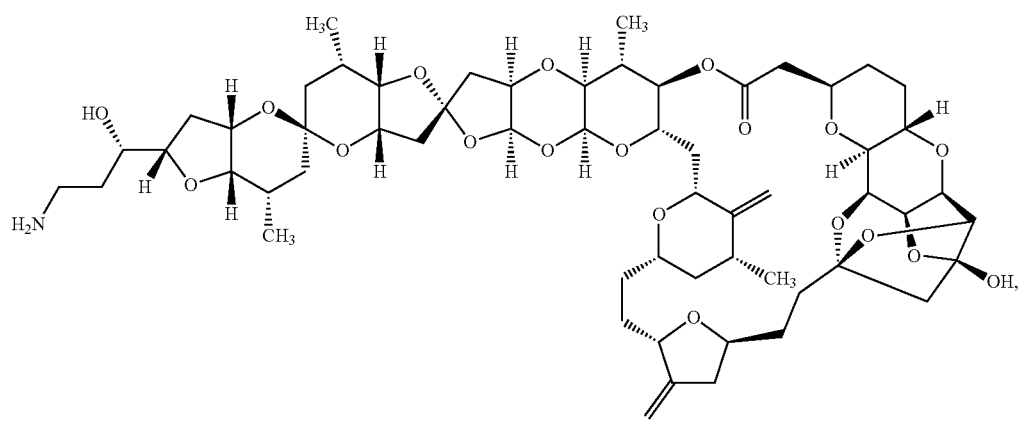
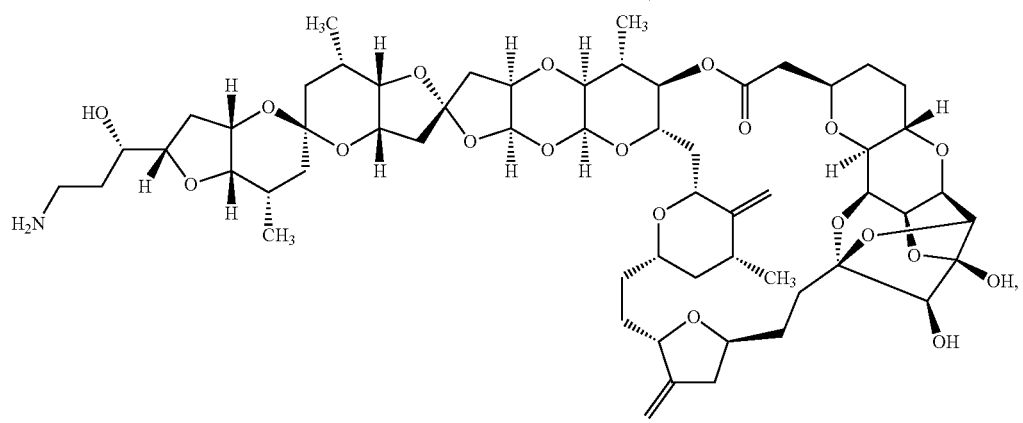

and pharmaceutically acceptable salts and isotopically labeled derivatives thereof.

In another aspect, the present invention provides compounds of Formula (III):

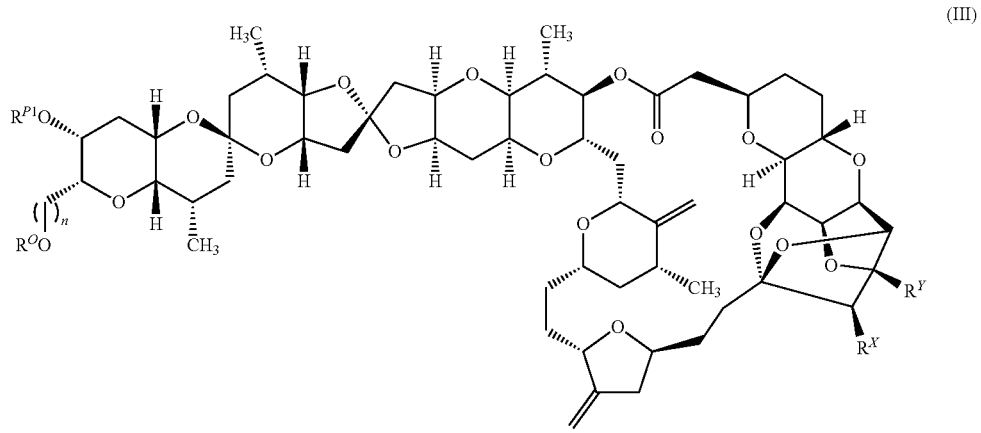

(III)

and pharmaceutically acceptable salts and isotopically labeled derivatives thereof, wherein:

$R^O$ is hydrogen, optionally substituted alkyl, optionally substituted acyl, or an oxygen protecting group;

$R^{P1}$ is hydrogen, optionally substituted alkyl, optionally substituted acyl, or an oxygen protecting group;

$R^X$ is hydrogen or $-OR^{Xa}$;

$R^Y$ is hydrogen or $-OR^{Ya}$;

$R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl; and n is 1 or 2.

In certain embodiments, the compound of Formula (III) is the following:

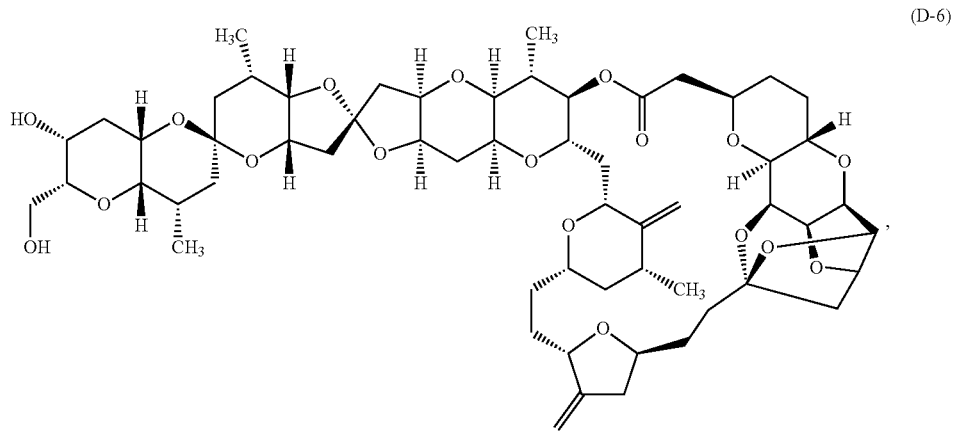 [SMILES: C=C1C[C@@H]2CC[C@@]34CC5O[C@H]6[C@@H](O3)[C@H]3O[C@H](CC[C@@H]3O[C@H]6C5O4)CC(=O)O[C@@H]3[C@@H](C)[C@@H]4O[C@@H]5C[C@]6(C[C@@H]7O[C@]8(C[C@H](C)[C@@H]9O[C@H](CO)[C@H](O)C[C@@H]9O8)C[C@H](C)[C@@H]7O6)O[C@@H]5C[C@@H]4O[C@H]3C[C@H]3O[C@@H](CC[C@@H]1O2)C[C@@H](C)C3=C]

(D-6)

or a pharmaceutically acceptable salt thereof. In certain embodiments, the compound of Formula (III) is not (D-6), or a pharmaceutically acceptable salt or isotopically labeled derivative thereof. In certain embodiments (D-6), and all pharmaceutically acceptable salts and isotopically labeled derivatives thereof, are excluded from the invention.

In certain embodiments, the compound of Formula (III) is of one of the following formulae:

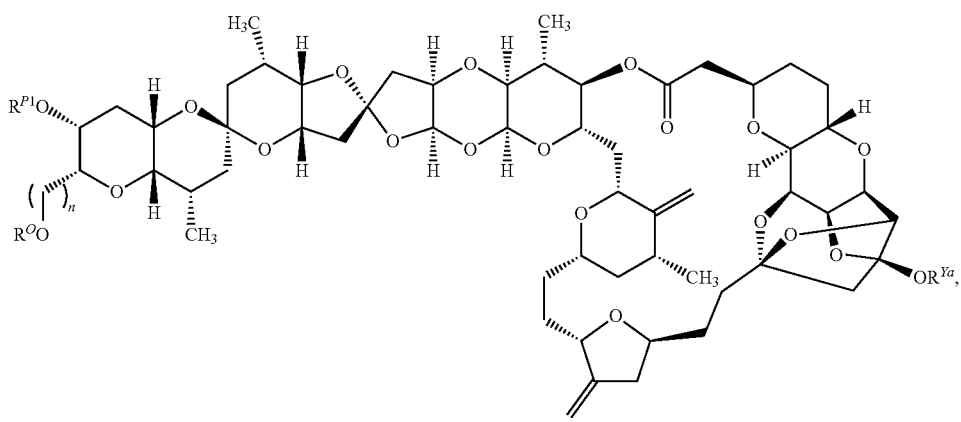
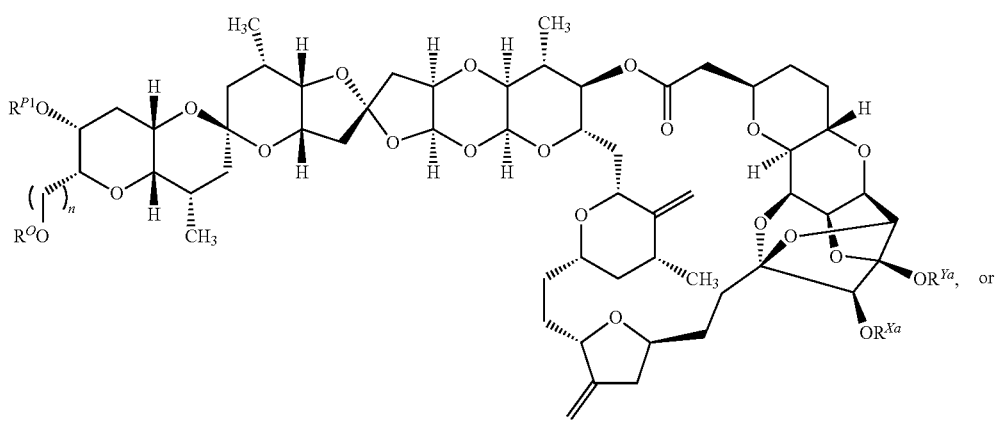
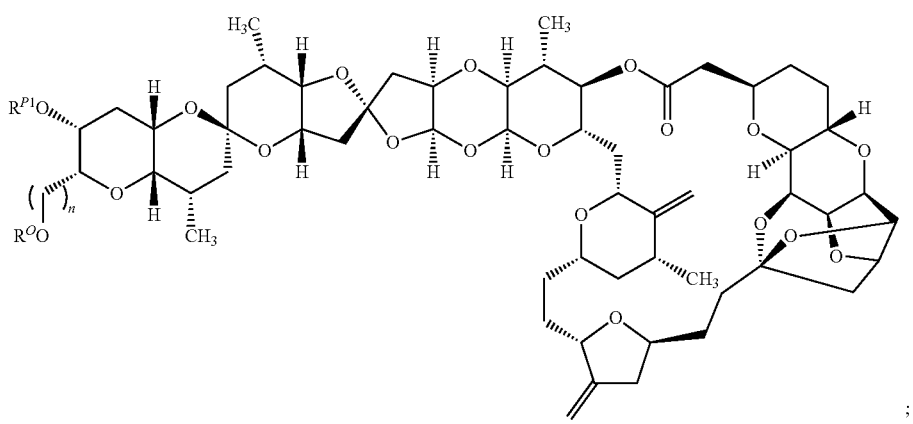
or a pharmaceutically acceptable salt or isotopically labeled derivative thereof.
In certain embodiments, the compound of Formula (III) is of one of the following formulae:

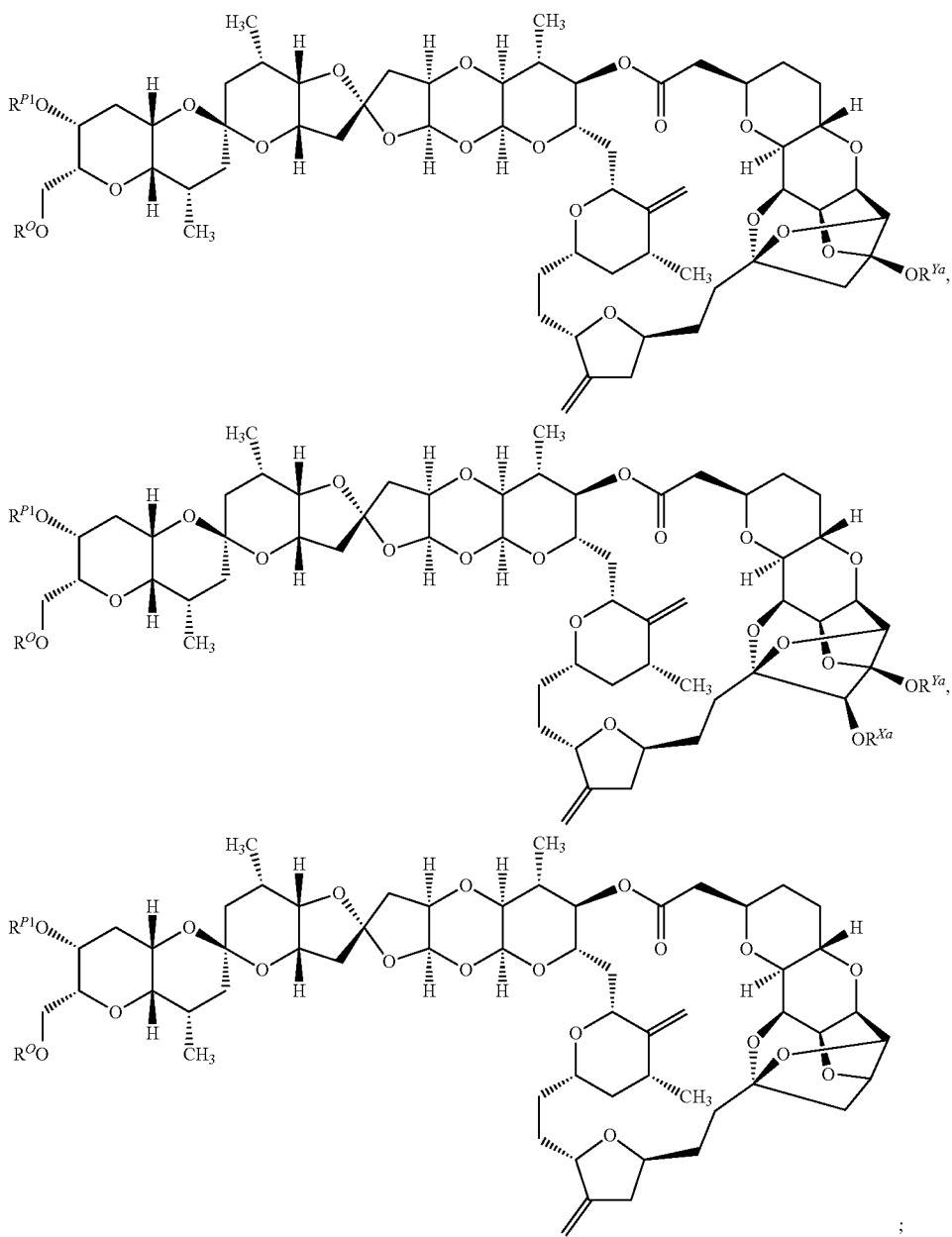
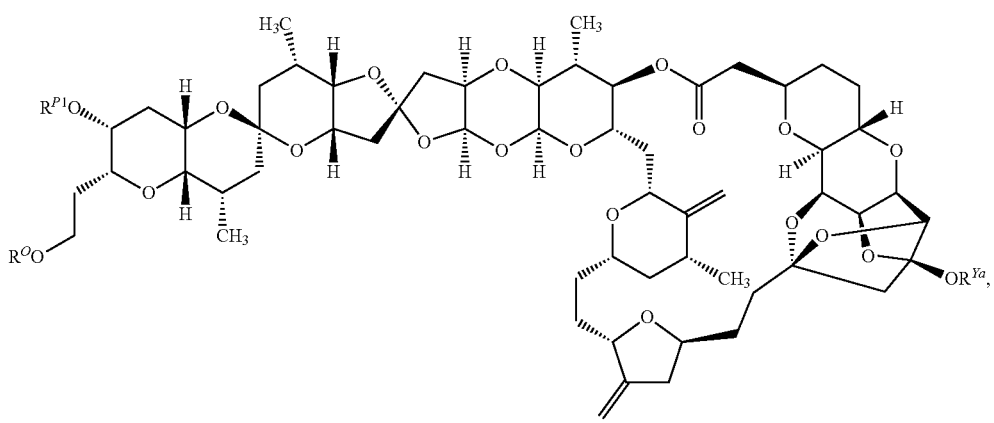

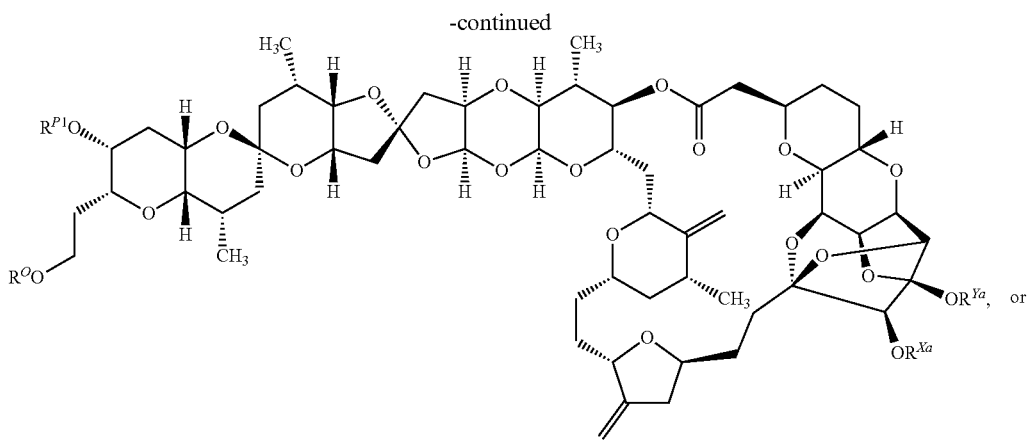
or a pharmaceutically acceptable salt or isotopically labeled derivative thereof.
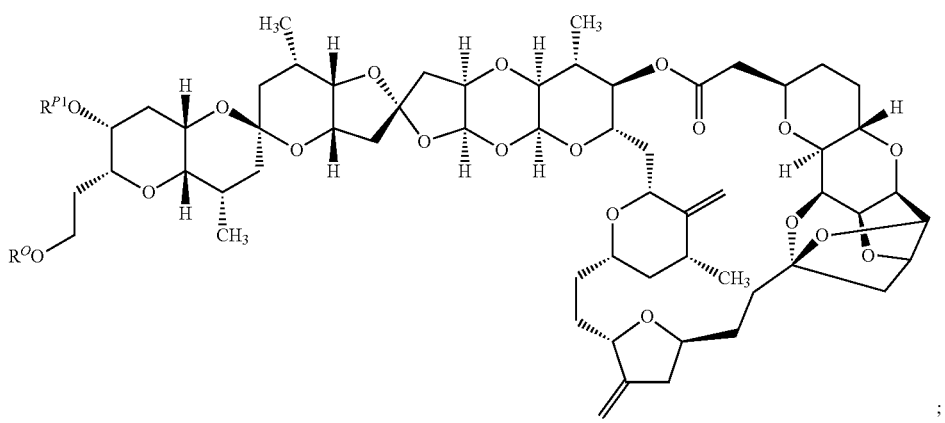
In certain embodiments, the compound of Formula (III) is selected from the group consisting of:
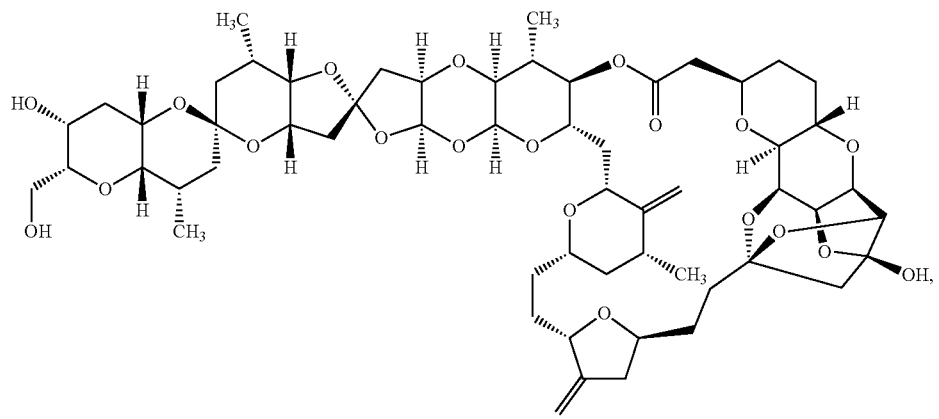

-continued
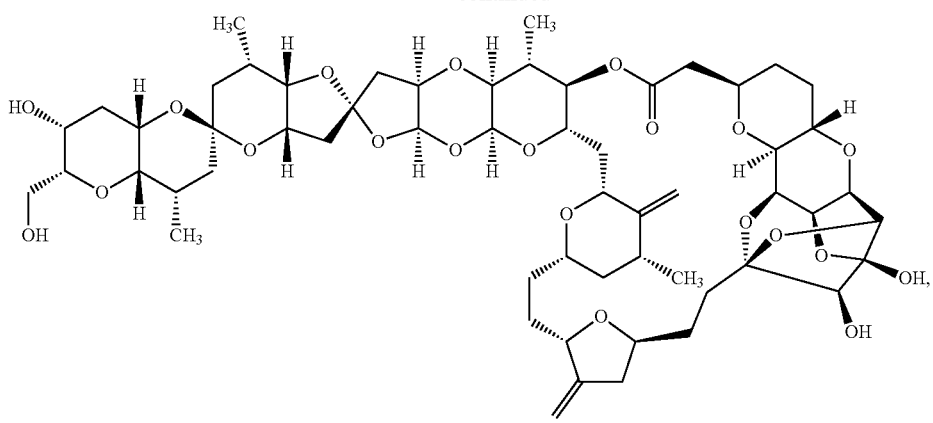
(E-2)
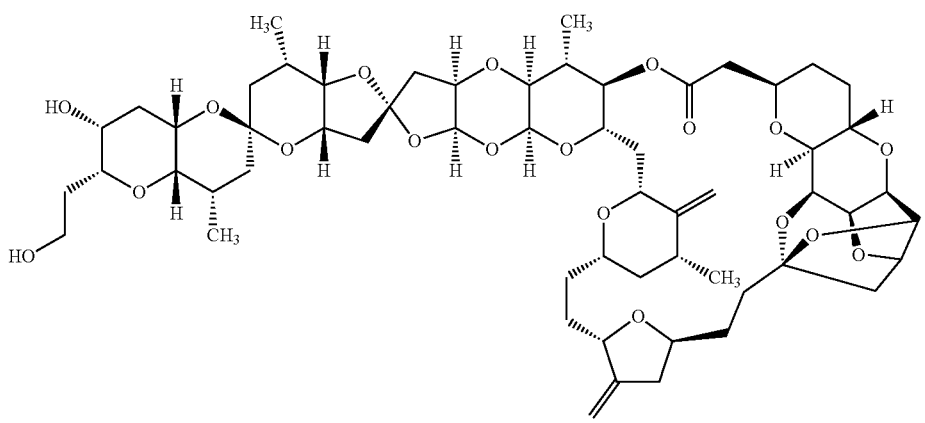
(J-1)
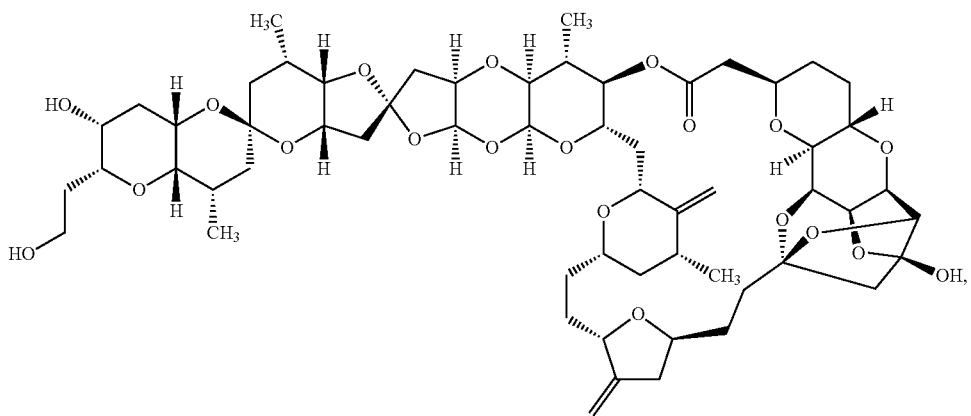
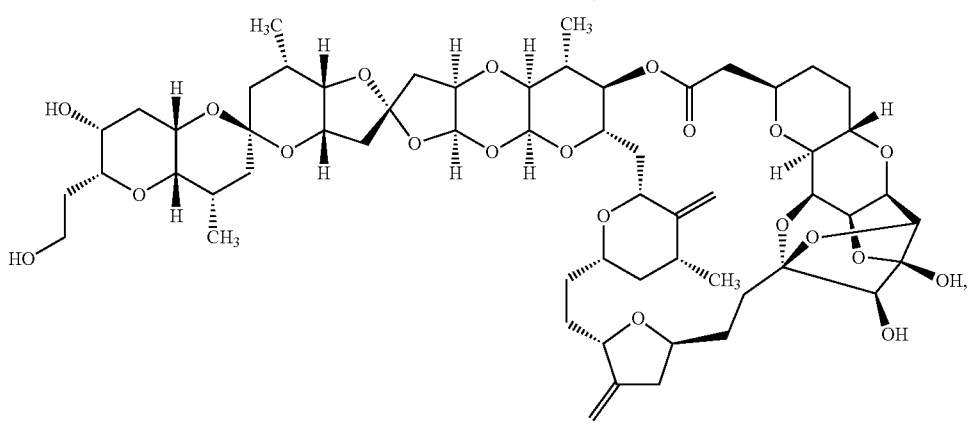

-continued
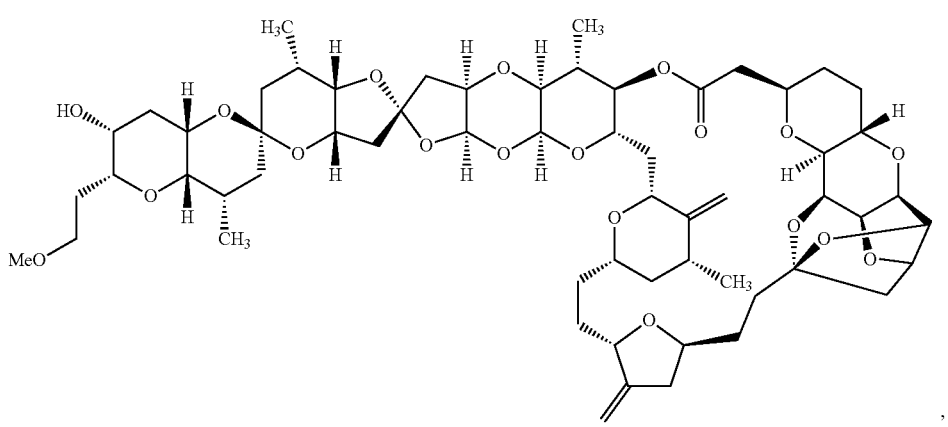
(I-2)
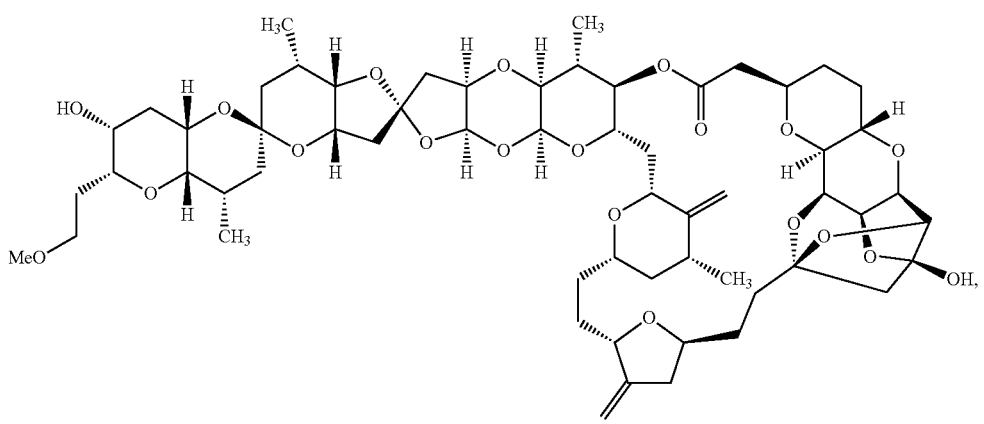
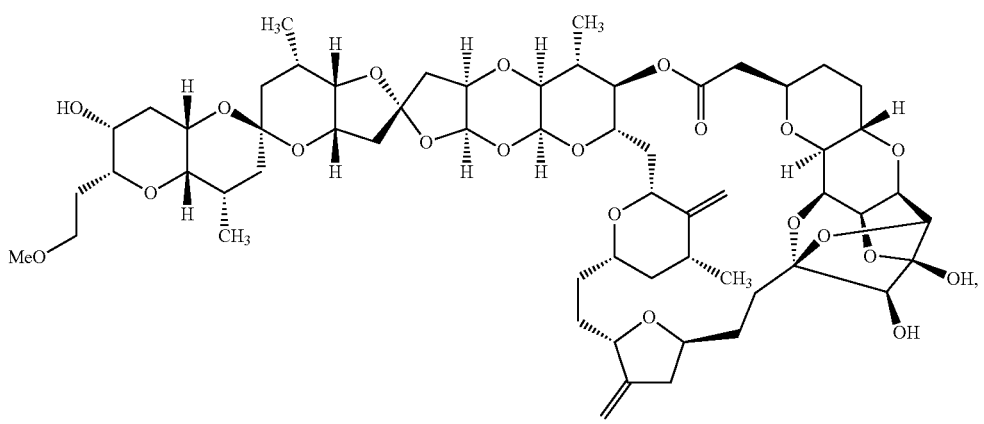
and pharmaceutically acceptable salts and isotopically labeled derivatives thereof.
In yet another aspect, the present invention provides compounds of Formula (IV):

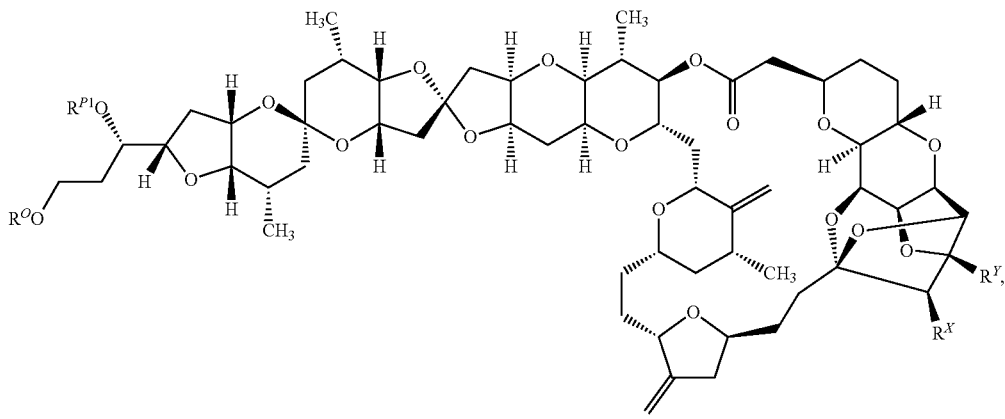

(IV)

and pharmaceutically acceptable salts and isotopically labeled derivatives thereof, wherein:

$R^O$ is hydrogen, optionally substituted alkyl, optionally substituted acyl, or an oxygen protecting group;

$R^{P1}$ is hydrogen, optionally substituted alkyl, optionally substituted acyl, or an oxygen protecting group;

$R^X$ is hydrogen or —$OR^{Xa}$;

$R^Y$ is hydrogen or —$OR^{Ya}$;

$R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl; and m is 0 or 1.

In certain embodiments, the compound of Formula (IV) is of one of the following formulae:

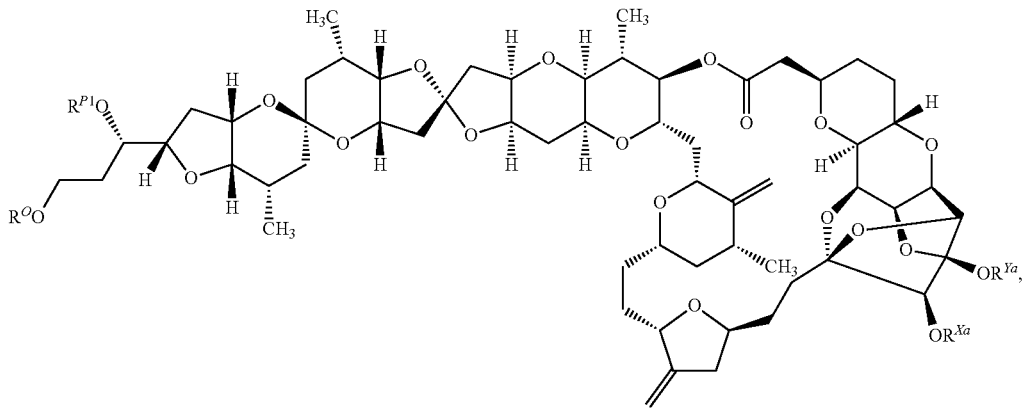

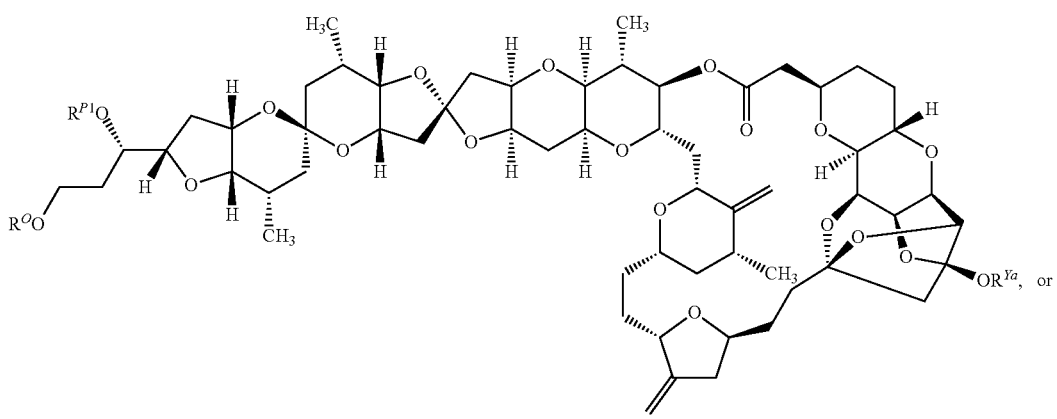

-continued
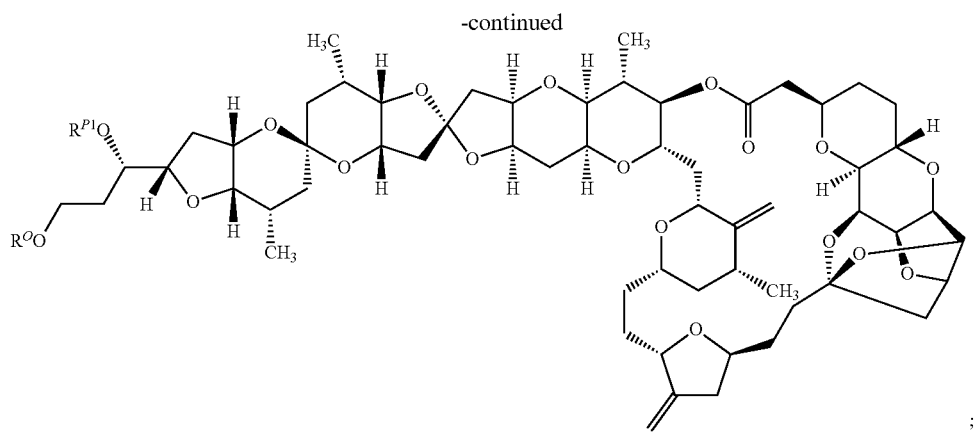
or a pharmaceutically acceptable salt or isotopically labeled derivative thereof.
In certain embodiments, the compound of Formula (IV) is selected from the group consisting of:
(M-3)
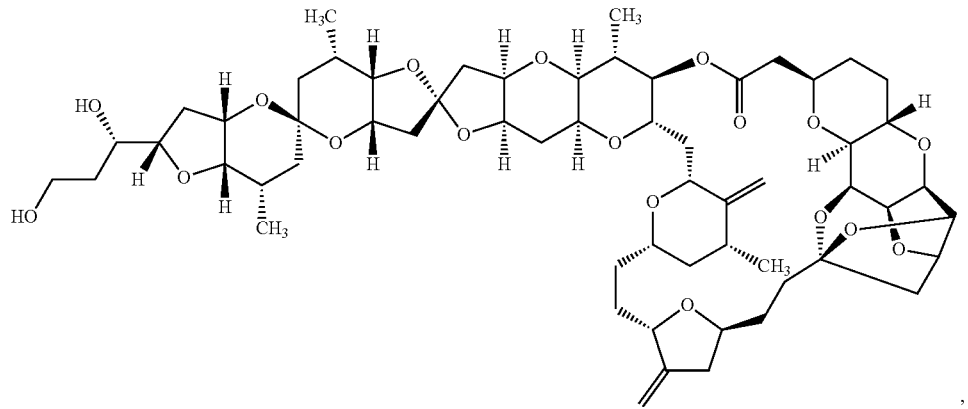
,
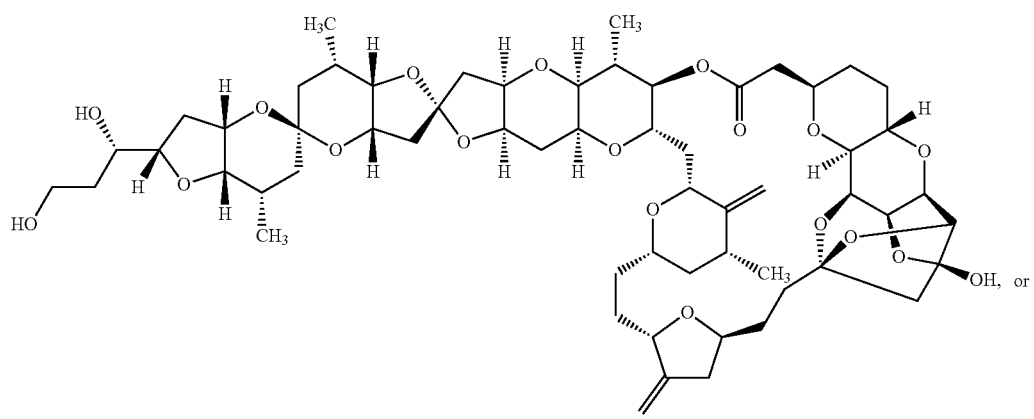
OH, or -continued

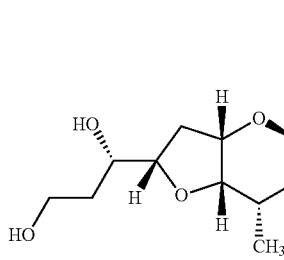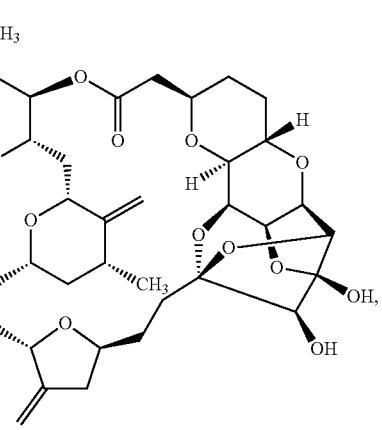

and pharmaceutically acceptable salts and isotopically labeled derivatives thereof.

The compounds provided herein may be optionally be in the form of a hydrate, solvate or polymorph, optionally in a pharmaceutically acceptable carrier or excipient. The present invention also provides stereoisomers of any one of the compounds described herein. Compounds provided herein may exist as a crystal polymorph, and the compound of the present invention may be in any of single crystal forms or a mixture of two or more crystal forms. Compounds provided herein can be in an amorphous form, or can be an anhydride or a solvate, such as a hydrate.

The present invention includes isotopically labeled derivatives of compounds provided herein, and pharmaceutically acceptable salts thereof. The isotopically labeled compound is equivalent to compounds provided herein, except that one or more atom(s) are replaced by atom(s) having an atomic mass or a mass number different from those usually found in nature. Examples of an isotope that can be incorporated into the compound of the present invention include isotopes of hydrogen, carbon, nitrogen, oxygen, phosphorus, fluorine, iodine, bromine and chlorine, such as $^2$H, $^3$H, $^{11}$C, $^{13}$C, $^{14}$C, $^{18}$F, $^{35}$S, $^{123}$I, and $^{125}$I.

The isotopically labeled compound, such as a compound into which a radioactive isotope of, for example, $^3$H and/or $^{14}$C is incorporated, is useful for a tissue distribution assay for a medicine and/or a matrix. The isotopes $^3$H and $^{14}$C are regarded to be useful because these isotopes can be easily prepared and detected. The isotopes $^{11}$C and $^{18}$F are useful in PET (positron emission tomography). The isotope $^{125}$I is regarded to be useful in SPECT (single photon emission computed tomography), and can be useful in brain imaging. Replacement by a heavier isotope such as $^2$H causes, because of its higher metabolic stability, some advantages, in a treatment, of, for example, extension of half-life in vivo or reduction of a necessary dose, and therefore, is regarded useful under given circumstances. The isotopically labeled compound can be similarly prepared by using a readily available isotopically labeled reagent instead of a non-isotopically labeled reagent and by performing processes disclosed in schemes and/or examples described below.

Compounds provided herein can be used as a chemical probe for capturing a target protein of a biologically active low molecular weight compound. Specifically, the compound of the present invention can be transformed into an affinity chromatography probe, a photoaffinity probe or the like by introducing a labeling group, a linker or the like into a moiety other than a structural moiety indispensable to activity expression of the compound by a method described in J. Mass Spectrum. Soc. Jpn. Vol. 51, No. 5, 2003, p. 492-498, WO 2007/139149, or the like.

Examples of the labeling group, the linker or the like used in such a chemical probe include groups belonging to the following groups (1) to (5). (1) Protein labeling groups such as photoaffinity labeling groups (such as a benzoyl group, a benzophenone group, an azide group, a carbonyl azide group, a diaziridine group, an enone group, a diazo group and a nitro group), and chemical affinity groups (such as a ketone group in which an alpha carbon atom is substituted by a halogen atom, a carbamoyl group, an ester group, an alkylthio group, a Michael acceptor of a,β-unsaturated ketone, ester, or the like, and an oxirane group); (2) cleavable linkers such as S—S, O—Si—O, a monosaccharide (such as a glucose group or a galactose group) and a disaccharide (such as lactose), and oligopeptide linkers that can be cleaved by an enzyme reaction; (3) fishing tag groups such as biotin and a 3-(4, 4-difluoro-5,7-dimethyl-4H-3a, 4a-diaza-4-bora-s-indacene-3-yl)propionyl group; (4) radioactive labeling groups such as $^{125}$I, $^{32}$P, $^3$H and $^{14}$C; fluorescence labeling groups such as fluorescein, rhodamine, dansyl, umbelliferone, 7-nitrofurazanyl, and a 3-(4,4-difluoro-5,7-dimethyl-4H-3a,4a-diaza-4-bora-s-indacene-3-yl) propionyl group; chemiluminescent groups such as luciferin and luminol; and markers capable of detecting heavy metal ions such as lanthanoid metal ions and radium ions; and (5) groups to be bonded to a solid phase carrier such as glass beads, a glass bed, a microliter plate, agarose beads, an agarose bed, polystyrene beads, a polystyrene bed, nylon beads and a nylon bed.

A probe prepared by introducing, into the compound of the present invention, a labeling group or the like selected from the above-described groups (1) to (5) by the method described in any of the aforementioned literatures or the like can be used as a chemical probe for identifying a marker protein useful for research of a novel potential drug target.

Examples of a "salt" used herein include salts with inorganic acids, salts with organic acids, and salts with acidic amino acids, and in particular, pharmaceutically acceptable salts are preferred. Besides, a salt of the compound of the present invention embraces an anhydride of a pharmaceutically acceptable salt thereof and a solvate, such as a hydrate, of the pharmaceutically acceptable salt. Preferable examples of a salt with an inorganic acid include salts with hydrochloric acid, hydrobromic acid, sulfuric acid, nitric acid, phosphoric acid and the like, and preferable examples of a salt with an organic acid include salts with acetic acid, succinic acid, fumaric acid, maleic acid, tartaric acid, citric acid, lactic acid, stearic acid, benzoic acid, methanesulfonic acid, ethanesulfonic acid, benzenesulfonic acid, p-toluenesulfonic acid and the like. Preferable examples of a salt with an acidic amino acid include salts with aspartic acid and glutamic acid and the like.

In the case where the compound according to the present invention is obtained as a salt of the compound or a hydrate of the compound, the salt and the hydrate can be converted to a free body of the compound by a conventional method.
Groups $R^{N1}$, $R^{N2}$, $R^O$, $R^{P1}$, $R^{P2}$, $R^X$, $R^Y$, n, and m All definitions provided below apply to all compounds of Formulae (I), (II), (II), and (IV) described herein.

As generally defined herein, $R^{N1}$ and $R^{N2}$ are independently hydrogen, optionally substituted alkyl, optionally substituted acyl, or a nitrogen protecting group, optionally wherein $R^{N1}$ and $R^{N2}$ are joined together with the intervening atoms to form optionally substituted heterocyclyl or optionally substituted heteroaryl. In certain embodiments, $R^{N1}$ is hydrogen. In certain embodiments, $R^{N1}$ is optionally substituted alkyl. In certain embodiments, $R^{N1}$ is optionally substituted acyl. In certain embodiments, $R^{N1}$ is a nitrogen protecting group. In certain embodiments, $R^{N1}$ is an ester protecting group. In certain embodiments, $R^{N1}$ is an alloc protecting group. "Alloc" is of the following formula:

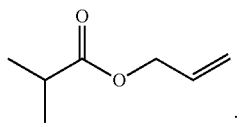

In certain embodiments, $R^{N2}$ is hydrogen. In certain embodiments, $R^{N2}$ is optionally substituted alkyl. In certain embodiments, $R^{N2}$ is optionally substituted acyl. In certain embodiments, $R^{N2}$ is a nitrogen protecting group. In certain embodiments, $R^{N2}$ is an ester protecting group. In certain embodiments, $R^{N2}$ is an alloc protecting group.

In certain embodiments, $R^{N1}$ and $R^{N2}$ are both hydrogen. In certain embodiments, $R^{N1}$ is hydrogen; and $R^{N2}$ is a nitrogen protecting group. In certain embodiments, $R^{N1}$ is hydrogen; and $R^{N2}$ is alloc. In certain embodiments, $R^{N1}$ and $R^{N2}$ are joined together with the intervening atoms to form optionally substituted heterocyclyl. In certain embodiments, $R^{N1}$ and $R^{N2}$ are joined together with the intervening atoms to form optionally substituted heteroaryl.

As generally defined herein, $R^{P1}$ is hydrogen, optionally substituted alkyl, optionally substituted acyl, or an oxygen protecting group. In certain embodiments, $R^{P1}$ is hydrogen. In certain embodiments, $R^{P1}$ is optionally substituted alkyl. In certain embodiments, $R^{P1}$ is optionally substituted acyl. In certain embodiments, $R^{P1}$ is an oxygen protecting group. In certain embodiments, $R^{P1}$ is silyl (e.g., trialkylsilyl). In certain embodiments, $R^{P1}$ is tert-butyldimethylsilyl (TBS or TBDMS).

As generally defined herein, n is 1 or 2. In certain embodiments, n is 1. In certain embodiments, n is 2.

As generally defined herein, m is 0 or 1. In certain embodiments, m is 0. In certain embodiments, m is 1.

As generally defined herein, $R^X$ is hydrogen or —$OR^{Xa}$. In certain embodiments, $R^X$ is hydrogen. In certain embodiments, $R^X$—$OR^{Xa}$. In certain embodiments, $R^X$ is —OH.

As generally defined herein, $R^{Xa}$ is hydrogen, optionally substituted alkyl, optionally substituted acyl, or an oxygen protecting group. In certain embodiments, $R^{Xa}$ is hydrogen. In certain embodiments, $R^{Xa}$ is optionally substituted alkyl. In certain embodiments, $R^{Xa}$ is optionally substituted acyl. In certain embodiments, $R^{Xa}$ is an oxygen protecting group.

As generally defined herein, $R^Y$ is hydrogen or —$OR^{Ya}$. In certain embodiments, $R^Y$ is hydrogen. In certain embodiments, $R^Y$ is —$OR^{Ya}$. In certain embodiments, $R^Y$ is —OH.

As generally defined herein, $R^{Ya}$ is hydrogen, optionally substituted alkyl, optionally substituted acyl, or an oxygen protecting group. In certain embodiments, $R^{Ya}$ is hydrogen. In certain embodiments, $R^{Ya}$ is optionally substituted alkyl. In certain embodiments, $R^{Ya}$ is optionally substituted acyl. In certain embodiments, $R^{Ya}$ is an oxygen protecting group.

In certain embodiments, $R^{Xa}$ and $R^{Ya}$ are joined together with the intervening atoms to form optionally substituted heterocyclyl (e.g., optionally substituted 5-membered heterocyclyl).

In certain embodiments, $R^X$ and $R^Y$ are hydrogen. In certain embodiments, $R^X$ is —$OR^{Xa}$; and $R^Y$ is —$OR^{Ya}$. In certain embodiments, $R^X$ and $R^Y$ are —OH. In certain embodiments, $R^X$ is hydrogen; and $R^Y$ is —$OR^{Ya}$. In certain embodiments, $R^X$ is hydrogen; and $R^Y$ is —OH.

As generally defined herein, $R^{P2}$ is hydrogen, optionally substituted alkyl, optionally substituted acyl, or an oxygen protecting group. In certain embodiments, $R^{P2}$ is hydrogen. In certain embodiments, $R^{P2}$ is optionally substituted alkyl. In certain embodiments, $R^{P2}$ is optionally substituted acyl. In certain embodiments, $R^{P2}$ is an oxygen protecting group. In certain embodiments, $R^{P2}$ is silyl (e.g., trialkylsilyl). In certain embodiments, $R^{P2}$ is tert-butyldimethylsilyl (TBS or TBDMS).

As generally defined herein, $R^O$ is hydrogen, optionally substituted alkyl, optionally substituted acyl, or an oxygen protecting group. In certain embodiments, $R^O$ is optionally substituted alkyl. In certain embodiments, $R^O$ is optionally substituted $C_{1-6}$ alkyl. In certain embodiments, $R^O$ is unsubstituted $C_{1-6}$ alkyl. In certain embodiments, $R^O$ is optionally substituted $C_{1-3}$ alkyl. In certain embodiments, $R^O$ is unsubstituted $C_{1-3}$ alkyl. In certain embodiments, $R^O$ is methyl, ethyl, n-propyl, iso-propyl, n-butyl, iso-butyl, sec-butyl, or tert-butyl. In certain embodiments, $R^O$ is methyl. In certain embodiments, $R^O$ is optionally substituted acyl. In certain embodiments, $R^O$ is an oxygen protecting group.

Pharmaceutical Compositions, Kits, and Administration

The present invention provides pharmaceutical compositions comprising a compound of Formula (I), (II), (III), or (IV), or a pharmaceutically acceptable salt or isotopically labeled derivative thereof, and a pharmaceutically acceptable excipient. In certain embodiments, the compound described herein, or pharmaceutically acceptable salt or isotopically labeled derivative thereof, is provided in an effective amount in the pharmaceutical composition (e.g., a therapeutically effective amount).

Pharmaceutical compositions described herein can be prepared by any method known in the art of pharmacology. In general, such preparatory methods include bringing a compound provided herein (i.e., the "active ingredient") into association with a carrier or excipient, and/or one or more other accessory ingredients, and then, if necessary and/or desirable, shaping, and/or packaging the product into a desired single- or multi-dose unit.

A pharmaceutical composition of the invention could be prepared according to the known method such as a method described in the general rules for preparations of the *Japanese Pharmacopoeia*, 16th edition, the *United States Pharmacopoeia*, and the *European Pharmacopoeia*, 9th edition. A pharmaceutical composition of the invention could be administered to patients appropriately depending on the dosage form.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

The compound provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds of the present invention and compositions thereof provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound provided herein required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell may be, in non-limiting examples, three doses a day, two doses a day, one dose a day, one dose every other day, one dose every third day, one dose every week, one dose every two weeks, one dose every three weeks, or one dose every four weeks, or even slow dose controlled delivery over a selected period of time using a drug delivery device. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is about or at least one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is about or at least three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.001 mg/kg and 0.01 mg/kg, between 0.01 mg/kg and 0.1 mg/kg, between 0.1 mg/kg and 1 mg/kg, inclusive of a compound provided herein. Examples are dosage forms with at least about 0.05, 0.1, 0.5, 1, 1.5, 2, 2.5, 3, 3.5, 4, 4.5, 5, 10, 5, 20, 25, or 50 mg of active compound, or its salt in a dosage form.

In certain embodiments, a dose (e.g., a single dose, or any of multiple doses) described herein includes independently between 1.0 µg/m$^2$ and 1.0 mg/m$^2$, inclusive, of a compound provided herein (e.g., Compound (1) or a pharmaceutically acceptable salt thereof). In certain embodiments, a dose (e.g., a single dose, or any dose of multiple doses) described herein includes independently between 1.0 µg/m$^2$ and 100.0 µg/m$^2$, between 1.0 µg/m$^2$ and 50 µg/m$^2$, between 10 µg/m$^2$ and 50 µg/m$^2$, or between 10 µg/m$^2$ and 30 µg/m$^2$, inclusive, of a compound provided herein (e.g., Compound (1) or a pharmaceutically acceptable salt thereof). Examples are dosage forms with approximately 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 µg of a compound provided herein (e.g., Compound (1) or a pharmaceutically acceptable salt thereof).

In certain embodiments, a compound provided herein (e.g., Compound (1) or a pharmaceutically acceptable salt thereof) is dosed approximately once every 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In certain embodiments, a compound provided herein (e.g., Compound (1) or a pharmaceutically acceptable salt thereof) is dosed approximately twice a month. In certain embodiments, a compound provided herein (e.g., Compound (1) or a pharmaceutically acceptable salt thereof) is dosed approximately once every 15 days for the duration of the treatment. In certain embodiments, a compound provided herein (e.g., Compound (1) or a pharmaceutically acceptable salt thereof) is dosed on day 1 and day 15 of a 28-day cycle. In certain embodiments, a compound provided herein (e.g., Compound (1) or a pharmaceutically acceptable salt thereof) is dosed at approximately 25 µg/m$^2$ on approximately day 1 and approximately day 15 of an approximately 28-day cycle. In certain embodiments, a compound provided herein (e.g., Compound (1) or a pharmaceutically acceptable salt thereof) is dosed at 25 µg/m$^2$ at on day 1 and day 15 of a 28-day cycle. The number of cycles will be decided by a physician.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Also encompassed by the disclosure are kits (e.g., pharmaceutical packs). The kits provided may comprise a pharmaceutical composition or compound provided herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound provided herein. In some embodiments, the pharmaceutical composition or compound provided in the first container and the second container are combined to form one unit dosage form. A kit described herein may include one or more additional pharmaceutical agents described herein as a separate composition.

Methods of Treatment and Uses

As shown herein, compounds of Formulae (I), (II), (III), and (IV) have significant tumor vascular remodeling effects and anti-CAF activity, and therefore, have potential use for the treatment of proliferative diseases (e.g., treatment of cancer and/or the inhibition of tumor growth).

Provided herein is a method of treating a proliferative disease in a subject, the method comprising administering to the subject an effective amount of a compound provided herein, or a pharmaceutically acceptable salt or isotopically labeled derivative thereof, or a pharmaceutical composition thereof. The present invention also provides a compound described herein, or a pharmaceutically acceptable salt or isotopically labeled derivative thereof, or a pharmaceutical composition thereof, for use in treating a proliferative disease in a subject. The present invention also provides the use of a compound provided herein, or a pharmaceutically acceptable salt or isotopically labeled derivative thereof, or a pharmaceutical composition thereof, for the manufacture of a medicament for the treating a proliferative disease. Examples of proliferative diseases are described herein.

Provided herein is a method of treating cancer in a subject, the method comprising administering to the subject an effective amount of a compound provided herein, or a pharmaceutically acceptable salt or isotopically labeled derivative thereof, or a pharmaceutical composition thereof. The present invention also provides a compound described herein, or a pharmaceutically acceptable salt or isotopically labeled derivative thereof, or a pharmaceutical composition thereof, for use in treating cancer in a subject. The present invention also provides the use of a compound provided herein, or a pharmaceutically acceptable salt or isotopically labeled derivative thereof, or a pharmaceutical composition thereof, for the manufacture of a medicament for the treating cancer.

Also provided herein is a method of inhibiting tumor growth in a subject, the method comprising administering to the subject a compound provided herein, or a pharmaceutically acceptable salt or isotopically labeled derivative thereof, or a pharmaceutical composition thereof. Also provided herein is a compound described herein, or a pharmaceutically acceptable salt or isotopically labeled derivative thereof, or a pharmaceutical composition thereof, for use in inhibiting tumor growth in a subject. The present invention also provides the use of a compound provided herein, or a pharmaceutically acceptable salt or isotopically labeled derivative thereof, or a pharmaceutical composition thereof, for the manufacture of a medicament for inhibiting tumor growth.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located.

In certain embodiments, the disease to be treated is cancer. The term "cancer" refers to a class of diseases characterized by the development of abnormal cells that proliferate uncontrollably and have the ability to infiltrate and destroy normal body tissues.

In certain embodiments, the cancer is head and neck cancer (e.g., squamous cell carcinoma of the head and neck (SCCHN), adenoid cystic carcinoma).

In certain embodiments, the cancer is oral cancer (e.g., buccal cavity cancer, lip cancer, tongue cancer, mouth cancer, pharynx cancer, hypopharynx cancer (e.g., hypopharyngeal carcinoma), throat cancer (e.g., laryngeal cancer, pharyngeal cancer, nasopharyngeal cancer, oropharyngeal cancer), salivary gland cancer).

In certain embodiments, the cancer is esophageal cancer (e.g., esophageal squamous cell carcinoma, esophageal adenocarcinoma, Barrett's adenocarcinoma, esophageal leiomyosarcoma).

In certain embodiments, the cancer is gastrointestinal cancer (e.g., anal cancer, colorectal cancer (e.g., colon cancer, rectal cancer, colorectal adenocarcinoma), gall bladder cancer, gastric cancer (e.g., stomach cancer (e.g., stomach adenocarcinoma)), gastrointestinal stromal tumor (GIST), small bowel cancer (e.g., appendix cancer, small bowel carcinoma, e.g., small bowel adenocarcinoma), small intestine cancer, large bowel cancer, large intestine cancer).

In certain embodiments, the cancer is cardiovascular cancer (e.g., primary cardiac tumors, angiosarcoma (e.g., lymphangiosarcoma, lymphangioendotheliosarcoma, hemangiosarcoma), endotheliosarcoma (e.g., Kaposi's sarcoma, multiple idiopathic hemorrhagic sarcoma), cardiac myxoma, cardiac rhabdomyoma).

In certain embodiments, the cancer is lung cancer (e.g., bronchus cancer (e.g., bronchogenic carcinoma, bronchial adenoma), alveolar carcinoma, mesothelioma, small cell lung cancer (SCLC), non-small cell lung cancer (NSCLC), lung adenocarcinoma, chondromatous hamartoma, papillary adenocarcinoma).

In certain embodiments, the cancer is a genitourinary cancer (e.g., bladder cancer (e.g., urothelial carcinoma), urethral cancer, kidney cancer (e.g., nephroblastoma a.k.a. Wilms' tumor, renal cell carcinoma), testicular cancer (e.g., seminoma, testicular embryonal carcinoma), germ cell cancer, prostate cancer (e.g., prostate adenocarcinoma), penile cancer (e.g., Paget's disease of the penis and scrotum)).

In certain embodiments, the cancer is a gynecological cancer (e.g., breast cancer (e.g., adenocarcinoma of the breast, papillary carcinoma of the breast, mammary cancer, medullary carcinoma of the breast, triple negative breast cancer, HER-2 positive breast cancer, HER2-negative breast cancer), endometrial cancer (e.g., uterine cancer (e.g., uterine sarcoma, choriocarcinoma), endometrial carcinoma), cervical cancer (e.g., cervical adenocarcinoma), ovarian cancer (e.g., cystadenocarcinoma, ovarian embryonal carcinoma, ovarian adenocarcinoma), germ cell cancer, vulvar cancer (e.g., Paget's disease of the vulva) vaginal cancer, fallopian tube cancer).

In certain embodiments, the cancer is a hematopoietic cancer (e.g., leukemia (e.g., acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), chronic lymphocytic leukemia (CLL) (e.g., B-cell CLL, T-cell CLL)); lymphoma (e.g., Hodgkin lymphoma (HL) (e.g., B-cell HL, T-cell HL)), non-Hodgkin lymphoma (NHL) (e.g., B-cell NHL such as diffuse large cell lymphoma (DLCL) (e.g., diffuse large B-cell lymphoma)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomads, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma, T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome)), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); heavy chain disease (e.g., alpha chain disease, gamma chain disease, mu chain disease); a myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); multiple myeloma (MM); plasma cell neoplasia; familiar hypereosinophilia; inflammatory myofibroblastic tumors; immunocytic amyloidosis). In certain embodiments, the cancer is leukemia. In certain embodiments, the cancer is acute lymphoblastic leukemia (ALL). In certain embodiments, the cancer is early T-cell precursor (ETP)-acute lymphoblastic leukemia (ALL).

In certain embodiments, the cancer is liver cancer (e.g., hepatocellular cancer (HCC) (e.g., hepatocellular carcinoma, hepatoblastoma, hepatocellular adenoma), malignant hepatoma, hemangiomas, biliary cancer (e.g., cholangiocarcinoma)).

In certain embodiments, the cancer is musculoskeletal cancer (e.g., bone cancer (e.g., osteosarcoma, osteoid osteoma, malignant fibrous histiocytoma, Ewing's sarcoma, chordoma, malignant giant cell tumor chordoma, chondrosarcoma osteochondroma, benign chondroma, chondroblastoma chondromyxofibroma, myelodysplastic syndrome (MDS)), muscle cancer (e.g., rhabdomyosarcoma, rhabdomyoma), connective tissue cancer, synovioma).

In certain embodiments, the cancer is a nervous system cancer (e.g., brain cancer (e.g., astrocytoma, medulloblastoma, glioma (e.g., astrocytoma, oligodendroglioma), glioblastomas, glioblastoma multiform, medulloblastoma, ependymoma, germinoma (i.e., pinealoma), oligodendroglioma, schwannoma, retinoblastoma, congenital tumors, craniopharyngioma), spinal cord cancer, neurofibroma (e.g., neurofibromatosis (NF) type 1 or type 2, schwannomatosis), neuroblastoma, primitive neuroectodermal tumors (PNT), meningeal cancer (e.g., meningioma, meningiosarcoma, gliomatosis), skull cancer, acoustic neuroma, ependymoma, hemangioblastoma, ocular cancer (e.g., intraocular melanoma, retinoblastoma)). In certain embodiments, the disease to be treated is a brain tumor. In certain embodiments, the disease is pleomorphic xenoanthrocytoma (PXA). In certain embodiments, the disease is pediatric pleomorphic xenoanthrocytoma (PXA).

In certain embodiments, the cancer is selected from endocrine/exocrine cancers (e.g., thyroid cancer (e.g., papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma), pancreatic cancer (e.g., pancreatic andenocarcinoma, intraductal papillary mucinous neoplasm (IPMN), Islet cell tumors, ductal adenocarcinoma, insulinoma, glucagonoma, vipoma), adrenal gland cancer, neuroendocrine cancer (e.g., gastroenteropancreatic neuroendoctrine tumor (GEP-NET), carcinoid tumor), sebaceous gland carcinoma, sweat gland carcinoma). In certain embodiments, the cancer is sweat gland cancer (e.g., sweat gland carcinoma)

In certain embodiments, the cancer is skin cancer (e.g., squamous cell carcinoma (SCC), keratoacanthoma (KA), melanoma, basal cell carcinoma (BCC), dermatofribroma).

In certain embodiments, the cancer is a soft tissue cancer (e.g., intraepithelial neoplasms, epithelial carcinomas, epithelial sarcomas, adenocarcinomas, adenomas, fibrosarcomas, fibromas, liposarcomas, lipomas, myxomas, teratomas).

In certain embodiments, the cancer is a rare cancer. The term "rare cancer" refers to cancers that occur in a relatively small number of patients. Rare cancers include, but are not limited to, sarcomas (e.g., soft tissue sarcoma, liposarcoma, uterine sarcoma, leiomyosarcoma, myxofibrosarcoma, osteosarcoma, angiosarcoma, Ewing's sarcoma, synovial sarcoma, rhabdomyosarcoma, intimal sarcoma), malignant lymphomas, thymic cancer (e.g., thymomas), mesothelioma, gastrointestinal stromal tumors (GISTs), neuroendocrine cancer, eye cancer, brain tumors, bone soft tissue tumors, skin cancer, and germ cell tumors.

Examples of proliferative diseases, cancers, and tumors are provided herein. In certain embodiments of the methods provided herein, the cancer is head and neck cancer (e.g., squamous cell carcinoma of the head and neck, adenoid cystic carcinoma, oral cancer, throat cancer, salivary gland cancer, tongue cancer). In certain embodiments, the cancer is breast cancer (e.g., HER2-positive breast cancer, HER2-negative breast cancer, triple negative breast cancer). In certain embodiments, the cancer is colorectal cancer (e.g., colon carcinoma). In certain embodiments, the cancer is esophageal cancer (e.g., esophageal adenocarcinoma). In certain embodiments, the cancer is uterine cancer (e.g., uterine sarcoma). In certain embodiments, the cancer is ovarian cancer. In certain embodiments, the cancer is a sarcoma (e.g., uterine sarcoma, fibrosarcoma, angiosarcoma, synovial sarcoma, soft tissue sarcoma, intimal sarcoma). In certain embodiments, the cancer is gastric cancer. In certain embodiments, the cancer is lung cancer (e.g., non-small cell lung cancer). In certain embodiments, the cancer is bladder cancer (e.g., urothelial carcinoma). In certain embodiments, the cancer is endometrial cancer. In certain embodiments, the cancer is small bowel cancer (e.g., small bowel carcinoma, e.g., small bowel adenocarcinoma). In certain embodiments, the cancer is sweat gland cancer (e.g., sweat gland carcinoma). In certain embodiments, the cancer is a rare cancer.

Combination Therapy

Besides administration as monotherapy, compounds provided herein (e.g., compounds of Formulae (I), (II), (III), and (IV)) can be administered in combination with other therapeutic agents or treatment modalities. In certain embodiments, the compound is administered in combination with an anti-cancer agent. "Anti-cancer agents" encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunomodulatory agents (e.g., IL-1, 2, 4, 6, or 12), immune cell growth factors (e.g., GM-CSF), and antibodies (e.g., Herceptin (trastuzumab), T-DM1, AVASTIN (bevacizumab), ERBITUX (cetuximab), Vectibix (panitumumab), Rituxan (rituximab), Bexxar (tositumomab), and other antibodies described above.

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mitomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Novartis), XL765 (Sanofi Aventis), PF-4691502 (Pfizer), GDC0980 (Genentech), SF1126 (Semafore) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, a compound provided herein, or a pharmaceutically acceptable salt or isotopically labeled derivative thereof, or a pharmaceutical composition thereof, is used in combination with radiation therapy (RT). In certain embodiments, the compound is administered in combination with surgery. In certain embodiments, the compound is administered in combination with an immunotherapy.

For example, a compound of the present invention can be administered in combination with another therapeutic agent, such as anti-EGFR therapy, anti-HER2 therapy, anti-PD-1 therapy, anti-PD-L1 therapy, or irradiation therapy.

In certain embodiments, a compound provided herein, or a pharmaceutically acceptable salt or isotopically labeled derivative thereof, or a pharmaceutical composition thereof, is administered in combination with an anti-EGFR therapy (e.g., anti-EGFR monoclonal antibody (mAb), such as cetuximab). For example, provided herein is a method of treating squamous cell carcinoma of the head and neck (SCCHN) in a subject comprising administering to said subject a compound provided herein, or a pharmaceutically acceptable salt or isotopically labeled derivative thereof, or a pharmaceutical composition thereof, in combination with an anti-EGFR (epidermal growth factor receptor) mAb therapy. In certain embodiments, the anti-EGFR mAb is cetuximab (CTX).

In certain embodiments, a compound provided herein, or a pharmaceutically acceptable salt or isotopically labeled derivative thereof, or a pharmaceutical composition thereof, is administered in combination with an anti-HER2 therapy (e.g., anti-HER2 monoclonal antibody (mAb), such as trastuzumab). For example, provided herein is a method of treating breast cancer in a subject in need thereof comprising administering to said subject a compound provided herein, or a pharmaceutically acceptable salt or isotopically labeled derivative thereof, or a composition thereof, in combination with an HER2 (human epidermal growth factor receptor) mAb therapy. In certain embodiments, the anti-HER2 mAb is trastuzumab.

In certain embodiments, a compound provided herein, or a pharmaceutically acceptable salt or isotopically labeled derivative thereof, or a pharmaceutical composition thereof, is administered in combination with an anti-PD-1 or anti-PD-L1 therapy (e.g., anti-PD-1 or anti-PD-L1 monoclonal antibody). For example, provided herein is a method of treating colorectal cancer in a subject in need thereof comprising administering to said subject a compound provided herein, or a pharmaceutically acceptable salt or isotopically labeled derivative thereof, or a composition thereof, in combination with an anti-PD-1 or anti-PD-L1 therapy (e.g., mAb therapy).

EXAMPLES

Synthesis of Compounds

General Procedures and Methods

The compound according to the present invention can be produced by the methods described in Examples below. However, these examples are only for illustrative purposes, and the compound according to the present invention is not limited to the specific examples mentioned below in any way.

In the Examples, unless specifically mentioned otherwise, the silica gel for purification by using silica gel column chromatography was Hi-Flash™ Column (Silica Gel, 30 µm 60 Å or 40 µm 60 Å, Yamazen Corporation), the silica gel for purification by using NH silica gel column chromatography was Chromatorex NH silica gel (Fuji Silysia Chemical LTD). Analytical thin layer chromatography (TLC) was performed with TLC silica gel 60 $F_{254}$, layer thickness 0.25 mm (Merck KGaA) or Chromatorex TLC NH silica gel $F_{254}$, layer thickness 0.25 mm (Fuji Silysia Chemical LTD). TLC plates were visualized by staining with p-anisaldehyde stain, phosphomolybdic acid stain or Hanessian's Stain.

All moisture sensitive reactions were conducted under an inert atmosphere. Reagents and solvents were commercial grade and were used as supplied, unless otherwise noted.

NMR spectra were recorded on a JEOL ECZ500R (500 MHz), JEOL ECZ400S (400 MHz), Varian Inova 500 (500 MHz), Varian Mercury 400 (400 MHz) or Bruker Avance (600 MHz) spectrometer. Chemical shifts are reported in parts per million (ppm). For $^1$H NMR spectra (CDCl$_3$, C$_6$D$_6$, and/or CD$_3$OD), the residual solvent peak was used as the internal reference (7.27 ppm in CDCl$_3$; 7.16 ppm in C$_6$D$_6$; 3.31 ppm in CD$_3$OD).

Analytical mass spectra (MS) results were obtained using a Waters Acquity UPLC equipped with a single quadrapole detector (SQ Detector 2) or LTQ Orbitrap XL™ (Thermoscientific).

High performance liquid chromatography (HPLC) was carried out with Shimadzu LC-10AD on a UV spectrophotometric detector (200 nm, Shimadzu SPD-10A).

The abbreviations used herein are as follows: AIBN: 2,2'-azobis(isobutyronitrile); Alloc: allyloxycarbonyl; 9-BBN: 9-borabicyclo[3.3.1]nonane; Bu$_3$SnH: tri-normal-butyltin hydride; (+)-CSA: (1S)-(+)-10-Camphorsulfonic acid; DMAP: 4-dimethylaminopyridine; DCM: dichloromethane; DDQ: 2,3-dichloro-5,6-dicyano-1,4-benzoquinone; DIBAL: diisobutylaluminium hydride; DMF: N,N-dimethylformamide; DMSO: dimethyl sulfoxide; Et$_3$N: triethylamine; EtOAc: ethyl acetate; HF-Pyridine: hydrogen fluoride pyridine; HPLC: high performance liquid chromatography; IPA: isopropyl alcohol; MeCN: acetonitrile; MeOH: methanol; MPM: para-methoxybenzyl; PPh$_3$: triphenylphosphine; t-BuOH: tertiary-butyl alcohol; tBuLi: tertiary-butyl lithium; TBME: methyl tertiary-butyl ether; TBAF: tetrabutylammonium fluoride; TBS: tertiary-butyldimethylsilyl; THF: tetrahydrofuran; TMS: trimethylsilyl; Ts: para-toluenesulfonyl.

The synthetic intermediates disclosed herein are considered part of the present invention.

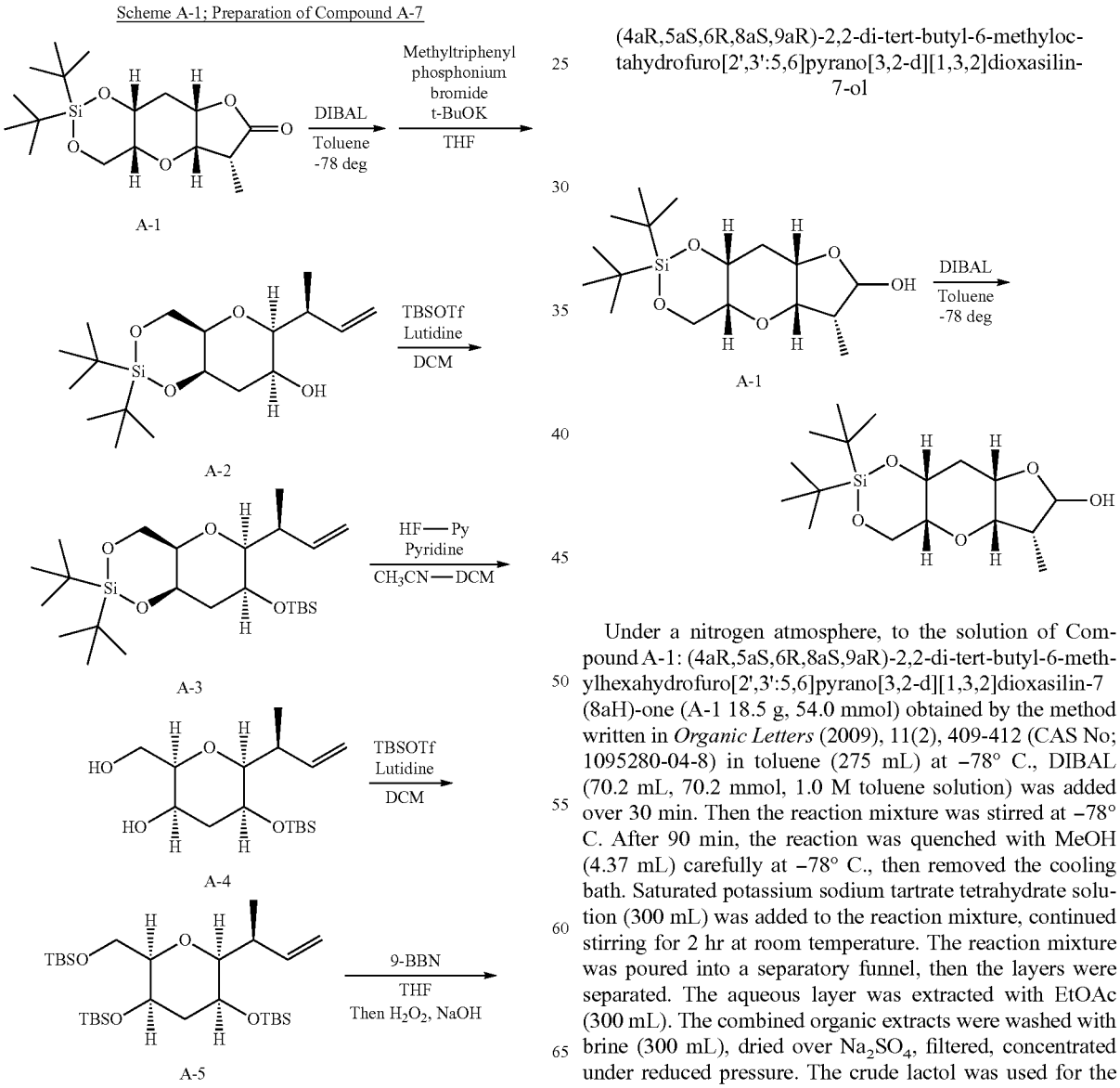

Example 1

(4aR,5aS,6R,8aS,9aR)-2,2-di-tert-butyl-6-methyloctahydrofuro[2',3':5,6]pyrano[3,2-d][1,3,2]dioxasilin-7-ol Under a nitrogen atmosphere, to the solution of Compound A-1: (4aR,5aS,6R,8aS,9aR)-2,2-di-tert-butyl-6-methylhexahydrofuro[2',3':5,6]pyrano[3,2-d][1,3,2]dioxasilin-7(8aH)-one (A-1 18.5 g, 54.0 mmol) obtained by the method written in *Organic Letters* (2009), 11(2), 409-412 (CAS No; 1095280-04-8) in toluene (275 mL) at −78° C., DIBAL (70.2 mL, 70.2 mmol, 1.0 M toluene solution) was added over 30 min. Then the reaction mixture was stirred at −78° C. After 90 min, the reaction was quenched with MeOH (4.37 mL) carefully at −78° C., then removed the cooling bath. Saturated potassium sodium tartrate tetrahydrate solution (300 mL) was added to the reaction mixture, continued stirring for 2 hr at room temperature. The reaction mixture was poured into a separatory funnel, then the layers were separated. The aqueous layer was extracted with EtOAc (300 mL). The combined organic extracts were washed with brine (300 mL), dried over Na$_2$SO$_4$, filtered, concentrated under reduced pressure. The crude lactol was used for the next reaction without purification.

Example 2

(4aR,6S,7S,8aR)-6-((S)-but-3-en-2-yl)-2,2-di-tert-butylhexahydropyrano[3,2-d][1,3,2]dioxasilin-7-ol (Compound A-2)

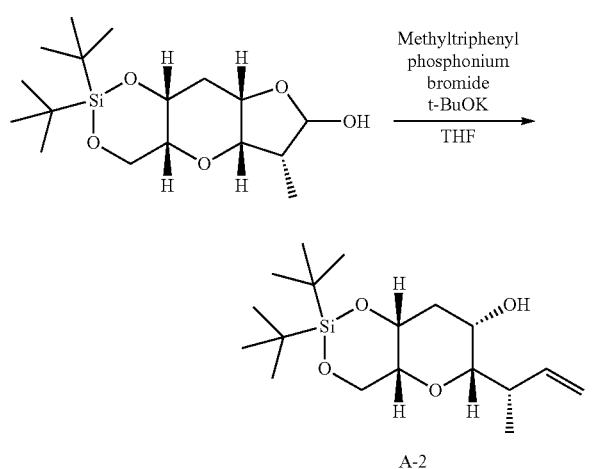

A-2

Under a nitrogen atmosphere, to the suspension of methyltriphenylphosphonium bromide (73.30 g, 205.2 mmol) in THF (200 mL), potassium tert-butoxide (17.27 g, 153.9 mmol) was added at −5° C. over 10 min, and then stirred for 60 min at −5° C. Solution of the crude lactol described in Example 1 in THF (40 mL) was transferred to the reaction mixture at −5° C. over 10 min, then stirred at −5° C. for 1 hr, at room temperature for 1 hr. The reaction mixture was quenched with ice-water (400 mL), then diluted with TBME (400 mL) and then the layers were separated. The aqueous layer was extracted with TBME (400 mL). The combined organic extracts were washed with brine (400 mL), dried over Na$_2$SO$_4$, filtered and concentrated under reduced pressure. The residue was suspended with Heptane/EtOAc=1/1 (100 mL). The resulting suspension was filtered, rinsed with Heptane/EtOAc=1/1 (100 mL) to remove triphenylphosphine derived material. Then filtrate was concentrated under reduced pressure. Flash chromatography of the residue on silica gel (400 g, Silica Gel 60, spherical, 40-50 μm, Kanto Chemical) using 0% to 20% EtOAc/Heptane gave the title compound (Compound A-2, 16.7 g, 90% yield).

$^1$H NMR (400 MHz, CHLOROFORM-d) δ ppm 1.03 (d, J=6.8 Hz, 3H) 1.05 (s, 9H) 1.07 (s, 9H) 1.75 (dt, J=14.5, 3.0 Hz, 1H) 2.37 (dt, J=14.5, 2.9 Hz, 1H) 2.65-2.76 (m, 1H) 3.03 (dd, J=9.8, 1.0 Hz, 1H) 3.31 (m, 1H) 3.69 (d, J=15.0 Hz, 1H) 3.75-3.79 (m, 1H) 4.16-4.31 (m, 2H) 4.41 (t, J=2.9 Hz, 1H) 4.95-5.09 (m, 2H) 6.02 (ddd, J=17.3, 10.5, 6.3 Hz, 1H).

Example 3

(4aR,6S,7S,8aR)-6-((S)-but-3-en-2-yl)-2,2-di-tert-butyl-7-((tert-butyldimethylsilyl)oxy)hexahydropyrano[3,2-d][1,3,2]dioxasiline (Compound A-3)

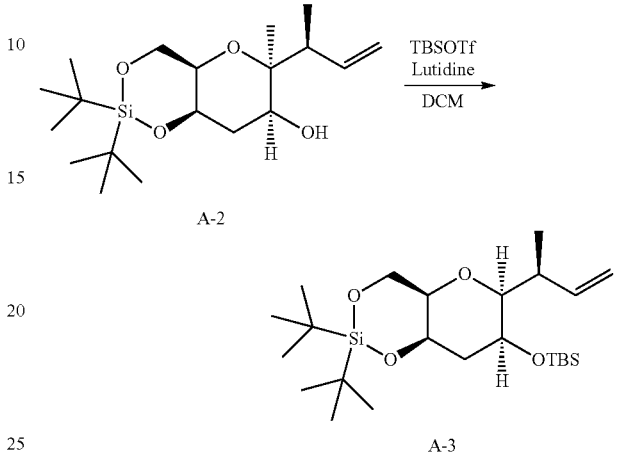

Under a nitrogen atmosphere, to a solution of Compound A-2: (4aR,6S,7S,8aR)-6-((S)-but-3-en-2-yl)-2,2-di-tert-butylhexahydropyrano[3,2-d][1,3,2]dioxasilin-7-ol (9.85 g, 28.8 mmol) described in Example 2 in DCM (150 mL) at 0° C. were added 2,6-lutidine (6.68 mL, 57.5 mmol) and tert-butyldimethylsilyl trifluoromethanesulfonate (9.25 mL, 40.3 mmol). The reaction mixture was stirred at 0° C. for 30 min, then at room temperature for 2 hr. The reaction mixture was diluted with diethyl ether. The organic layer was washed with 0.5 N HCl aq, sat.NaHCO$_3$aq and then brine. The combined organic layers were dried over MgSO$_4$, filtered (small amount of SiO$_2$) and concentrated under reduced pressure. Flash chromatography of the residue on silica gel using 0% to 15% EtOAc/Heptane gave the title compound (Compound A-3, 12.0 g, 91% yield).

$^1$H NMR (500 MHz, CHLOROFORM-d) δ ppm 0.10 (s, 3H) 0.19 (s, 3H) 0.91 (s, 9H) 0.96 (d, J=6.3 Hz, 3H) 1.02 (s, 9H) 1.06 (s, 9H) 1.73 (dt, J=15.0, 4.0 Hz, 1H) 2.26 (dt, J=15.0, 2.5 Hz, 1H) 2.66-2.74 (m, 1H) 2.95 (dd, J=9.5, 2.2 Hz, 1H) 3.17 (m, 1H) 3.81-3.84 (m, 1H) 4.12-4.22 (m, 2H) 4.24 (t, J=2.7 Hz, 1H) 4.93-5.06 (m, 2H) 6.08 (ddd, J=17.3, 10.5, 6.3 Hz, 1H).

Example 4

(2R,3R,5S,6S)-6-((S)-but-3-en-2-yl)-5-((tert-butyldimethylsilyl)oxy)-2-(hydroxymethyl)tetrahydro-2H-pyran-3-ol (Compound A-4)

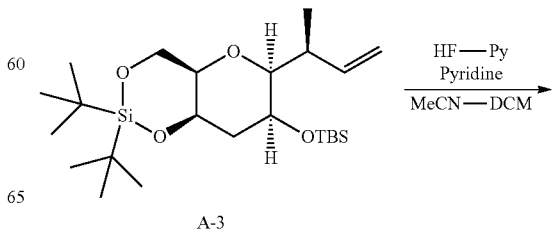

A-3

-continued

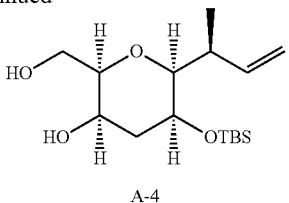

A-4

Under a nitrogen atmosphere, to a solution of Compound A-3: (4aR,6S,7S,8aR)-6-((S)-but-3-en-2-yl)-2,2-di-tert-butyl-7-((tert-butyldimethylsilyl)oxy)hexahydropyrano[3,2-d][1,3,2]dioxasiline (12 g, 26.3 mmol) described in Example 3 in MeCN (120 mL) and DCM (40 mL) at −10° C. was added pre-mixed solution of HF-Pyridine (4.0 mL) and pyridine (20 mL) in 20 mL of MeCN. The reaction mixture was stirred at −10° C. for 15 min, then at room temperature for 1 hr. The reaction mixture was quenched with sat.NaHCO₃aq at 0° C. and diluted with DCM, then the layers were separated. The aqueous layer was extracted with DCM. The combined organic extracts were washed with brine. The combined organic layer was dried over MgSO₄, filtered and concentrated under reduced pressure. Flash chromatography of the residue on silica gel using 15% to 60% EtOAc/Heptane gave the title compound (Compound A-4, 8.4 g, Quant. yield).

$^1$H NMR (500 MHz, CHLOROFORM-d) δ ppm 0.13 (s, 3H) 0.19 (s, 3H) 0.94 (s, 9H) 0.96 (d, J=6.8 Hz, 3H) 1.72 (dt, J=14.6, 2.9 Hz, 1H) 2.15 (dd, J=9.8, 2.4 Hz, 1H) 2.23 (dt, J=14.6, 2.9 Hz, 1H) 2.55-2.65 (m, 1H) 3.03 (d, J=9.8 Hz, 1H) 3.41-3.46 (m, 1H) 3.49 (d, J=11.7 Hz, 1H) 3.62-3.72 (m, 2H) 3.92 (ddd, J=11.7, 8.3, 2.4 Hz, 1H) 4.02 (t, J=2.7 Hz, 1H) 5.01-5.12 (m, 2H) 5.93 (ddd, J=17.4, 10.4, 7.3 Hz, 1H).

Example 5

(((2S,3S,5R,6R)-2-((S)-but-3-en-2-yl)-6-(((tert-butyldimethylsilyl)oxy)methyl)tetrahydro-2H-pyran-3,5-diyl)bis(oxy))bis(tert-butyldimethylsilane) (Compound A-5)

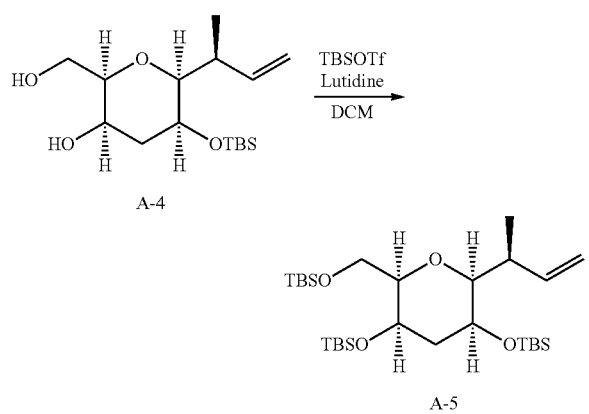

Under a nitrogen atmosphere, to a solution of Compound A-4: (2R,3R,5S,6S)-6-((S)-but-3-en-2-yl)-5-((tert-butyldimethylsilyl)oxy)-2-(hydroxymethyl)tetrahydro-2H-pyran-3-ol (997 mg, 3.15 mmol) described in Example 4 in DCM (10 mL) at 5° C. was added 2,6-lutidine (1.83 mL, 15.8 mmol) and tert-butyldimethylsilyl trifluoromethanesulfonate (2.17 mL, 9.45 mmol). The reaction mixture was stirred at room temperature for 5 hr. The reaction mixture was diluted with diethyl ether and quenched with sat. NaHCO₃aq, then the layers were separated. The combined organic extracts were successively washed with 0.5 N HCl aq, sat.NaHCO₃ aq, and then brine. The organic layer was dried over MgSO₄, filtered and concentrated under reduced pressure. Flash chromatography of the residue on silica gel using 0% to 5% EtOAc/Heptane (containing 1% Et₃N) gave the title compound (Compound A-5, 1.69 g, 98% yield).

$^1$H NMR (500 MHz, CHLOROFORM-d) δ ppm 0.02-0.08 (m, 15H) 0.11 (s, 3H) 0.89 (s, 9H) 0.90-0.92 (m, 18H) 0.94 (d, J=6.8 Hz, 3H) 1.82 (dt, J=14.9, 4.8 Hz, 1H) 2.00 (dt, J=14.9, 2.9 Hz, 1H) 2.62-2.72 (m, 1H) 2.93 (dd, J=9.3, 2.0 Hz, 1H) 3.27-3.34 (m, 1H) 3.66-3.79 (m, 3H) 3.83-3.87 (m, 1H) 4.91-5.07 (m, 2H) 6.11 (ddd, J=17.3, 10.7, 6.1 Hz, 1H).

Example 6

(S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butan-1-ol (Compound A-6)

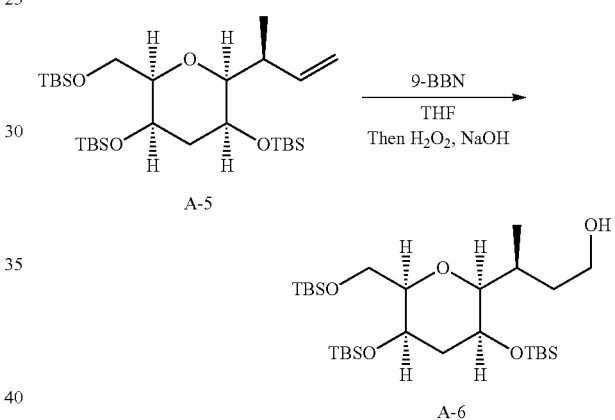

To a solution of Compound A-5: (((2S,3S,5R,6R)-2-((S)-but-3-en-2-yl)-6-(((tert-butyldimethylsilyl)oxy)methyl)tetrahydro-2H-pyran-3,5-diyl)bis(oxy))bis(tert-butyldimethylsilane) (1.32 g, 2.42 mmol) described in Example 5 in THF (10 mL) at 0° C. was added 9-BBN (9.69 mL, 0.5 M THF solution, 4.84 mmol). The reaction mixture was stirred at 0° C. for 1 hr and at room temperature for 1.5 hr. 3.0 M NaOH aq (3 mL, 9.00 mmol) and hydrogen peroxide (35% in water, 3 mL) were added to the reaction mixture at 0° C. The reaction mixture was stirred at 0° C. for 30 min, then at room temperature for 1 hr. The reaction mixture was quenched with sat. Na₂SO₃ aq and then the layers were separated. The aqueous layer was extracted with EtOAc (3 times). The combined organic extracts were washed with brine, dried over Na₂SO₄, filtered and concentrated under reduced pressure. Flash chromatography of the residue on silica gel using 0% to 20% EtOAc/Heptane gave the title compound (Compound A-6, 1.36 g, 100% yield).

$^1$H NMR (500 MHz, CHLOROFORM-d) δ ppm 0.03 (s, 3H) 0.05-0.08 (m, 12H) 0.10 (s, 3H) 0.88 (d, J=6.8 Hz, 3H) 0.89-0.93 (m, 27H) 1.55-1.65 (m, 1H) 1.82 (dt, J=15.4, 4.4 Hz, 1H) 1.87-1.96 (m, 1H) 1.97-2.03 (m, 1H) 2.17-2.26 (m, 1H) 2.67 (dd, J=7.8, 3.9 Hz, 1H) 2.98-3.10 (m, 1H) 3.34-3.40 (m, 1H) 3.59-3.86 (m, 6H)

ESI-MS (m/z): 563.64 [M+H]⁺, 585.62 [M+Na]⁺

Example 7

(S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butanal (Compound A-7)

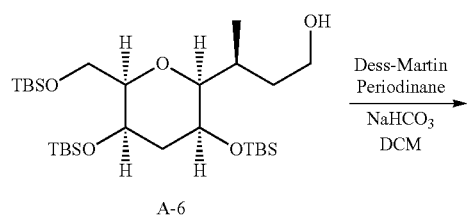

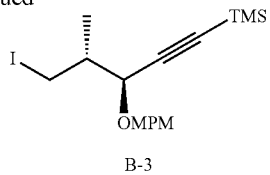

Under a nitrogen atmosphere, to a solution of Compound A-6: (S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butan-1-ol (1100 mg, 1.954 mmol) described in Example 6 in DCM (30 mL) at 5° C. were added NaHCO$_3$ (41.0 mg, 0.49 mmol) and Dess-Martin periodinane (1077 mg, 2.54 mmol). The reaction mixture was stirred at room temperature. After 3 hr, the reaction mixture was diluted with DCM and quenched with sat.NaHCO$_3$aq and sat. Na$_2$SO$_3$ aq, then the layers were separated. The aqueous layer was extracted with DCM. The combined organic extracts were washed with brine, dried over MgSO$_4$, filtered and concentrated under reduced pressure. Flash chromatography of the residue on silica gel using 0% to 25% EtOAc/Heptane gave the title compound (Compound A-7, 950 mg, 87% yield).

$^1$H NMR (500 MHz, CHLOROFORM-d) δ ppm 0.00 (s, 3H) 0.03-0.08 (m, 12H) 0.11 (s, 3H) 0.88 (s, 9H) 0.91-0.92 (m, 21H) 1.82 (dt, J=15.0, 4.5 Hz, 1H) 2.01 (dt, J=15.0, 2.5 Hz, 1H) 2.28 (ddd, J=16.0, 7.3, 2.4 Hz, 1H) 2.53-2.58 (m, 1H) 2.74 (ddd, J=16.0, 5.5, 2.0 Hz, 1H) 2.94 (dd, J=9.0, 1.7 Hz, 1H) 3.29 (td, J=5.9, 2.0 Hz, 1H) 3.68 (d, J=5.9 Hz, 2H) 3.75-3.82 (m, 1H) 3.82-3.90 (m, 1H) 9.73 (t, J=2.4 Hz, 1H).

Scheme B; Preparation of Compound B-3

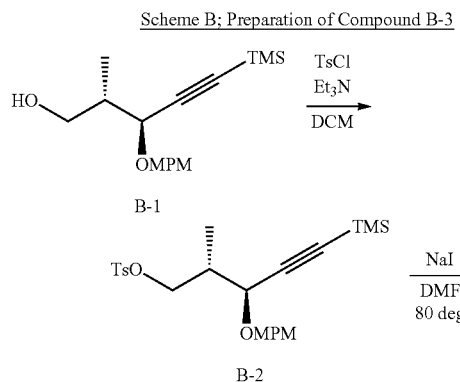

Example 8

(2S,3S)-3-((4-methoxybenzyl)oxy)-2-methyl-5-(trimethylsilyl)pent-4-yn-1-yl 4-methylbenzenesulfonate (Compound B-2)

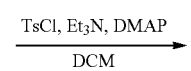

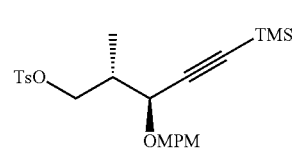

Under a nitrogen atmosphere, to the solution of Compound B-1: (2S,3S)-3-((4-methoxybenzyl)oxy)-2-methyl-5-(trimethylsilyl)pent-4-yn-1-ol (11.08 g, 36.15 mmol) obtained by the method written in WO 9317690 A1/U.S. Pat. No. 5,436,238 A (CAS No; 157323-41-6) in DCM (330 mL), Et$_3$N (12.6 mL, 90.4 mmol) and p-toluenesulfonyl chloride (8.27 g, 43.4 mmol) were added at room temperature. The reaction mixture was stirred at room temperature overnight. The mixture was washed with sat.NaHCO$_3$ and brine, dried over MgSO$_4$, filtered, then concentrated under reduced pressure. Flash chromatography of the residue on silica gel (Silica Gel 60, spherical, 40-50 μm, Kanto Chemical) using 0% to 10% EtOAc/Heptane gave the title compound (Compound B-2, 17.7 g, 93% yield).

$^1$H NMR (500 MHz, CHLOROFORM-d) δ ppm 0.17 (s, 9H) 1.02 (d, J=6.8 Hz, 3H) 2.10-2.18 (m, 1H) 2.44 (s, 3H) 3.82 (s, 3H) 3.99 (d, J=6.8 Hz, 1H) 4.04-4.07 (m, 2H) 4.33 (d, J=11.2 Hz, 1H) 4.66 (d, J=11.2 Hz, 1H) 6.87 (d, J=8.3 Hz, 2H) 7.21 (d, J=8.3 Hz, 2H) 7.33 (d, J=8.8 Hz, 2H) 7.77 (d, J=8.8 Hz, 2H).

Example 9

((3S,4R)-5-iodo-3-((4-methoxybenzyl)oxy)-4-methylpent-1-yn-1-yl)trimethylsilane (Compound B-3)

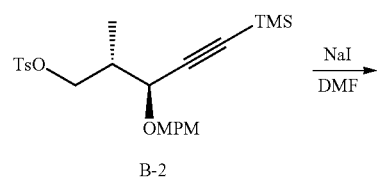

-continued

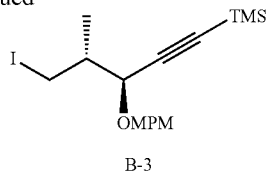

B-3

Under a nitrogen atmosphere, to the solution of Compound B-2: (2S,3S)-3-((4-methoxybenzyl)oxy)-2-methyl-5-(trimethylsilyl)pent-4-yn-1-yl 4-methylbenzenesulfonate (17.7 g, 38.4 mmol) described in Example 8 in DMF (360 mL), NaI (7.49 g, 50.0 mmol) was added at room temperature. The reaction mixture was stirred at 80° C. for 2 hr.

Another 2.0 g of NaI was added to the reaction mixture. The reaction was stirred for 1.5 hr at 80° C., then cooled to room temperature. The mixture was diluted with diethyl ether, washed with water and brine, dried over $MgSO_4$, filtered and concentrated under reduced pressure. Flash chromatography of the residue on silica gel (Silica Gel 60, spherical, 40-50 μm, Kanto Chemical) using 10% to 20% EtOAc/Heptane gave the title compound (Compound B-3, 14.3 g, 89% yield).

$^1$H NMR (500 MHz, CHLOROFORM-d) δ ppm 0.21 (s, 9H) 1.10 (d, J=6.8 Hz, 3H) 1.74-1.84 (m, 1H) 3.30-3.37 (m, 2H) 3.82 (s, 3H) 3.96 (d, J=7.3 Hz, 1H) 4.44 (d, J=11.2 Hz, 1H) 4.73 (d, J=11.2 Hz, 1H) 6.89 (d, J=8.8 Hz, 2H) 7.30 (d, J=8.8 Hz, 2H).

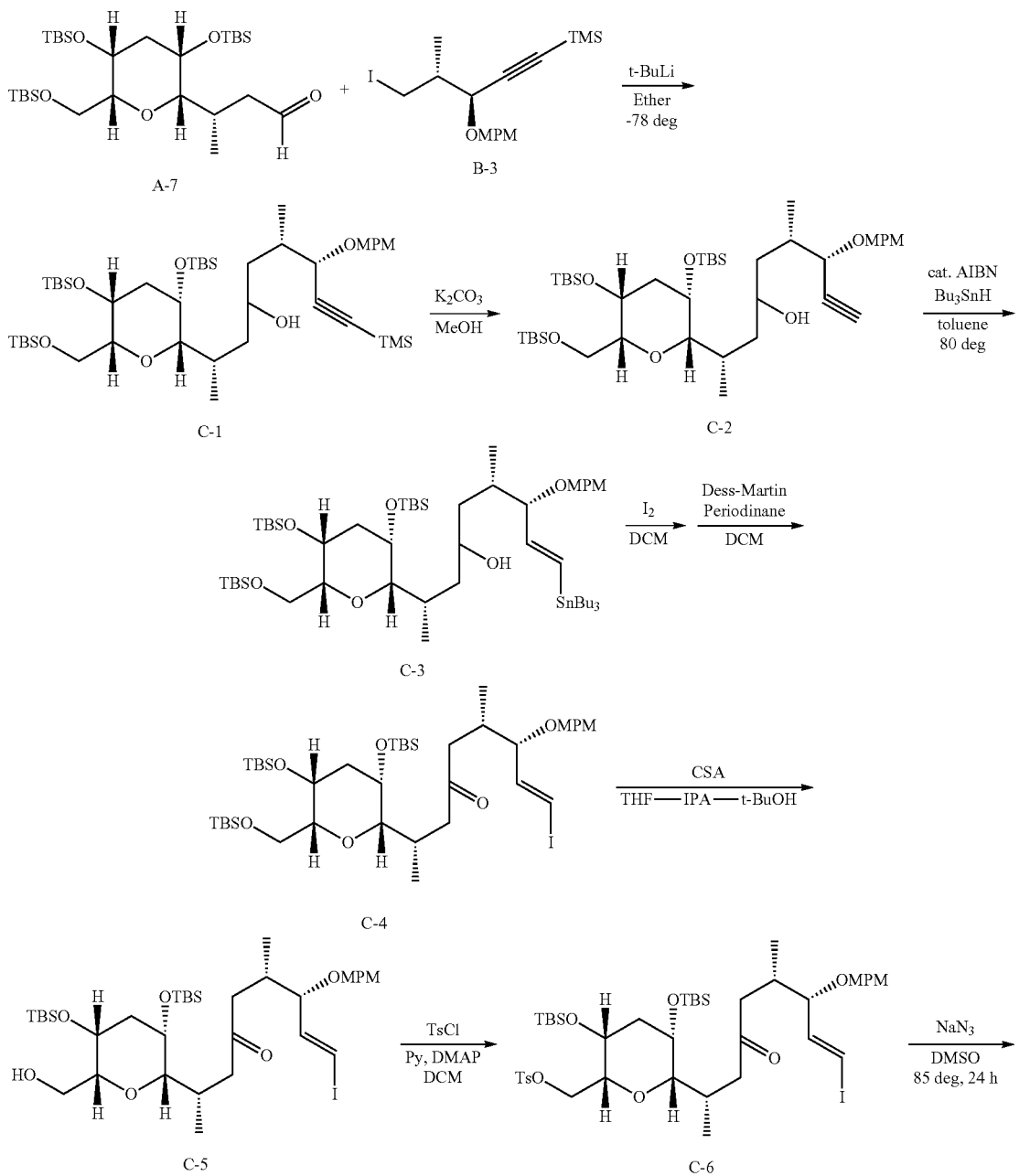

Scheme C-1; Preparation of Compound C-8

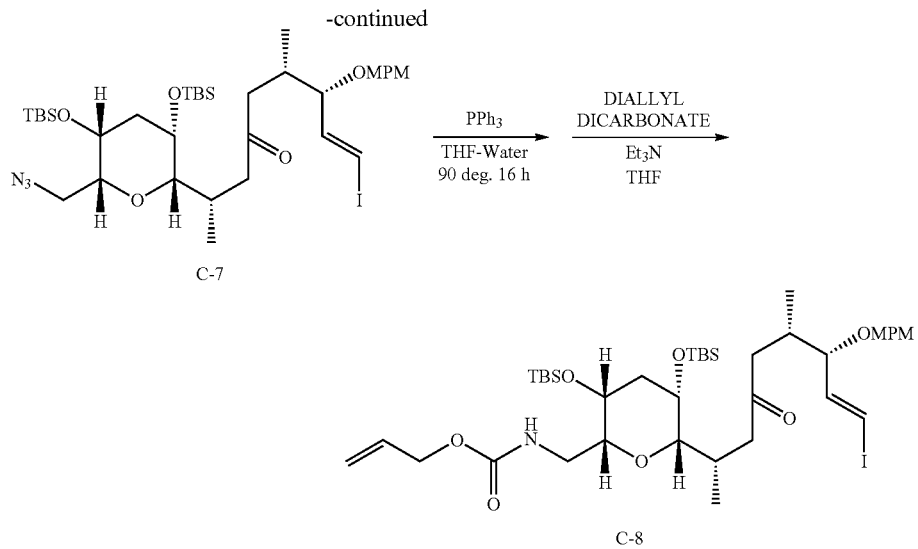

Example 10

(2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methyl-9-(trimethylsilyl)non-8-yn-4-ol (Compound C-1)

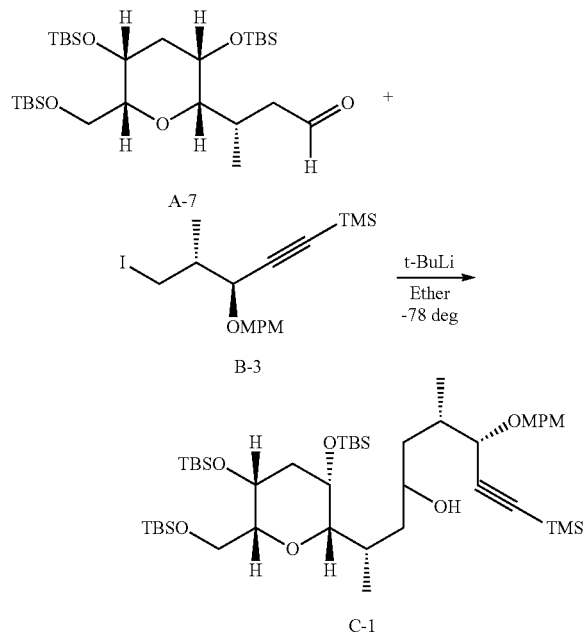

Under an argon atmosphere, to a solution of Compound B-3: ((3S,4R)-5-iodo-3-((4-methoxybenzyl)oxy)-4-methylpent-1-yn-1-yl)trimethylsilane (1408 mg, 3.382 mmol) described in Example 9 in diethyl ether (25 mL) at −78° C. was added tert-butyllithium (1.61M in pentane, 4.11 mL, 6.62 mmol). The reaction mixture was stirred at −78° C. for 45 min. Compound A-7: (S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butanal (825 mg, 1.47 mmol) described in Example 7 in 5.0 mL of diethyl ether was added to the reaction mixture at −78° C. The reaction mixture was stirred at −78° C. for 60 min. The reaction mixture was quenched with sat.NH$_4$Cl aq. Organic layer was washed with brine, dried over Na$_2$SO$_4$, then concentrated under reduced pressure. Flash chromatography of the residue on silica gel using 0% to 25% EtOAc/Heptane gave the title compound (Compound C-1, 1167 mg, 93% yield).

$^1$H NMR (500 MHz, CHLOROFORM-d) δ ppm 0.00-0.12 (m, 21H) 0.15-0.24 (m, 6H) 0.82-0.96 (m, 30H) 1.03 (d, J=6.3 Hz, 3H) 1.38-1.55 (m, 1H) 1.68-1.99 (m, 4H) 2.10-2.30 (m, 2H) 2.76-2.87 (m, 1H) 3.15 (d, J=9.75 Hz, 1H) 3.33-3.38 (m, 1H) 3.56-4.02 (m, 9H) 4.37-4.50 (m, 1H) 4.64-4.78 (m, 1H) 6.83-6.88 (m, 2H) 7.23-7.35 (m, 2H).

Example 11

(2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methyl-9-(tributylstannyl)non-8-en-4-ol (Compound C-3)

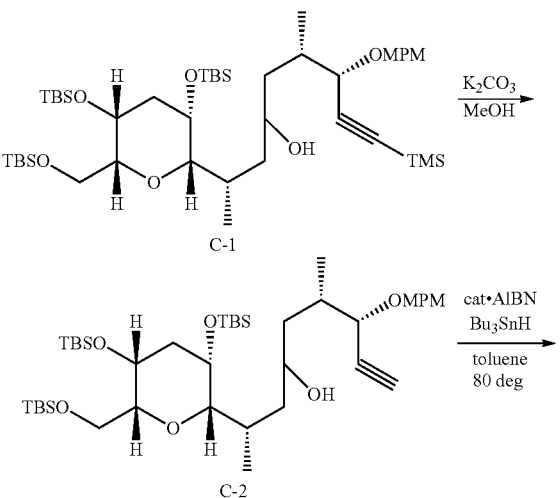

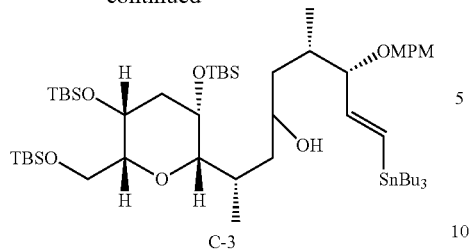

C-3

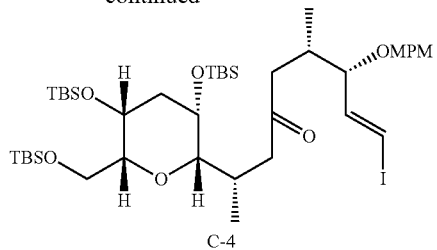

C-4

To a solution of Compound C-1: (2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methyl-9-(trimethylsilyl)non-8-yn-4-ol (1165 mg, 1.37 mmol) described in Example 10 in MeOH (20 mL) at 20° C. was added $K_2CO_3$ (189 mg, 1.37 mmol). The reaction mixture was stirred at 20° C. for 2 hr. The reaction mixture was diluted with EtOAc and quenched with sat.$NH_4Cl$ aq, then the layers were separated. The aqueous layer was extracted with EtOAc. The combined organic extracts were washed with brine, dried over $MgSO_4$, filtered and concentrated under reduced pressure. Flash chromatography of the residue on silica gel using 0% to 15% EtOAc/Heptane gave Compound C-2: (2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methylnon-8-yn-4-ol (1050 mg, 98% yield). ESI-MS (m/z): 801.50 $[M+Na]^+$ Under a nitrogen atmosphere, to a solution of Compound C-2: (2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methylnon-8-yn-4-ol (780 mg, 1.00 mmol) obtained above in toluene (15 mL) at 20° C. were added tri-n-butyltin hydride (2.5 mL, 9.36 mmol) and 2,2'-azobis(isobutyronitrile) (82 mg, 0.50 mmol). The reaction mixture was stirred at 90° C. for 15 min. The reaction mixture was concentrated under reduced pressure. Flash chromatography of the residue on silica gel using 0% to 15% EtOAc/Heptane gave the title compound (Compound C-3, 970 mg, 91% yield).

$^1$H NMR (500 MHz, CHLOROFORM-d) δ ppm 0.02-0.13 (m, 18H) 0.84-0.96 (m, 48H) 1.22-1.37 (m, 6H) 1.47-1.56 (m, 7H) 1.72-1.90 (m, 3H) 1.95-2.03 (m, 1H) 2.11-2.28 (m, 2H) 2.82-2.86 (m, 1H) 3.08-3.15 (m, 1H) 3.33-3.40 (m, 1H) 3.43-3.53 (m, 1H) 3.58-3.87 (m, 8H) 4.25-4.31 (m, 1H) 4.49-4.54 (m, 1H) 5.83 (dd, J=19.3, 7.6 Hz, 1H) 6.05-6.13 (m, 1H) 6.83-6.90 (m, 2H) 7.24 (d, J=8.8 Hz, 2H).

Example 12

(2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-one (Compound C-4)

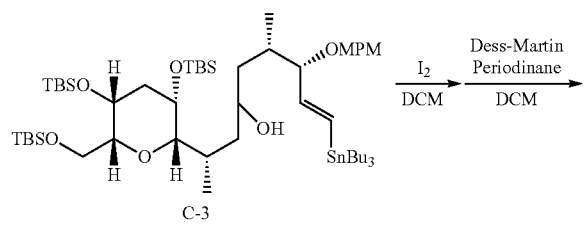

Under a nitrogen atmosphere, to a solution of Compound C-3: (2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methyl-9-(tributylstannyl)non-8-en-4-ol (970 mg, 0.91 mmol) described in Example 11 in 30 mL of DCM at 5° C. was added iodine (242 mg, 0.95 mmol) in DCM (6 mL) until it maintained the iodine color. The reaction mixture was quenched with sat.$Na_2SO_3$ aq and the layers were separated. The aqueous layer was extracted with DCM. The combined organic extracts were washed with brine. The combined organic layers were dried over $Na_2SO_4$, filtered and concentrated under reduced pressure. Flash chromatography of the residue on silica gel using 0% to 25% EtOAc/Heptane gave (2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-ol (768 mg, 93% yield).

Under a nitrogen atmosphere, to a solution of (2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-ol (768 mg, 0.85 mmol) obtained above in DCM (25 mL) at room temperature was added $NaHCO_3$ (17.8 mg, 0.21 mmol) and Dess-Martin periodinane (485 mg, 1.14 mmol). The reaction mixture was stirred at room temperature for 4 hr. The reaction mixture was diluted with DCM and quenched with sat.$NaHCO_3$ aq and sat.$Na_2SO_3$ aq, and then the layers were separated. The aqueous layer was extracted with DCM. The combined organic extracts were washed with brine, dried over $MgSO_4$, filtered and concentrated under reduced pressure. Flash chromatography of the residue on silica gel using 0% to 20% EtOAc/Heptane gave the title compound (Compound C-4, 776 mg, Quant. yield).

$^1$H NMR (500 MHz, CHLOROFORM-d) δ ppm 0.00 (s, 3H) 0.03-0.07 (m, 12H) 0.10 (s, 3H) 0.81 (d, J=6.3 Hz, 3H) 0.84 (d, J=6.3 Hz, 3H) 0.89 (s, 9H) 0.91 (s, 9H) 0.92 (s, 9H) 1.80 (dt, J=15.0, 4.5 Hz, 1H) 1.99 (dt, J=15.0, 2.5 Hz, 1H) 2.17 (dd, J=16.6, 10.2 Hz, 1H) 2.20-2.29 (m, 2H) 2.43-2.48 (m, 1H) 2.54 (d, J=12.7 Hz, 1H) 2.87 (dd, J=9.0, 1.7 Hz, 1H) 2.99 (dd, J=16.6, 2.9 Hz, 1H) 3.27 (td, J=5.8, 2.4 Hz, 1H) 3.50-3.56 (m, 1H) 3.66-3.74 (m, 2H) 3.75-3.78 (m, 1H) 3.80 (s, 3H) 3.81-3.85 (m, 1H) 4.26 (d, J=11.7 Hz, 1H) 4.50 (d, J=11.7 Hz, 1H) 6.26 (d, J=14.6 Hz, 1H) 6.42 (dd, J=14.6, 7.8 Hz, 1H) 6.87 (d, J=8.3 Hz, 2H) 7.21 (d, J=8.3 Hz, 2H). ESI-MS (m/z): 927.39 $[M+Na]^+$

Example 13

(2S,6S,7S,E)-2-((2S,3S,5R,6R)-3,5-bis((tert-butyldimethylsilyl)oxy)-6-(hdydroxymethyl)tetrahydro-2H-pyran-2-yl)-9-iodo-7-((4-methoxybenzyl)oxy)-6-methylnon-8-en-4-one (Compound C-5)

Example 14

((2R,3R,5S,6S)-3,5-bis((tert-butyldimethylsilyl)oxy)-6-((2S,6S,7S,E)-9-iodo-7-((4-methoxybenzyl)oxy)-6-methyl-4-oxonon-8-en-2-yl)tetrahydro-2H-pyran-2-yl)methyl 4-methylbenzenesulfonate (Compound C-6)

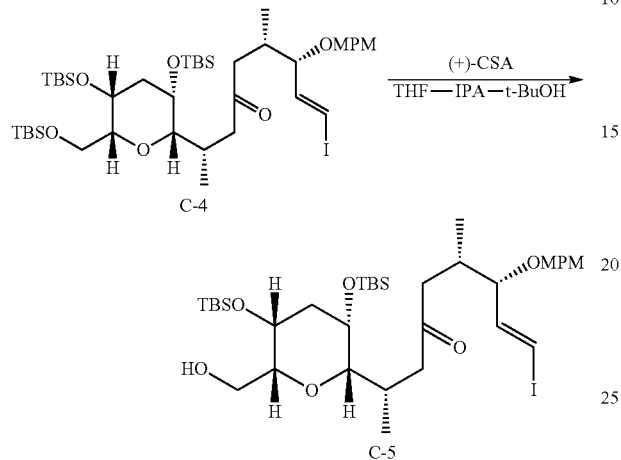

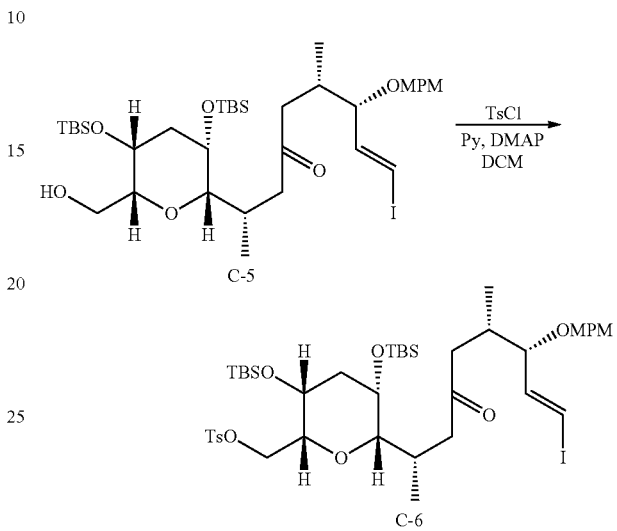

To a solution of Compound C-4: (2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-one (600 mg, 0.66 mmol) described in Example 12 in THF (5.0 mL), IPA (5.0 mL) and t-BuOH (5.0 mL) at 4° C. was added (1S)-(+)-10-Camphorsulfonic acid (154 mg, 0.66 mmol). The reaction mixture was stirred at 4° C. for 20 hr. The reaction mixture was diluted with EtOAc and quenched with sat.NaHCO$_3$aq, then the layers were separated. The aqueous layer was extracted with EtOAc. The combined organic extracts were washed with brine, dried over MgSO$_4$, filtered and concentrated under reduced pressure. Flash chromatography of the residue on silica gel using 0% to 35% EtOAc/Heptane gave the title compound (Compound C-5, 500 mg, 95% yield).

$^1$H NMR (500 MHz, CHLOROFORM-d) δ ppm 0.01 (s, 3H) 0.04 (s, 3H) 0.07 (s, 3H) 0.11 (s, 3H) 0.86-0.91 (m, 15H) 0.93 (s, 9H) 1.83 (dt, J=14.9, 4.8 Hz, 1H) 1.93-2.00 (dt, J=14.9, 4.8 Hz, 1H) 2.19-2.26 (m, 1H) 2.29 (dd, J=14.9, 5.6 Hz, 1H) 2.39 (dd, J=16.6, 8.3 Hz, 1H) 2.44-2.66 (m, 4H) 2.91 (dd, J=9.5, 1.7 Hz, 1H) 3.36-3.41 (m, 1H) 3.48 (td, J=11.3, 2.7 Hz, 1H) 3.59 (t, J=7.1 Hz, 1H) 3.74-3.78 (m, 2H) 3.80 (s, 3H) 3.85 (m, 1H) 4.25 (d, J=11.2 Hz, 1H) 4.46 (d, J=11.2 Hz, 1H) 6.28 (d, J=14.6 Hz, 1H) 6.43 (dd, J=14.6, 7.8 Hz, 1H) 6.87 (d, J=8.8 Hz, 2H) 7.21 (d, J=8.8 Hz, 2H). ESI-MS (m/z): 813.30 [M+Na]$^+$ Under a nitrogen atmosphere, to a solution of Compound C-5: (2S,6S,7S,E)-2-((2S,3S,5R,6R)-3,5-bis((tert-butyldimethylsilyl)oxy)-6-(hydroxymethyl)tetrahydro-2H-pyran-2-yl)-9-iodo-7-((4-methoxybenzyl)oxy)-6-methylnon-8-en-4-one (500 mg, 0.63 mmol) described in Example 13 in DCM (10 mL) at 5° C. were added pyridine (2.54 mL, 31.6 mmol), p-toluenesulfonyl chloride (723 mg, 3.79 mmol) and 4-dimethylaminopyridine (77 mg, 0.63 mmol). The reaction mixture was stirred at room temperature for 24 hr. p-Toluenesulfonyl chloride (150 mg, 0.79 mmol) was added to the reaction mixture at room temperature. Then, the reaction mixture was stirred at room temperature for 8 hr. The reaction mixture was diluted with DCM and quenched with sat.NaHCO$_3$aq, then the layers were separated. The aqueous layer was extracted with DCM. The combined organic extracts were washed with brine, dried over Na$_2$SO$_4$, filtered and concentrated under reduced pressure. Flash chromatography of the residue on silica gel using 0% to 25% EtOAc/Heptane gave the title compound (Compound C-6, 560 mg, 94% yield).

$^1$H NMR (500 MHz, CHLOROFORM-d) δ ppm 0.01 (s, 3H) 0.04 (s, 3H) 0.04 (s, 3H) 0.08 (s, 3H) 0.81 (d, J=6.8 Hz, 3H) 0.83 (s, 9H) 0.86 (d, J=6.8 Hz, 3H) 0.89 (s, 9H) 1.81 (dt, J=14.9, 4.5 Hz, 1H) 1.91-1.96 (m, 1H) 2.15-2.32 (m, 3H) 2.36-2.42 (m, 1H) 2.43 (s, 3H) 2.57 (d, J=12.7 Hz, 1H) 2.77 (dd, J=16.6, 3.4 Hz, 1H) 2.87 (dd, J=9.0, 1.7 Hz, 1H) 3.53-3.58 (m, 2H) 3.70-3.75 (m, 1H) 3.80-3.85 (m, 1H) 3.81 (s, 3H) 4.06 (dd, J=10.0, 5.0 Hz, 1H) 4.08-4.16 (m, 1H) 4.28 (d, J=11.2 Hz, 1H) 4.51 (d, J=11.2 Hz, 1H) 6.30 (d, J=14.6 Hz, 1H) 6.45 (dd, J=14.6, 7.8 Hz, 1H) 6.88 (d, J=8.8 Hz, 2H) 7.24 (d, J=8.8 Hz, 2H) 7.31 (d, J=8.3 Hz, 2H) 7.76 (d, J=8.3 Hz, 2H).

Example 15

(2S,6S,7S,E)-2-((2S,3S,5R,6R)-6-(azidomethyl)-3,5-bis((tert-butyldimethylsilyl)oxy)tetrahydro-2H-pyran-2-yl)-9-iodo-7-((4-methoxybenzyl)oxy)-6-methylnon-8-en-4-one (Compound C-7)

Example 16

(((2R,3R,5S,6S)-3,5-bis((tert-butyldimethylsilyl)oxy)-6-((2S,6S,7S,E)-9-iodo-7-((4-methoxybenzyl)oxy)-6-methyl-4-oxonon-8-en-2-yl)tetrahydro-2H-pyran-2-yl)methyl)carbamate (Compound C-8)

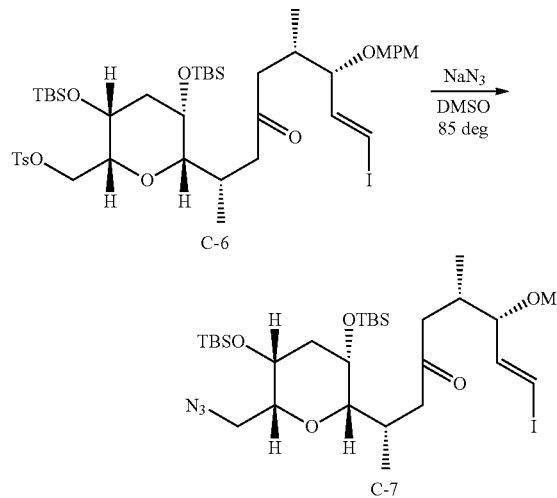

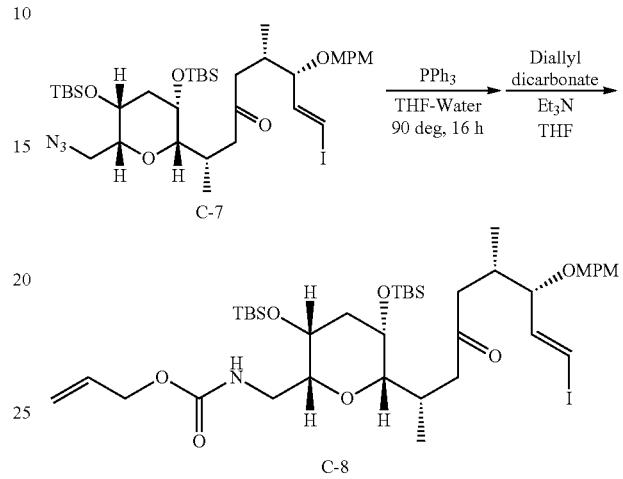

Under a nitrogen atmosphere, to a solution of Compound C-6: ((2R,3R,5S,6S)-3,5-bis((tert-butyldimethylsilyl)oxy)-6-((2S,6S,7S,E)-9-iodo-7-((4-methoxybenzyl)oxy)-6-methyl-4-oxonon-8-en-2-yl)tetrahydro-2H-pyran-2-yl) methyl 4-methylbenzenesulfonate (560 mg, 0.59 mmol) described in Example 14 in DMSO (5.6 mL) at 20° C. was added sodium azide (385 mg, 5.92 mmol). The reaction mixture was stirred at 85° C. After 2 hr, sodium azide (100 mg, 1.54 mmol) was added to the reaction mixture, then the reaction mixture was stirred at 85° C. for 14 hr. The reaction mixture was diluted with EtOAc and quenched with $H_2O$, then the layers were separated. The organic extracts were successively washed with water and brine. The combined organic layers were dried over $Na_2SO_4$, filtered and concentrated under reduced pressure to give a crude residue. Flash chromatography of the residue on silica gel using 0% to 15% EtOAc/Heptane gave the title compound (Compound C-7, 298 mg, 62% yield).

$^1$H NMR (500 MHz, CHLOROFORM-d) δ ppm 0.03 (s, 3H) 0.06 (s, 3H) 0.07 (s, 3H) 0.10 (s, 3H) 0.84 (d, J=6.8 Hz, 3H) 0.85 (d, J=6.8 Hz, 3H) 0.91 (s, 9H) 0.92 (s, 9H) 1.86 (dt, J=15.0, 4.7 Hz, 1H) 1.98 (dt, J=15.0, 2.9 Hz, 1H) 2.19-2.32 (m, 3H) 2.41-2.49 (m, 1H) 2.58 (d, J=12.7 Hz, 1H) 2.94 (dd, J=16.6, 2.9 Hz, 1H) 2.98 (dd, J=8.8, 2.0 Hz, 1H) 3.02 (dd, J=12.7, 2.9 Hz, 1H) 3.47 (dt, J=8.8, 2.7 Hz, 1H) 3.49-3.54 (m, 1H) 3.63 (dd, J=12.7, 8.8 Hz, 1H) 3.69-3.73 (m, 1H) 3.81 (s, 3H) 3.83-3.88 (m, 1H) 4.26 (d, J=11.7 Hz, 1H) 4.50 (d, J=11.7 Hz, 1H) 6.26 (d, J=14.6 Hz, 1H) 6.42 (dd, J=14.6, 7.8 Hz, 1H) 6.87 (d, J=8.8 Hz, 2H) 7.22 (d, J=8.8 Hz, 2H).

To a solution of Compound C-7: (2S,6S,7S,E)-2-((2S,3S,5R,6R)-6-(azidomethyl)-3,5-bis((tert-butyldimethylsilyl)oxy)tetrahydro-2H-pyran-2-yl)-9-iodo-7-((4-methoxybenzyl)oxy)-6-methylnon-8-en-4-one (298 mg, 0.37 mmol) described in Example 15 in THF (10 mL) and water (1.0 mL) at 20° C. was added triphenylphosphine (1437 mg, 5.478 mmol). The reaction mixture was stirred at 70° C. for 1.5 hr. The reaction mixture was concentrated under reduced pressure to give a crude amine. To a solution of the crude amine obtained above in THF (10 mL) at 5° C. were added $Et_3N$ (0.51 mL, 3.66 mmol) and diallyl dicarbonate (341 mg, 1.83 mmol). The reaction mixture was stirred at room temperature for 60 min. The reaction mixture was concentrated under reduced pressure. Flash chromatography of the residue on silica gel using 0% to 25% EtOAc/Heptane gave the title compound (Compound C-8, 300 mg, 94% yield).

$^1$H NMR (500 MHz, CHLOROFORM-d) δ ppm 0.05-0.07 (m, 9H) 0.11 (s, 3H) 0.85 (d, J=6.3 Hz, 3H) 0.87 (d, J=6.3 Hz, 3H) 0.90 (s, 9H) 0.93 (s, 9H) 1.80 (dt, J=15.0, 4.4 Hz, 1H) 1.96 (dt, J=15.0, 2.8 Hz, 1H) 2.16-2.29 (m, 2H) 2.32-2.39 (m, 1H) 2.53-2.60 (m, 3H) 2.86 (d, J=7.3 Hz, 1H) 3.04-3.11 (m, 1H) 3.30-3.34 (m, 1H) 3.38-3.48 (m, 1H) 3.58 (t, J=7.1 Hz, 1H) 3.70-3.76 (m, 1H) 3.80 (s, 3H) 3.81-3.84 (m, 1H) 4.25 (d, J=11.2 Hz, 1H) 4.46 (d, J=11.2 Hz, 1H) 4.53-4.63 (m, 2H) 5.19 (dd, J=10.7, 1.5 Hz, 1H) 5.32 (d, J=17.1 Hz, 1H) 5.47 (d, J=6.8 Hz, 1H) 5.88-5.99 (m, 1H) 6.28 (d, J=14.6 Hz, 1H) 6.43 (dd, J=14.6, 7.8 Hz, 1H) 6.87 (d, J=8.8 Hz, 2H) 7.21 (d, J=8.8 Hz, 2H). ESI-MS (m/z): 896.34 [M+Na]$^+$ Scheme D-1; Preparation of Compound D-7-1
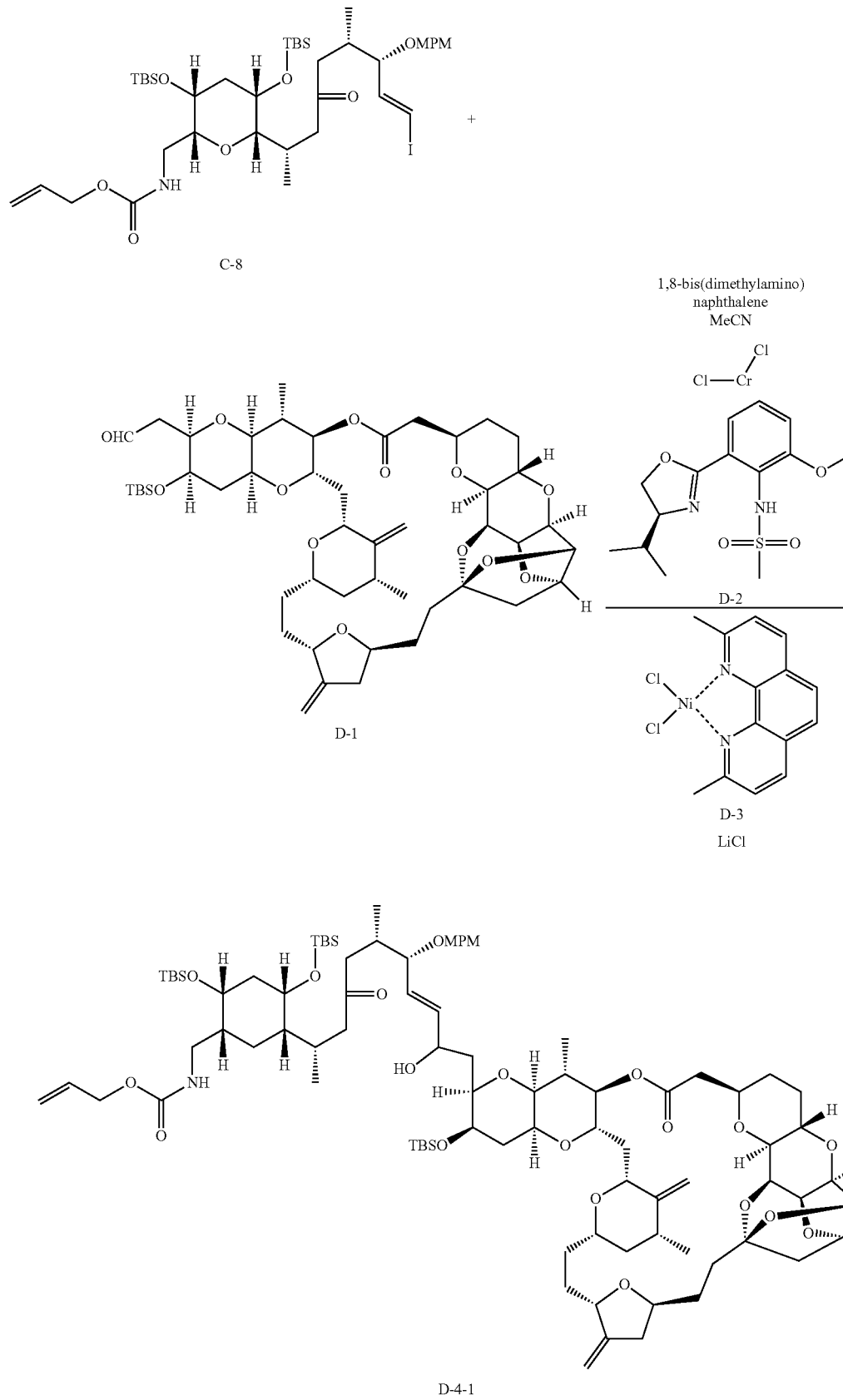

-continued
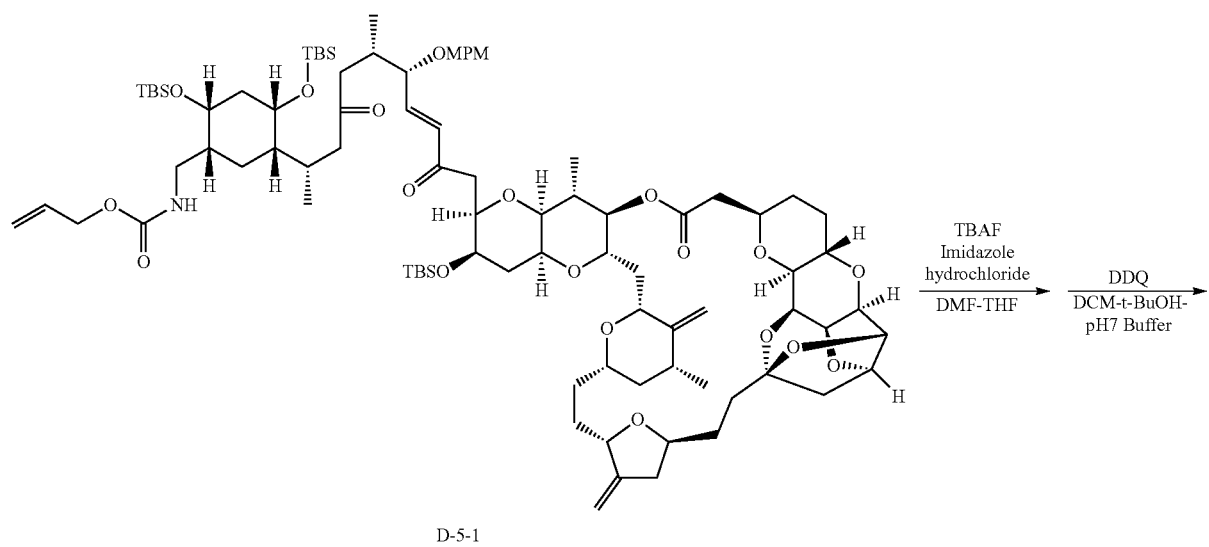
D-5-1
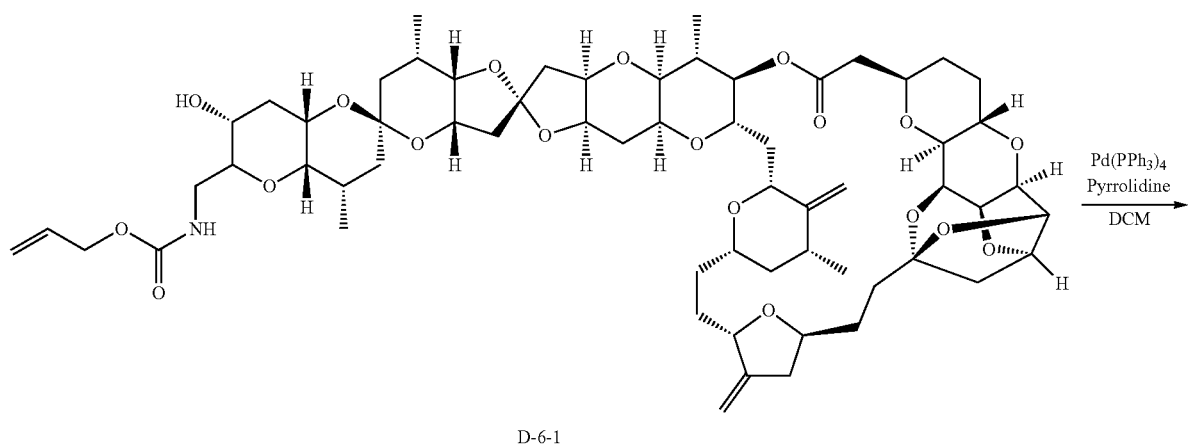
D-6-1
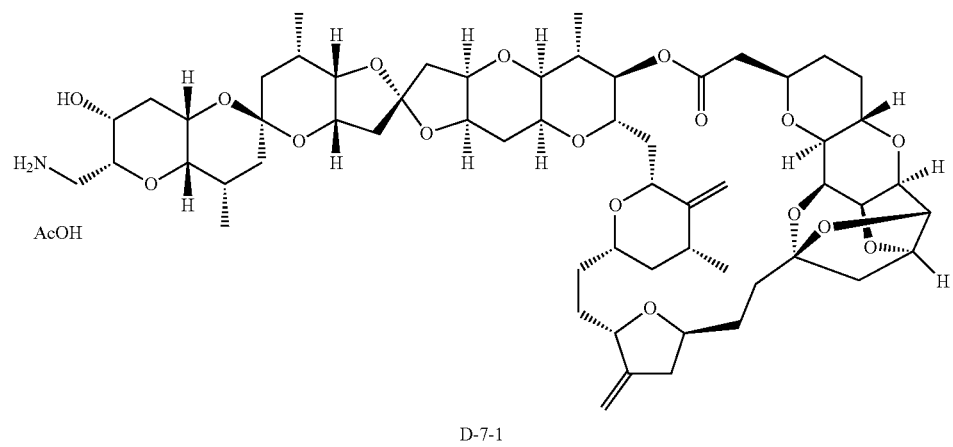
D-7-1

Example 17
Compound D-4-1
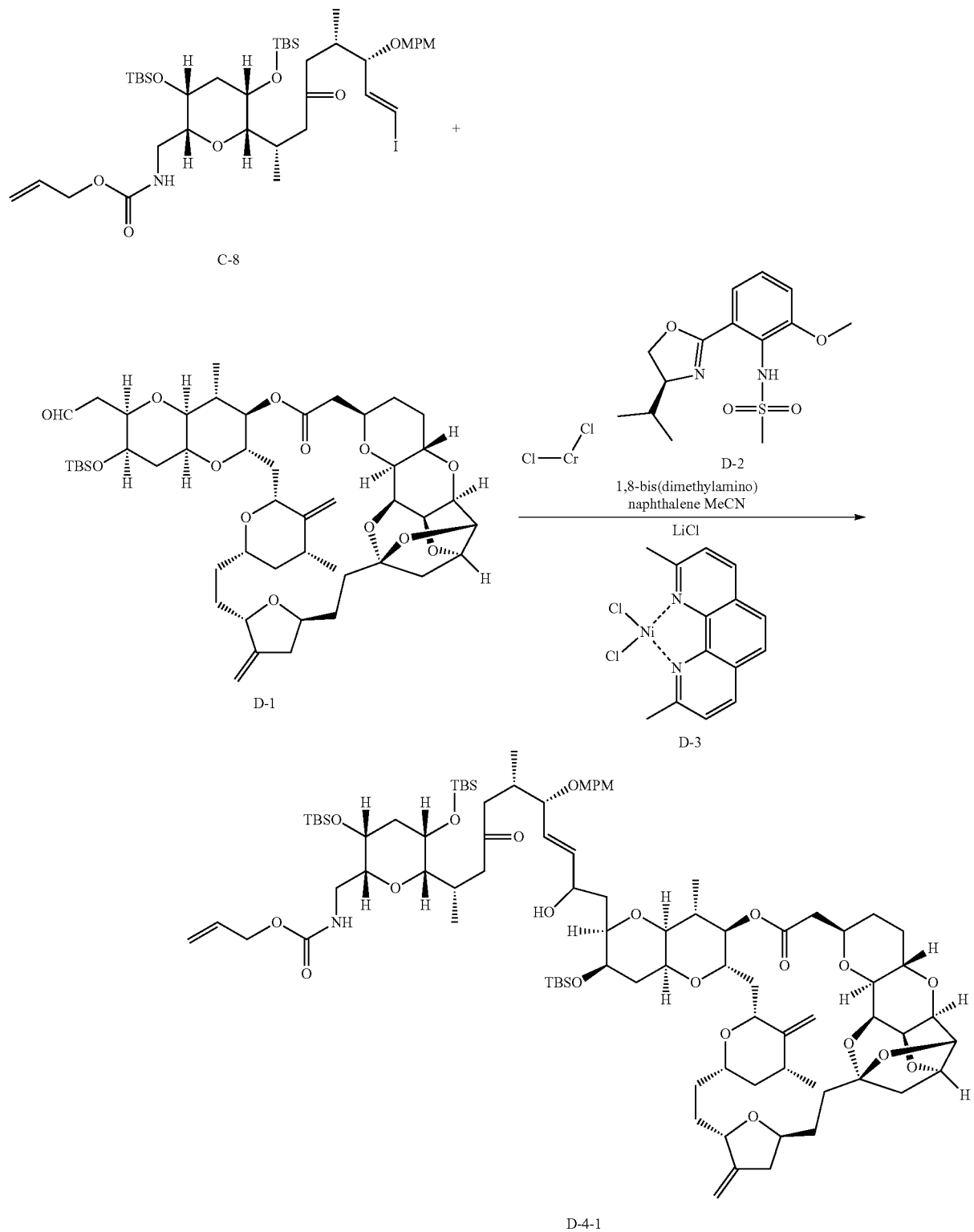
Under a nitrogen atmosphere (in a glove box), to a solution of Compound D-2: (S)—N-(2-(4-isopropyl-4,5-dihydrooxazol-2-yl)-6-methoxyphenyl)methanesulfonamide (155 mg, 0.497 mmol) obtained by the method written in Organic Letters (2002), 4 (25), 4431-4434 (CAS No; 546141-34-8) and 1,8-bis(dimethylamino)naphthalene (107 mg, 0.497 mmol) in MeCN (0.75 mL) was added chromium (II) chloride (55.5 mg, 0.452 mmol) and then the resulting mixture was stirred in the glove box at room temperature for 1 hr. The resulting green solution was added to a mixture of Compound C-8: allyl (((2R,3R,5S,6S)-3,5-bis((tert-butyldimethylsilyl)oxy)-6-((2S,6S,7S,E)-9-iodo-7-((4-methoxybenzyl)oxy)-6-methyl-4-oxonon-8-en-2-yl)tetrahydro-2H-pyran-2-yl)methyl)carbamate (99.0 mg, 0.113 mmol) described in Example 16, Compound D-1(80.0 mg, 0.09 mmol) obtained by the method written in *Journal of the American Chemical Society* (1992), 114 (8), 3162-3164 (CAS No; 157322-23-1), Compound D-3: dichloro(2,9-dimethyl-1,10-phenanthroline)nickel (0.46 mg, 1.36 µmol) obtained by the method written in *Journal of the American Chemical Society* (2009), 131(42), 15387-15393 (CAS No; 21361-04-6) and lithium chloride (3.83 mg, 0.09 mmol). The reaction mixture was stirred in the glove box at room temperature for 60 min. The reaction mixture was then taken out of the glove box, diluted with diethyl ether-EtOAc (5.0 mL-5.0 mL), then Florisil® (1600 mg, 15.94 mmol) (CAS No; 1343-88-0) was added to the mixture. Then mixture was stirred at room temperature for 30 min. The mixture was filtered (Celite®), washed with EtOAc/Heptane=2/1, then filtrate was concentrated under reduced pressure. Flash chromatography of the residue on silica gel using 3% to 55% EtOAc/Heptane gave the title compound (Compound D-4-1, 140 mg, 95% yield).

Example 18

Compound D-5-1

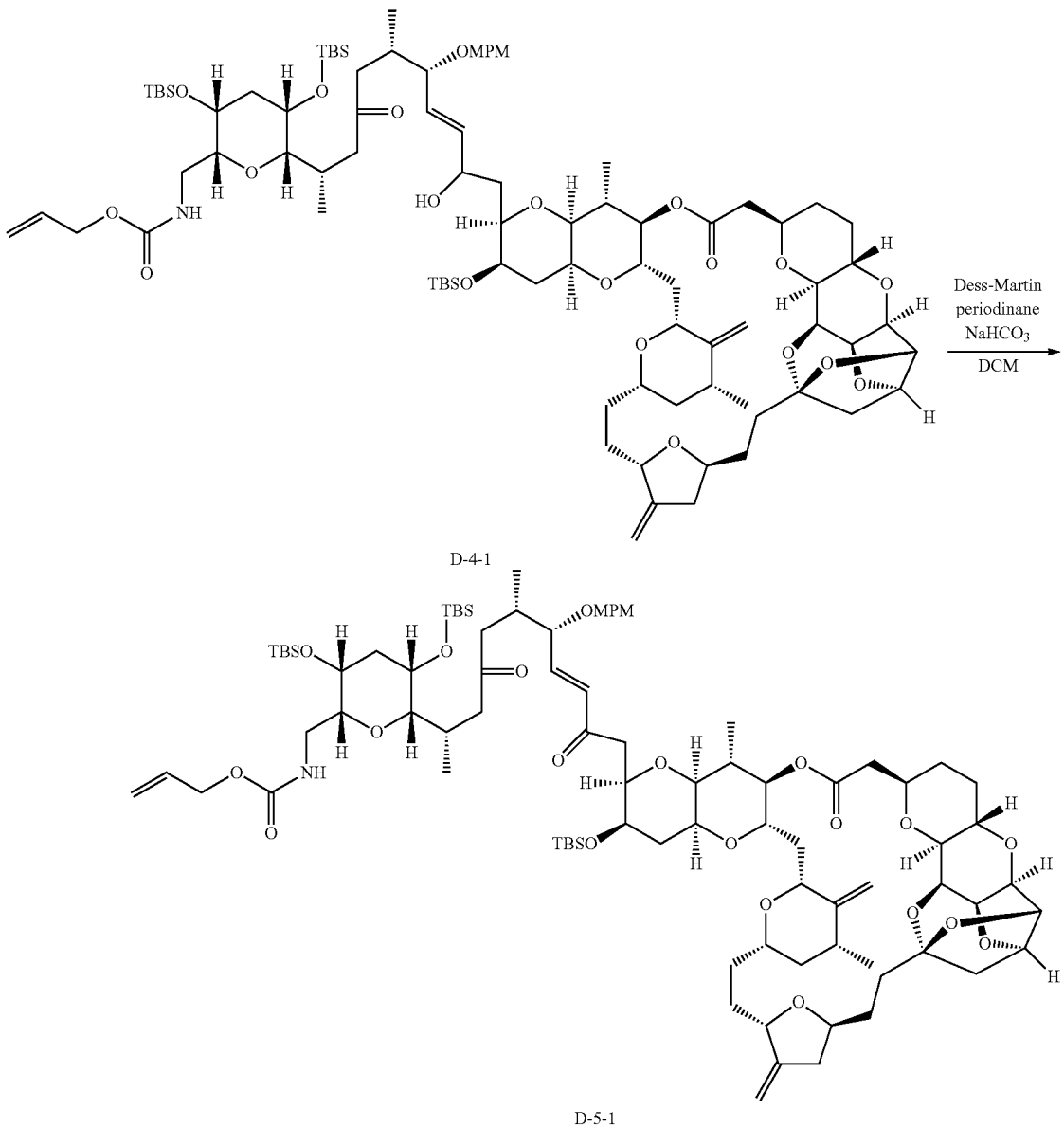

Under a nitrogen atmosphere, to a solution of Compound D-4-1 (140 mg, 0.09 mmol) described in Example 17 in DCM (5.0 mL) at 5° C. were added NaHCO$_3$ (28.8 mg, 0.34 mmol) and Dess-Martin periodinane (72.7 mg, 0.17 mmol). The reaction mixture was stirred at room temperature for 60 min. The reaction mixture was diluted with DCM and quenched with sat. NaHCO₃aq and sat. Na₂SO₃ aq, and then the layers were separated. The aqueous layer was extracted with DCM. The combined organic extracts were washed with brine, dried over Na₂SO₄, filtered and concentrated under reduced pressure. Flash chromatography of the residue on silica gel using 2% to 60% EtOAc/Heptane gave the title compound (Compound D-5-1, 120 mg, 86%).

¹H NMR (500 MHz, BENZENE-d6) δ ppm 0.01-0.05 (m, 9H) 0.10-0.12 (m, 6H) 0.15 (s, 3H) 0.76 (d, J=6.1 Hz, 3H) 0.96 (s, 9H) 1.02 (s, 9H) 1.04 (s, 9H) 0.95-1.10 (m, 7H) 1.20 (d, J=7.3 Hz, 3H) 1.31-1.37 (m, 3H) 1.41 (dd, J=12.8, 4.9 Hz, 1H) 1.40-1.58 (m, 4H) 1.59-1.64 (m, 1H) 1.69-1.89 (m, 3H) 1.90-1.99 (m, 2H) 2.02-2.25 (m, 8H) 2.26-2.48 (m, 6H) 2.49-2.70 (m, 6H) 2.71-2.84 (m, 2H) 3.00-3.07 (m, 1H) 3.12-3.30 (m, 4H) 3.36 (s, 3H) 3.40 (br.s, 1H) 3.44-3.53 (m, 2H) 3.65 (dd, J=6.4, 4.0 Hz, 1H) 3.69-3.84 (m, 4H) 3.86-4.03 (m, 4H) 4.07-4.17 (m, 3H) 4.27-4.29 (m, 1H) 4.27 (d, J=11.0 Hz, 1H) 4.48-4.58 (m, 1H) 4.49 (d, J=11.0 Hz, 1H) 4.65-4.70 (m, 2H) 4.68 (d, J=5.5 Hz, 1H) 4.74-4.86 (m, 2H) 4.78 (s, 1H) 4.93 (s, 1H) 5.05 (d, J=10.4 Hz, 1H) 5.09 (br. s., 1H) 5.19 (br. s., 1H) 5.30 (dd, J=17.1, 1.2 Hz, 1H) 5.82 (d, J=8.0 Hz, 1H) 5.86-5.96 (m, 1H) 6.46 (d, J=15.9 Hz, 1H) 6.84-6.92 (m, 3H) 7.31 (d, J=8.6 Hz, 2H).

Example 19

Compound D-6-1

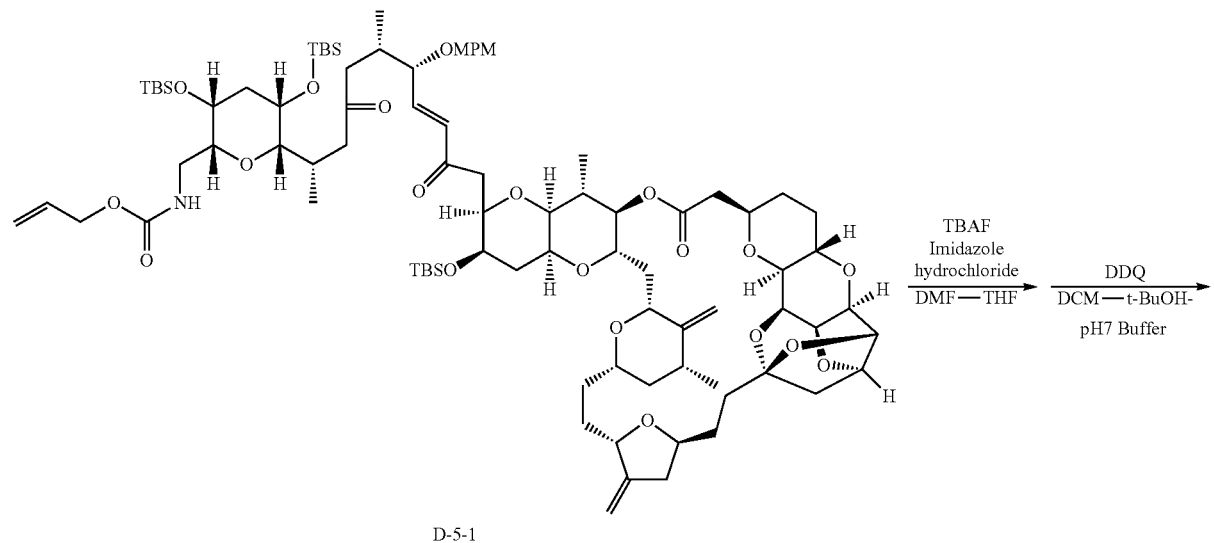

D-5-1

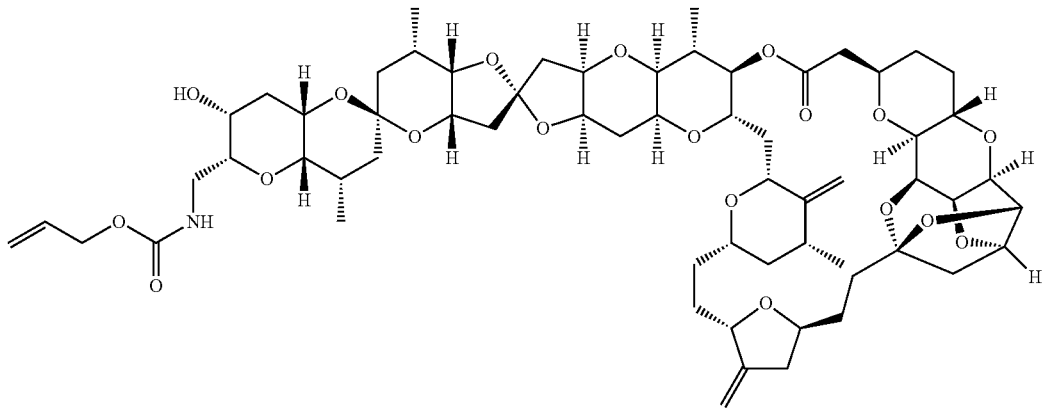

D-6-1

Imidazole hydrochloride (155 mg, 1.48 mmol) was dissolved in DMF (2.9 mL) to give a 0.5 M imidazole hydrochloride solution in DMF. 1.0 mL of this solution was mixed with 1.0 mL of TBAF (1.0 M, THF solution) to give a premixed solution of 0.5 M TBAF and 0.25 M imidazole hydrochloride in THF-DMF (1:1). Under a nitrogen atmosphere, to a solution of Compound D-5-1 (80.0 mg, 0.05 mmol) described in Example 18 in DMF (7.0 mL) at 20° C. were added 0.588 mL of premixed solution of TBAF (0.5 M) and imidazole hydrochloride (0.25 M) in THF-DMF (1:1) prepared above. The reaction mixture was stirred at room temperature for 14 hr. 1.6 g of $CaCO_3$ and 4.0 g of Dowex® 50WX8 (hydrogen form, 200-400 mesh, SIGMA-ALDRICH) were added to the reaction mixture. The mixture was stirred at room temperature for 2 hr. Then mixture was diluted with EtOAc, then filtered (Celite®), washed with EtOAc. Filtrate was concentrated under reduced pressure to give a crude residue. 1000 mg of $CaCO_3$ and 2.25 g of Dowex® 50WX8 were added to the EtOAc (6.0 mL) solution of the crude residue. The mixture was stirred at room temperature for 2.5 hr. Then mixture was diluted with EtOAc, filtered (Celite®), washed with EtOAc. Filtrate was concentrated under reduced pressure to give a crude residue (63.0 mg). To a solution of the crude residue (63.0 mg) obtained above in DCM (6.0 mL), t-BuOH (0.6 mL) and pH 7 Phosphate Buffer (0.6 mL, 1/15 M) at room temperature was added DDQ (111 mg, 0.49 mmol). The reaction mixture was stirred at room temperature for 45 min. The reaction mixture was quenched with sat. $NaHCO_3$ aq, then diluted with DCM and the layers were separated. The aqueous layer was extracted with DCM (3 times). The combined organic extracts were dried over $Na_2SO_4$, filtered and concentrated under reduced pressure. Flash chromatography of the residue on NH silica gel using 10% to 100% EtOAc/Heptane, then 10% MeOH/EtOAc gave a roughly purified title compound (Compound D-6-1, 15.0 mg, 27%).

$^1$H NMR (500 MHz, METHANOL-d4) δ ppm 0.97 (d, J=7.0 Hz, 3H) 0.97 (d, J=7.0 Hz, 3H) 1.00-1.02 (m, 1H) 1.05 (d, J=7.3 Hz, 3H) 1.09 (d, J=6.3 Hz, 3H) 1.31-1.45 (m, 6H) 1.46-1.63 (m, 5H) 1.64-1.75 (m, 3H) 1.80-1.86 (m, 2H) 1.87-1.93 (m, 2H) 1.94-2.11 (m, 9H) 2.13-2.27 (m, 8H) 2.33 (d, J=2.4 Hz, 2H) 2.39 (dd, J=13.4, 6.1 Hz, 1H) 2.44 (dd, J=17.6, 2.0 Hz, 1H) 2.55 (dd, J=17.6, 9.3 Hz, 1H) 2.75-2.84 (m, 1H) 2.97 (dd, J=9.3, 2.0 Hz, 1H) 3.21 (dd, J=6.6, 4.6 Hz, 1H) 3.32 (m, 1H) 3.41-3.46 (m, 1H) 3.57 (br. s., 1H) 3.60 (d, J=11.7 Hz, 1H) 3.67-3.74 (m, 2H) 3.78 (br. s., 1H) 3.86-3.90 (m, 2H) 3.97 (d, J=2.4 Hz, 1H) 4.02-4.11 (m, 4H) 4.17 (dd, J=6.6, 4.6 Hz, 1H) 4.23 (dd, J=11.5, 2.2 Hz, 1H) 4.29 (br.s, 1H) 4.31 (td, J=9.3, 3.9 Hz, 1H) 4.44 (d, J=10.2 Hz, 1H) 4.51 (d, J=5.4 Hz, 2H) 4.59 (t, J=4.9 Hz, 1H) 4.61 (dd, J=7.3, 4.9 Hz, 1H) 4.69 (t, J=4.6 Hz, 1H) 4.80 (s, 1H) 4.85-4.87 (m, 1H) 5.01 (s, 1H) 5.05 (s, 1H) 5.16 (dd, J=10.7, 1.0 Hz, 1H) 5.28 (dd, J=17.1, 2.0 Hz, 1H) 5.92 (m, 1H). ESI-MS (m/z): 1172.57 [M+Na]$^+$ Example 20

Compound D-7-1

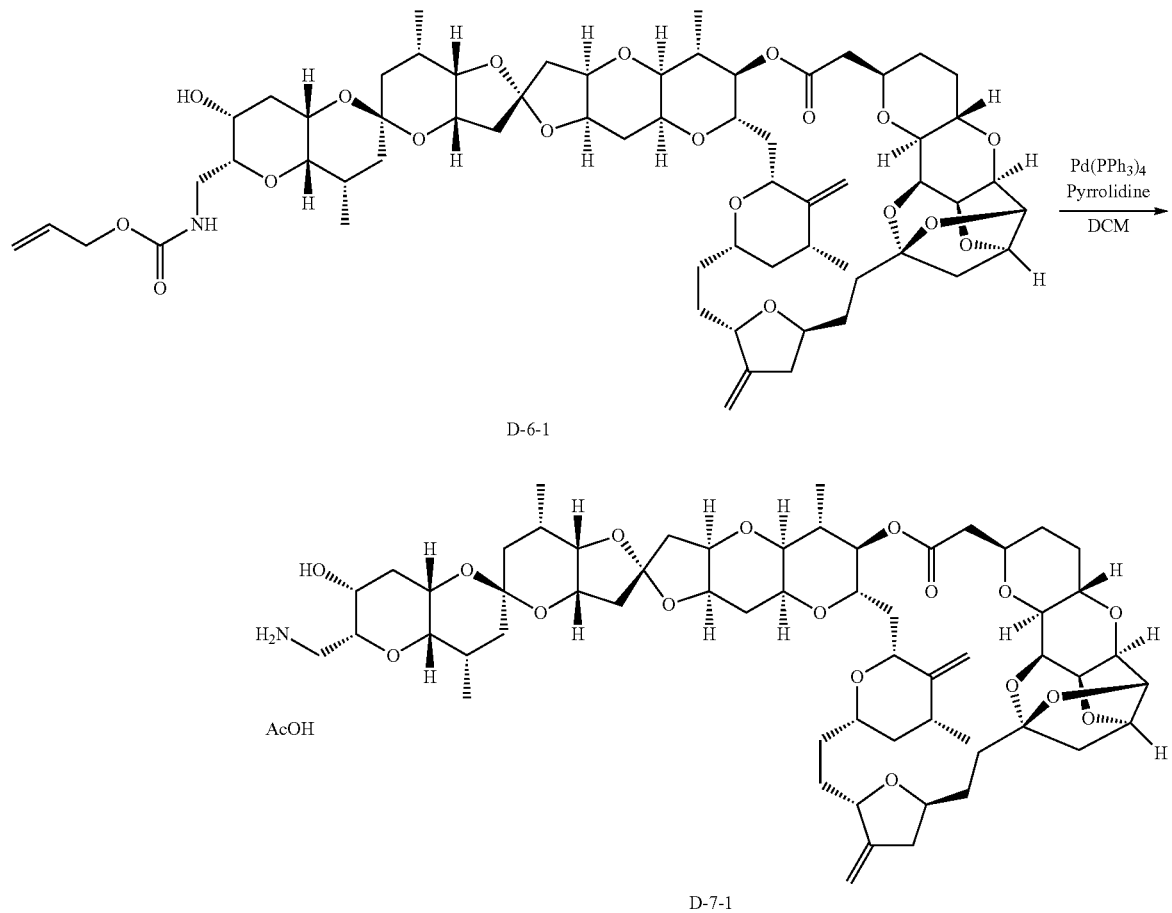

Under a nitrogen atmosphere, to a solution of Compound D-6-1 (15.0 mg, 0.013 mmol) described in Example 19, pyrrolidine (10.8 μL, 0.13 mmol) in DCM (2.0 mL) at room temperature was added tetrakis(triphenylphosphine)palladium(0) (7.53 mg, 6.52 μmol). The reaction mixture was stirred at room temperature for 30 min. The reaction mixture was concentrated under reduced pressure. Flash chromatography of the residue on NH silica gel using 50% EtOAc/Heptane, then 0% to 20% MeOH/EtOAc to give a roughly purified product. Obtained roughly purified product was purified by HPLC to give the title compound (D-7-1, 7.0 mg, 47%, retention time=13.8 min).

HPLC Conditions:

Column: YMC Pak Pro C18 (20 mm×250 mm)

Detection wavelength: 200 nm

Column temperature: room temperature

Mobile phase: MeCN-Water (0.05% AcOH)

Flow rate: 8 mL/min

Eluate:

MeCN/Water 25% (iso, 2 min), then

MeCN/Water 25% to 60% (Gradient, 20 min)

$^1$H NMR (500 MHz, METHANOL-d4) δ ppm 0.99 (d, J=6.7 Hz, 3H) 1.00-1.03 (m, 1H) 1.04 (d, J=7.3 Hz, 3H) 1.06 (d, J=7.3 Hz, 3H) 1.10 (d, J=6.1 Hz, 3H) 1.29-1.63 (m, 10H) 1.65-1.78 (m, 3H) 1.79-1.89 (m, 2H) 1.92-2.12 (m, 10H) 1.93 (s, 3H) 2.13-2.36 (m, 9H) 2.41 (dd, J=13.5, 6.1 Hz, 1H) 2.45 (dd, J=17.6, 2.2 Hz, 1H) 2.56 (dd, J=17.6, 9.8 Hz, 1H) 2.75-2.84 (m, 1H) 2.98 (dd, J=9.8, 1.8 Hz, 1H) 3.12 (dd, J=12.8, 3.7 Hz, 1H) 3.22 (dd, J=6.4, 4.6 Hz, 1H) 3.26 (dd, J=13.2, 7.8 Hz, 1H) 3.39 (d, J=1.8 Hz, 1H) 3.61 (d, J=12.8 Hz, 1H) 3.63-3.68 (m, 2H) 3.68-3.76 (m, 2H) 3.81-3.94 (m, 3H) 4.00 (d, J=2.5 Hz, 1H) 4.03-4.15 (m, 4H) 4.18 (dd, J=6.4, 4.6 Hz, 1H) 4.25 (ddd, J=11.0, 4.3, 1.8 Hz, 1H) 4.27-4.36 (m, 2H) 4.46 (d, J=11.0 Hz, 1H) 4.57-4.65 (m, 2H) 4.70 (t, J=4.6 Hz, 1H) 4.81 (d, J=1.2 Hz, 1H) 5.02 (br. s, 1H) 5.06 (d, J=1.8 Hz, 1H). ESI-MS (m/z): 1066.96 [M+H]$^+$, 1090.19 [M+Na]$^+$ Compound (1) (salt free form of Compound D-7-1): $^1$H NMR (600 MHz, METHANOL-d4) δ ppm 0.98 (d, J=7.2 Hz, 3H) 1.00 (d, J=6.8 Hz, 3H) 1.02 (m, 1H) 1.05 (d, J=6.8 Hz, 3H) 1.09 (d, J=6.4 Hz, 3H) 1.28-1.45 (m, 5H) 1.46-1.59 (m, 4H) 1.57-1.63 (m, 1H) 1.65-1.71 (m, 1H) 1.70-1.75 (m, 2H) 1.79-1.86 (m, 2H) 1.91 (dt, J=14.9, 3.1 Hz, 1H) 1.94-2.11 (m, 8H) 2.14-2.34 (m, 9H) 2.39 (dd, J=13.2, 6.0 Hz, 1H) 2.44 (dd, J=17.4, 1.9 Hz, 1H) 2.56 (dd, J=17.6, 9.6 Hz, 1H) 2.69 (dd, J=13.2, 4.2 Hz, 1H) 2.79 (ddq, J=15.9, 7.6, 2.0 Hz, 1H) 2.92 (dd, J=13.2, 8.3 Hz, 1H) 2.97 (dd, J=9.6, 1.7 Hz, 1H) 3.21 (dd, J=6.4, 4.9 Hz, 1H) 3.29 (m, 1H) 3.34 (dd, J=8.3, 4.15 Hz, 1H) 3.58 (br. s., 1H) 3.60 (br.d, J=11.3 Hz, 1H) 3.68-3.73 (m, 2H) 3.80 (br. s., 1H) 3.84-3.90 (m, 2H) 3.98 (d, J=2.3 Hz, 1H) 4.03-4.13 (m, 4H) 4.17 (dd, J=6.4, 4.9 Hz, 1H) 4.24 (ddd, J=11.3, 4.5, 1.5 Hz, 1H) 4.29 (dd, J=4.0, 1.9 Hz, 1H) 4.32 (td, J=10.2, 4.2 Hz, 1H) 4.44 (br. d, J=11.0 Hz, 1H) 4.59 (t, J=4.5 Hz, 1H) 4.62 (dd, J=7.4, 4.7 Hz, 1H) 4.69 (t, J=4.7 Hz, 1H) 4.80 (br. s., 1H) 4.87 (s, 1H) 5.00 (br. s., 1H) 5.05 (br.d, J=1.1 Hz, 1H)

ESI-MS (m/z): 1066.57 [M+H]$^+$, 1088.55 [M+Na]$^+$

Synthesis of Compound (D-6)

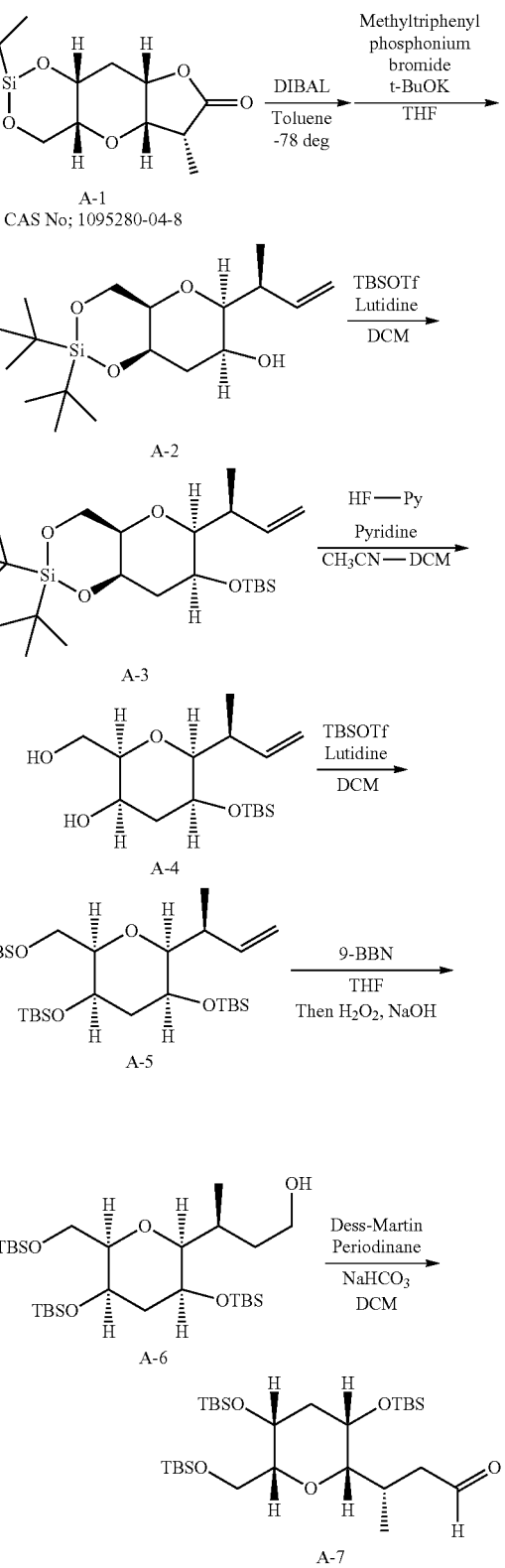

Scheme A; Preparation of Compound A-7

Example 21

(S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butanal (Compound A-7)

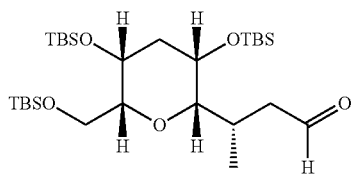

A-7

The title compound A-7 was obtained from compound A-1: (4aR,5aS,6R,8aS,9aR)-2,2-di-tert-butyl-6-methylhexahydrofuro[2',3':5,6]pyrano[3,2-d][1,3,2]dioxasilin-7(8aH)-one prepared by the method written in Organic Letters (2009), 11(2), 409-412 (CAS No; 1095280-04-8) as shown in Scheme A.

$^1$H NMR (500 MHz, CHLOROFORM-d) ppm 0.00 (s, 3H) 0.03-0.08 (m, 12H) 0.11 (s, 3H) 0.88 (s, 9H) 0.91-0.92 (m, 21H) 1.82 (dt, J=15.0, 4.5 Hz, 1H) 2.01 (dt, J=15.0, 2.5 Hz, 1H) 2.28 (ddd, J=16.0, 7.3, 2.4 Hz, 1H) 2.53-2.58 (m, 1H) 2.74 (ddd, J=16.0, 5.5, 2.0 Hz, 1H) 2.94 (dd, J=9.0, 1.7 Hz, 1H) 3.29 (td, J=5.9, 2.0 Hz, 1H) 3.68 (d, J=5.9 Hz, 2H) 3.75-3.82 (m, 1H) 3.82-3.90 (m, 1H) 9.73 (t, J=2.4 Hz, 1H)

Scheme B; Preparation of Compound B-3

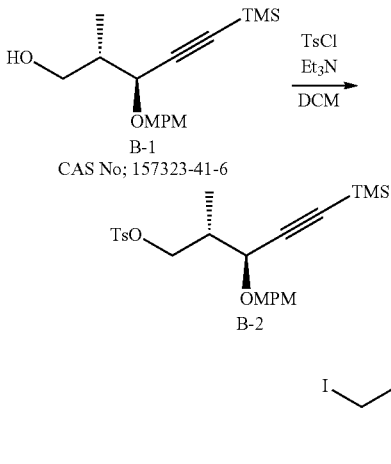

Example 22

((3S,4R)-5-iodo-3-((4-methoxybenzyl)oxy)-4-methylpent-1-yn-1-yl)trimethylsilane (Compound B-3)

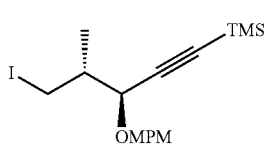

B-3

The title compound B-3 was obtained from compound B-1: (2S,3S)-3-((4-methoxybenzyl)oxy)-2-methyl-5-(trimethylsilyl)pent-4-yn-1-ol prepared by the method written in WO 93/17690 A1/U.S. Pat. No. 5,436,238 A (CAS No; 157323-41-6) as shown in Scheme B.

$^1$H NMR (500 MHz, CHLOROFORM-d) δ ppm 0.21 (s, 9H) 1.10 (d, J=6.8 Hz, 3H) 1.74-1.84 (m, 1H) 3.30-3.37 (m, 2H) 3.82 (s, 3H) 3.96 (d, J=7.3 Hz, 1H) 4.44 (d, J=11.2 Hz, 1H) 4.73 (d, J=11.2 Hz, 1H) 6.89 (d, J=8.8 Hz, 2H) 7.30 (d, J=8.8 Hz, 2H).

Scheme C; Preparation of Compound C-4

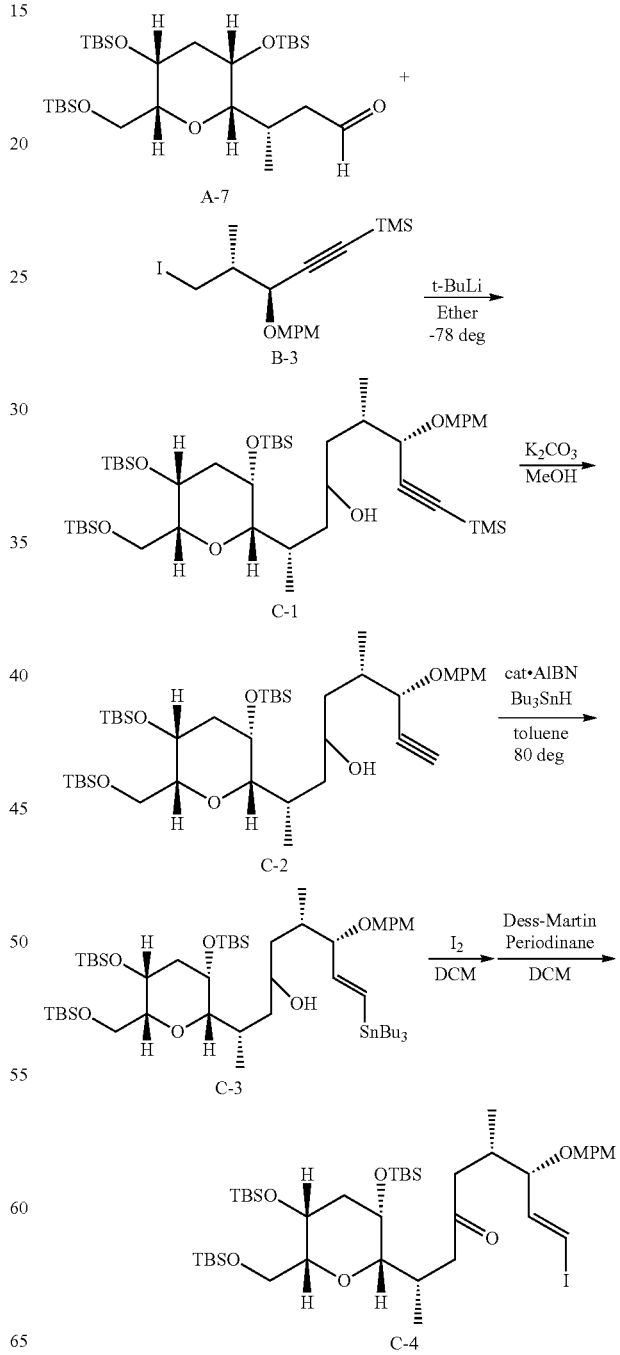

Example 23

(2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-one (Compound C-4)

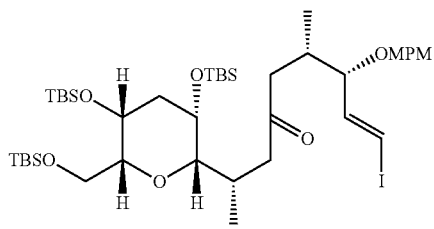

The title compound C-4 was obtained from Compound A-7: (S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butanal and Compound B-3: ((3S,4R)-5-iodo-3-((4-methoxybenzyl)oxy)-4-methylpent-1-yn-1-yl)trimethylsilane according to the procedure for the preparation of Compound C-8, as shown in Scheme C.

$^1$H NMR (500 MHz, CHLOROFORM-d) δ ppm 0.00 (s, 3H) 0.03-0.07 (m, 12H) 0.10 (s, 3H) 0.81 (d, J=6.3 Hz, 3H) 0.84 (d, J=6.3 Hz, 3H) 0.89 (s, 9H) 0.91 (s, 9H) 0.92 (s, 9H) 1.80 (dt, J=15.0, 4.5 Hz, 1H) 1.99 (dt, J=15.0, 2.5 Hz, 1H) 2.17 (dd, J=16.6, 10.2 Hz, 1H) 2.20-2.29 (m, 2H) 2.43-2.48 (m, 1H) 2.54 (d, J=12.7 Hz, 1H) 2.87 (dd, J=9.0, 1.7 Hz, 1H) 2.99 (dd, J=16.6, 2.9 Hz, 1H) 3.27 (td, J=5.8, 2.4 Hz, 1H) 3.50-3.56 (m, 1H) 3.66-3.74 (m, 2H) 3.75-3.78 (m, 1H) 3.80 (s, 3H) 3.81-3.85 (m, 1H) 4.26 (d, J=11.7 Hz, 1H) 4.50 (d, J=11.7 Hz, 1H) 6.26 (d, J=14.6 Hz, 1H) 6.42 (dd, J=14.6, 7.8 Hz, 1H) 6.87 (d, J=8.3 Hz, 2H) 7.21 (d, J=8.3 Hz, 2H). ESI-MS (m/z): 927.4 [M+Na]$^+$ Scheme D; Preparation of Compound D-6

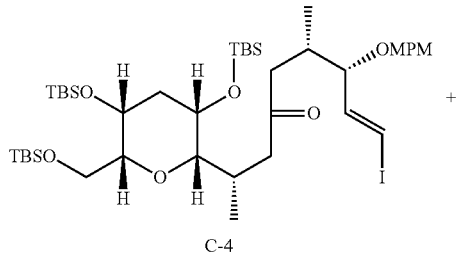

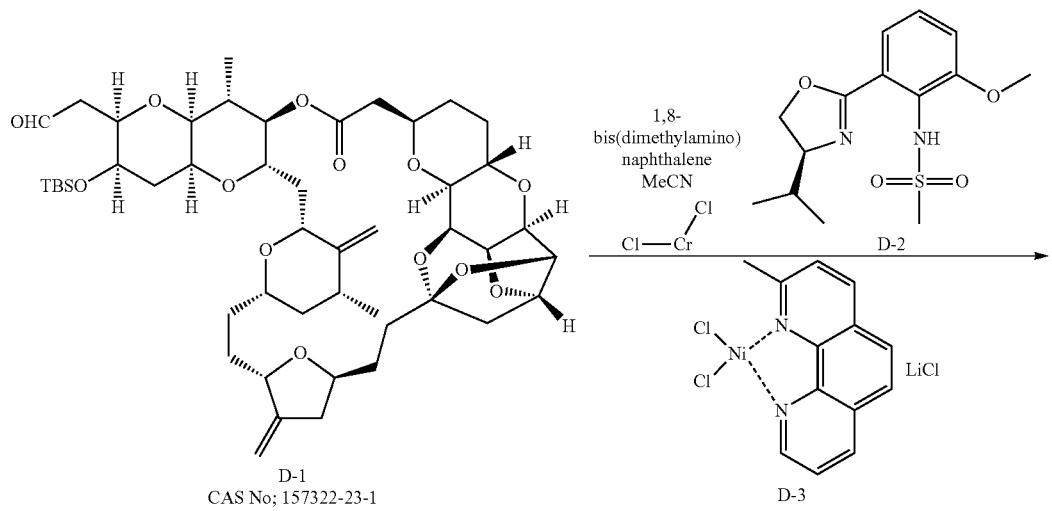

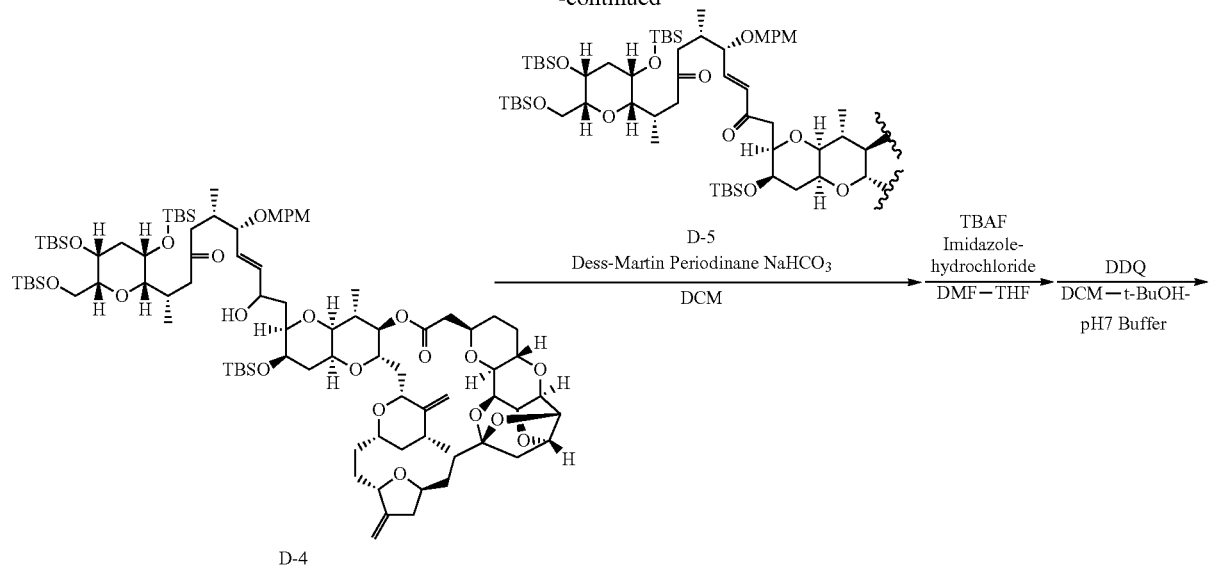
D-5
Example 24
Compound D-4
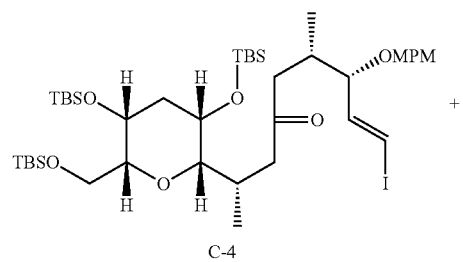

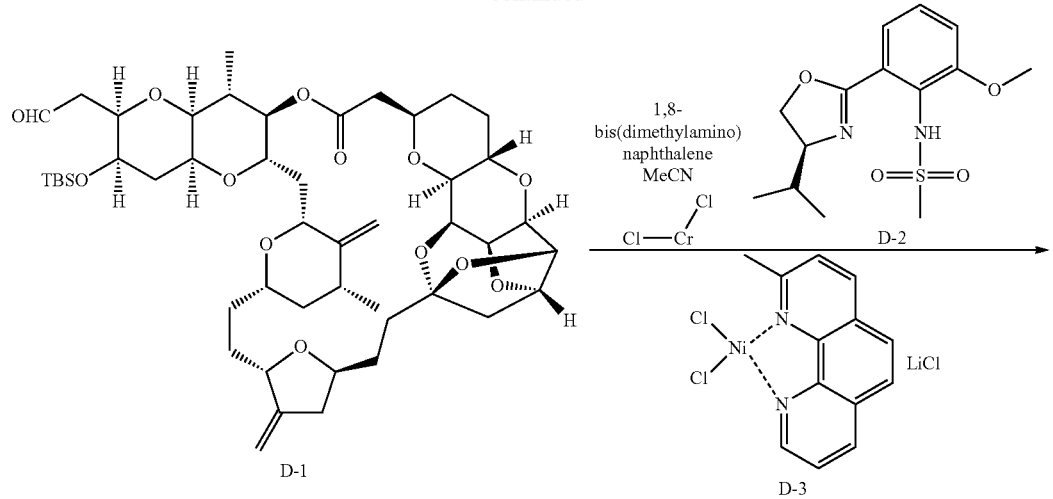

D-1

D-2

D-3

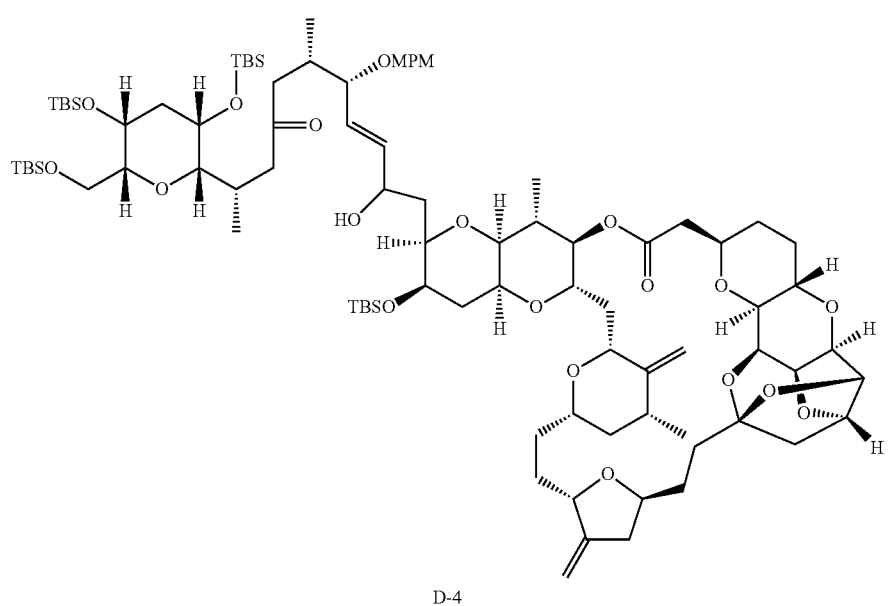

D-4

Under a nitrogen atmosphere (in a glove box), to a solution of Compound D-2: (S)—N-(2-(4-isopropyl-4,5-dihydrooxazol-2-yl)-6-methoxyphenyl)methanesulfonamide (29.1 mg, 0.093 mmol) obtained by the method written in Organic Letters (2002), 4 (25), 4431-4434 (CAS No; 546141-34-8) and 1,8-bis(dimethylamino)naphthalene (20.0 mg, 0.093 mmol) in MeCN (0.3 mL) was added chromium (II) chloride (10.4 mg, 0.085 mmol) and then the resulting mixture was stirred in the glove box at room temperature for 1 hr. The resulting solution was added to the pre-mixture of Compound C-4: (2S,6S,7S,E)-2-((2S,3S,5R,6R)-3,5-bis ((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-one (18.4 mg, 0.02 mmol) described in Example 23, Compound D-1 (15.0 mg, 0.017 mmol) obtained by the method written in Journal of the American Chemical Society (1992), 114 (8), 3162-3164 (CAS No; 157322-23-1), Compound D-3: dichloro(2,9-dimethyl-1,10-phenanthroline)nickel (0.09 mg, 0.254 μmol) obtained by the method written in Journal of the American Chemical Society (2009), 131(42), 15387-15393 (CAS No; 21361-04-6) and lithium chloride (1.0 mg, 0.024 mmol). The reaction mixture was stirred in the glove box at room temperature for 60 min. The reaction mixture was then taken out from the glove box, diluted with diethyl ether (0.45 mL), then Florisil® (300 mg, 2.99 mmol) (CAS No; 1343-88-0) was added to the mixture. Then mixture was stirred at room temperature for 30 min. The mixture was filtered (Celite®), washed with EtOAc/Heptane=1/1, then filtrate was concentrated under reduced pressure. Flash chromatography of the residue on silica gel using 3% to 45% EtOAc/Heptane gave the title compound (Compound D-4, 25.5 mg, 90% yield).

Example 25

Compound D-5

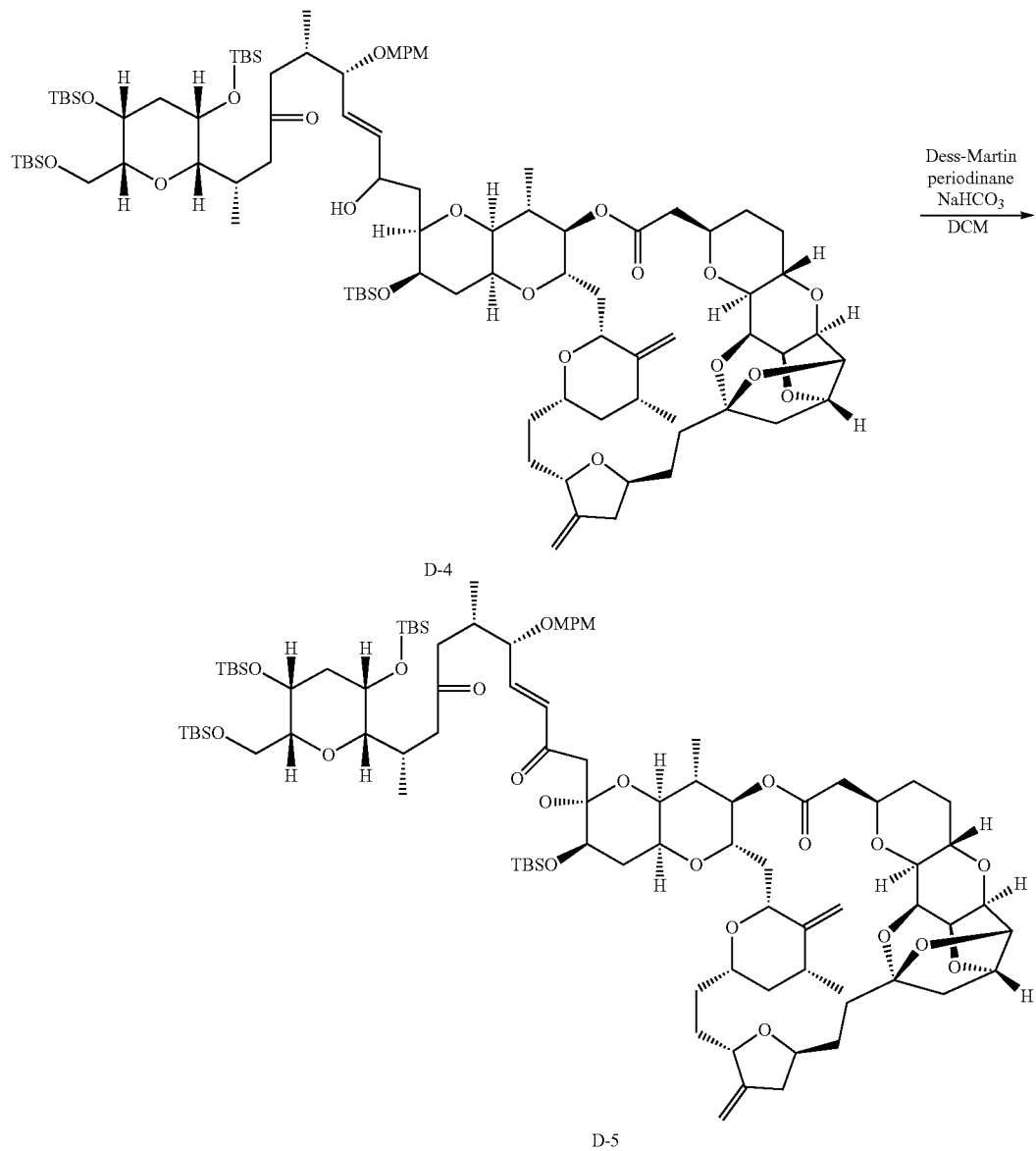

Under a nitrogen atmosphere, to a solution of Compound D-4 (25.0 mg, 0.015 mmol) described in Example 24 in DCM (1.5 mL) at 0° C. were added NaHCO$_3$ (0.38 mg, 4.51 μmol) and Dess-Martin periodinane (12.7 mg, 0.03 mmol). The reaction mixture was stirred at room temperature for 5 hr. Dess-Martin periodinane (4.0 mg, 9.43 μmol) was added to the reaction mixture, then the reaction mixture was stirred at room temperature for 3 hr. The reaction mixture was diluted with DCM and quenched with sat.NaHCO$_3$aq and sat.Na$_2$SO$_3$ aq, and then the layers were separated. The aqueous layer was extracted with DCM. The combined organic extracts were washed with brine, dried over Na$_2$SO$_4$, filtered and concentrated under reduced pressure. Flash chromatography of the residue on silica gel using 3% to 40% EtOAc/Heptane gave the title compound (Compound D-5, 20 mg, 80%). $^1$H NMR (500 MHz, CHLOROFORM-d) δ ppm −0.01-0.01 (m, 6H) 0.03-0.08 (m, 15H) 0.10 (s, 3H) 0.80 (d, J=6.3 Hz, 3H) 0.84 (d, J=6.8 Hz, 3H) 0.87 (s, 9H) 0.88 (s, 9H) 0.91 (s, 9H) 0.91 (s, 9H) 0.94-0.98 (m, 1H) 1.04 (d, J=6.8 Hz, 3H) 1.07 (d, J=6.3 Hz, 3H) 1.29-1.51 (m, 5H) 1.60-1.68 (m, 3H) 1.68-1.77 (m, 2H) 1.80 (dt, J=14.8, 4.6 Hz, 1H) 1.86-2.03 (m, 7H) 2.06-2.27 (m, 9H) 2.29 (d, J=2.4 Hz, 2H) 2.37 (dd, J=16.3, 4.6 Hz, 1H) 2.41-2.50 (m, 1H) 2.54 (d, J=13.7 Hz, 1H) 2.64 (dd, J=16.6, 7.3 Hz, 1H) 2.76-2.90 (m, 3H) 2.91-3.04 (m, 3H) 3.24-3.30 (m, 1H) 3.41 (dd, J=5.6, 4.1 Hz, 1H) 3.54-3.59 (m, 1H) 3.66-3.75 (m, 3H) 3.75-3.78 (m, 1H) 3.80 (s, 3H) 3.81-3.84 (m, 1H) 3.86-3.96 (m, 3H) 4.03-4.09 (m, 2H) 4.20 (dd, J=6.8, 4.9 Hz, 1H) 4.24 (d, J=11.2 Hz, 1H) 4.33 (br. s., 2H) 4.39-4.45 (m, 2H) 4.47 (d, J=11.7 Hz, 1H) 4.57 (d, J=7.3 Hz, 1H) 4.60 (t, J=4.4 Hz, 1H) 4.69 (t, J=4.6 Hz, 1H) 4.75 (s, 1H) 4.83 (s, 1H) 5.00 (d, J=13.2 Hz, 2H) 6.23 (d, J=16.1 Hz, 1H) 6.66 (dd, J=16.1, 6.8 Hz, 1H) 6.87 (d, J=8.8 Hz, 2H) 7.21 (d, J=8.8 Hz, 2H).

Example 26

Compound D-6

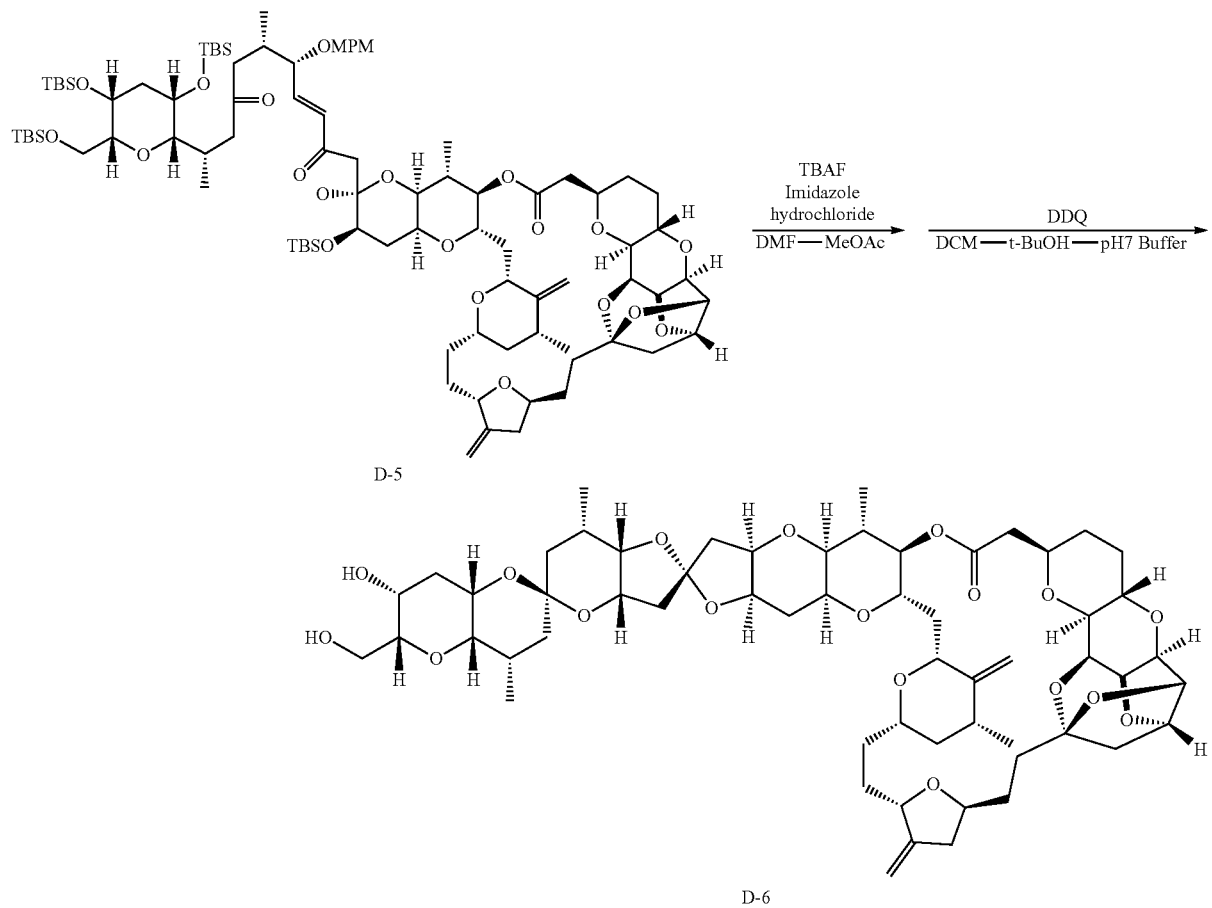

One milliliter of TBAF (1.0 mmol, 1.0 M THF solution) was co-evaporated with toluene (3×1 mL). To the residue was added imidazole hydrochloride (52 mg, 0.5 mmol) and DMF (2.0 mL) to give a premixed solution of 0.5 M TBAF and 0.25 M imidazole hydrochloride in DMF. Under a nitrogen atmosphere, to a solution of Compound D-5 (20.7 mg, 0.012 mmol) described in Example 25 in DMF (0.9 mL) and MeOAc (0.1 mL) at room temperature was added 0.241 mL of premixed solution of TBAF (0.5 M) and imidazole hydrochloride (0.25 M) in DMF prepared above. The reaction mixture was stirred at room temperature for 18 hr. The reaction mixture was added with 210 mg of $CaCO_3$ and 520 mg of Dowex® 50WX8 (hydrogen form, 200-400 mesh, SIGMA-ALDRICH). The mixture was diluted with EtOAc (0.3 mL) and stirred at room temperature for 1 hr. The mixture was diluted with EtOAc (3 mL), then filtered through Celite®, washed with EtOAc. The filtrate was concentrated under reduced pressure to give a crude residue. The residue was added EtOAc (3 mL). The solution was added with 210 mg of $CaCO_3$ and 520 mg of Dowex® 50WX8. The mixture was stirred at room temperature for 1 hr. The mixture was diluted with EtOAc, filtered through Celite®, washed with EtOAc. The filtrate was concentrated under reduced pressure to give a crude residue (16.7 mg). To a solution of the crude residue (16.7 mg) obtained above in DCM (2.1 mL), t-BuOH (0.21 mL), and pH7 Phosphate Buffer (0.21 mL, 1/15 M) at room temperature was added DDQ (28.3 mg, 0.125 mmol). The reaction mixture was stirred vigorously at room temperature for 50 min. The reaction mixture was poured into sat. $NaHCO_3$aq. (8 mL) with vigorous stirring at room temperature, then diluted with DCM (10 mL) and the layers were separated. The aqueous layer was extracted with DCM (2×5 mL). The combined organic extracts were dried over $Na_2SO_4$, filtered and concentrated under reduced pressure. Flash chromatography of the residue on NH silica gel (FUJI SILYSIA CHEMICAL LTD, Chromatorex® NH silica gel) using 0% to 100% EtOAc/Heptane, then 5% MeOH/EtOAc gave a roughly purified title compound (4.9 mg). The obtained product was purified by HPLC to give the title compound (Compound D-6, 2.2 mg, 16.5%).Retention time=8.7 min HPLC Conditions Column: YMC Pak Pro C18 (10 mm I.D.×250 mm)
Detection wavelength: 205 nm
Column temperature: room temperature
Mobile phase: MeCN-Water
Flow rate: 4.7 mL/min
Eluate:
MeCN/Water 60% (iso, 2 min), then
MeCN/Water 60% to 99% (gradient, 10 min), then
MeCN/Water 99% (iso, 11 min)

$^1$H NMR (500 MHz, METHANOL-d4) δ ppm 0.97 (d, J=6.8 Hz, 3H) 0.99 (d, J=7.3 Hz, 3H) 1.00-1.05 (m, 1H) 1.05 (d, J=7.3 Hz, 3H) 1.09 (d, J=6.8 Hz, 3H) 1.30-1.57 (m, 8H) 1.57-1.62 (m, 1H) 1.64-1.70 (m, 1H) 1.70-1.75 (m, 2H)

1.78-1.86 (m, 2H) 1.90 (ddd, J=14.8, 3.2, 3.2 Hz, 1H) 1.94-2.12 (m, 9H) 2.13-2.25 (m, 4H) 2.25-2.34 (m, 5H) 2.39 (dd, J=13.2, 5.8 Hz, 1H) 2.44 (dd, J=17.4, 2.3 Hz, 1H) 2.55 (dd, J=17.6, 9.7 Hz, 1H) 2.76-2.83 (m, 1H) 2.97 (dd, J=9.7, 1.9 Hz, 1H) 3.21 (dd, J=6.6, 4.6 Hz, 1H) 3.30 (m, 1H) 3.41 (dd, J=6.1, 6.1 Hz, 1H) 3.60 (d, J=11.7 Hz, 1H) 3.65 (d, J=2.9 Hz, 1H) 3.65-3.68 (m, 2H) 3.68-3.74 (m, 2H) 3.80 (br. s., 1H) 3.84-3.91 (m, 2H) 3.98 (dd, J=4.7, 2.2 Hz, 1H) 4.03-4.13 (m, 4H) 4.17 (dd, J=6.6, 4.6 Hz, 1H) 4.23 (ddd, J=11.6, 4.6, 2.0 Hz, 1H) 4.28-4.30 (m, 1H) 4.32 (dd, J=10.2, 4.2 Hz, 1H) 4.44 (d, J=11.2 Hz, 1H) 4.59 (dd, J=4.4, 4.4 Hz, 1H) 4.61 (dd, J=7.6, 4.8 Hz, 1H) 4.69 (dd, J=4.6, 4.6 Hz, 1H) 4.80 (d, J=1.2 Hz, 1H) 4.86-4.87 (m, 1H) 5.01 (br. s., 1H) 5.06 (d, J=1.5 Hz, 1H). ESI-MS (m/z): 1089.5 $[M+Na]^+$ Synthesis of Compound (E-2)

Example 27

Compound E-2

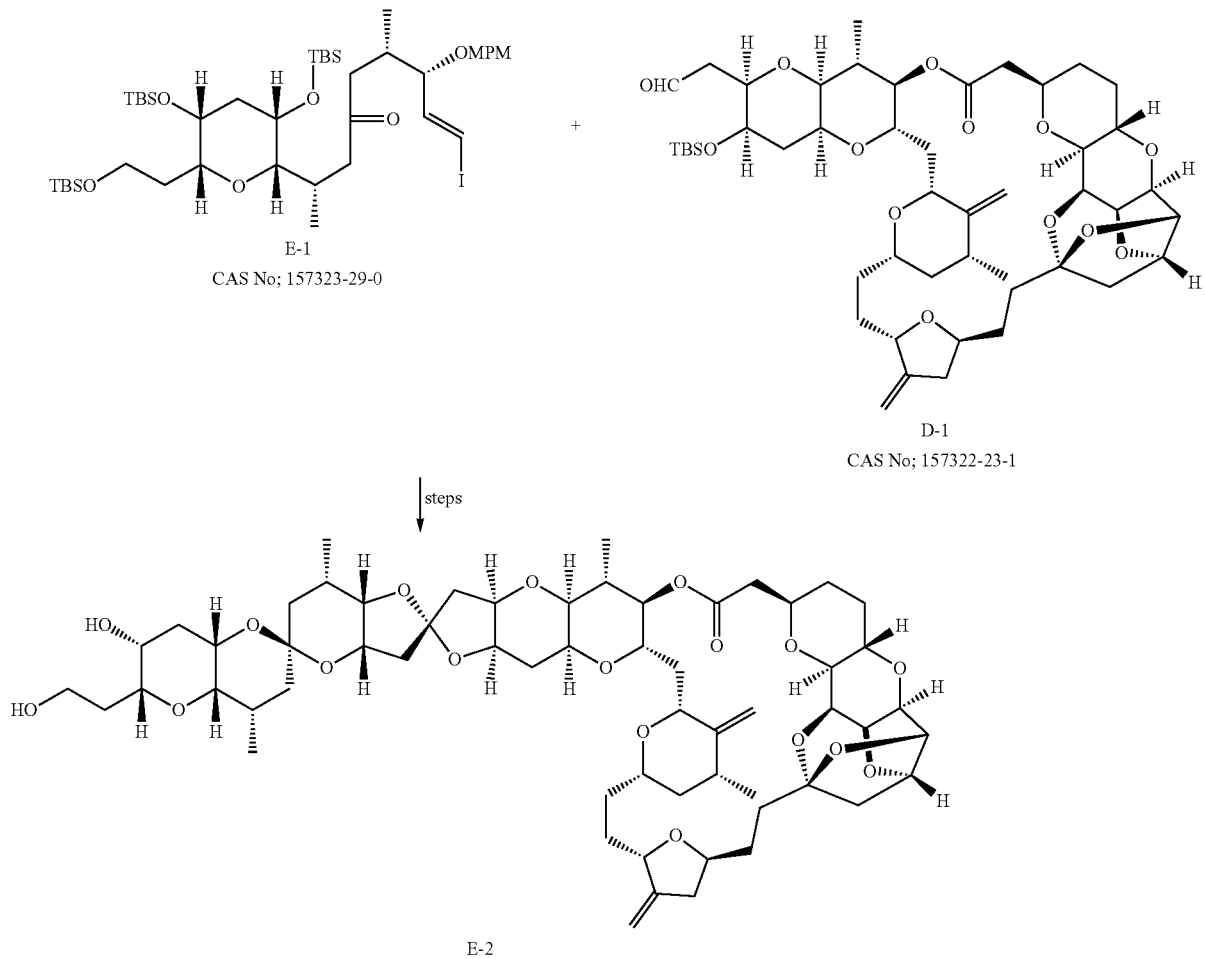

The title compound E-2 was obtained from compound E-1: (2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-ol (CAS No; 157323-29-0) prepared by the method written in WO 93/17690 A1, and Compound D-1 (CAS No; 157322-23-1) prepared by the method written in *Journal of the American Chemical Society* 1992, 114, 3162-3164, using the same procedures described for the preparation of compounds D-4, D-5, and D-6 (Example 24, 25, and 26). Retention time=14.7 min.

HPLC Conditions
   Column: YMC Pak Pro C18 (4.6 mm I.D.×250 mm)
   Detection wavelength: 200 nm
   Column temperature: room temperature
   Mobile phase: MeCN-Water
   Flow rate: 1 ml/min
   Eluate:
   MeCN/Water 40% to 98% (Gradient, 20 min), then
   MeCN/Water 98% (iso, 10 min)

$^1$H NMR (600 MHz, METHANOL-d4) δ ppm 0.96-0.98 (m, 6H) 1.01 (d, J=11.7 Hz, 1H) 1.05 (d, J=6.8 Hz, 3H) 1.09 (d, J=6.4 Hz, 3H) 1.30-1.56 (m, 7H) 1.63-1.71 (m, 3H) 1.72 (d, J=10.6 Hz, 1H) 1.79-1.86 (m, 2H) 1.89-2.12 (m, 11H) 2.13-2.21 (m, 3H) 2.22-2.32 (m, 6H) 2.39 (dd, J=13.2, 6.0 Hz, 1H) 2.44 (dd, J=17.8, 2.3 Hz, 1H) 2.55 (dd, J=17.4, 9.4 Hz, 1H) 2.79 (dd, J=15.7, 5.5 Hz, 1H) 2.97 (dd, J=9.4, 1.5 Hz, 1H) 3.21 (dd, J=6.4, 4.9 Hz, 1H) 3.28 (br. s., 2H) 3.47 (br. s., 1H) 3.51 (dd, J=9.1, 3.8 Hz, 1H) 3.60 (d, J=11.7 Hz, 1H) 3.66-3.70 (m, 1H) 3.67-3.71 (m, 1H) 3.68-3.73 (m, 2H) 3.78 (br. s., 1H) 3.86 (br. s., 1H) 3.86-3.90 (m, 1H) 3.98 (q, J=2.3 Hz, 1H) 4.03-4.08 (m, 1H) 4.07-4.10 (m, 1H) 4.09-

4.12 (m, 1H) 4.10-4.12 (m, 2H) 4.17 (dd, J=6.4, 4.9 Hz, 1H) 4.23 (ddq, J=11.0, 4.2, 1.9 Hz, 1H) 4.29 (t, J=1.9 Hz, 1H) 4.32 (td, J=10.6, 4.5 Hz, 1H) 4.44 (d, J=11.0 Hz, 1H) 4.59 (t, J=4.3 Hz, 1H) 4.62 (dd, J=7.4, 4.7 Hz, 1H) 4.69 (t, J=4.7 Hz, 1H) 4.84 (br. s., 1H) 4.87 (br. s., 1H) 5.00 (br. s., 1H) 5.05 (br. s., 1H). ESI-MS (m/z): 1103.6 [M+Na]$^+$
Synthesis of Compound (G-4)
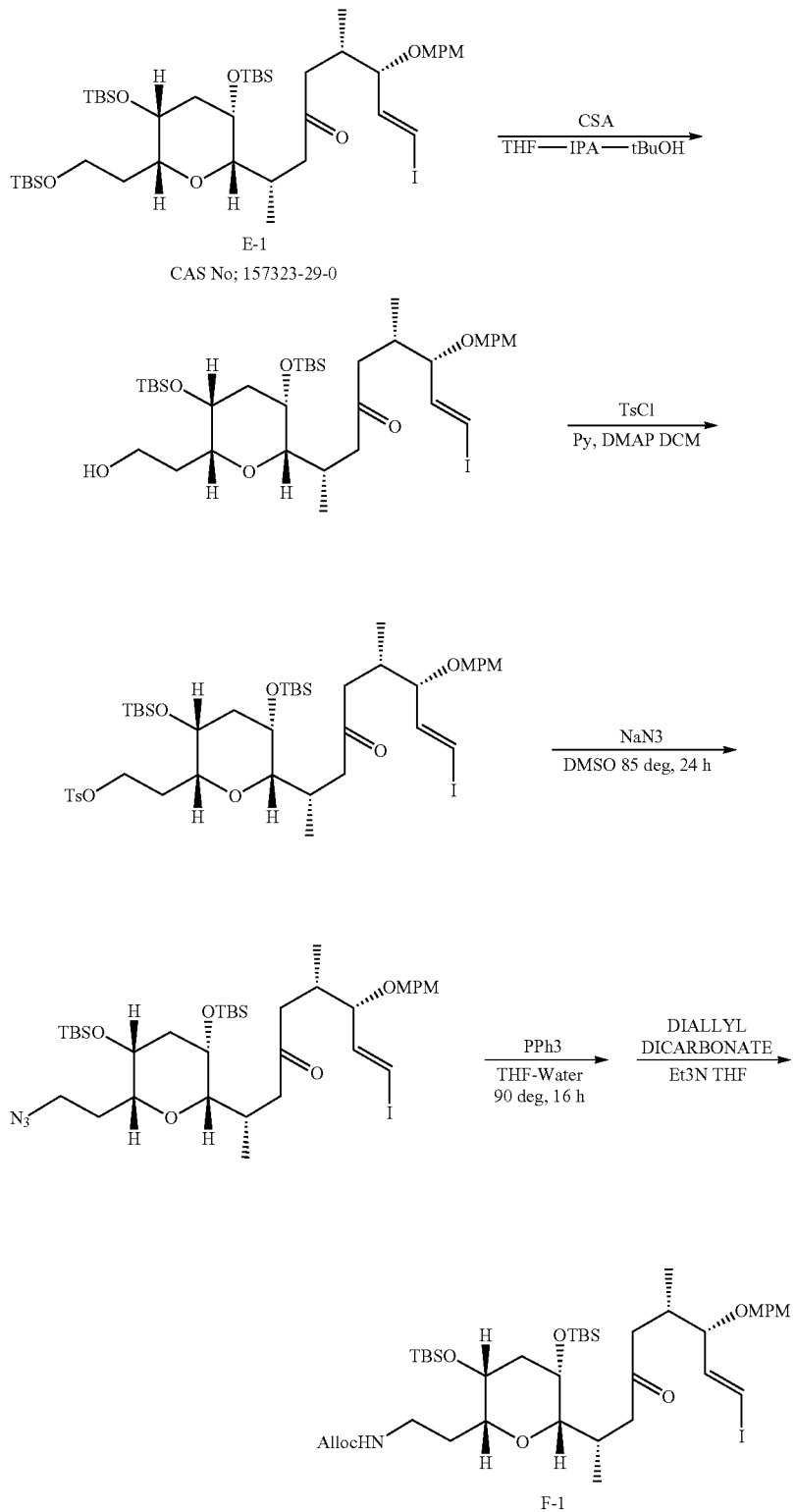

Scheme G; Preparation of Compound G-4
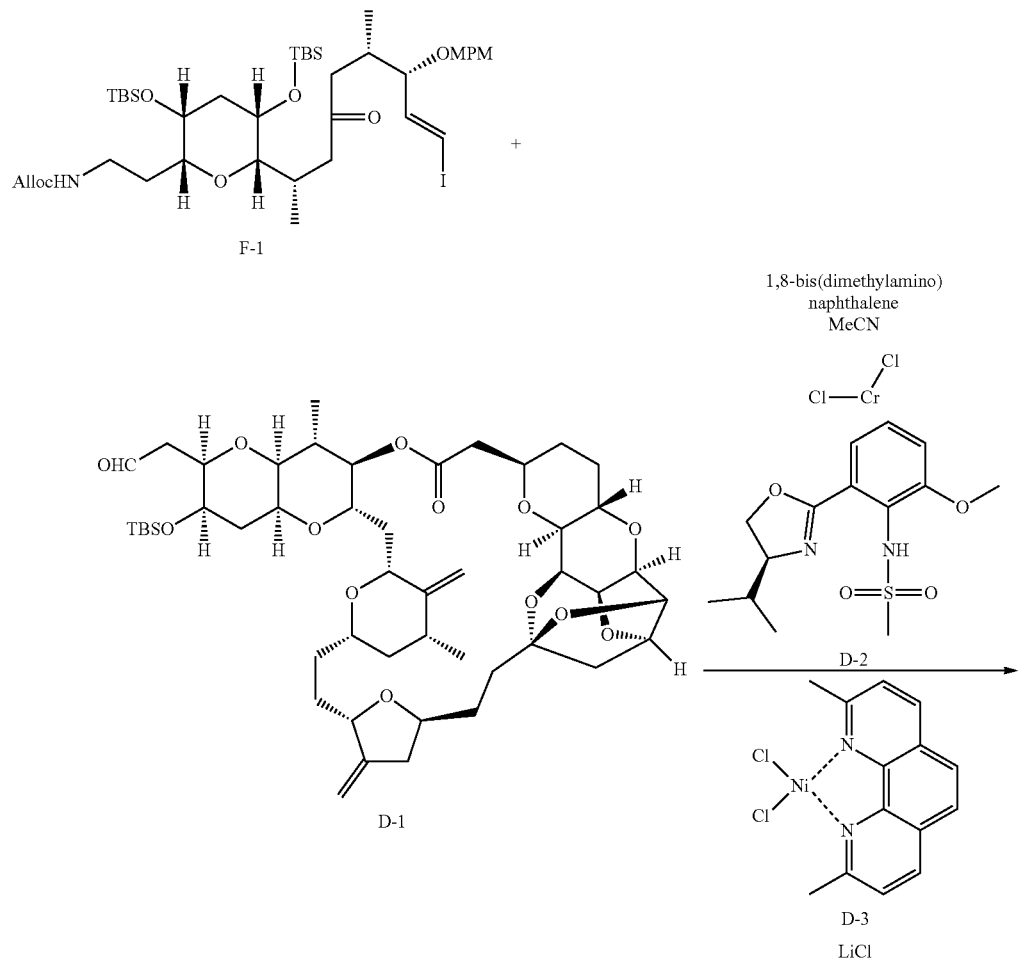
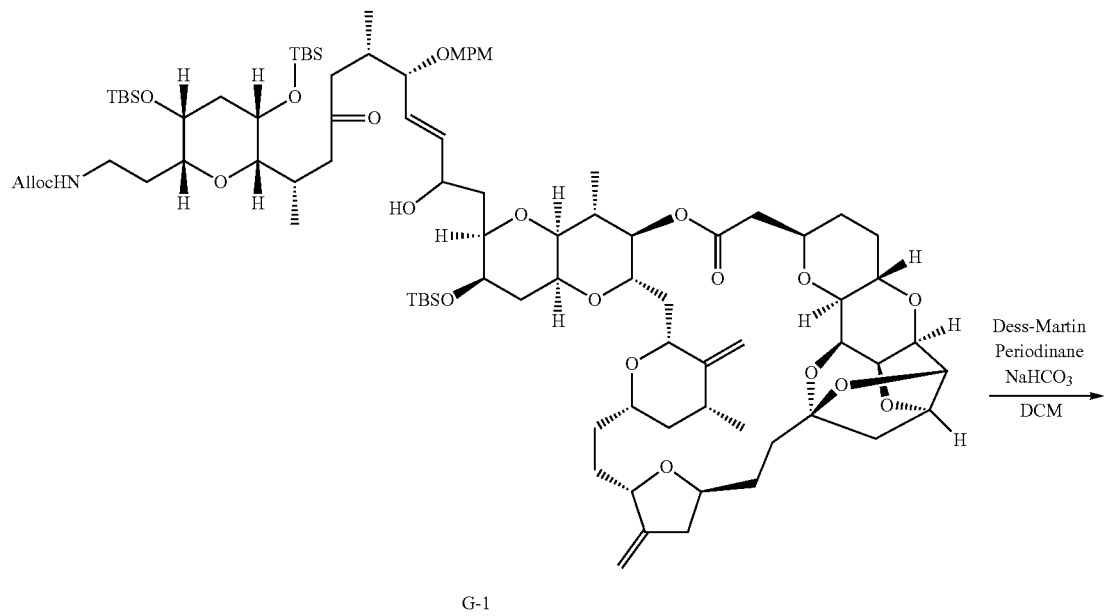

-continued
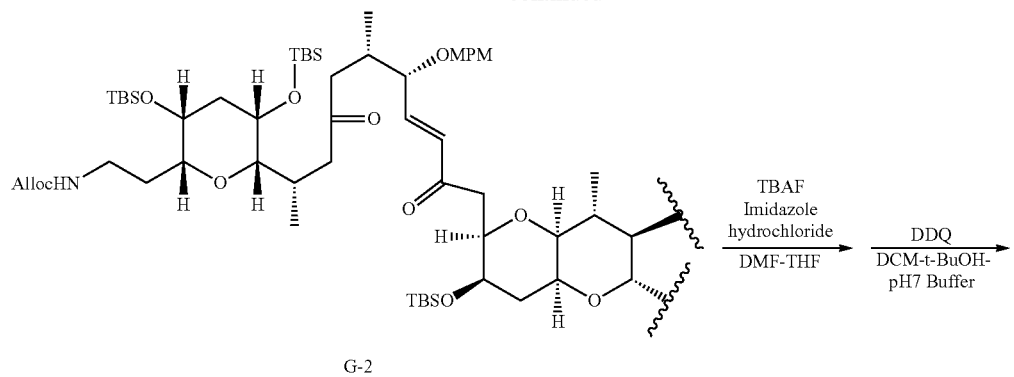
G-2
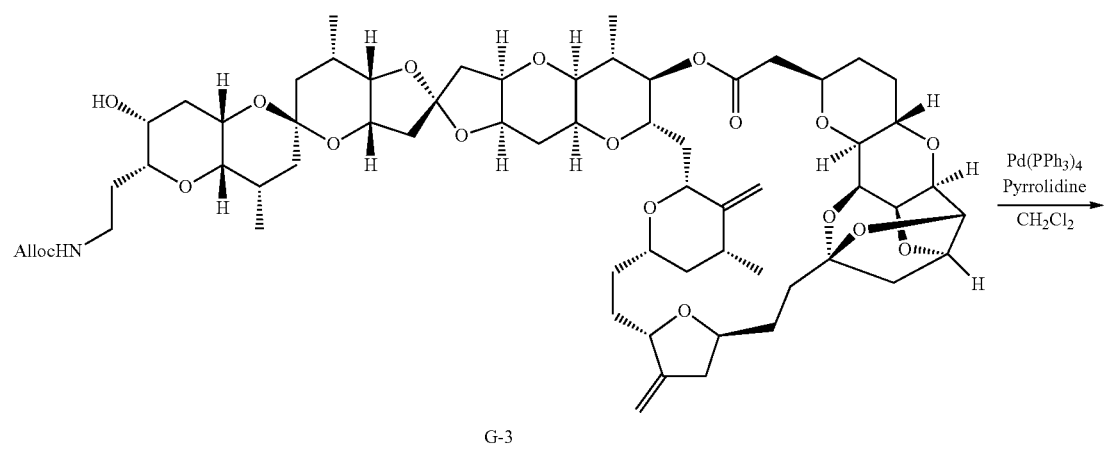
G-3
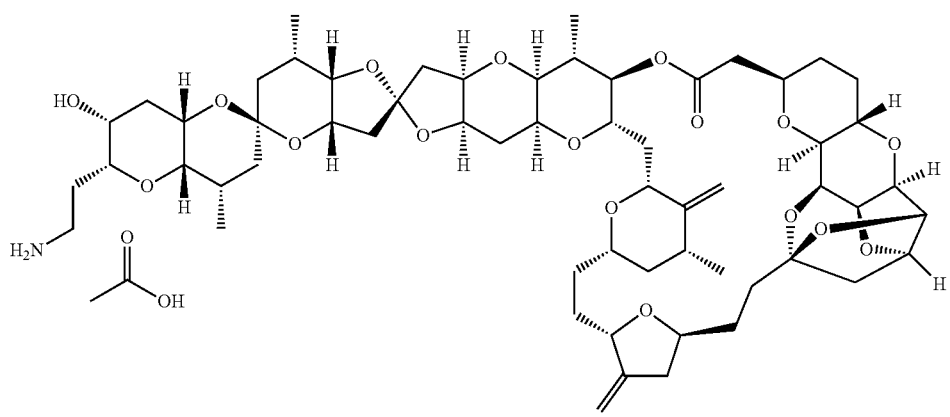
G-4

Example 28

Compound G-4

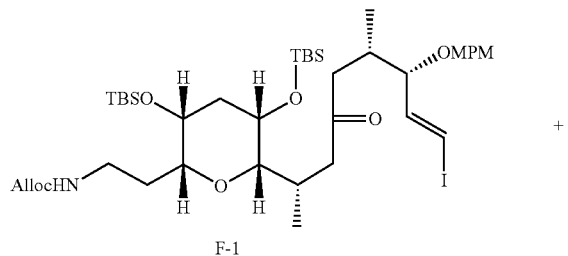

F-1

+

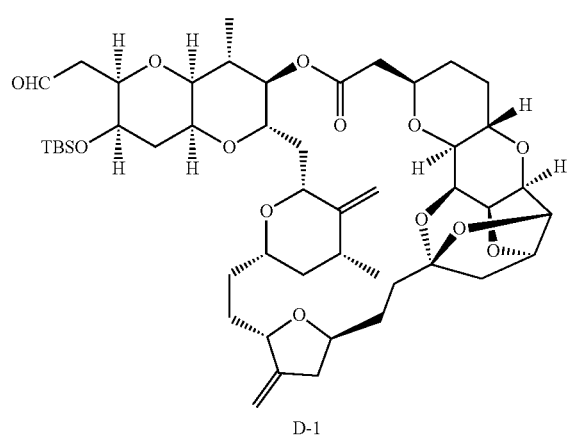

D-1

↓ steps

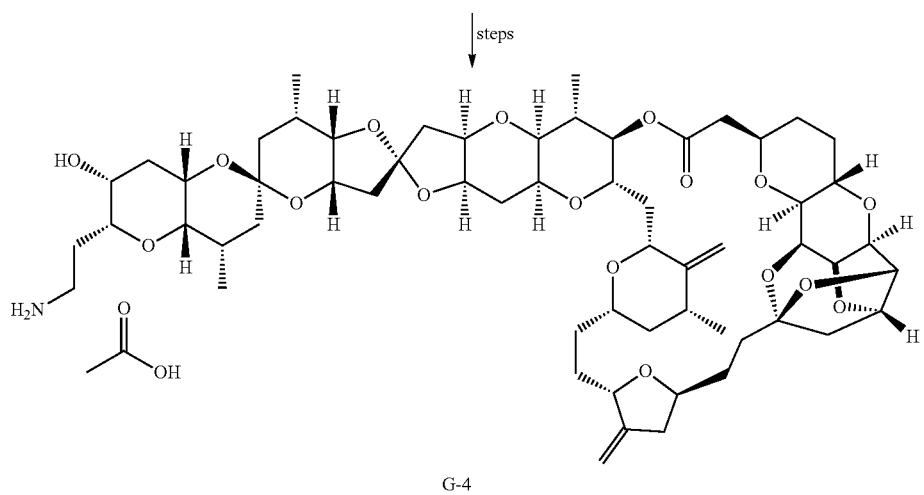

G-4

The title compound G-4 was obtained as an acetic acid salt from compound F-1: allyl-(2-((2R,3R,5S,6S)-3,5-bis((tert-butyldimethylsilyl)oxy)-6-((2S,6S,7S,E)-9-iodo-7-((4-methoxybenzyl)oxy)-6-methyl-4-oxonon-8-en-2-yl)tetrahydro-2H-pyran-2-yl)ethyl)carbamate (prepared by the procedure described in Scheme F), and compound D-1 (CAS No; 157322-23-1) prepared by the method written in *Journal of the American Chemical Society* 1992, 114, 3162-3164, the entire contents of which is incorporated herein by reference, based on the procedure described in Scheme G. Retention time=10.7 min.

HPLC Conditions
  Column: YMC Pak Pro C18 (10 mm I.D.×250 mm)
  Detection wavelength: 200 nm
  Column temperature: room temperature
  Mobile phase: MeCN-Water (0.05% AcOH)
  Flow rate: 4.0 mL/min
  Eluate:
    MeCN/Water 25% (iso, 2 min), then
    MeCN/Water 25% to 60% (gradient, 20 min), then
    MeCN/Water 60% (iso, 1 min)

$^1$H NMR (500 MHz, METHANOL-d4) δ ppm 0.99 (d, J=6.7 Hz, 6H) 1.00-1.03 (m, 1H) 1.06 (d, J=6.7 Hz, 3H) 1.10 (d, J=6.1 Hz, 3H) 1.26-1.64 (m, 11H) 1.65-2.37 (m, 25H) 2.40 (dd, J=13.4, 6.1 Hz 1H) 2.45 (dd, J=17.1, 1.8 Hz, 1H) 2.56 (dd, J=17.7, 9.2 Hz, 1H) 2.76-2.84 (m, 1H) 2.98 (dd, J=9.8, 1.8 Hz, 1H) 3.01-3.17 (m, 2H) 3.22 (dd, J=6.7, 4.9 Hz, 1H) 3.34 (dd, J=6.1, 4.3 Hz, 1H) 3.48-3.53 (m, 2H) 3.61 (d, J=11.6 Hz 1H) 3.69-3.75 (m, 2H) 3.82 (br. s., 1H) 3.85-3.92 (m, 2H) 3.99 (br. s., 1H) 4.04-4.14 (m, 4H) 4.18 (dd, J=6.7, 4.2 Hz, 1H) 4.25 (ddd, J=11.6, 4.9, 1.8 Hz, 1H) 4.29-4.35 (m, 2H) 4.46 (d, J=11.0 Hz, 1H) 4.58-4.63 (m, 2H) 4.70 (t, J=7.2, 4.6 Hz, 1H) 4.81 (br. s., 1H) 5.02 (br. s., 1H) 5.06 (br. s., 1H). ESI-MS (m/z): 1080.6 [M+H]$^+$, 1102.6 [M+Na]$^+$.

Synthesis of Compound (H-2)

Example 29

Compound H-2

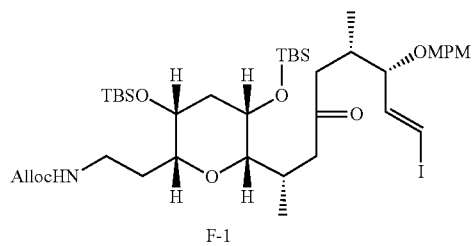

F-1

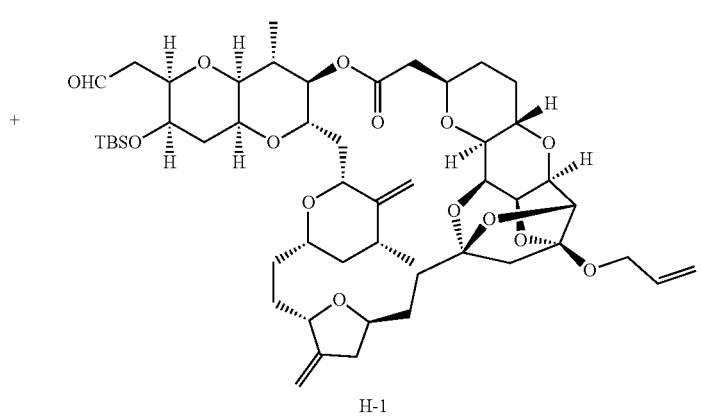

H-1
CAS No; 1353268-98-0

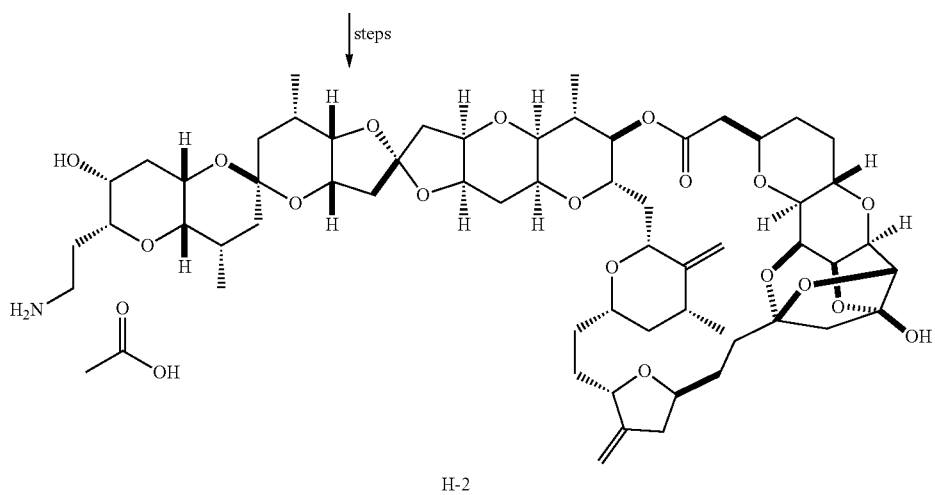

H-2

The title compound H-2 was obtained as an acetic acid salt from compound F-1: allyl-2-((2R,3R,5S,6S)-3,5-bis((tert-butyldimethylsilyl)oxy)-6-((2S,6S,7S,E)-9-iodo-7-((4-methoxybenzyl)oxy)-6-methyl-4-oxonon-8-en-2-yl)tetrahydro-2H-pyran-2-yl)ethyl)carbamate prepared by the method written in Scheme F, and compound H-1 (CAS No; 1353268-98-0) prepared by the method written in *Journal of the American Chemical Society* 2012, 134, 893-896, the entire contents of which is incorporated herein by reference, and based on the procedure described in Scheme G. Retention time=10.2 min.

HPLC Conditions
Column: YMC Pak Pro C18 (10 mm I.D.×250 mm)
Detection wavelength: 200 nm
Column temperature: room temperature
Mobile phase: MeCN-Water (0.05% AcOH)
Flow rate: 4.0 ml/min
Eluate:
MeCN/Water 20% (iso, 2 min), then
MeCN/Water 20% to 80% (Gradient, 20 min)

$^1$H NMR (400 MHz, METHANOL-$d_4$) δ ppm 0.99 (d, J=7.0 Hz, 6H) 1.02-1.04 (m, 1H) 1.06 (d, J=7.0 Hz, 3H) 1.11 (d, J=6.6 Hz, 3H) 1.24-1.45 (m, 7H) 1.46-1.54 (m, 2H) 1.54-1.61 (m, 2H) 1.62-1.77 (m, 5H) 1.78-1.89 (m, 4H) 1.90-2.16 (m, 7H) 2.16-2.36 (m, 9H) 2.39 (dd, J=13.3, 5.9 Hz 2H) 2.55 (dd, J=19.9, 3.5 Hz, 1H) 2.75-2.85 (m, 1H) 2.95 (dd, J=9.8, 2.0 Hz, 1H) 3.01-3.17 (m, 2H) 3.22 (dd, J=6.4, 4.5 Hz, 2H) 3.46-3.53 (m, 2H) 3.61 (d, J=10.5 Hz 1H) 3.67-3.76 (m, 2H) 3.80-3.84 (m, 1H) 3.84-3.92 (m, 2H) 3.97-4.01 (m, 1H) 4.03-4.14 (m, 3H) 4.17 (dd, J=4.1, 1.4 Hz, 1H) 4.21-4.27 (m, 1H) 4.27-4.34 (m, 2H) 4.39-4.43 (m, 1H) 4.44 (d, J=10.6 Hz, 1H) 4.62 (dd, J=7.2, 4.5 Hz, 1H) 4.82 (br. s., 1H) 4.88 (br. s., 1H) 5.02 (br. s., 1H) 5.06 (br. s., 1H). ESI-MS (m/z): 1096.6 [M+H]$^+$, 1118.6 [M+Na]$^+$.

Synthesis of Compound (I-2)
Scheme I; Preparation of Compound I-1
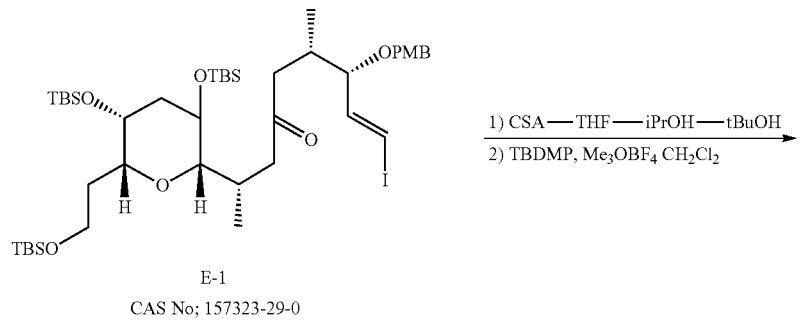
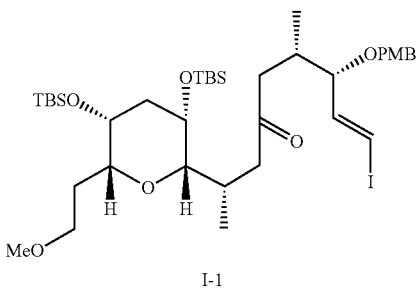
Example 30
Compound I-2
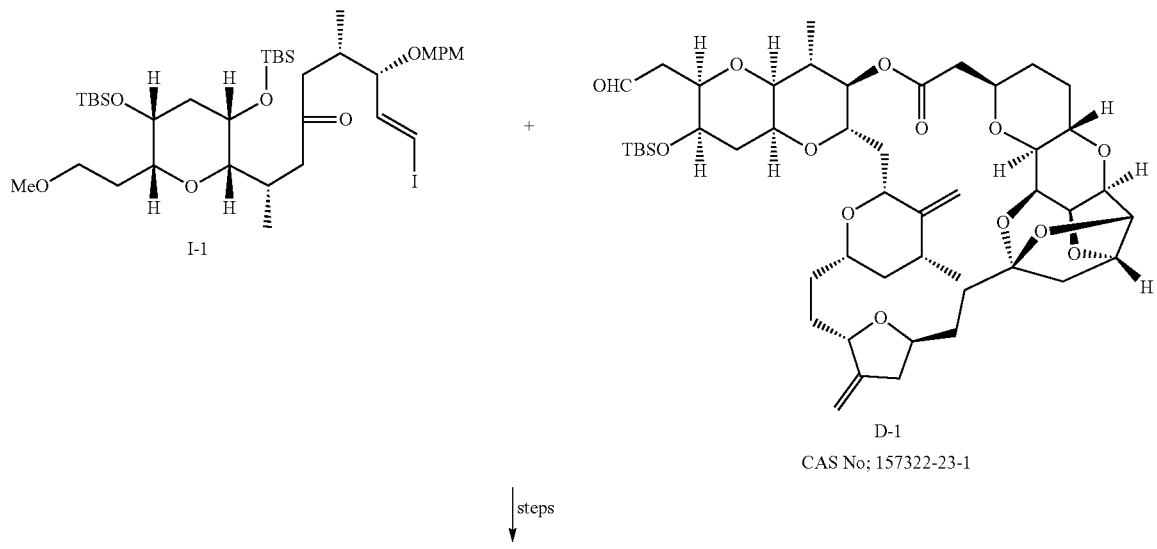

-continued

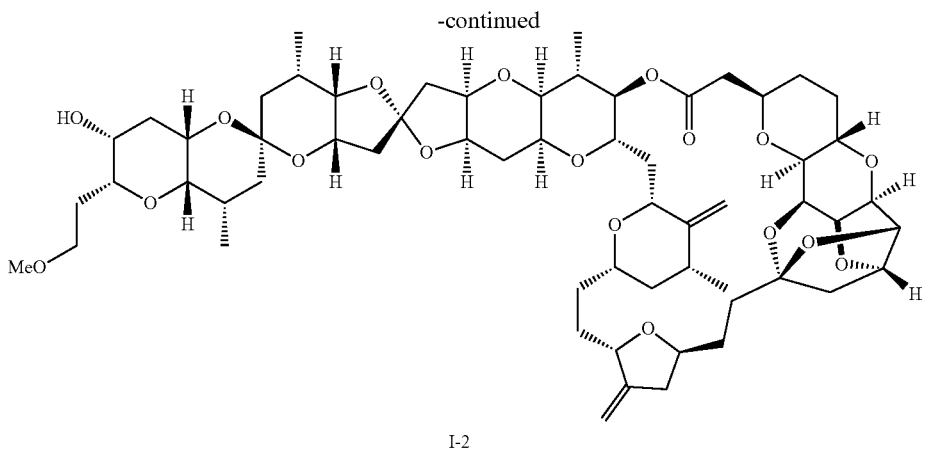

I-2

The title compound I-2 was obtained from compound I-1: (2S,6S,7S,E)-2-((2S,3S,5R,6R)-3,5-bis((tert-butyldimethylsilyl)oxy)-6-(2-methoxyethyl)tetrahydro-2H-pyran-2-yl)-9-iodo-7-((4-methoxybenzyl)oxy)-6-methylnon-8-en-4-one obtained by the method written in Scheme I, and compound D-1 (CAS No; 157322-23-1), using the procedures described for the preparation of Compounds D-4, D-5, and D-6 (Example 24, 25, and 26).

$^1$H NMR (500 MHz, METHANOL-d4) δ ppm 0.98 (d, J=6.8 Hz, 6H) 1.00-1.03 (m, 1H) 1.06 (d, J=6.8 Hz, 3H) 1.10 (d, J=5.8 Hz, 3H) 1.29-1.63 (m, 11H) 1.65-1.78 (m, 3H) 1.78-2.13 (m, 12H) 2.13-2.36 (m, 9H) 2.39 (dd, J=14.1, 5.4 Hz, 1H) 2.45 (d, J=17.1 Hz, 1H) 2.57 (dd, J=17.5, 9.7 Hz, 1H) 2.76-2.84 (m, 1H) 2.98 (d, J=10.2 Hz, 1H) 3.19-3.24 (m, 1H) 3.31-3.32 (m, 1H) 3.32 (s, 3H) 3.49-3.57 (m, 4H) 3.61 (d, J=11.2 Hz, 1H) 3.68-3.76 (m, 2H) 3.79 (br. s., 1H) 3.84-3.92 (m, 2H) 3.98 (br. s., 1H) 4.03-4.15 (m, 4H) 4.18 (t, J=5.8 Hz, 1H) 4.25 (d, J=10.2 Hz, 1H) 4.28-4.36 (m, 2H) 4.45 (d, J=11.2 Hz, 1H) 4.58-4.65 (m, 2H) 4.70 (br. t, J=5.4 Hz, 1H) 4.81 (br. s., 1H) 4.87 (br. s., 1H) 5.02 (br. s., 1H) 5.06 (br. s., J=1.5 Hz, 1H). ESI-MS (m/z): 1117.6 [M+Na]+.

Synthesis of Compound (J-1)

Example 31

Compound J-1

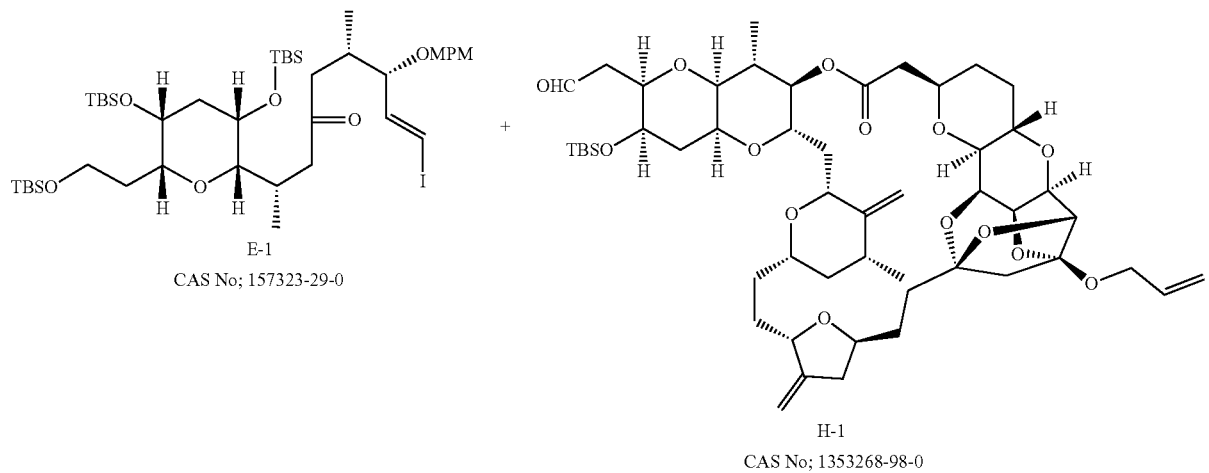

E-1
CAS No; 157323-29-0

H-1
CAS No; 1353268-98-0

↓ steps

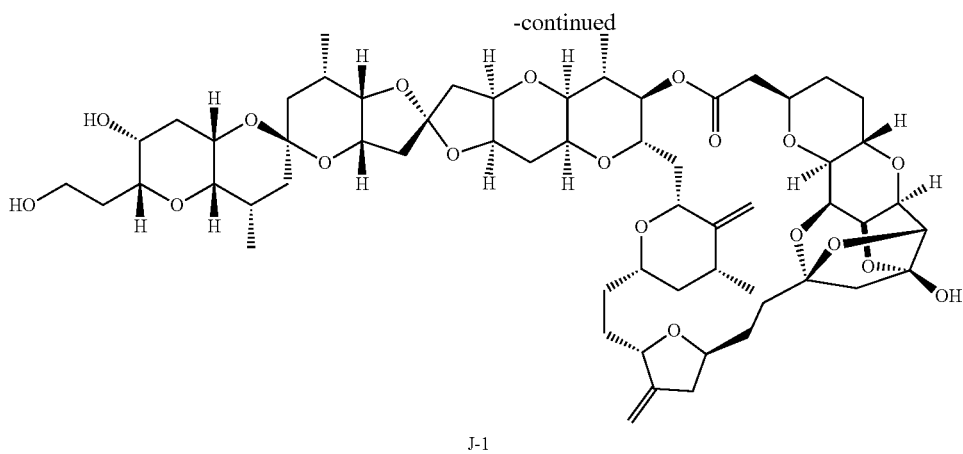

J-1

The title compound J-1 was obtained from compound E-1: (2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-ol (CAS No; 157323-29-0) and compound H-1 (CAS No; 1353268-98-0), based on the procedure described in Scheme G. Retention time=12.8 min.
HPLC Conditions
Column: YMC Pak Pro C18 (10 mm I.D.×250 mm)
Detection wavelength: 200 nm
Column temperature: room temperature
Mobile phase: MeCN-Water
Flow rate: 4.5 ml/min
Eluate:
MeCN/Water 35% (iso, 2 min), then
MeCN/Water 35% to 99% (Gradient, 20 min)

$^1$H NMR (500 MHz, METHANOL-d4) δ ppm 0.97 (d, J=2.9 Hz, 3H) 0.99 (d, J=2.9 Hz, 3H) 1.00-1.03 (m, 1H) 1.05 (d, J=7.3 Hz, 3H) 1.11 (d, J=7.3 Hz, 3H) 1.30-1.44 (m, 6H) 1.48-1.57 (m, 4H) 1.61-1.76 (m, 4H) 1.79-1.87 (m, 3H) 1.91-1.98 (m, 3H) 2.00-2.14 (m, 8H) 2.24-2.35 (m, 5H) 2.37-2.44 (m, 6H) 2.55 (dd, J=17.6, 9.8 Hz, 1H) 2.68-2.87 (m, 1H) 2.94 (dd, J=9.8, 2.0 Hz, 1H) 3.22 (dd, J=6.6, 4.7 Hz, 1H) 3.22 (dd, J=6.6, 4.7 Hz, 1H) 3.26-3.36 (m, 2H) 3.42-3.56 (m, 2H) 3.60 (d, J=11.7 Hz, 1H) 3.65-3.75 (m, 3H) 3.79 (br. s., 1H) 3.83-3.93 (m, 2H) 3.98 (d, J=2.4 Hz, 1H) 4.02-4.36 (m, 3H) 4.37-4.51 (m, 2H) 4.62 (dd, J=7.6, 4.6, Hz, 1H) 4.82 (br. s., 1H) 4.89 (br. s., 1H) 5.01 (br. s., 1H) 5.06 (br. s., 1H). ESI-MS (m/z): 1119.6 [M+Na]$^+$.

Synthesis of Compound (K-2)

Scheme K; Preparation of Compound K-1

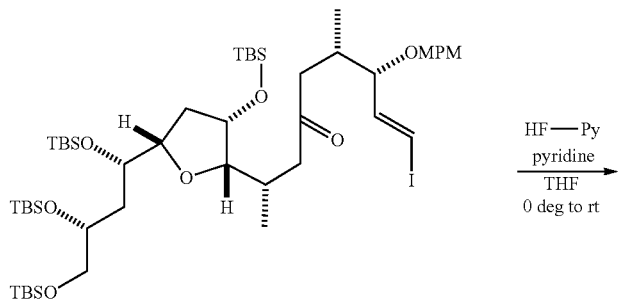

CAS No; 2036069-72-2
Tetrahedron Lett. 1992, 33, 1553.

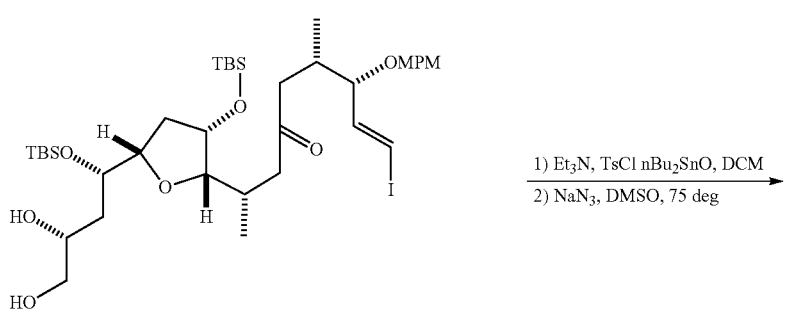

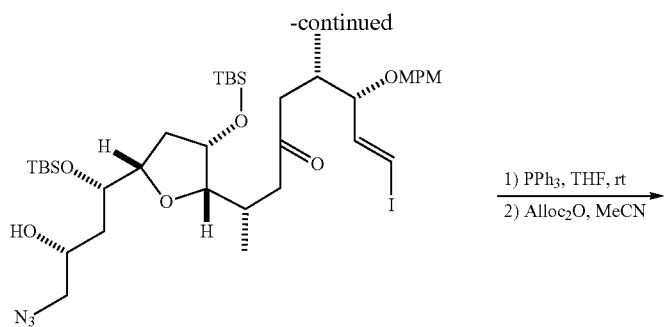
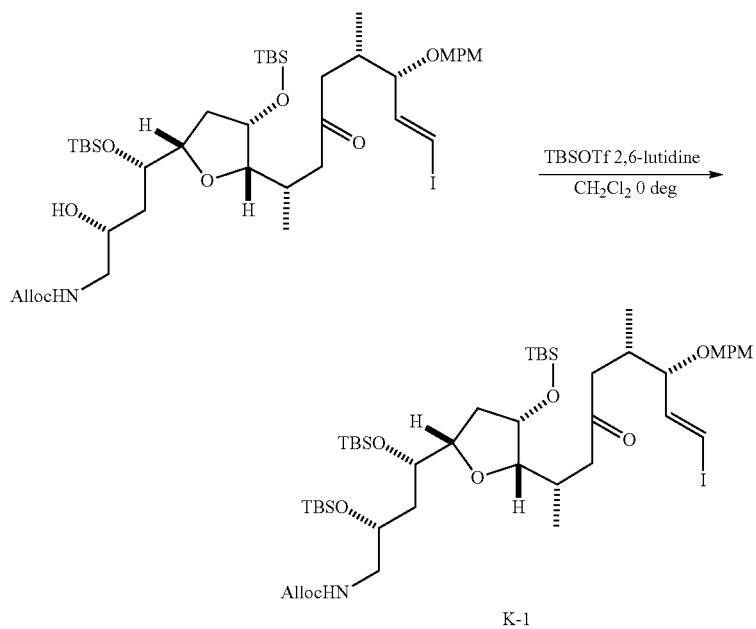
Example 32
Compound K-2
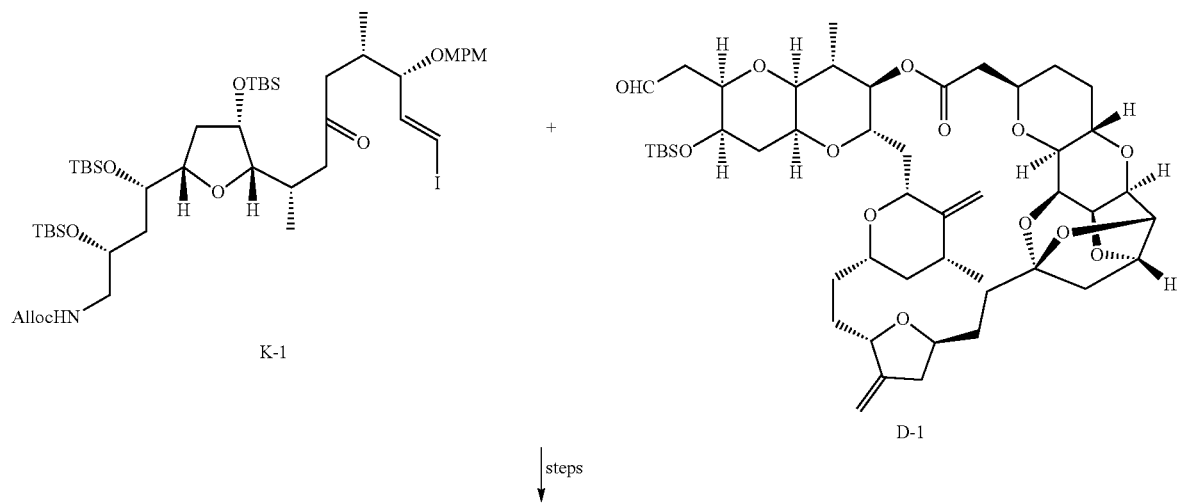
↓ steps

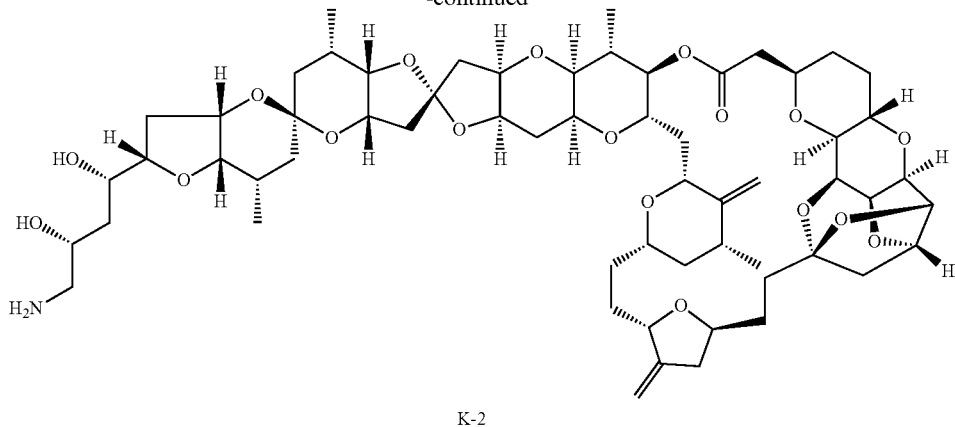

K-2

The title compound K-2 was obtained from compound K-1: allyl ((2R,4S)-2,4-bis((tert-butyldimethylsilyl)oxy)-4-((2S,4S,5S)-4-((tert-butyldimethylsilyl)oxy)-5-((2S,6S,7S,E)-9-iodo-7-((4-methoxybenzyl)oxy)-6-methyl-4-oxonon-8-en-2-yl)tetrahydrofuran-2-yl)butyl)carbamate prepared by the method written in Scheme K, and compound D-1 (CAS No; 157322-23-1), based on the procedure described in Scheme G. Retention time=9.5 min.

HPLC Conditions
  Column: YMC Pak Pro C18 (10 mm I.D.×250 mm)
  Detection wavelength: 200 nm
  Column temperature: room temperature
  Mobile phase: MeCN-Water (0.05% AcOH)
  Flow rate: 4 ml/min
  Eluate:
  MeCN/Water 25% (iso, 2 min), then
  MeCN/Water 25% to 80% (Gradient, 20 min)

$^1$H NMR (500 MHz, METHANOL-$d_4$) δ ppm 0.96 (d, J=6.8 Hz, 3H) 1.01 (d, J=7.3 Hz, 3H) 1.00-1.03 (m, 1H) 1.05 (d, J=7.3 Hz, 3H) 1.09 (d, J=6.3 Hz, 3H) 1.19-1.63 (m, 9H) 1.64-1.76 (m, 4H) 1.77-1.89 (m, 3H) 1.91-2.21 (m, 11H) 2.12-2.21 (m, 3H) 2.22-2.44 (m, 7H) 2.44 (dd, J=17.5, 1.9 Hz, 1H) 2.55 (dd, J=17.6, 9.3 Hz, 1H) 2.75-2.87 (m, 2H) 2.97 (dd, J=9.8, 2.0 Hz, 1H) 3.05 (d, J=11.7 Hz, 1H) 3.21 (dd, J=6.3, 4.4 Hz, 1H) 3.58 (br. s., 1H) 3.60 (d, J=12.2 Hz, 1H) 3.69 (br. s., 1H) 3.73 (d, J=10.2 Hz, 1H) 3.77 (br. s., 1H) 3.84-3.90 (m, 2H) 3.98-4.13 (m, 7H) 4.17 (dd, J=6.1, 4.6 Hz, 1H) 4.24 (d, J=11.2 Hz, 1H) 4.29 (d, J=3.9 Hz, 1H) 4.32 (dd, J=9.8, 3.9 Hz, 1H) 4.45 (d, J=10.2 Hz, 1H) 4.58-4.62 (m, 2H) 4.69 (t, J=4.6 Hz, 1H) 4.80 (s, 1H) 4.84 (s, 1H) 5.02 (br. s., 1H) 5.06 (br. s., 1H). ESI-MS (m/z): 1110.6. [M+H]$^+$, 1132.6 [M+Na]$^+$.

Synthesis of Compound (L-6)

Scheme L; Preparation of Compound L-6

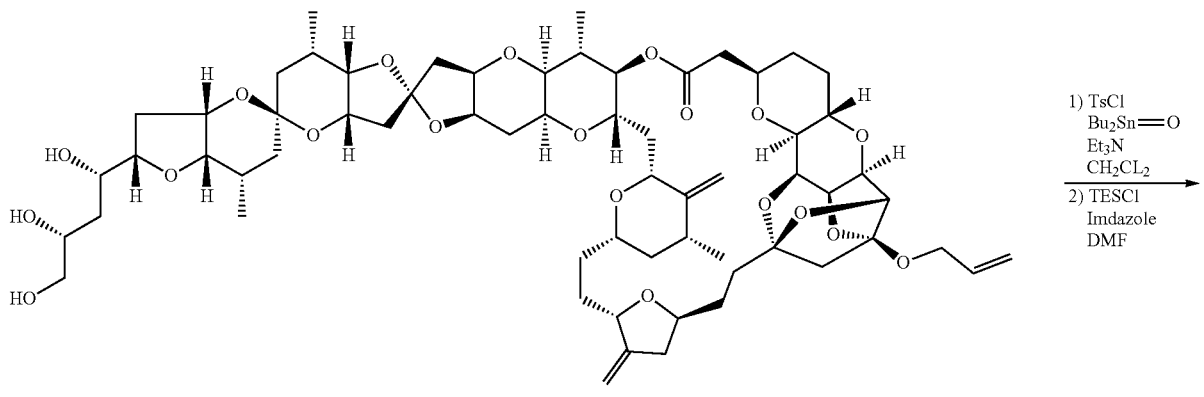

L-1
CAS No; 1353269-09-6

-continued
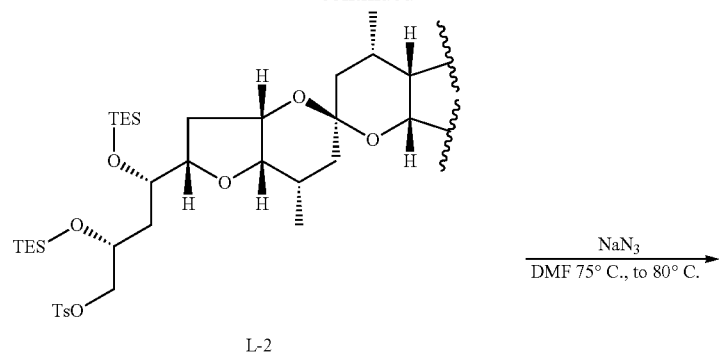
L-2
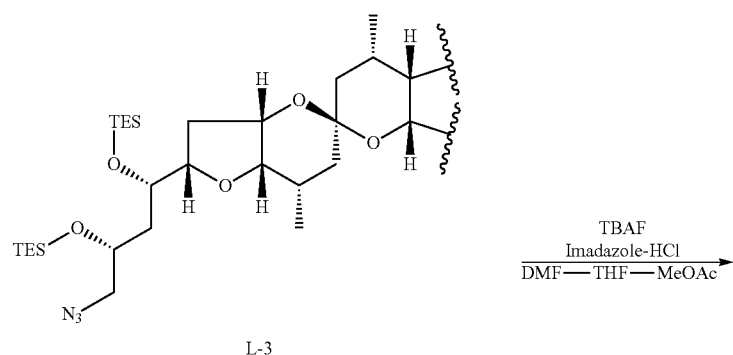
L-3
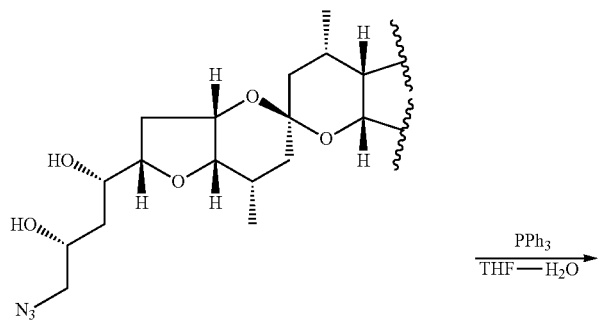
L-4
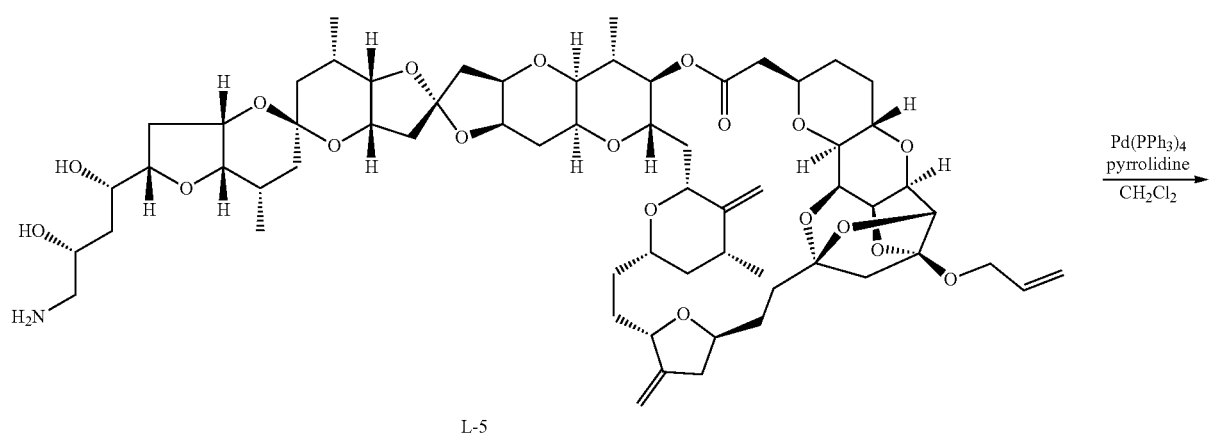
L-5

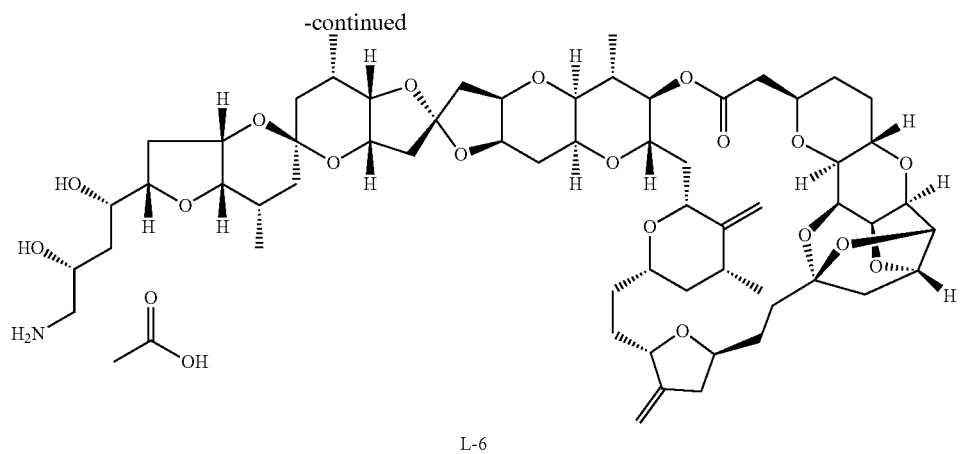

L-6

Example 33

Compound L-6

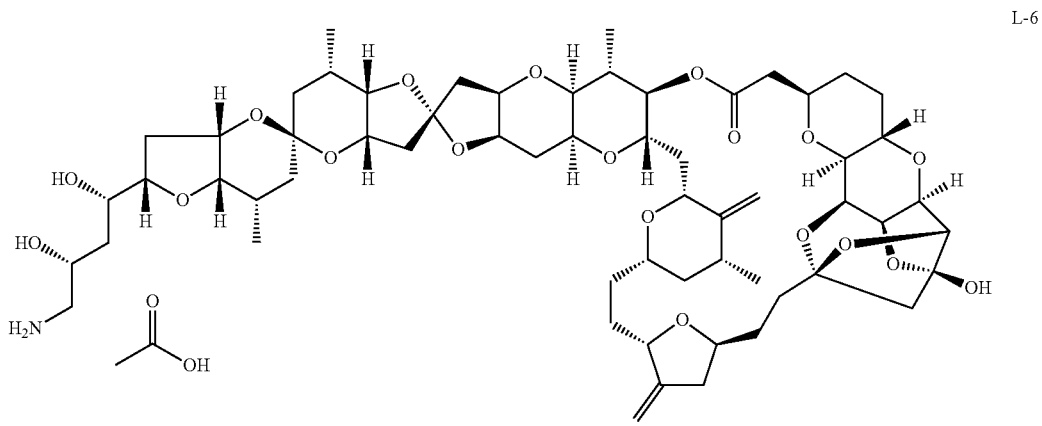

L-6

The title compound L-6 was obtained as an acetic acid salt from compound L-1 (CAS No; 1353269-09-6) prepared by the method written in *Journal of the American Chemical Society* 2012, 134, 893-896, the entire contents of which is incorporated herein by reference, by the method described in Scheme L. Retention time=5.6 min.

HPLC Conditions
Column: YMC Pak Pro C18 (10 mm I.D.×250 mm)
Detection wavelength: 205 nm
Column temperature: room temperature
Mobile phase: MeCN-Water (0.05% AcOH)
Flow rate: 4.7 mL/min
Eluate:
MeCN/Water 25% (iso, 2 min), then
MeCN/Water 25% to 80% (gradient, 20 min), then
MeCN/Water 80% (iso, 2 min)

$^1$H NMR (500 MHz, METHANOL-$d_4$) δ ppm 0.94-1.03 (m, 7H) 1.05 (d, J=7.3 Hz, 3H) 1.10 (d, J=6.8 Hz, 3H) 1.21-2.41 (m, 36H) 2.44 (dd, J=17.6, 2.2 Hz, 1H) 2.54 (dd, J=17.6, 9.2 Hz, 1H) 2.75-2.83 (m, 1H) 2.94 (dd, J=9.5, 1.7 Hz, 1H) 3.19-3.23 (m, 1H) 3.31-3.33 (m, 1H) 3.53-3.73 (m, 7H) 3.78 (br. s., 1H) 3.84-3.90 (m, 2H) 3.97-4.12 (m, 4H) 4.16 (dd, J=3.9, 1.0 Hz, 1H) 4.21 (dd, J=5.6, 3.2 Hz, 1H) 4.21-4.26 (m, 1H) 4.26-4.33 (m, 2H) 4.38-4.46 (m, 2H) 4.58-4.63 (m, 2H) 4.81 (br. s., 1H) 4.86-4.87 (m, 1H) 5.01 (br. s., 1H) 5.06 (br. s., 1H). ESI-MS (m/z):1126.6 [M+H]$^+$, 1148.6 [M+Na]$^+$.

Synthesis of Compound (M-3)

Scheme M: Preparation of Compound M-1 and M-2
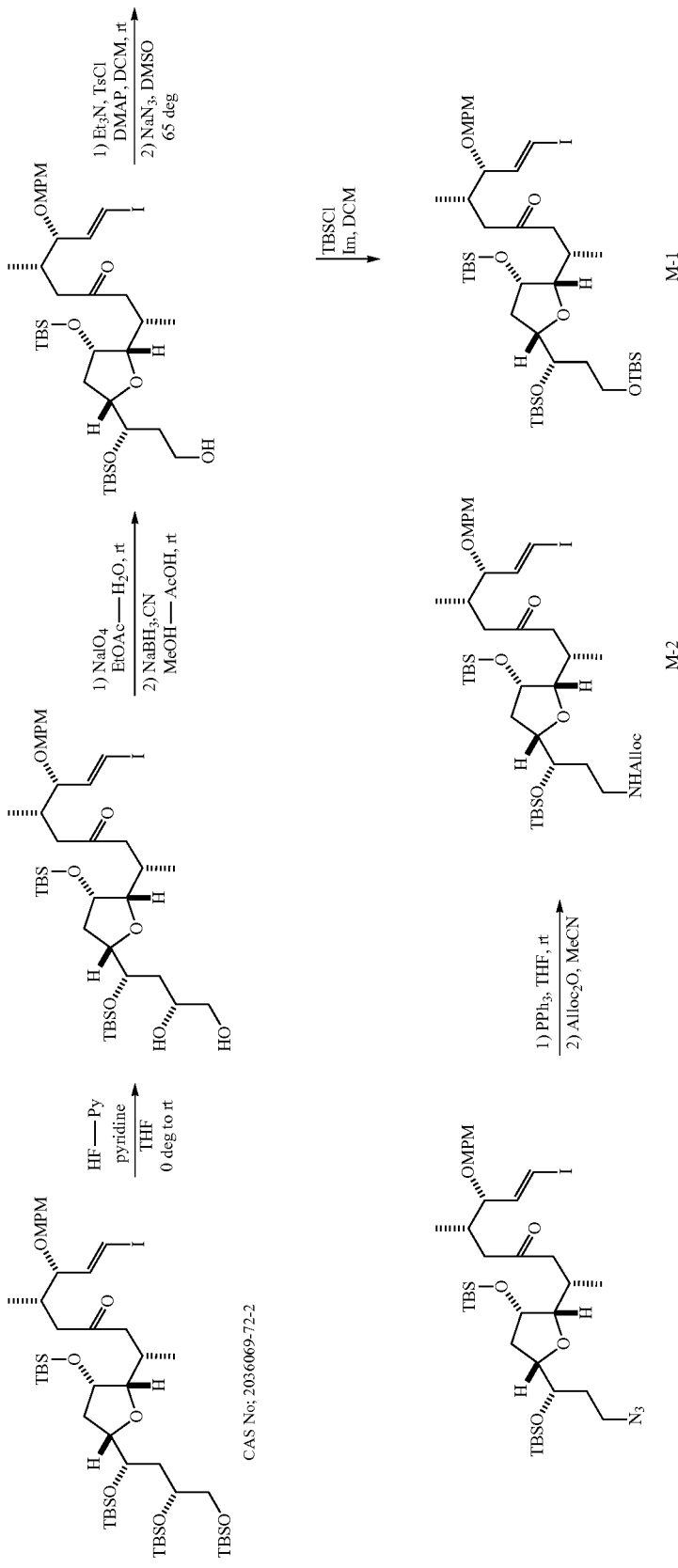

Example 34

Compound M-3

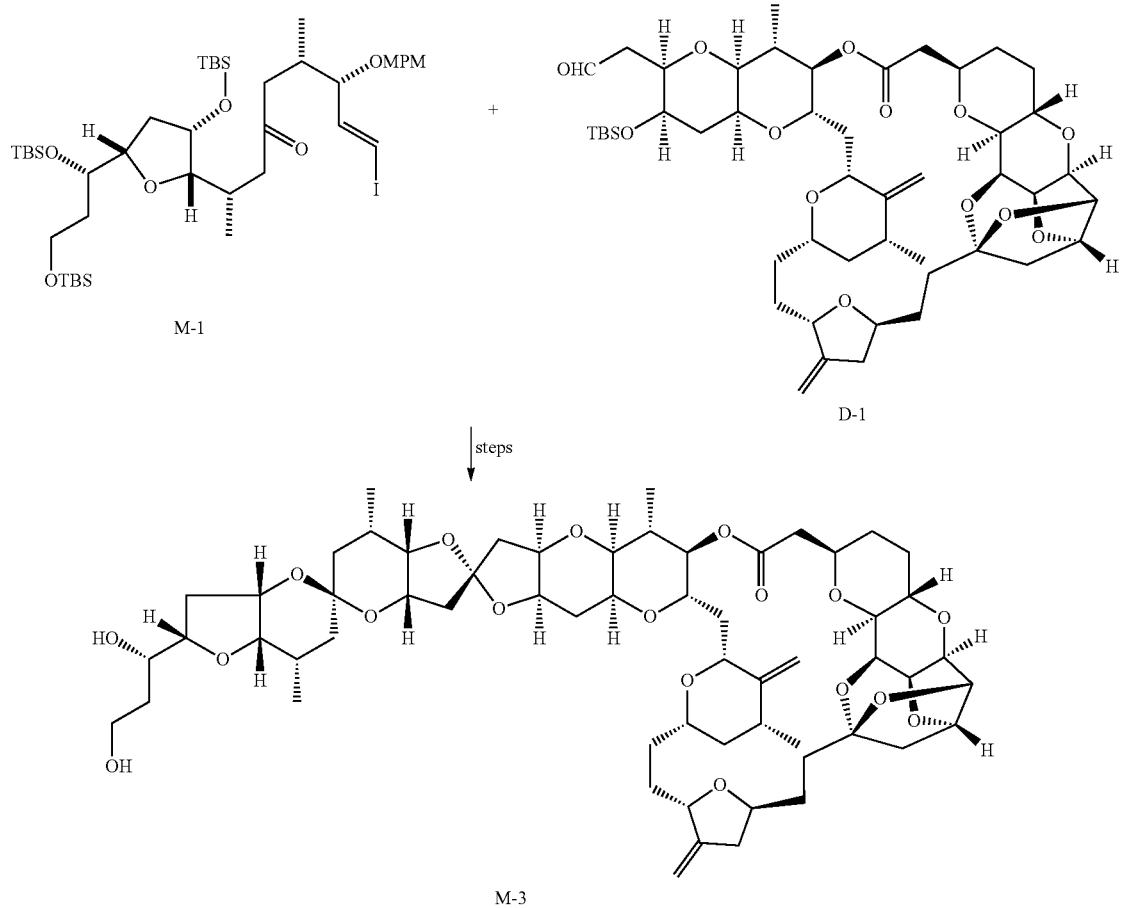

M-1

D-1

↓ steps

M-3

The title compound M-3 was obtained from compound M-1: (2S,6S,7S,E)-2-((2S,3S,5S)-3-((tert-butyldimethylsilyl)oxy)-5-((S)-2,2,3,3,9,9,10,10-octamethyl-4,8-dioxa-3,9-disilaundecan-5-yl)tetrahydrofuran-2-yl)-9-iodo-7-((4-methoxybenzyl)oxy)-6-methylnon-8-en-4-one prepared by the method written in Scheme M, and Compound D-1 (CAS No; 157322-23-1), using the procedures described for the preparation of Compounds D-4, D-5, and D-6 (Example 24, 25, and 26).

$^1$H NMR (500 MHz, METHANOL-d4) δ ppm 0.96 (d, J=6.8 Hz, 3H) 1.00-1.03 (m, 1H) 1.02 (d, J=7.3 Hz, 3H) 1.06 (d, J=7.3 Hz, 3H) 1.10 (d, J=6.8 Hz, 3H) 1.29-1.63 (m, 10H) 1.65-1.78 (m, 5H) 1.79-1.89 (m, 3H) 1.92-2.12 (m, 7H) 2.13-2.36 (m, 10H) 2.40 (dd, J=13.4, 6.1 Hz, 1H) 2.45 (dd, J=17.5, 2.4 Hz, 1H) 2.56 (dd, J=18.0, 9.7 Hz, 1H) 2.76-2.84 (m, 1H) 2.98 (dd, J=9.7, 1.9 Hz, 1H) 3.22 (dd, J=6.3, 4.9 Hz, 1H) 3.31-3.32 (m, 1H) 3.55 (m, 1H) 3.61 (d, J=11.7 Hz, 1H) 3.67-3.76 (m, 5H) 3.84-3.91 (m, 2H) 3.95 (sept, J=4.9 Hz, 1H) 4.03-4.11 (m, 4H) 4.12 (dd, J=6.6, 4.1 Hz, 1H) 4.18 (dd, J=6.3, 4.4 Hz, 1H) 4.24 (ddd, J=11.2, 9.0, 2.3 Hz, 1H) 4.28-4.31 (m, 1H) 4.32 (dd, J=10.2, 4.4 Hz, 1H) 4.46 (d, J=10.7 Hz, 1H) 4.60 (t, J=3.9 Hz, 1H) 4.62 (dd, J=7.3, 3.9 Hz, 1H) 4.70 (t, J=4.4 Hz, 1H) 4.81 (d, J=1.5 Hz, 1H) 4.87 (s, 1H) 5.02 (br. s., 1H) 5.06 (d, J=1.5 Hz, 1H). ESI-MS (m/z): 1103.6 [M+Na]$^+$.

Synthesis of Compound (N-1)

Example 35

Compound N-1

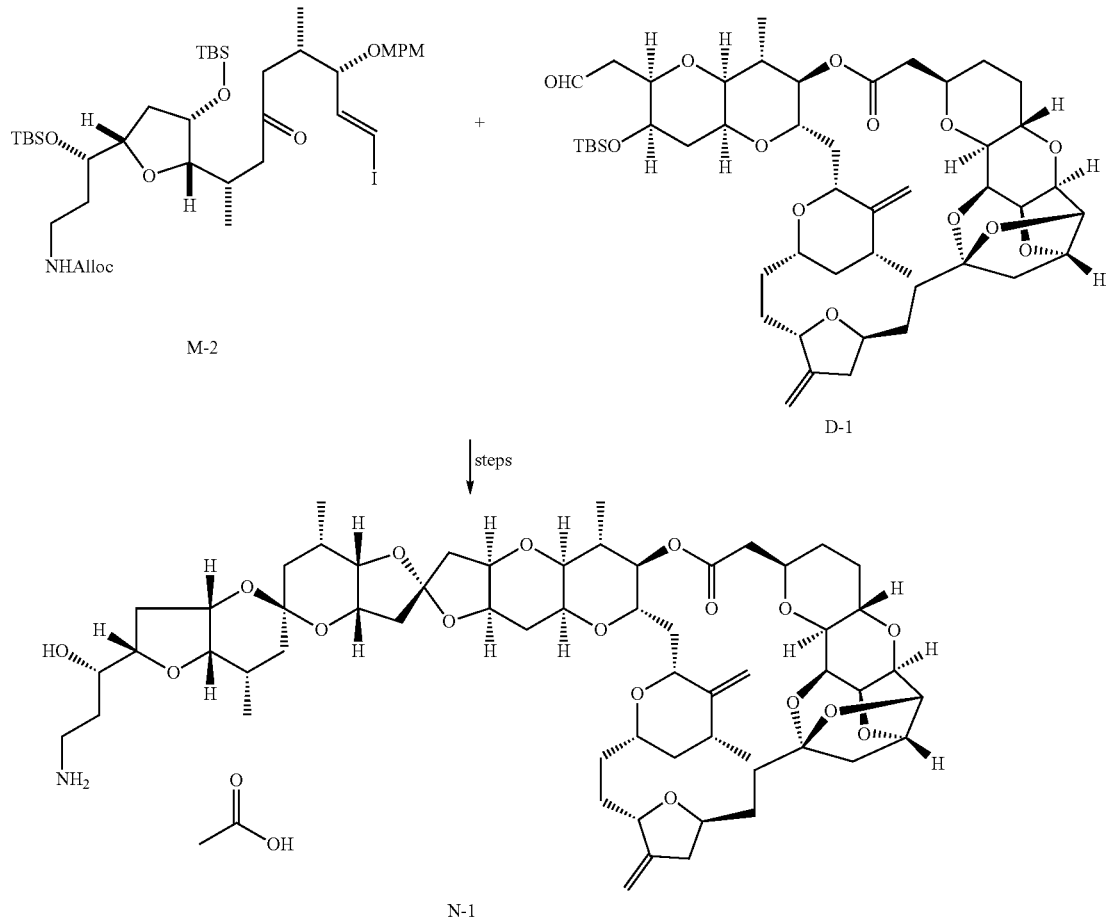

The title compound N-1 was obtained as an acetic acid salt from compound M-2: allyl-((S)-3-((tert-butyldimethylsilyl)oxy)-3-((2S,4S,5S)-4-((tert-butyldimethylsilyl)oxy)-5-((2S,6S,7S,E)-9-iodo-7-((4-methoxybenzyl)oxy)-6-methyl-4-oxonon-8-en-2-yl)tetrahydrofuran-2-yl)propyl)carbamate prepared by the method written in Scheme M, and Compound D-1 (CAS No; 157322-23-1), by the same procedure described in Scheme G. Retention time=8.4 min.

HPLC Conditions
  Column: YMC Pak Pro C18 (10 mm I.D.×250 mm)
  Detection wavelength: 200 nm
  Column temperature: room temperature
  Mobile phase: MeCN-Water (0.05% AcOH)
  Flow rate: 4.5 ml/min
  Eluate:
    MeCN/Water 25% (iso, 2 min), then
    MeCN/Water 25% to 80% (Gradient, 20 min)

$^1$H NMR (500 MHz, METHANOL-$d_4$) δ ppm 0.97 (d, J=6.8 Hz 3H) 1.01 (m, 1H) 1.02 (d, J=7.8 Hz 3H) 1.07 (d, J=7.3 Hz 3H) 1.10 (d, J=6.3 Hz, 3H) 1.26-1.41 (m, 6H) 1.42-1.56 (m, 4H) 1.56-1.64 (m, 2H) 1.64-1.78 (m, 4H) 1.81-1.88 (m, 3H) 1.97-2.11 (m, 7H) 2.12-2.22 (m, 2H) 2.23-2.37 (m, 9H) 2.40 (dd, J=13.2, 3.9 Hz, 1H) 2.45 (dd, J=17.1, 2.4 Hz, 1H) 2.56 (dd, J=17.8, 10.0 Hz 1H) 2.75-2.87 (m, 1H) 2.98 (dd, J=9.3, 1.9 Hz, 1H) 3.06-3.14 (m, 2H) 3.22 (dd, J=5.8, 4.4 Hz, 1H) 3.59 (br. s., 1H) 3.61 (d, J=11.2 Hz, 1H) 3.68-3.76 (m, 3H) 3.85-3.92 (m, 2H) 3.98-4.03 (m, 1H) 4.04-4.14 (m, 4H) 4.16-4.20 (m, 1H) 4.22-4.28 (m, 1H) 4.28-4.35 (m, 2H) 4.46 (d, J=11.21 Hz, 1H) 4.58-4.64 (m, 2H) 4.70 (t, J=4.9 Hz 1H) 4.81 (br. s., 1H) 4.87 (br. s., 1H) 5.03 (br. s., 1H) 5.07 (br. s., 1H). ESI-MS (m/z): 1080.6 [M+H]$^+$, 1102.6 [M+Na]$^+$.

Pharmacological Test Examples

General Information

Natural Halichondrin compounds and modified compounds thereof are known in the literature (See, e.g., D. Uemura et al. "Norhalichondrin A: An Antitumor Polyether Macrolide from a Marine Sponge" *J. Am. Chem. Soc.*, 107, 4796 (1985); Marc Litaudon et al. "Antitumor Polyether Macrolides: New and Hemisynthetic Halichondrins from the New Zealand Deep-Water Sponge *Lissodendoryx* sp." *J. Org. Chem.*, 1997, 62, 1868-1871). However, most of them are not easily available. For example, Dr. Uemura et. al. isolated 12.5 mg of Halichondrin B, 35.0 mg of Norhalichondrin A and 17.2 mg of Homohalichondrin A from as much as 600 kg of *Halichondria okadai* Kadota (See, e.g., D. Uemura et al. "Norhalichondrin A: An Antitumor Polyether Macrolide from a Marine Sponge" *J. Am. Chem.*

Soc., 107, 4796 (1985)). Among natural Halichondrin compounds, Halichondrin B shows the strongest anti-tumor activities against B-16 melanoma cells in vitro and is highly active against L-1210 Leukemia in vivo (See, e.g., D. Uemura et al. "Norhalichondrin A: An Antitumor Polyether Macrolide from a Marine Sponge" *J. Am. Chem. Soc.*, 107, 4796 (1985)). Halichondrin C is also active in various in vivo models but unstable in aqueous solution in comparison with Halichondrin B. Norhalichondrin B is much weaker than Halichondrin B not only in vitro but also in vivo See, e.g., D. Uemura et al. "Norhalichondrin A: An Antitumor Polyether Macrolide from a Marine Sponge" *J. Am. Chem. Soc.*, 107, 4796 (1985)). The following pharmacological tests use Halichondrin B (Hali-B) as reference compounds as needed.

Pharmacological Test Example 1. FaDu Growth Inhibition Assay

In this assay, the growth inhibitory activity of test compounds in a human squamous cell carcinoma of the head and neck (SCCHN) cell line FaDu was measured. FaDu cells were maintained in an RPMI-1640 (Wako Pure Chemical Industries, Ltd., 187-02021) medium containing 10% fetal bovine serum (FBS: Nichirei, 12D168), and penicillin and streptomycin in a 5% $CO_2$ incubator (37° C.). To each well of a 96 well plate (Becton, Dickinson and Company, 353219), 75 µL of FaDu cell suspension adjusted to a concentration of $4\times10^4$ cells/mL with the culture medium was added, and the cells were incubated overnight in a 5% $CO_2$ incubator (37° C.). On the next day, 25 µL of Compound (1) or Halichondrin B in three-fold dilution series suspended in the culture medium was added to each well, and the resultant was incubated for 3 days in a 5% $CO_2$ incubator (37° C.). Then, cell viability was determined by CellTiter-Glo® Luminescent Cell Viability Assay (Promega) with EnVision 2103 Multilabel Reader (Perkin-Elmer, Wellesley, Mass.). Value of the wells containing cells without adding the test compounds was defined as 100% and the value of the wells containing no cells was defined as 0%. The concentration of the test compound necessary for inhibiting the cell growth by 50% (i.e., an $IC_{50}$ value) was calculated, and shown in Table 1.

TABLE 1

| Test compound | FaDu ($IC_{50}$ (nM)) |
| --- | --- |
| Halichondrin B | 0.124 |
| Compound (1) | 0.0714 |

Pharmacological Test Example 2. MDA-MB231 Growth Inhibition Assay

In this assay, the growth inhibitory activity of test compounds in a human breast cancer cell line MDA-MB231 was measured. MDA-MB231 cells were maintained in Dulbecco's Modified Eagle's medium (Wako Pure Chemical Industries, Ltd., 044-29765) medium containing 10% fetal bovine serum (FBS: Nichirei, 12D168), and penicillin and streptomycin in a 5% $CO_2$ incubator (37° C.). To each well of a 96 well plate (Becton, Dickinson and Company, 353219), 75 µL of MDA-MB231 cell suspension adjusted to a concentration of $4\times10^4$ cells/mL with the culture medium was added, and the cells were incubated overnight in a 5% $CO_2$ incubator (37° C.). On the next day, 25 µL of Compound (1) or Halichondrin B in three-fold dilution series suspended in the culture medium was added to each well, and the resultant was incubated for 3 days in a 5% $CO_2$ incubator (37° C.). Then, cell viability was determined by CellTiter-Glo® Luminescent Cell Viability Assay (Promega) with EnVision 2103 Multilabel Reader (Perkin-Elmer, Wellesley, Mass.). Value of the wells containing cells without adding the test compounds was defined as 100% and the value of the wells containing no cells was defined as 0%. The concentration of the test compound necessary for inhibiting the cell growth by 50% (i.e., an $IC_{50}$ value) was calculated, and shown in Table 2.

TABLE 2

| Test compound | MDA-MB231 ($IC_{50}$ (nM)) |
| --- | --- |
| Halichondrin B | 1.000 |
| Compound (1) | 0.109 |

Pharmacological Test Example 3. HCC1954 Growth Inhibition Assay

In this assay, the growth inhibitory activity of test compounds in a human breast cancer cell line HCC1954 was measured. HCC1954 cells were maintained in an RPMI-1640 medium modified to contain 2 mM L-glutamine, 10 mM HEPES, 1 mM sodium pyruvate, 4500 mg/L glucose, and 1500 mg/L sodium bicarbonate (ATCC 30-2001) containing 10% fetal bovine serum (FBS: Nichirei, 12D168), and penicillin and streptomycin in a 5% $CO_2$ incubator (37° C.). To each well of a 96 well plate (Becton, Dickinson and Company, 353219), 75 µL of HCC1954 cell suspension adjusted to a concentration of $4\times10^4$ cells/mL with the culture medium was added, and the cells were incubated overnight in a 5% $CO_2$ incubator (37° C.). On the next day, 25 µL of Compound (1) or Halichondrin B in three-fold dilution series suspended in the culture medium was added to each well, and the resultant was incubated for 3 days in a 5% $CO_2$ incubator (37° C.). Then, cell viability was determined by CellTiter-Glo® Luminescent Cell Viability Assay (Promega) with EnVision 2103 Multilabel Reader (Perkin-Elmer, Wellesley, Mass.). Value of the wells containing cells without adding the test compounds was defined as 100% and the value of the wells containing no cells was defined as 0%. The concentration of the test compound necessary for inhibiting the cell growth by 50% (i.e., an $IC_{50}$ value) was calculated, and shown in Table 3.

TABLE 3

| Test compound | HCC1954 ($IC_{50}$ (nM)) |
| --- | --- |
| Halichondrin B | 0.154 |
| Compound (1) | 0.0668 |

Pharmacological Test Example 4. Antitumor Effects in FaDu Subcutaneous Xenograft Model in Mice as Monotherapy A human squamous cell carcinoma of the head and neck (SCCHN) cell line FaDu, which had been cultured in an RPMI-1640 medium containing 10% FBS, and penicillin and streptomycin, was adjusted to a concentration of $4.8\times10^7$ cells/mL with Hanks' Balanced Salt Solution to prepare a cell suspension. The cell suspension was inoculated in a volume of 100 μL into a subcutaneous part of a right flank of nude mice, 7 weeks of ages (CAnN.Cg-Foxn1nu/CrlCrlj, female, Charles River Laboratories Japan Inc.). Nine days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)×
Shortest diameter (mm)×Shortest diameter
(mm)/2

Relative tumor volume (RTV)=Tumor volume (day
$X$)/Tumor volume (the first day) Tumor Regression (%)=(1−minimum RTV)×100

On the basis of the volumes of tumors obtained on the first day of administration, the mice were grouped such that averages of the tumor volumes were substantially equal among the groups. Each test compound was dissolved in DMSO and a solution was stored at the freezer before use. Immediately before the administration, the stock solution was diluted in saline with 100 μM of hydroxypropyl-β-cyclodextrin. Each evaluation sample was intravenously administered at a maximum tolerable dose (MTD). Incidentally, the experiment was conducted on groups each consisting of 4 mice. Tumor regression (%) of each test compound was shown in Table 4.

TABLE 4

| Test compound | Dose (mg/kg) | Tumor Regression (%) |
|---|---|---|
| Halichondrin B | 0.05 | 0 |
| Compound (1) | 0.2 | 43 |

Pharmacological Test Example 5. Antitumor Activity Against OSC-19 in Subcutaneous Xenograft Model in Mice as Monotherapy A human squamous cell carcinoma of the head and neck (SCCHN) cell line OSC-19, which had been cultured in an DMEM/Ham's F-12 (1:1) medium containing 10% FBS, and penicillin and streptomycin, was adjusted to a concentration of 1×10$^8$ cells/ml with PBS to prepare a cell suspension, and the suspension was mixed with Matrigel™ (BD Bioscience, #366237) in a ratio of 1:1 to prepare a cell suspension in a concentration of 5×10$^7$ cell/mL. The cell suspension was inoculated in a volume of 100 μL into a subcutaneous part of a right flank of nude mice, 5 weeks of ages (CAnN.Cg-Foxn1nu/CrlCrlj, female, Charles River Laboratories Japan, Inc.). Six days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)×
Shortest diameter (mm)×Shortest diameter
(mm)/2

Relative tumor volume (RTV)=Tumor volume (day
$X$)/Tumor volume (the first day) Tumor Regression (%)=(1−minimum RTV)×100

On the basis of the volumes of tumors obtained on the first day of administration, the mice were grouped such that averages of the tumor volumes were substantially equal among the groups. The experiment was conducted on groups each consisting of 6 mice. Test compound was dissolved in saline and intravenously administered at doses from 0.06 mg/kg to 0.18 mg/kg once a week for 2 weeks (Q7Dx2 schedule). Tumor regression (%) of each test dose is shown in Table 5.

TABLE 5

| Test compound | Dose (mg/kg) | Tumor Regression (%) |
|---|---|---|
| Compound (1) | 0.06 | 59 |
| Compound (1) | 0.18 | 90 |

Pharmacological Test Example 6. Antitumor Activity Against HCC1806 in Subcutaneous Xenograft Model in Mice as Monotherapy A human breast cancer cell line HCC1806, which had been cultured in an RPMI-1640 medium containing 10% FBS, and penicillin and streptomycin, was adjusted to a concentration of 1×10$^8$ cells/mL with PBS to prepare a cell suspension, and the suspension was mixed with Matrigel™ (BD Bioscience, #366237) in a ratio of 1:1 to prepare a cell suspension in a concentration of 5×10$^7$ cell/mL. The cell suspension was inoculated in a volume of 100 μL into a subcutaneous part of a right flank of nude mice, 5 weeks of ages (CAnN.Cg-Foxn1nu/CrlCrlj, female, Charles River Laboratories Japan, Inc.). Twelve days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)×
Shortest diameter (mm)×Shortest diameter
(mm)/2

Relative tumor volume (RTV)=Tumor volume (day
$X$)/Tumor volume (the first day) Tumor Regression (%)=(1−minimum RTV)×100

On the basis of the volumes of tumors obtained on the first day of administration, the mice were grouped such that averages of the tumor volumes were substantially equal among the groups. The experiment was conducted on groups each consisting of 6 mice. Test compound was dissolved in saline and intravenously administered at 0.18 mg/kg once a week for 2 weeks (Q7Dx2 schedule). Tumor regression (%) for Compound (1) is shown in Table 6.

TABLE 6

| Test compound | Dose (mg/kg) | Tumor Regression (%) |
|---|---|---|
| Compound (1) | 0.18 | 90 |

Pharmacological Test Example 7. Antitumor Effects in FaDu Subcutaneous Xenograft Model in Combination with Cetuximab in Mice A human squamous cell carcinoma of the head and neck (SCCHN) cell line FaDu, which had been cultured in an RPMI-1640 medium containing 10% FBS, and penicillin and streptomycin, was adjusted to a concentration of 5×10$^7$ cells/mL with Hanks' Balanced Salt Solution to prepare a cell suspension. The cell suspension was inoculated in a volume of 100 L into a subcutaneous part of a right flank of nude mice, 7 weeks of ages (CAnN.Cg-Foxn1nu/CrlCrlj, female, Charles River Laboratories Japan Inc.). Ten days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)× Shortest diameter (mm)×Shortest diameter (mm)/2

Relative tumor volume (RTV)=Tumor volume (day X)/Tumor volume (the first day) Tumor Regression on day 35(%)=(1−RTV on day 35)×100

On the basis of the volumes of tumors obtained on the first day of administration, the mice were grouped such that averages of the tumor volumes were substantially equal among the groups. Each test compound was dissolved in DMSO and a solution was stored at the freezer before use. Immediately before the administration, the stock solution was diluted in saline with 100 μM of hydroxypropyl-β-cyclodextrin. Each test compound and was intravenously administered at doses from ¼ MTD to ½ MTD in combination with cetuximab (Erbitux, Merck Serono Co., Ltd.). Incidentally, the experiment was conducted on groups each consisting of 4 mice. Tumor regression on day 35(%) of each test compound are shown in Table 7.

TABLE 7

| Test compound | Dose (mg/kg) | Cetuximab (mg/kg) | Tumor Regression on day 35 (%) |
| --- | --- | --- | --- |
| — | — | 20 | −242 |
| Halichondrin B | 0.0125 | 20 | −38 |
|  | 0.025 | 20 | −2 |
| Compound (1) | 0.05 | 20 | 38 |
|  | 0.1 | 20 | 60 |

Pharmacological Test Example 8. Antitumor Activity in KPL-4 Subcutaneous Xenograft Model in Combination with Trastuzumab in Mice A human HER-2 positive breast cancer cell line KPL-4, which had been cultured in an RPMI-1640 medium containing 10% FBS, and penicillin and streptomycin, was adjusted to a concentration of 1×10$^8$ cells/mL with Hank's Balanced Salt Solution to prepare a cell suspension. The cell suspension was inoculated in a volume of 100 μL into a subcutaneous part of a right flank of nude mice, 7 weeks of ages (CAnN.Cg-Foxn1nu/CrlCrlj, female, Charles River Laboratories Japan, Inc.). Sixteen days after the cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)× Shortest diameter (mm)×Shortest diameter (mm)/2

Relative tumor volume (RTV)=Tumor volume (day X)/Tumor volume (the first day) Tumor Regression (%)=(1−minimum RTV)×100

On the basis of the volumes of tumors obtained on the first day of administration, the mice were grouped such that averages of the tumor volumes were substantially equal among the groups. The experiment was conducted on groups each consisting of 6 mice. Each test compound was dissolved in DMSO and a solution was stored at the freezer before use. Immediately before the administration, the stock solution was diluted in saline. The test compound was intravenously administered at 0.09 mg/kg or 0.18 mg/kg in combination with trastuzumab (Herceptin, Genentech, Inc.). Tumor regression for Compound (1) is shown in Table 8.

TABLE 8

| Test compound | Dose (mg/kg) | Trastuzumab (mg/kg) | Tumor Regression (%) |
| --- | --- | --- | --- |
| — | — | 10 | 0 |
| Compound (1) | 0.09 | — | 43 |
|  | 0.09 | 10 | 83 |
|  | 0.18 | — | 87 |
|  | 0.18 | 10 | 100 |

Pharmacological Test Example 9. Effect on CD31-Positive Vessel in the FaDu Subcutaneous Model in Mice A human squamous cell carcinoma of the head and neck (SCCHN) cell line FaDu, which had been cultured in an RPMI-1640 medium containing 10% FBS, and penicillin and streptomycin, was adjusted to a concentration of 5×10$^7$ cells/mL with PBS to prepare a cell suspension. The cell suspension was inoculated in a volume of 100 μL into a subcutaneous part of a right flank of nude mice, 7 weeks of ages (CAnN.Cg-Foxn1nu/CrlCrlj, female, Charles River Laboratories Japan, Inc.). Ten days after cell inoculation, a test compound in saline with 100 μM of hydroxypropyl-β-cyclodextrin was intravenously administered at doses from 1/2 MTD to MTD. The experiment was conducted on groups each consisting of 3 mice. Five days after administration, tumor samples were collected and fixed with IHC Zinc Fixative (BD Pharmingen) at 4° C. for 24 hr. Paraffin-embedded tissues were sectioned (3 μm), mounted on positively charged slides, and air-dried. Immunohistochemical staining of CD31 was conducted using Ventana autostainer model Discover XT (Roche Diagnostics) according to the manufacture's protocol. Sections were deparaffinized, conditioned and the antigens were retrieved with CC1 (Ventana Medical Systems). Slides were blocked with Blocker A and Blocker B (Endogenous biotin blocking kit, Roche Diagnostics). Rat anti-mouse IgG CD31 antibody (Dianova GmbH) was applied at 2 μg/mL. Sections were incubated with the antibody for 6 hr, followed by 32 minutes incubation with biotinylated anti-rat IgG antibody (Jackson ImmunoResearch Laboratories) at 2.2 μg/mL. The detection was performed with Streptavidin-HRP D for 16 min, followed by incubation with DAB D and DAB H$_2$O$_2$ D (DABMap kit, Ventana Medical Systems, Inc) for 8 min. Slides were counterstained with Hematoxylin II (Roche Diagnostics) for 16 min, followed by incubation with Bluing reagent for 4 min. Sections were dehydrated in graded ethanols, defatted in xylene replacement and covered with DPX (Merck KGaA).

Immunostained slides were scanned using Vectra 2 Automated Slide Imaging System (Perkin Elmer Inc.). The number of blood vessels in the whole tumor was quantified by counting the CD31-positive objects using in Form 2 software (PerkinElmer Inc.) Area of the tumor region was measured by assessing the hematoxylin-staining area using inform 2 software (PerkinElmer Inc.) The number of blood vessels was normalized by the area of the tumor region. An increase rate of the blood vessel number of the test compound-dosing group was calculated with the below formula, and shown in Table 9.

Increase rate of blood vessel number (%)=((blood vessel number of the test compound-dosing group−blood vessel number of the control group)/blood vessel number of the control group)×100

TABLE 9

| Test compound | Dose (mg/kg) | Increase rate of blood vessel number (%) |
|---|---|---|
| Halichondrin B | 0.025 | 31 |
|  | 0.05 | 39 |
| Compound (1) | 0.10 | 69 |
|  | 0.20 | 154 |

Pharmacological Test Example 10. Effect on α-SMA Positive-CAFs in the FaDu Subcutaneous Model A human squamous cell carcinoma of the head and neck (SCCHN) cell line FaDu, which had been cultured in an RPMI-1640 medium containing 10% FBS, and penicillin and streptomycin, was adjusted to a concentration of $5 \times 10^7$ cells/mL with PBS to prepare a cell suspension. The cell suspension was inoculated in a volume of 100 µL into a subcutaneous part of a right flank of nude mice, 5 to 6 weeks of ages (CAnN.Cg-Foxn1nu/CrlCrlj, female, Charles River Laboratories Japan, Inc.). Ten days after cell inoculation, a test compound in saline with 100 µM of hydroxypropyl-β-cyclodextrin was intravenously administered at ½ MTD and MTD. The experiment was conducted on groups each consisting of 3 mice. Two days after administration, tumor samples were collected and fixed with IHC Zinc Fixative (BD Pharmingen) at 4° C. for 24 hr. Paraffin-embedded tissues were sectioned (3 µm), mounted on positively charged slides, and air-dried for 6 hr. Immunohistochemical staining of α-SMA was conducted using Ventana autostainer model Discover XT (Roche Diagnostics). Sections were deparaffinized, conditioned and the antigens were retrieved with proprietary buffers, EZPrep and CC1 (Ventana Medical Systems). Mouse anti-α-SMA monoclonal antibody conjugated with alkaline phosphatase (clone 1A4, Sigma) was applied at 5 µg/mL. Sections were incubated with the antibody for 6 hr. The detection was performed with Red-Map kit (Ventana Medical Systems, Inc). Sections were dehydrated in graded ethanols, defatted in xylene replacement and covered with DPX (Merck KGaA). The serial tumor slices were deparaffinized and stained with Mayer's hematoxylin (Muto Pure Chemicals) for 1 min. Sections were dehydrated in graded ethanols, defatted in xylene replacement and covered with DPX (Merck KGaA).

Immunostained slides were scanned using Vectra 2 Automated Slide Imaging System (Perkin Elmer Inc.). The area of the α-SMA-positive region in the whole tumor was quantified by counting the α-SMA-positive objects using in Form 2 software (PerkinElmer Inc.). Area of the tumor region was measured by assessing the hematoxylin-staining area using in Form 2 software (PerkinElmer Inc.). The area of the α-SMA positive region was normalized by the area of the tumor region. A suppression rate of the α-SMA positive area of the test compound-dosing group was calculated with the below formula, and shown in Table 10.

TABLE 10

| Test compound | Dose (mg/kg) | Suppression rate of α-SMA positive area (%)[a] |
|---|---|---|
| Halichondrin B | 0.025 | 7 |
|  | 0.05 | 3 |
| Compound (1) | 0.10 | 21 |
|  | 0.20 | 28 |

[a]Suppression rate of α-SMA positive area (%) = −((α-SMA positive area of the test compound-dosing group − α-SMA positive area of the control group)/α-SMA positive area of the control group) × 100

Pharmacological Test Example 11. HSC-2 Orthotopic Transplantation Mouse Model

Luciferase-transduced HSC-2-Luc cells were established by retrovirus-mediated gene transfer. First, the DNA fragment encoding firefly luciferase was obtained from pGL3-enhancer plasmid (GenBank #:U47297), and subcloned into the retroviral vector pCX4pur (GenBank #: AB086386). Then, helper-free recombinant retroviruses were produced by transfecting the above retroviral expression vector together with pGP and pE-Ampho plasmids (Takara Bio; Shiga, Japan), into 293T cells (ATCC; Manassas, USA). Next, HSC-2 cells were infected with the recombinant retroviruses, and were cultured for two weeks in the presence of puromycin (2 µg/mL). The infected cells were selected from a polyclonal proliferative population of the culture.

Under anesthesia, the human SCCHN cell line, HSC-2-Luc was inoculated into tongue of female nude mice ($1 \times 10^6$ cells in 50 µL of PBS), 6 weeks of ages (CAnN.Cg-Foxn1nu/CrlCrlj mice; Charles River, Inc.; Shizuoka, Japan). Seven days after transplantation, the tumor volume was analyzed using bioluminescence signal from HSC-2-Luc cells. For bioluminescence imaging, 0.1 mL of 15 mg/mL D-luciferin (Promega, Madison, Wis.) was injected intraperitoneally into nude mice under 1% to 2% inhaled isoflurane anesthesia. The bioluminescence signal was monitored using the IVIS SPECTRUM series (PerkinElmer, Waltham, Mass.), consisting of a highly sensitive, cooled chargecoupled device camera. Living Image software (PerkinElmer, Waltham, Mass.) was used to grid the imaging data and integrate the total bioluminescence signal in each region-of-interest (ROI). All bioluminescence images were acquired with a 1 second exposure. Data were analyzed using total photon flux emission (photons/second) in the ROIs.

On the basis of the total photon flux emission obtained on the first day of administration, the mice were grouped such that averages of the total photon flux emission were substantially equal among the groups. Compound (1) or cisplatin was intravenously administered with or without cetuximab (Erbitux, Merck Serono Co., Ltd.) once a week for 3 weeks (Q7Dx3 schedule). Two experiments were conducted using the identical procedure and all data were collected from the experiments. Each group consisted of 16 mice.

Figure 6A:
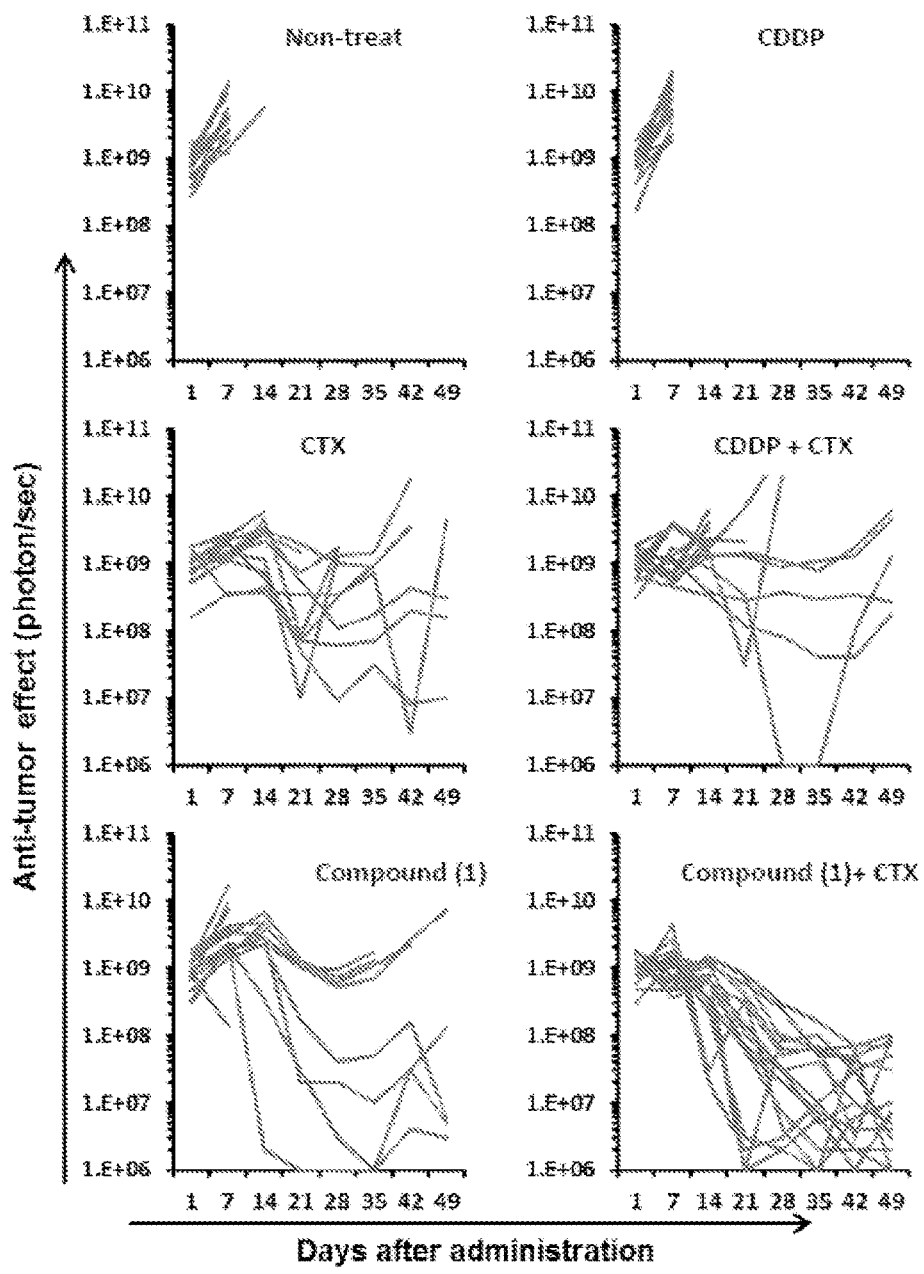
FIG. 6A-6B show anti-tumor effect of Compound (1) in HSC-2 orthotopic transplantation mouse model.
Figure 6B:
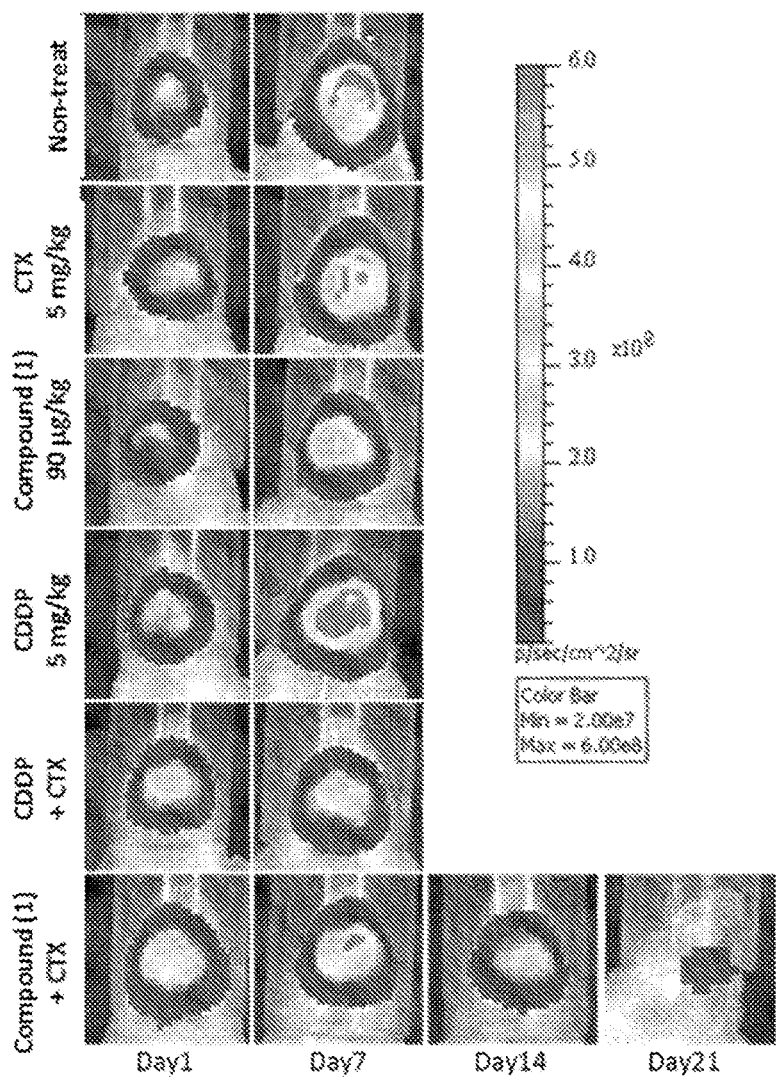
Figure 7A:
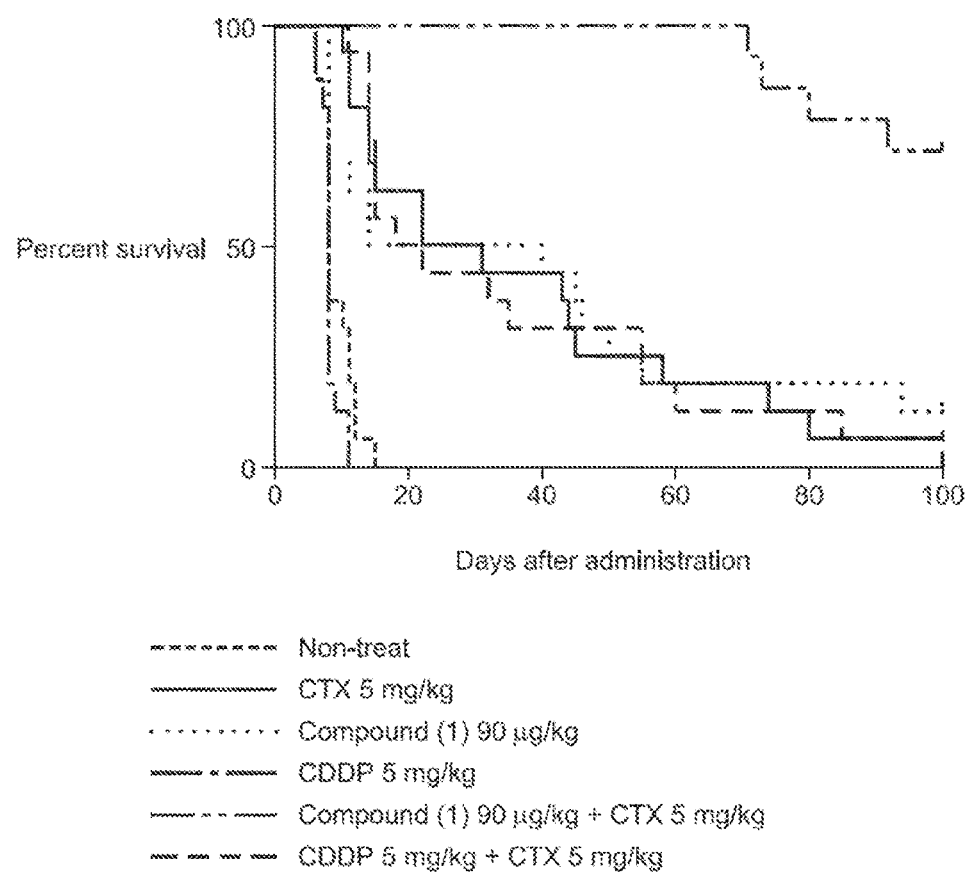
FIG. 7A-7B show survival advantage of Compound (1) in combination with cetuximab in HSC-2 orthotopic transplantation mouse model.
Figure 7B:
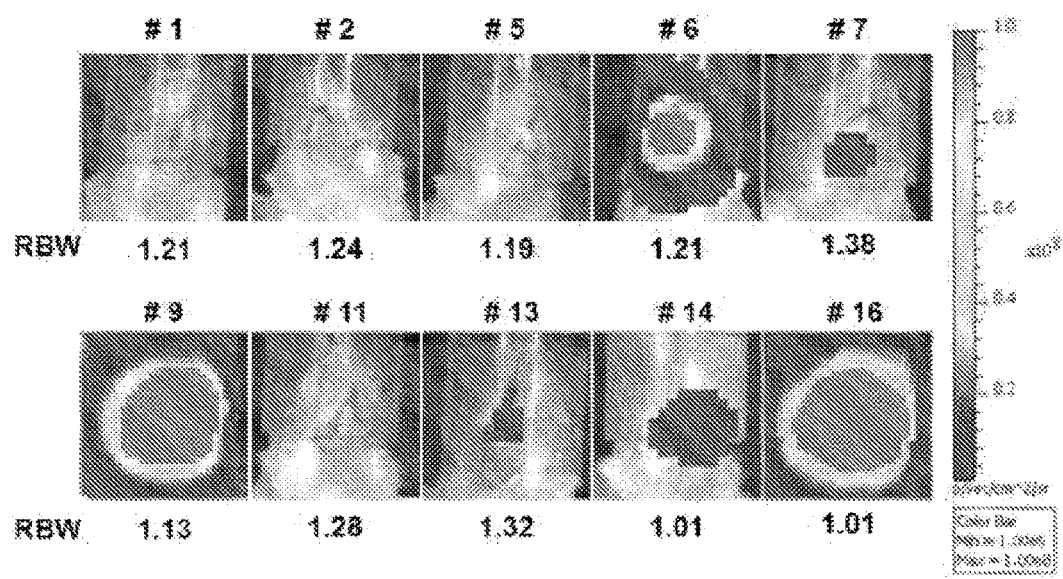
Figure 8A:
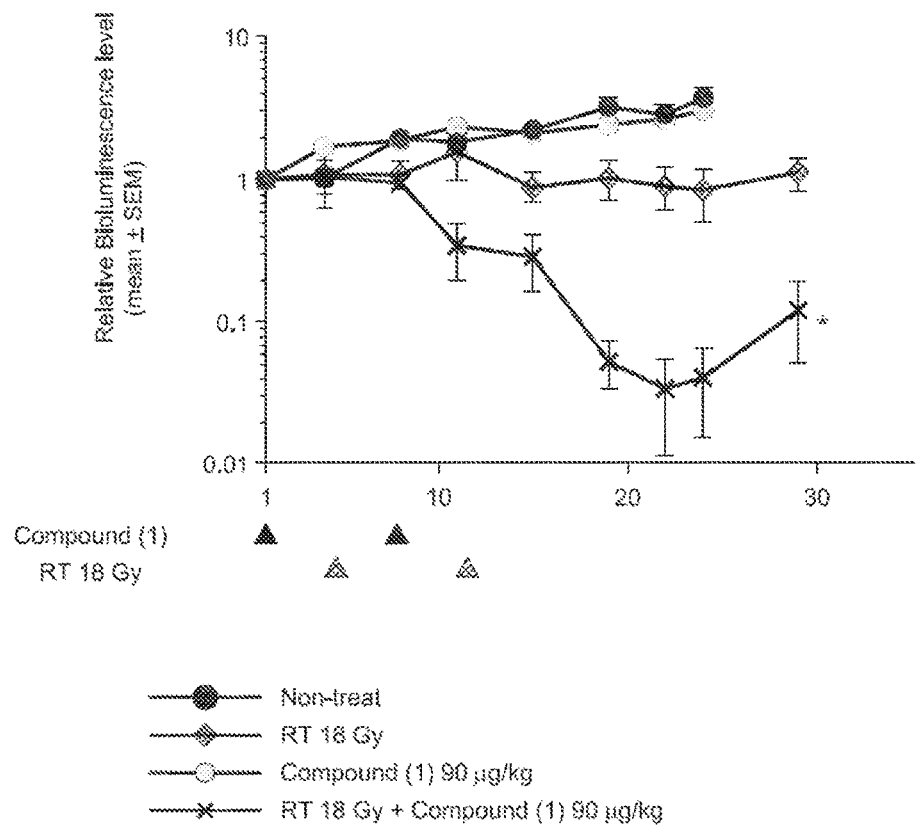
FIG. 8A-8B show anti-tumor effect of Compound (1) in combination with radiation therapy in FaDu mouse xenograft model.
Figure 8B:
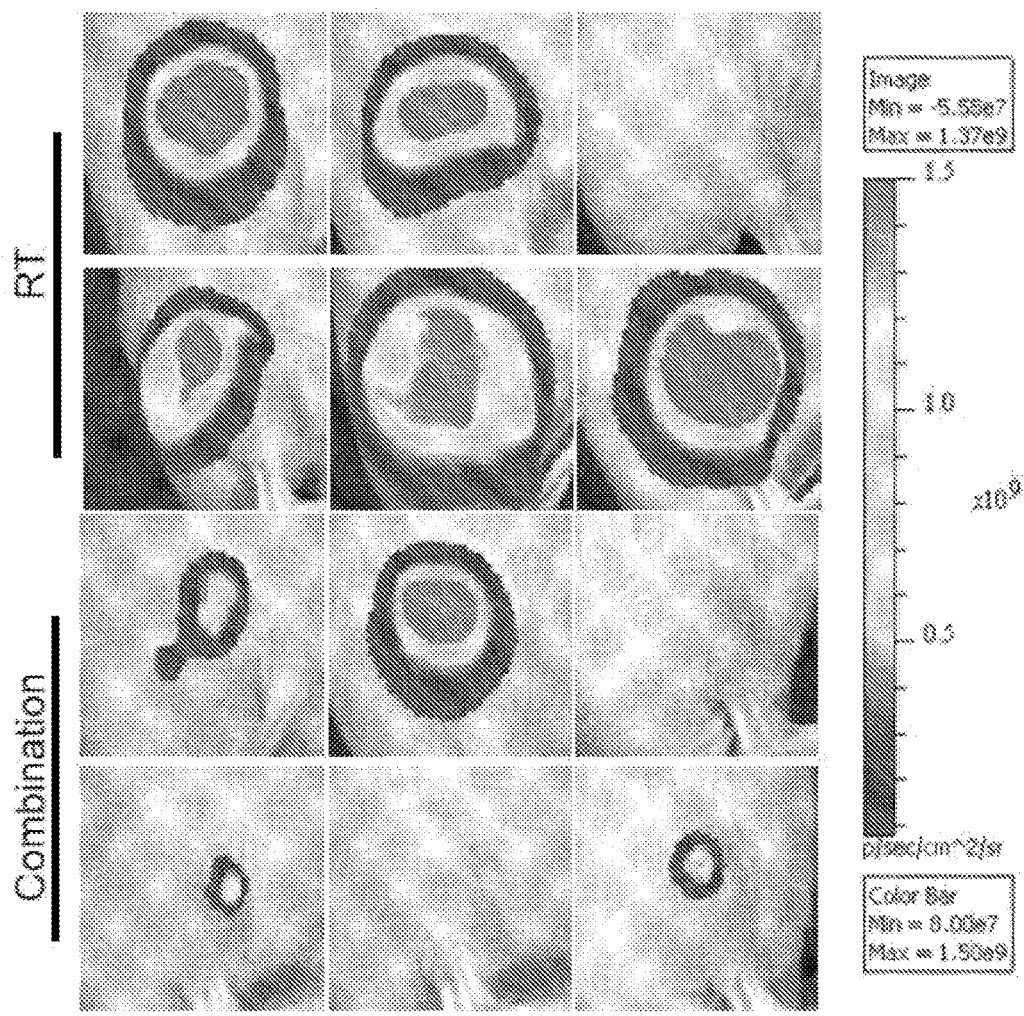
Figure 9:
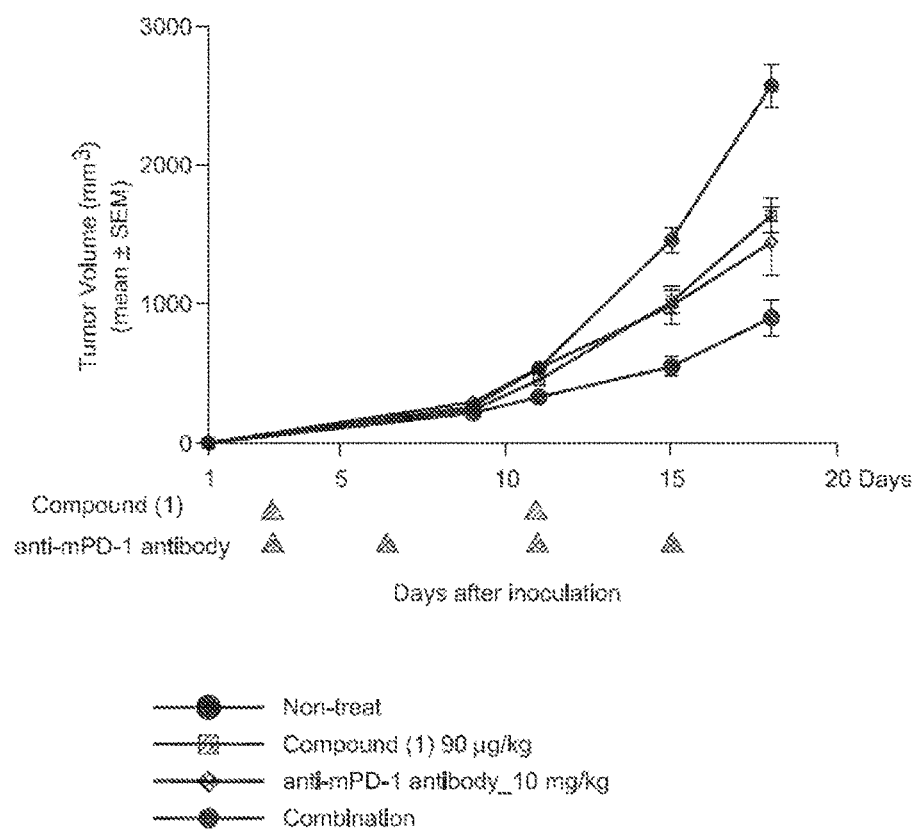
FIG. 9 shows anti-tumor activities of Compound (1) in combination with anti-mPD-1 antibody. CT26 s.c. syngeneic mouse model (colon carcinoma) was treated with Compound (1) and anti-mPD-1 antibody in Q7D schedule and twice a week schedule, respectively, for 3 weeks. Results show means±SEM of tumor volumes ($mm^3$) (n=8).

The imaging data showed that only the treatment of Compound (1) with cetuximab clearly reduced the bioluminescence signal in all mice after Day 14 (FIG. 6A-6B). Median survival time (MST) was calculated for each group of treatment as the median of the days of death. Increase Life Span (ILS) was calculated by the following formula: ILS (%)=(MST of animals treated with test compound−MST of control animals)/MST of control animals x 100. ILS (%) of each test compound is shown in Table 11.

TABLE 11

| Test compound | Dose (mg/kg) | Cetuximab (mg/kg) | ILS (%) |
|---|---|---|---|
| — | — | 5 | 231 |
| Cisplatin | 5 | — | 0 |
| | 5 | 5 | 150 |
| Compound (1) | 0.09 | — | 238 |
| | 0.09 | 5 | >1150 |

Pharmacological Test Example 12. FaDu s.c. Xenograft Model in Combination with Radiation Luciferase-transduced FaDu-Luc cells were established by retrovirus-mediated gene transfer. First, the DNA fragment encoding firefly luciferase was obtained from pGL3-enhancer plasmid (GenBank #:U47297), and subcloned into the retroviral vector pCX4pur (GenBank #: AB086386). Then, helper-free recombinant retroviruses were produced by transfecting the above retroviral expression vector together with pGP and pE-Ampho plasmids (Takara Bio; Shiga, Japan), into 293T cells (ATCC; Manassas, USA). Next, FaDu cells were infected with the recombinant retroviruses, and were cultured for two weeks in the presence of puromycin (2 µg/mL). The infected cells were selected from a polyclonal proliferative population of the culture.

A luciferase-transduced human SCCHN cell line FaDu-Luc, which had been cultured in an RPMI-1640 medium containing 10% FBS, and penicillin and streptomycin, was adjusted to a concentration of $5 \times 10^7$ cells/mL with Hank's Balanced Salt Solution to prepare a cell suspension. The cell suspension was inoculated in a volume of 100 µL into a subcutaneous part of a right thigh of nude mice, 6 weeks of ages (CAnN.Cg-Foxn1nu/CrlCrlj, female, Charles River Laboratories Japan, Inc.). Thirteen days after the cell inoculation, the tumor volume was analyzed using bioluminescence signal from FaDu-Luc cells. For bioluminescence imaging, 0.1 mL of 15 mg/mL D-luciferin (Promega, Madison, Wis.) was injected intraperitoneally into nude mice under 1% to 2% inhaled isoflurane anesthesia. The bioluminescence signal was monitored using the IVIS SPECTRUM series (PerkinElmer, Waltham, Mass.), consisting of a highly sensitive, cooled chargecoupled device camera. Living Image software (PerkinElmer, Waltham, Mass.) was used to grid the imaging data and integrate the total bioluminescence signal in each region-of-interest (ROI). All bioluminescence images were acquired with a 1 second exposure. Data were analyzed using total photon flux emission (photons/second) in the ROIs. The total photon flux emission was calculated in accordance with the following calculation formulae:

Relative bioluminescence level=Total photon flux emission (day $X$)/Total photon flux emission (the first day)

Tumor Regression (%)=(1−minimum Relative bioluminescence level)×100

On the basis of the total photon flux emission obtained on the first day of administration, the mice were grouped such that averages of the total photon flux emission were substantially equal among the groups. The experiment was conducted on groups each consisting of 6 mice. Compound (1) was administrated via tail vein injection on day 1 and 8. Irradiation was performed 18 Gy on day 4 and day 11. Tumor regression for Compound (1) is shown in Table 12.

TABLE 12

| Test compound | Dose (mg/kg) | Radiation (Gy) | Tumor Regression (%) |
|---|---|---|---|
| — | — | 18 | 16 |
| Compound (1) | 0.09 | — | 0 |
| | 0.09 | 18 | 97 |

Pharmacological Test Example 13. Antitumor Activity in CT26 Subcutaneous Syngeneic Model in Combination with Anti-mPD-1 Antibody in Mice A murine undifferentiated colon carcinoma cell line CT26, which had been cultured in an RPMI-1640 medium containing 10% FBS, and penicillin and streptomycin, was adjusted to a concentration of $2 \times 10^7$ cells/mL with Hank's Balanced Salt Solution to prepare a cell suspension. On day 1, the cell suspension was inoculated in a volume of 100 µL into a subcutaneous part of a right flank of BALB/c mice, 6 weeks of ages (BALB/cAnNCrlCrlj, female, Charles River Laboratories Japan, Inc.). Two days after the cell inoculation, the mice were randomly divided into four groups and each group consists of 8 mice. The shortest diameter and the longest diameter of a tumor in each mouse were measured by using an electronic digital caliper (Digimatic™ caliper, Mitutoyo Corporation), so as to calculate the volume of the tumor in accordance with the following calculation formula:

Tumor volume (mm³)=Longest diameter (mm)× Shortest diameter (mm)×Shortest diameter (mm)/2

T/C=(mean tumor volume of treated group)/(mean tumor volume of control group) Inhibition of tumor growth (%)=(1−T/C)×100

The test compound was intravenously administered at 0.09 mg/kg on days 3 and 11. Anti-mPD-1 antibody (BE0146, Bio X Cell) was intravenously administered at 10 mg/kg on days 3, 7, 11, and 15. Inhibition of tumor growth on day 15(%) of each test compound is shown in Table 13.

TABLE 13

| Test compound | Dose (mg/kg) | Anti-mPD-1 antibody (mg/kg) | Inhibition of tumor growth on day 15 (%) |
|---|---|---|---|
| — | — | 10 | 32 |
| Compound (1) | 0.09 | — | 30 |
| | 0.09 | 10 | 62 |

Figure 10A:
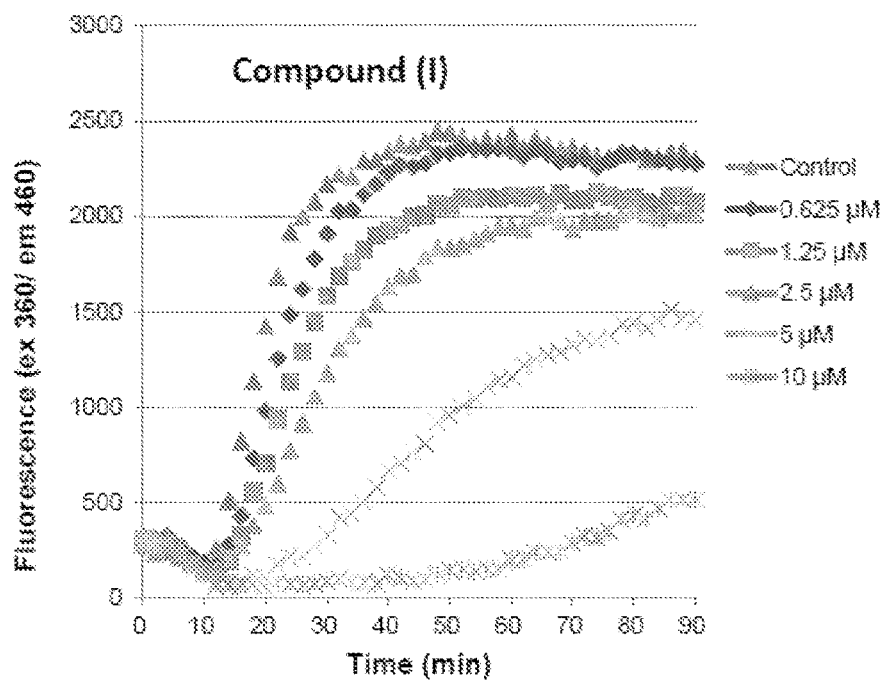
FIG. 10A shows a cell-free tubulin polymerization assay. Compound (1) has inhibitory activity on tubulin polymerization.

Pharmacological Test Example 14. Effect on Tubulin Polymerization In Vitro (FIG. 10A)

Tubulin Polymerization Assay kit was purchased from Cytoskeleton, Inc. (Cat. #BK011P). The kit contained 1 bottle of lyophilized tubulin protein purified from porcine brain, 3 tubes of lyophilized GTP, 2 bottles of lyophilized assay buffer, and 1 bottle of tubulin glycerol buffer. Assay buffer was prepared by dissolving the contents in 10 mL of deionized and sterilized water. This solution contained 80 mmol/L piperazine-N,N'-bis[2-ethanesulfonic acid] sesquisodium salt, 2.0 mmol/L magnesium chloride, 0.5 mmol/L ethylene glycol-bis(2-amino-ethyl ether) N,N,N',N'-tetraacetic acid, pH 6.9, and 10 µmol/L fluorescent reporter. The buffer was stored at −70° C. until use. Tubulin glycerol buffer consisted of 80 mmol/L piperazine-N,N'-bis[2-ethanesulfonic acid] sesquisodium salt, 2.0 mmol/L magnesium chloride, 0.5 mmol/L ethylene glycol-bis(2-amino-ethyl ether) N,N,N',N'-tetra-acetic acid, and 60% v/v glycerol, pH 6.9. It was stored at 4° C. until use. GTP stock solution was prepared by dissolving the contents of each tube in 100 μL of deionized and sterilized water to achieve a concentration of 100 mmol/L GTP. Aliquots of this stock were stored at −70° C. until use. Tubulin stock solution (10 mg/mL) was prepared by dissolving the tubulin powder adding 1.1 mL of the mixture of assay buffer and GTP stock solution (100:1, v/v). Aliquots were frozen in liquid nitrogen, and then stored at −70° C. until use.

In the tubulin polymerization assay, reaction mixture was prepared by mixing 820 μL of assay buffer, 17.6 μL of GTP stock solution, and 600 μL of tubulin glycerol buffer. Reaction mixture (1015 μL) was combined with 240 μL of the tubulin stock solution. This solution was called as tubulin reaction mixture and used for the measurement of test and control wells. No tubulin reaction mixture was prepared by mixing 89.85 μL of reaction mixture and 21.25 μL of assay buffer for the measurement of blank wells. The Compound (1) solution (6.25-100 μmol/L; final concentrations 0.625-10 μmol/L), or vehicle was added at 5 μL to individual wells of a 96-well half-area microtiter plate. Tubulin reaction mixture or no tubulin reaction mixture was added at 45 μL to each well of the plate. Fluorescence emission at 460 nm (excitation wavelength at 360 nm) was measured every 2 minutes for 90 minutes using the SpectraMax® M5e microplate reader (Molecular Devices). Tubulin polymerization was followed by fluorescence enhancement due to the incorporation of a fluorescence reporter into microtubules as polymerization occurred. The assay was performed in duplicate. The assay demonstrated that Compound (1) inhibited tubulin polymerization in a concentration-dependent manner. The fluorescence intensity in each time point was calculated by the following formulas:

Fluorescence intensity=mean fluorescence measurement of test wells or control wells−mean fluorescence measurement of blank wells; blank well: with vehicle without tubulin; control well: with vehicle and tubulin; test well: with compounds and tubulin.

Figure 10B:
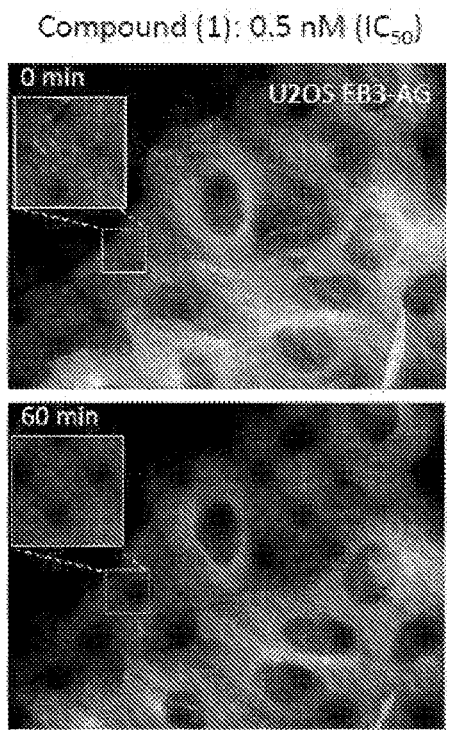
FIG. 10B shows a microtubule dynamics assay. Compound (1) also has inhibitory activity on microtubule dynamics.

Pharmacological Test Example 15. Cell-Based Microtubule Dynamics Assay (FIG. 10B)

A cell-based microtubule (MT) dynamics assay was conducted with the U2OS-EB3-AG osteosarcoma cell line, in which the fusion protein of EB3 (a microtubule plus end binding protein) and Azami-Green (EB3-AG) was stably expressed. U2OS-EB3-AG cells were culture in RPMI-1640 medium containing 10% FBS, and penicillin-streptomycin, at 37° C. in a humidified 5% $CO_2$ atmosphere. The MT dynamics in the live cells can be visualized as the movement of the comet-like structure of EB3-AG. U2OS-EB3-AG cells plated on glass-base culture plates (EZVIEW plate, AGC Techno Glass, Japan) were treated with Compound (1) at the indicated concentration and the microtubule dynamics were monitored by time-lapse imaging using fluorescent microscope with 60-fold magnification oil-immersed objective lens (BZ-X710, KEYENCE, Japan). The still images at the indicated time points were presented in FIG. 10B. Higher magnification views of the boxed areas were shown in inlets. When treated with Compound (1) at 0.5 nM ($IC_{50}$ value for antiproliferative activity in U2OS-EB3-AG cells), the comet-like structures became hard to observe at around 60 minutes after the addition of the compound. These results clearly demonstrated that Compound (1) had the ability to suppress the MT dynamics.

Figures 11, 12:
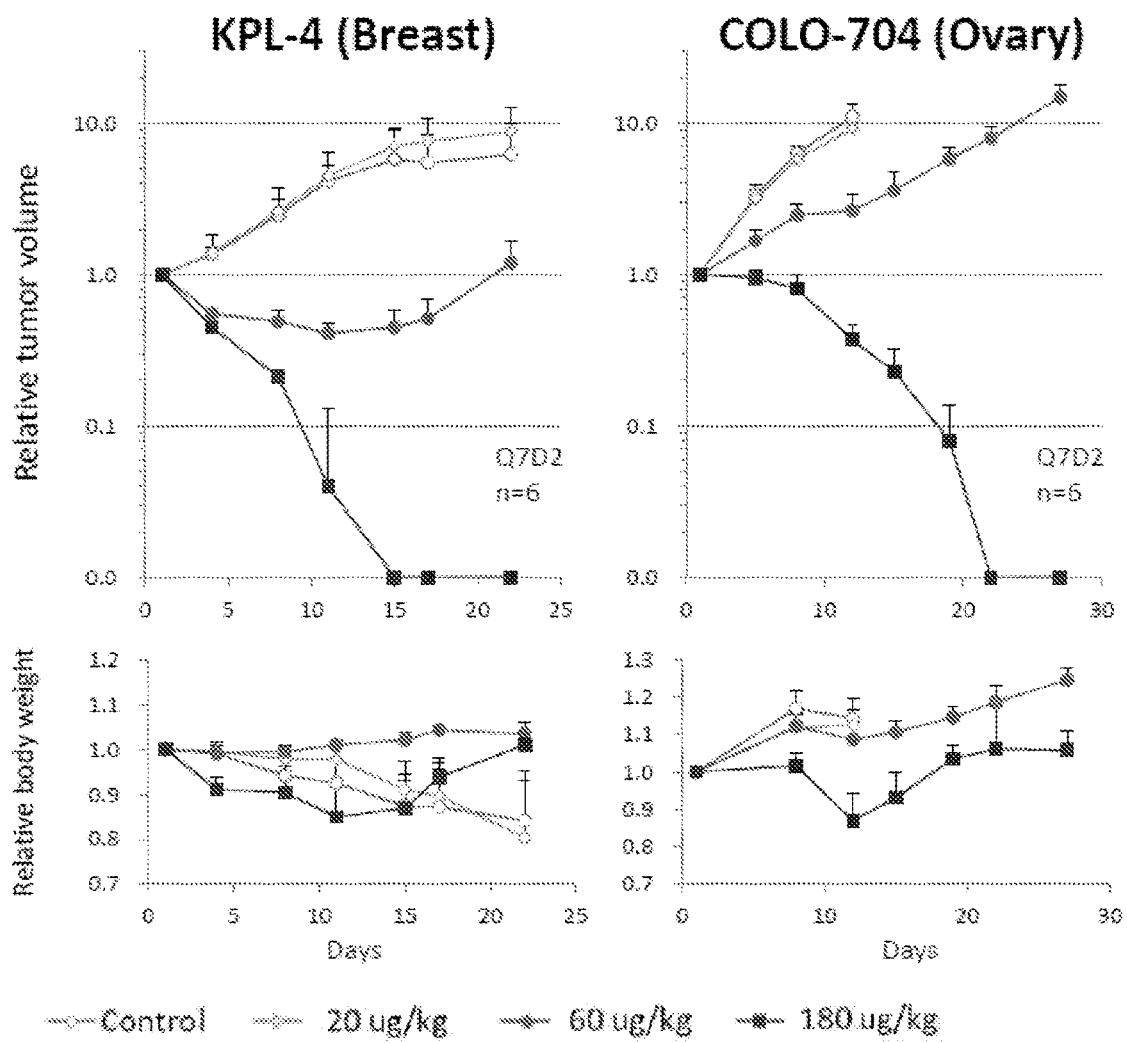
FIG. 11 shows that Compound (1) is a potent antiproliferative agent in esophageal cancer (OE21, OE33, and TE-8) and uterine cancer (MES-SA, MES-SA/Dx5-Rx1) cell lines.
FIG. 12 shows that Compound (1) has potent anti-tumor activity in subcutaneous xenograft models of breast and ovarian cancer (KPL-4 and COLO-704, respectively) as a monotherapy.

Pharmacological Test Example 16. In Vitro Antiproliferative Activity (FIG. 11)

The in vitro antiproliferative assays for Compound (1) were conducted using a small panel of cancer cell lines including human squamous cell carcinoma of the esophagus (OE21, TE-8), human adenosarcoma of the esophagus (OE33), and human uterine sarcoma (MES-SA, MES-SA-Dx5-Rx1). All cell lines were cultured in RPMI-1640 medium containing 10% FBS, and penicillin-streptomycin (culture medium), in a 5% $CO_2$ incubator (37° C.). To each well of a 96 well plate (Becton, Dickinson and Company, 353219), 75 μL of cell suspension adjusted to a concentration of $4\times10^4$ cells/mL with the culture medium was added, and the cells were incubated overnight in a 5% $CO_2$ incubator (37° C.). On the next day, 25 μL of Compound (1) in three-fold dilution series suspended in the culture medium was added to each well, and the resultant was incubated for 72 hours in a 5% $CO_2$ incubator (37° C.). Then, cell viability was determined by CellTiter-Glo® Luminescent Cell Viability Assay (Promega) with 2013 EnVision™ Multilabel Reader (Perkin-Elmer, Wellesley, Mass.). Value of the wells containing cells without adding the test compounds was defined as 100% and the value of the wells containing no cells was defined as 0%. The concentration of Compound (1) necessary for inhibiting the cell growth by 50% (i.e., an $IC_{50}$ value) was calculate, and is shown in FIG. 11. The P-gp susceptibility was calculated as the ratio of the $IC_{50}$ value in MES-SA-Dx5-Rx1 cells, which overexpress P-gp, to the $IC_{50}$ value in MES-SA cells.

Pharmacological Test Example 17. Antitumor Effects in the KPL-4 Xenograft Models in Mice as Monotherapy; Antitumor Effects in the COLO-704 Xenograft Models in Mice as Monotherapy (FIG. 12)

A human HER-2 positive breast cancer cell line KPL-4, which had been cultured in a DMEM containing 10% FBS, and penicillin-streptomycin, was adjusted to a concentration of $1\times10^8$ cells/mL with Hanks' Balanced Salt Solution to prepare a cell suspension. The cell suspension was inoculated in a volume of 100 μL into a subcutaneous part of a right flank of nude mice, 8 weeks of ages (CAnN.Cg-Foxn1nu/CrlCrlj, female, Charles River Laboratories Japan Inc.). Eleven days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume ($mm^3$)=Longest diameter (mm)× Shortest diameter (mm)×Shortest diameter (mm)/2

Relative tumor volume (RTV)=Tumor volume (day X)/Tumor volume (the first day) Relative body weight (RBW)=Body weight (day X)/Body weight (the first day)

On the basis of the volumes of tumors obtained on Day 1, the mice were grouped such that averages of the tumor volumes were substantially equal among the groups. The experiment was conducted on groups each consisting of six mice. The test compound was dissolved in DMSO and a solution was stored in the freezer before use. Immediately before the administration, the stock solution was diluted with saline. The test compound in saline was intravenously once-weekly administered at 20 µg/kg, 60 µg/kg, or 180 µg/kg for 2 weeks (on Day 1 and Day 8). The tumor regression was observed in 60 µg/kg- and 180 µg/kg-treated groups, and the administration at 180 µg/kg completely eradicated the xenograft tumors in all mice on Day 15.

A human ovarian cancer cell line COLO-704, which had been cultured in a RPMI-1640 containing 10% FBS, and penicillin-streptomycin, was adjusted to a concentration of $1 \times 10^8$ cells/mL with Hanks' Balanced Salt Solution to prepare a cell suspension. The cell suspension was inoculated in a volume of 100 µL into a subcutaneous part of a right flank of nude mice, 5 weeks of ages (CAnN.Cg-Foxn1nu/CrlCrlj, female, Charles River Laboratories Japan Inc.). Nine days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm³)=Longest diameter (mm)× Shortest diameter (mm)×Shortest diameter (mm)/2

Relative tumor volume (RTV)=Tumor volume (day X)/Tumor volume (the first day)

Relative body weight (RBW)=Body weight (day X)/Body weight (the first day)

On the basis of the volumes of tumors obtained on Day 1, the mice were grouped such that averages of the tumor volumes were substantially equal among the groups. The experiment was conducted on groups each consisting of six mice. The test compound was dissolved in DMSO and a solution was stored in the freezer before use. Immediately before the administration, the stock solution was diluted with saline. The test compound in saline was intravenously once-weekly administered at 20 µg/kg, 60 µg/kg, or 180 µg/kg for 2 weeks (on Day 1 and Day 8). The compound treatment induced tumor regression at 180 µg/kg and tumor growth delay at 60 µg/kg. The administration at 180 µg/kg completely eradicated the xenograft tumors in all mice on Day 22.

Figure 13:
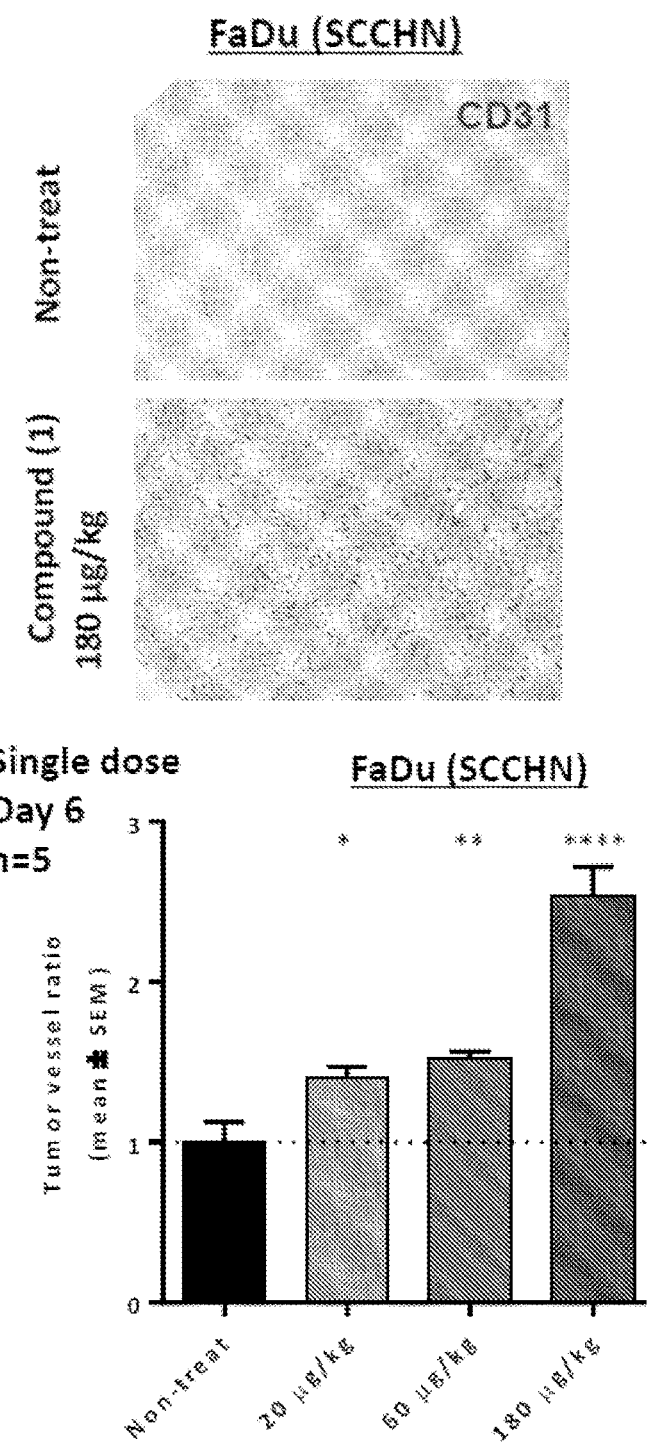
FIG. 13 shows the effect of Compound (1) on tumor microenvironments. As shown, Compound (1) increases microvessel density. * P<0.05,  P<0.01, **P<0.0001 versus non-treat (Dunnett multiple comparison test).

Pharmacological Test Example 18. Effect on CD31-Positive Vessel in the FaDu Subcutaneous Model in Mice (FIG. 13)

A human squamous cell carcinoma of the head and neck (SCCHN) cell line FaDu, which had been cultured in an RPMI-1640 medium containing 10% FBS, and penicillin-streptomycin (culture medium), was adjusted to a concentration of $5 \times 10^7$ cells/mL with culture medium to prepare a cell suspension. The cell suspension was inoculated in a volume of 100 µL into a subcutaneous part of a right flank of nude mice, 6 weeks of ages (CAnN.Cg-Foxn1nu/CrlCrlj, female, Charles River Laboratories Japan, Inc.). Ten days after cell inoculation, the mice were grouped such that averages of the tumor volumes were substantially equal among the groups. The experiment was conducted on groups each consisting of 6 mice. Each test compound was dissolved in DMSO and a solution was stored in the freezer before use. Immediately before the administration, the stock solution was diluted with saline. The test compound in saline was intravenously administered at 20 µg/kg, 60 µg/kg, or 180 µg/kg. Five days after the single administration, tumor samples were collected and fixed with IHC Zinc Fixative (BD Pharmingen) at 4° C. for 24 hours. Paraffin-embedded tissues were sectioned (3 µm), mounted on positively charged slides, and air-dried. Immunohistochemical staining of CD31 was conducted using Ventana autostainer model Discover XT (Roche Diagnostics) according to the manufacture's protocol. Sections were deparaffinized, conditioned and the antigens were retrieved with CC1 (Ventana Medical Systems). Slides were blocked with Blocker A and Blocker B (Endogenous biotin blocking kit, Roche Diagnostics). Rat anti-mouse IgG CD31 antibody (Dianova GmbH) was applied at 2 µg/mL. Sections were incubated with the antibody for 6 hours, followed by 32 minutes incubation with biotinylated anti-rat IgG antibody (Jackson ImmunoResearch Laboratories) at 2.2 µg/mL. The detection was performed with Streptavidin-HRP D for 16 minutes, followed by incubation with DAB D and DAB $H_2O_2$ D (DABMap kit, Ventana Medical Systems, Inc.) for 8 minutes. Slides were counterstained with Hematoxylin II (Roche Diagnostics) for 16 min, followed by incubation with Bluing reagent for 4 minutes. Sections were dehydrated in graded ethanols, defatted in xylene replacement and covered with DPX @(Merck KGaA). Immunostained slides were scanned using Vectra® 2 Automated Slide Imaging System (Perkin Elmer Inc.). The number of blood vessels in the whole tumor was quantified by counting the CD31-positive objects using inform 2 software (PerkinElmer Inc.) Area of the tumor region was measured by assessing the hematoxylin-staining area using inform 2 software (PerkinElmer Inc.) The number of blood vessels was normalized by the area of the tumor region. The single administration of test compound at doses of 20, 60, and 180 µg/kg increased the tumor blood vessel number. The ratios of blood vessel number in the test compound-dosing groups compared to non-treat group were calculated with the below formula:

Tumor vessel ratio=blood vessel number of the test compound-dosing group/blood vessel number of the non-treat group)

Figure 14:
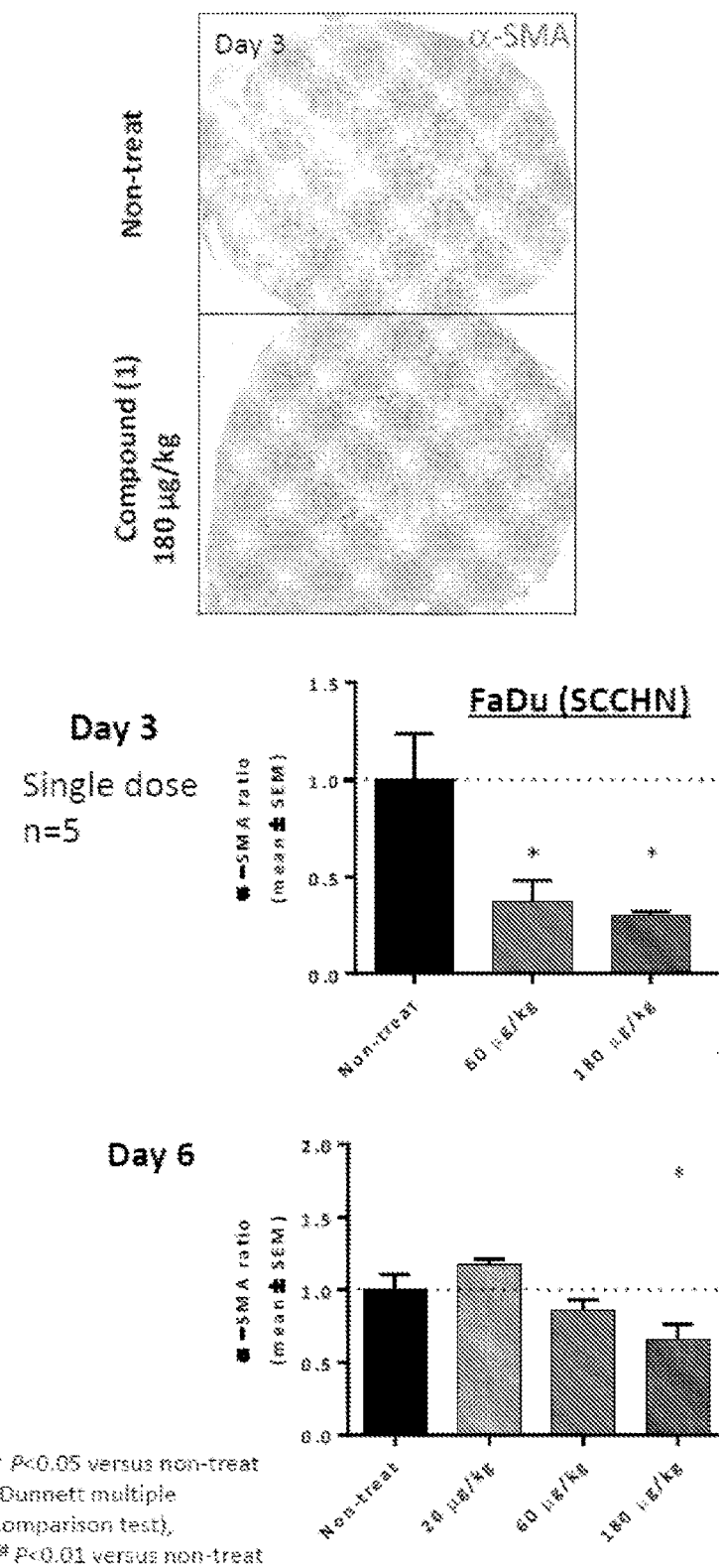
FIG. 14 shows the effect of Compound (1) on tumor microenvironments. As shown, Compound (1) reduces α-SMA positive CAFs.

Pharmacological Test Example 19. Effect on α-SMA-Positive CAFs in the FaDu Subcutaneous Model in Mice (FIG. 14)

A human squamous cell carcinoma of the head and neck (SCCHN) cell line FaDu, which had been cultured in an RPMI-1640 medium containing 10% FBS, and penicillin-streptomycin (culture medium), was adjusted to a concentration of $5 \times 10^7$ cells/mL with culture medium to prepare a cell suspension. The cell suspension was inoculated in a volume of 100 µL into a subcutaneous part of a right flank of nude mice, 6 weeks of ages (CAnN.Cg-Foxn1nu/CrlCrlj, female, Charles River Laboratories Japan, Inc.). Ten days after cell inoculation, the mice were grouped such that averages of the tumor volumes were substantially equal among the groups. The experiment was conducted on groups each consisting of 5 mice. Each test compound was dissolved in DMSO and a solution was stored in the freezer before use. Immediately before the administration, the stock solution was diluted with saline. The test compound in saline was intravenously administered at 20 µg/kg, 60 µg/kg, or 180 µg/kg. Two days or 5 days after the single administration, tumor samples were collected and fixed with IHC Zinc Fixative (BD Pharmingen) at 4° C. for 24 hours. Paraffin-embedded tissues were sectioned (3 µm), mounted on positively charged slides, and air-dried. Sections were deparaffinized, conditioned and the antigens were retrieved using microwave with 1 mM EDTA at pH 6.0. Sections were blocked with 1% of BSA in TBS. Mouse anti-α-SMA monoclonal antibody conjugated with alkaline phosphatase (clone 1A4, Sigma) was applied at 5 µg/mL. Sections were incubated with the antibody for 2.5 hr. The detection was performed with Fast red II substrate kit (Nichirei Bioscience Inc.). Sections were counterstained with Mayer's Hematoxylin (Muto Pure Chemicals) for 50 seconds. Sections were dehydrated in graded ethanols, defatted in xylene replacement and covered with DPX (Merck KGaA). Immunostained slides were scanned using Vectra 2 Automated Slide Imaging System (Perkin Elmer Inc.). The area of α-SMA-positive region in the whole tumor was quantified by counting the α-SMA-positive objects using inform 2 software (PerkinElmer Inc.) Area of the tumor region was measured by assessing the hematoxylin-staining area using inform 2 software (PerkinElmer Inc.). The area of the α-SMA-positive region was normalized by the area of the tumor region. The single administration of test compound significantly reduced the α-SMA positive area at doses of 60 and 180 µg/kg on Day 3 and at a dose of 180 µg/kg on Day 6. A suppression rate of the α-SMA-positive area of the test compound-dosing group was calculated with the below formula:

α-SMA ratio=α-SMA area of the test compound-dosing group/α-SMA area of the non-treat group

Figure 15:
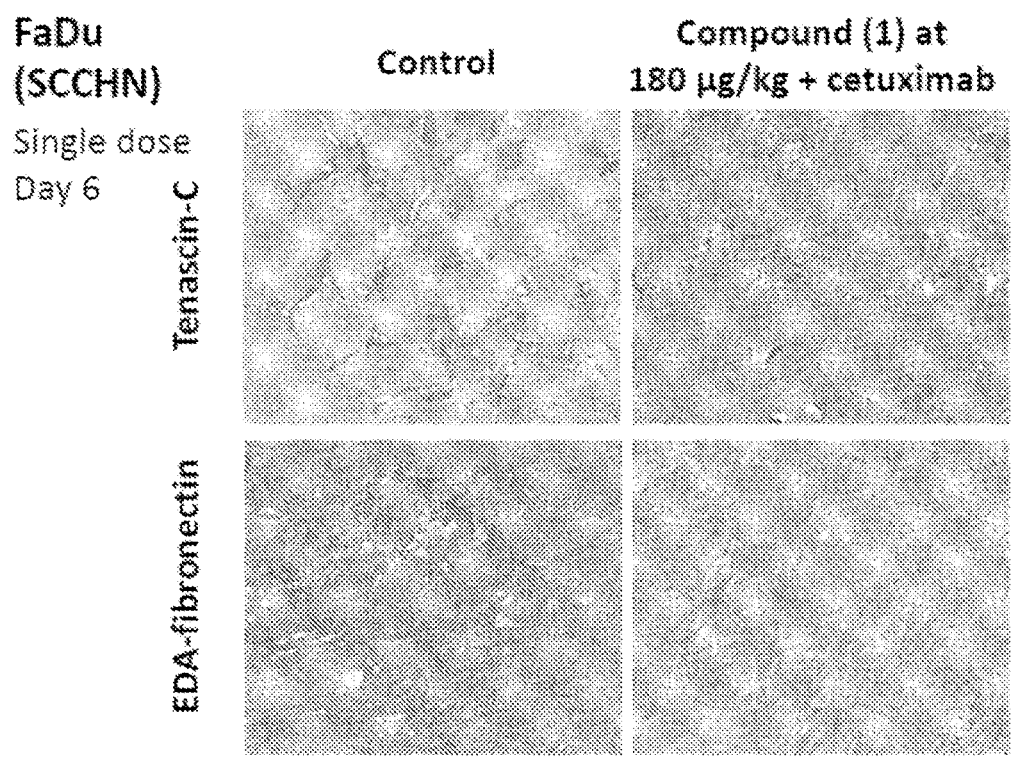
FIG. 15 shows that Compound (1) decreases ECM proteins from CAFs in FaDu subcutaneous xenograft model. FaDu xenograft tumors were collected on Day 6 after single administration of Compound (1) 180 μg/kg+cetuximab on Day 1.

Pharmacological Test Example 20. Effects on Tenascin-C and EDA-Fibronectin in the FaDu Subcutaneous Model in Mice (FIG. 15)

A human squamous cell carcinoma of the head and neck (SCCHN) cell line FaDu, which had been cultured in an RPMI-1640 medium containing 10% FBS, and penicillin-streptomycin (culture medium), was adjusted to a concentration of $5 \times 10^7$ cells/mL with culture medium to prepare a cell suspension. The cell suspension was inoculated in a volume of 100 µL into a subcutaneous part of a right flank of nude mice, 6 weeks of ages (CAnN.Cg-Foxn1nu/CrlCrlj, female, Charles River Laboratories Japan, Inc.). Ten days after cell inoculation, the mice were grouped such that averages of the tumor volumes were substantially equal among the groups. The experiment was conducted on groups each consisting of 5 mice. Compound (1) was dissolved in DMSO and a solution was stored in the freezer before use. Compound (1) (180 µg/kg) and Cetuximab (CTX, Erbitux®, Merck Serono Co. Ltd.) (10 mg/kg) was diluted with saline and intravenously injected on Day 1. Five days after the single administration, tumor samples were collected and fixed with IHC Zinc Fixative (BD Pharmingen) at 4° C. for 24 hr. Paraffin-embedded tissues were sectioned (3 µm), mounted on positively charged slides, and air-dried. Sections were deparaffinized, conditioned and the antigens were retrieved using microwave with 1 mM EDTA at pH 6.0 for Tenascin-C. For EDA-fibronectin, the antigens retrieval procedure was not necessary. Sections were incubated with BLOXALL Blocking Solution (Vector Labs) for 10 min to block endogenous peroxidase, and with Mouse on Mouse Ig Blocking Reagent (Vector Labs) for 1 hour, and then with 2.5% normal horse serum for 30 minutes. For immunohistochemical staining of Tenascin-C, mouse anti-Tenascin-C monoclonal antibody (clone 4C8MS, IBL) was applied at 5 µg/mL. Sections were incubated with the antibody overnight at 4° C. For immunohistochemical staining of EDA-fibronectin, mouse anti-EDA-fibronectin monoclonal antibody (clone IST-9, Abcam) was applied at 1.5 µg/mL. Sections were incubated with the antibody for 1 hour at room temperature. The detection was performed with Mouse On Mouse ImmPRESS™ Peroxidase Polymer Kit (Vector Labs). Sections were counterstained with Mayer's Hematoxylin (Muto Pure Chemicals) for 50 sec. Sections were dehydrated in graded ethanols, defatted in xylene replacement and covered with DPX (Merck KGaA). Immunostained slides were scanned using Vectra 2 Automated Slide Imaging System (Perkin Elmer Inc.). The expression levels of both Tenascin-C and ED-A fibronectin were reduced in the Compound (1) and CTX treated tumors compared with control tumors.

Figure 16:
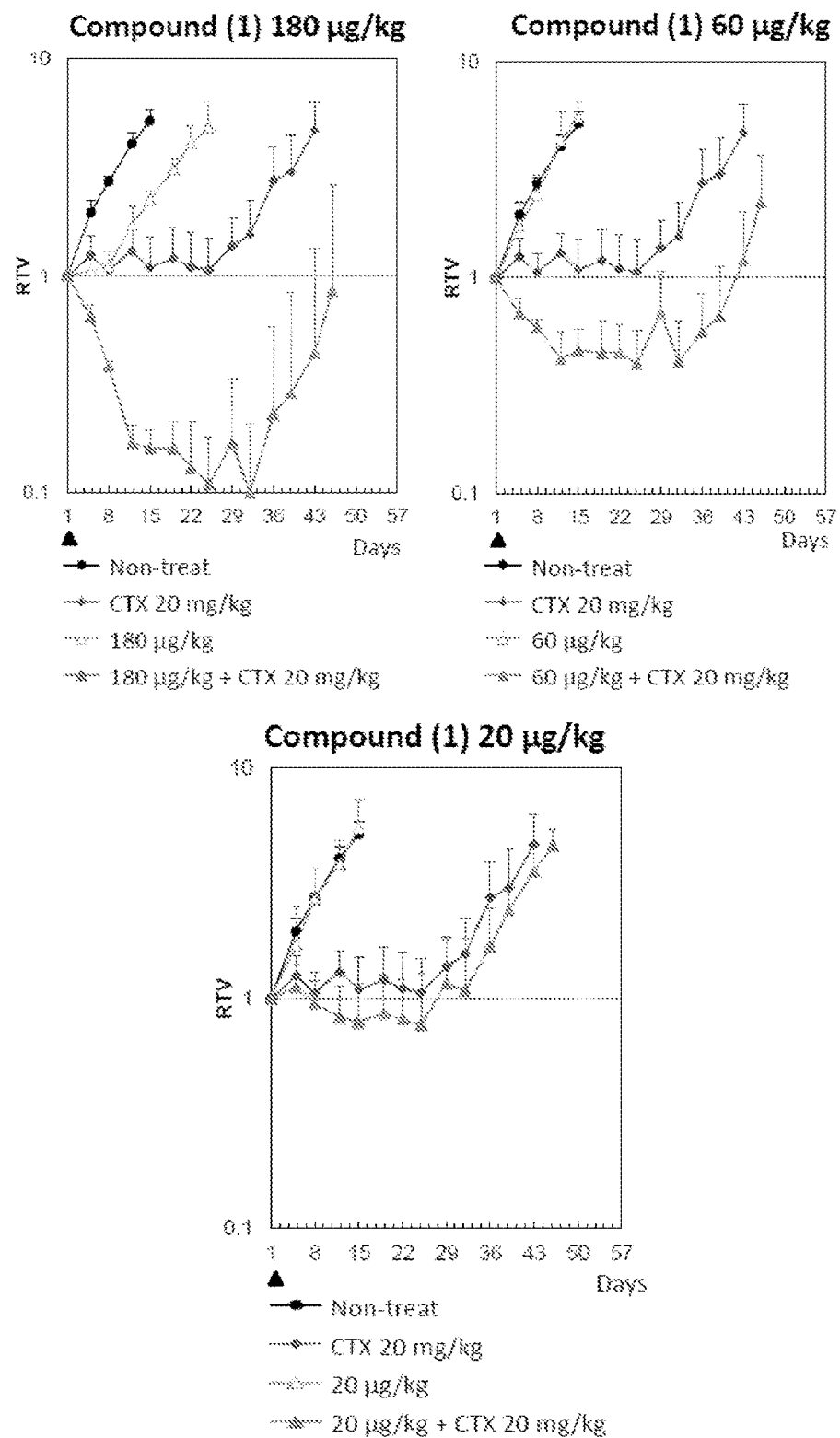
FIG. 16 shows that Compound (1) exhibits a dose-dependent combinational effect with cetuximab in a FaDu subcutaneous xenograft model. Single dose, n=6. Compound (1) and cetuximab (CTX) were administered on Day 1 in the FaDu xenograft model.

Pharmacological Test Example 21. Antitumor Effects in FaDu Subcutaneous Xenograft Model in Combination with Cetuximab in Mice (FIG. 16)

A human squamous cell carcinoma of the head and neck (SCCHN) cell line FaDu, which had been cultured in an RPMI-1640 medium containing 10% FBS, and penicillin-streptomycin, was adjusted to a concentration of $5 \times 10^7$ cells/mL with Hanks' Balanced Salt Solution to prepare a cell suspension. The cell suspension was inoculated in a volume of 100 µL into a subcutaneous part of a right flank of athymic mice (CAnN.Cg-Foxn1nu/CrlCrlj, female, 7 weeks old, Charles River Japan Inc.). Ten days after cell inoculation (Day 1), the length and the width of a tumor in each mouse were measured by using an electronic digital caliper (Mitutoyo Corporation), so as to calculate the volume of the tumor in accordance with the following calculation formula:

Tumor volume (mm³)=Longest diameter (mm)×Shortest diameter (mm)×Shortest diameter (mm)/2

Relative tumor volume (RTV)=Tumor volume (day $X$)/Tumor volume (the first day)

On the basis of TV, the mice were randomly grouped (Day 1). Each group was consisted in six mice. Compound (1) was dissolved in DMSO and a solution was stored in the freezer before use. Compound (1) (20, 60, or 180 µg/kg) and Cetuximab (CTX, Erbitux®, Merck Serono Co., Ltd.) (10 mg/kg) was diluted with saline and intravenously injected on Day 1. Changes of RTV of each group were shown in FIG. 16. At doses of 180 µg/kg and 60 µg/kg, antitumor efficacies of Compound (1) with CTX were stronger than that of CTX monotherapy with tumor regression. The antitumor efficacy of Compound (1) at doses of 20 µg/kg in combination with CTX tended to be stronger than that of CTX monotherapy.

Figure 17:
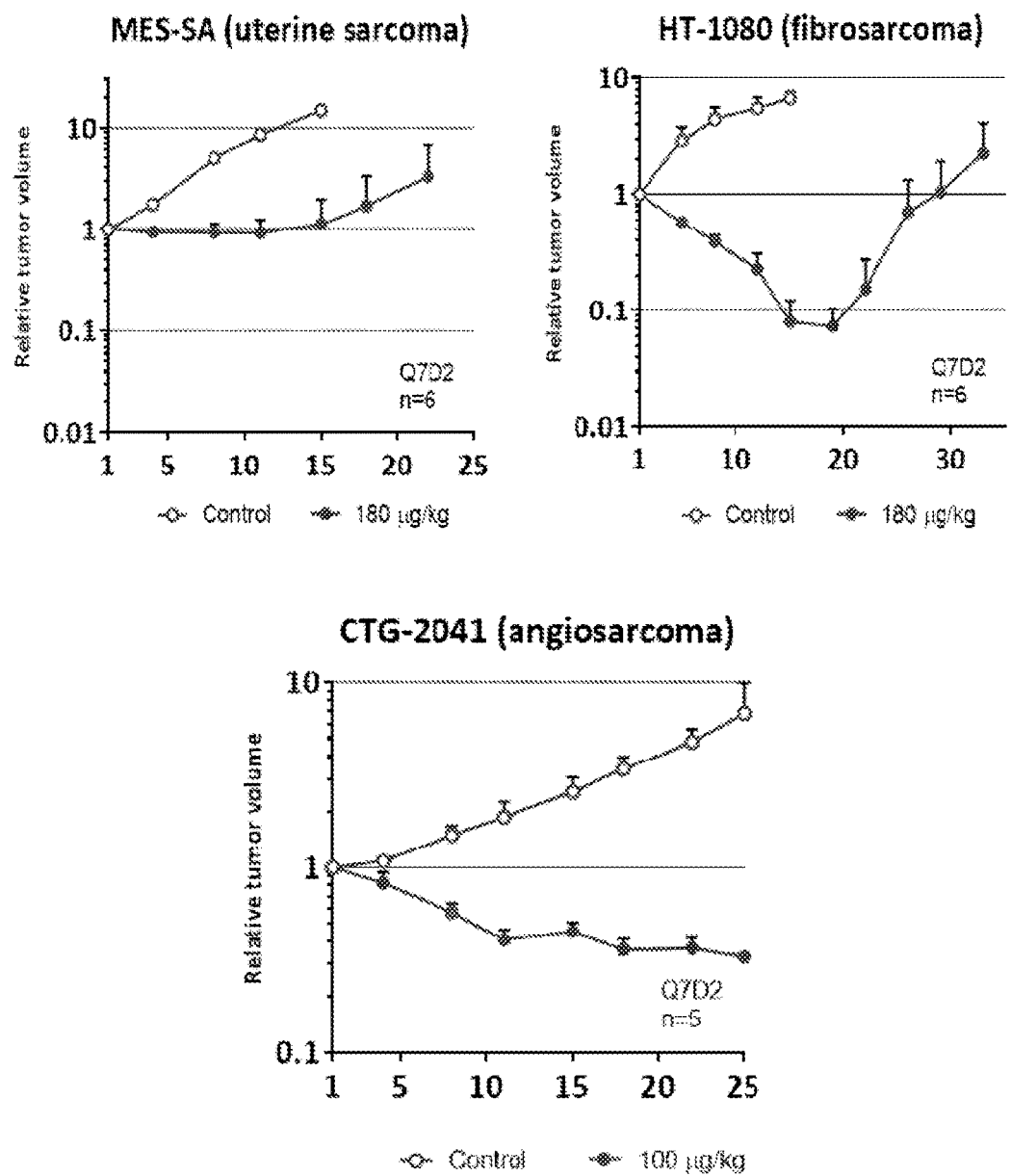
FIG. 17 shows antitumor effects in the soft tissue sarcoma xenograft models in mice as monotherapy. MES-SA (human uterine sarcoma), HT-1080 (human fibrosarcoma), and CTG-2041 (human angiosarcoma) are shown.

Pharmacological Test Example 22. Antitumor Effects in the Soft Tissue Sarcoma Xenograft Models in Mice as Monotherapy (FIG. 17)

MES-SA

A human uterine sarcoma cell line MES-SA, which had been cultured in an RPMI-1640 containing 10% FBS, and penicillin-streptomycin, was adjusted to a concentration of $2 \times 10^8$ cells/mL with Hanks' Balanced Salt Solution to prepare a cell suspension, and the suspension was mixed with Geltrex® (Thermo Fisher Scientific Inc., #A1413202) in a ratio of 1:1 to prepare a cell suspension in a concentration of $1 \times 10^8$ cells/mL. The cell suspension was inoculated in a volume of 100 µL into a subcutaneous part of a right flank of nude mice, 6 weeks of ages (CAnN.Cg-Foxn1nu/CrlCrlj, female, Charles River Laboratories Japan Inc.). Six days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)×
Shortest diameter (mm)×Shortest diameter
(mm)/2

Relative tumor volume (RTV)=Tumor volume (day
$X$)/Tumor volume (the first day)

On the basis of the volumes of tumors obtained on Day 1, the mice were grouped such that averages of the tumor volumes were substantially equal among the groups. The experiment was conducted on groups each consisting of 6 mice. The test compound was dissolved in DMSO and a solution was stored in the freezer before use. Immediately before the administration, the stock solution was diluted with saline. The test compound in saline was intravenously once-weekly administered at 180 μg/kg for 2 weeks (on Day 1 and Day 8). The antitumor activity was observed with tumor growth delay in the treated group.

HT-1080

A human fibrosarcoma cell line HT-1080, which had been cultured in an E-MEM containing 10% FBS, NEAA and antibiotics was adjusted to a concentration of 3×10$^7$ cells/mL with medium to prepare a cell suspension. The cell suspension was inoculated in a volume of 100 μL into a subcutaneous part of a right flank of athymic mice (CAnN.Cg-Foxn1nu/CrlCrlj, female, 6 weeks old, Charles River Japan Inc.). Six days after cell inoculation (Day 1), the length and the width of a tumor in each mouse were measured by using an electronic digital caliper (Mitutoyo Corporation), so as to calculate the volume of the tumor in accordance with the following calculation formula:

Tumor volume (mm$^3$)=Longest diameter (mm)×
Shortest diameter (mm)×Shortest diameter
(mm)/2

Relative tumor volume (RTV)=Tumor volume (day
$X$)/Tumor volume (the first day)

On the basis of TV, the mice were randomly grouped (Day 1). Each group was consisted in six mice. Compound (1) was dissolved in DMSO and a solution was stored in the freezer before use. Compound (1) (180 μg/kg) was diluted with saline and intravenously injected on Day 1 and Day 8. Changes of RTV of each group was shown in FIG. 17. The antitumor activity was observed with tumor regression in the treated group.

CTG-2041

Tumor fragments of human angiosarcoma CTG-2041 were implanted s.c. in the left flank of female mice. Tumor growth was monitored twice a week using digital caliper, so as to calculate the volume of the tumor in accordance with the following calculation formula:

Tumor volume (mm$^3$)=Longest diameter (mm)×
Shortest diameter (mm)×Shortest diameter
(mm)/2

Relative tumor volume (RTV)=Tumor volume (day
$X$)/Tumor volume (the first day)

When the volume of tumors reached approximately 200 mm$^3$, animals are matched by tumor volume into treatment or control groups and dosing initiated on Day 1. Each group was consisted with five mice. Compound (1) was dissolved in DMSO and a solution was stored in the freezer before use. Compound (1) (100 μg/kg) diluted in saline and intravenously injected on Day 1 and Day 8. Changes of RTV of each group were shown in FIG. 17. The antitumor activity was observed with tumor regression in the treated group.

Figure 18:
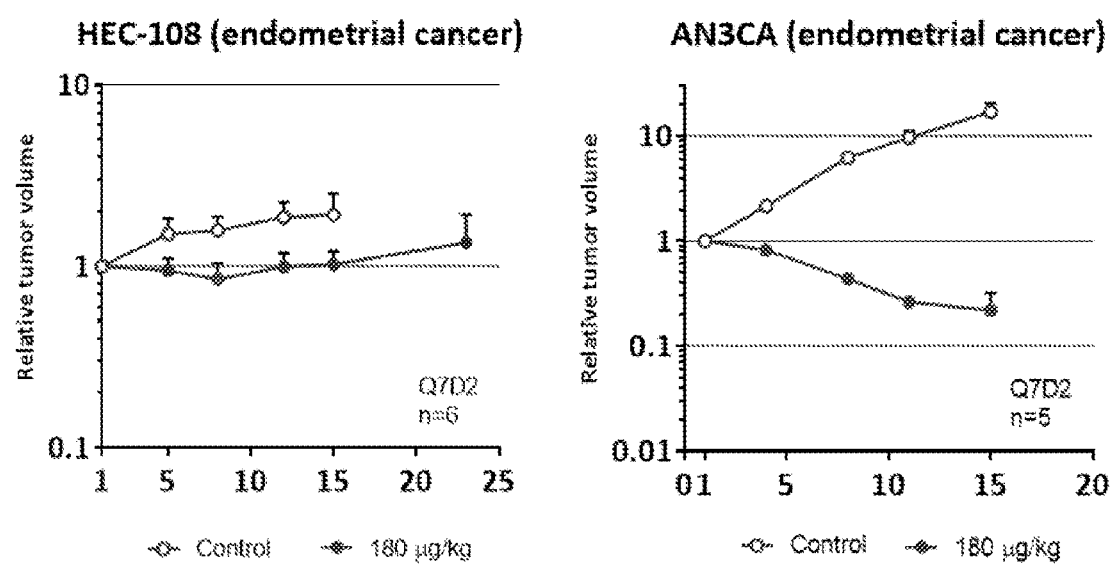
FIG. 18 shows antitumor effects in endometrial cancer xenograft models in mice as monotherapy. HEC-108 and AN3CA (endometrial cancer) are shown.

Pharmacological Test Example 23. Antitumor Effects in the Endometrial Cancer Sarcoma Xenograft Models in Mice as Monotherapy (FIG. 18)

HEC-108

A human endometrial cancer cell line HEC-108, which had been cultured in an E-MEM containing 15% FBS and antibiotics were adjusted to a concentration of 7.14×10$^7$ cells/mL with medium to prepare a cell suspension. The cell suspension was inoculated in a volume of 150 μL into a subcutaneous part of a right flank of athymic mice (CAnN.Cg-Foxn1nu/CrlCrlj, female, 6 weeks old, Charles River Japan Inc.). Thirteen days after cell inoculation (Day 1), the length and the width of a tumor in each mouse were measured by using an electronic digital caliper (Mitutoyo Corporation), so as to calculate the volume of the tumor in accordance with the following calculation formula:

Tumor volume (mm$^3$)=Longest diameter (mm)×
Shortest diameter (mm)×Shortest diameter
(mm)/2

Relative tumor volume (RTV)=Tumor volume (day
$X$)/Tumor volume (the first day)

On the basis of TV, the mice were randomly grouped (Day 1). Each group was consisted in six mice. Compound (1) was dissolved in DMSO and a solution was stored in the freezer before use. Compound (1) (180 μg/kg) was diluted in saline and intravenously injected on Day 1 and Day 8. Changes of RTV of each group was shown in FIG. 18. The antitumor activity was observed with tumor growth delay in the treated group.

AN3CA

A human endometrial cancer cell line AN3CA, which had been cultured in an E-MEM containing 10% FBS, and penicillin-streptomycin, was adjusted to a concentration of 1.4×10$^8$ cells/mL with Hanks' Balanced Salt Solution to prepare a cell suspension, and the suspension was mixed with Geltrex© (Thermo Fisher Scientific Inc., #A1413202) in a ratio of 1:1 to prepare a cell suspension in a concentration of 7×10$^7$ cells/mL. The cell suspension was inoculated in a volume of 100 μL into a subcutaneous part of a right flank of nude mice, 6 weeks of ages (CAnN.Cg-Foxn1nu/CrlCrlj, female, Charles River Laboratories Japan Inc.). Twelve days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)×
Shortest diameter (mm)×Shortest diameter
(mm)/2

Relative tumor volume (RTV)=Tumor volume (day
$X$)/Tumor volume (the first day)

On the basis of the volumes of tumors obtained on Day 1, the mice were grouped such that averages of the tumor volumes were substantially equal among the groups. The experiment was conducted on groups each consisting of five mice. The test compound was dissolved in DMSO and a solution was stored in the freezer before use. Immediately before the administration, the stock solution was diluted with saline. The test compound in saline was intravenously once-weekly administered at 180 µg/kg for 2 weeks (on Day 1 and Day 8). The antitumor activity was observed with tumor regression in the treated group.

Pharmacological Test Example 24. Growth Inhibition in NCI-H23, HCC1954, and MES-SA Cell Lines NCI-H23 Growth Inhibition Assay In this assay, the growth inhibitory activities of Compound D-6 (Example 26), E-2, G-4, H-2, I-2, J-1, K-2, L-6, M-3, and N-1 in a human lung cancer cell line NCI-H23 were measured. NCI-H23 cells were maintained in RPM-1640 (Wako Pure Chemical Industries, Ltd., 187-02021) medium containing 10% fetal bovine serum (FBS: Sigma, 172012), and penicillin and streptomycin (Wako Pure Chemical Industries, Ltd., 168-23191) in a 5% $C_{O2}$ incubator (37° C.). To each well of a 96 well plate (Becton, Dickinson and Company, 353219), 75 µL of NCI-H23 cell suspension adjusted to a concentration of $4\times10^4$ cells/mL with the culture medium was added, and the cells were incubated overnight in a 5% $CO_2$ incubator (37° C.). On the next day, 25 µL of each compound in three-fold dilution series suspended in the culture medium was added to each well, and the resultant was incubated for 3 days in a 5% $CO_2$ incubator (37° C.). Then, cell viability was determined by CellTiter-Glo® Luminescent Cell Viability Assay (Promega) with EnVision 2103 Multilabel Reader (Perkin-Elmer, Wellesley, Mass.). Value of the wells containing cells without adding the test substance was defined as 100% and the value of the wells containing no cells was defined as 0%. The concentration of the test substance necessary for inhibiting the cell growth by 50% (i.e., an $IC_{50}$ value) was calculated, and summarized in Table 14.

HCC1954 Growth Inhibition Assay

In this assay, the growth inhibitory activities of Compound D-6 (Example 26), E-2, G-4, H-2, I-2, J-1, K-2, L-6, M-3, and N-1 in a human breast cancer cell line HCC1954 were measured. HCC1954 cells were maintained in RPMI-1640 medium modified to contain 2 mM L-glutamine, 10 mM HEPES, 1 mM sodium pyruvate, 4500 mg/L glucose, and 1500 mg/L sodium bicarbonate (ATCC 30-2001) containing 10% fetal bovine serum (FBS: Sigma, 172012), and penicillin and streptomycin (Wako Pure Chemical Industries, Ltd., 168-23191) in a 5% $CO_2$ incubator (37° C.). To each well of a 96 well plate (Becton, Dickinson and Company, 353219), 75 µL of HCC1954 cell suspension adjusted to a concentration of $4\times10^4$ cells/mL with the culture medium was added, and the cells were incubated overnight in a 5% $CO_2$ incubator (37° C.). On the next day, 25 µL of each compound in three-fold dilution series suspended in the culture medium was added to each well, and the resultant was incubated for 3 days in a 5% $CO_2$ incubator (37° C.). Then, cell viability was determined by CellTiter-Glo® Luminescent Cell Viability Assay (Promega) with EnVision 2103 Multilabel Reader (Perkin-Elmer, Wellesley, Mass.). Value of the wells containing cells without adding the test substance was defined as 100% and the value of the wells containing no cells was defined as 0%. The concentration of the test substance necessary for inhibiting the cell growth by 50% (i.e., an $IC_{50}$ value) was calculated, and summarized in Table 14.

MES-SA Growth Inhibition Assay

In this assay, the growth inhibitory activities of Compound D-6 (Example 26), E-2, G-4, H-2, I-2, J-1, K-2, L-6, M-3, and N-1 in a human lung cancer cell line MES-SA were measured. MES-SA cells were maintained in RPM-1640 (Wako Pure Chemical Industries, Ltd., 187-02021) medium containing 10% fetal bovine serum (FBS: Sigma, 172012), and penicillin and streptomycin (Wako Pure Chemical Industries, Ltd., 168-23191) in a 5% $CO_2$ incubator (37° C.). To each well of a 96 well plate (Becton, Dickinson and Company, 353219), 75 µL of MES-SA cell suspension adjusted to a concentration of $4\times10^4$ cells/mL with the culture medium was added, and the cells were incubated overnight in a 5% $CO_2$ incubator (37° C.). On the next day, 25 µL of each compound in three-fold dilution series suspended in the culture medium was added to each well, and the resultant was incubated for 3 days in a 5% $CO_2$ incubator (37° C.). Then, cell viability was determined by CellTiter-Glo® Luminescent Cell Viability Assay (Promega) with EnVision 2103 Multilabel Reader (Perkin-Elmer, Wellesley, Mass.). Value of the wells containing cells without adding the test substance was defined as 100% and the value of the wells containing no cells was defined as 0%. The concentration of the test substance necessary for inhibiting the cell growth by 50% (i.e., an $IC_{50}$ value) was calculated, and summarized in Table 14.

TABLE 14

| Compound | Cell growth inhibition $IC_{50}$ (nM) | | |
|---|---|---|---|
|  | NCI-H23 | HCC1954 | MES-SA |
| Compound D-6 (Example 26) | 0.0220 | 0.0104 | 0.0138 |
| Compound E-2 | 0.595 | 0.0805 | 0.856 |
| Compound G-4 | 0.136 | 0.0335 | 0.326 |
| Compound H-2 | 0.286 | 0.123 | 0.146 |
| Compound I-2 | 0.103 | 0.00624 | 0.0570 |
| Compound J-1 | 0.00992 | 0.00308 | 0.0102 |
| Compound K-2 | 0.461 | 0.0700 | 0.341 |
| Compound L-6 | 6.81 | 0.269 | 2.79 |
| Compound M-3 | 0.0199 | 0.0101 | 0.0141 |
| Compound N-1 | 1.53 | 0.0800 | 2.88 |

Figure 19A:
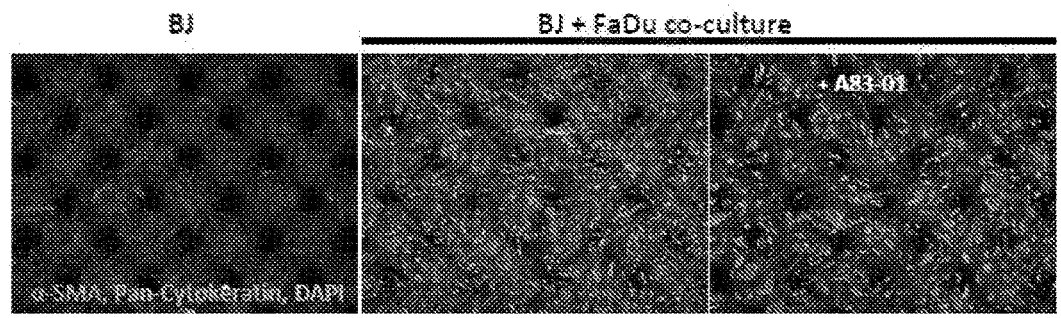
FIGS. 19A-19H show that Compound (1) reduced TGF-β-induced α-SMA expression in an in vitro CAF-inducing system.
Figures 19B, 19C, 19D, 19E:
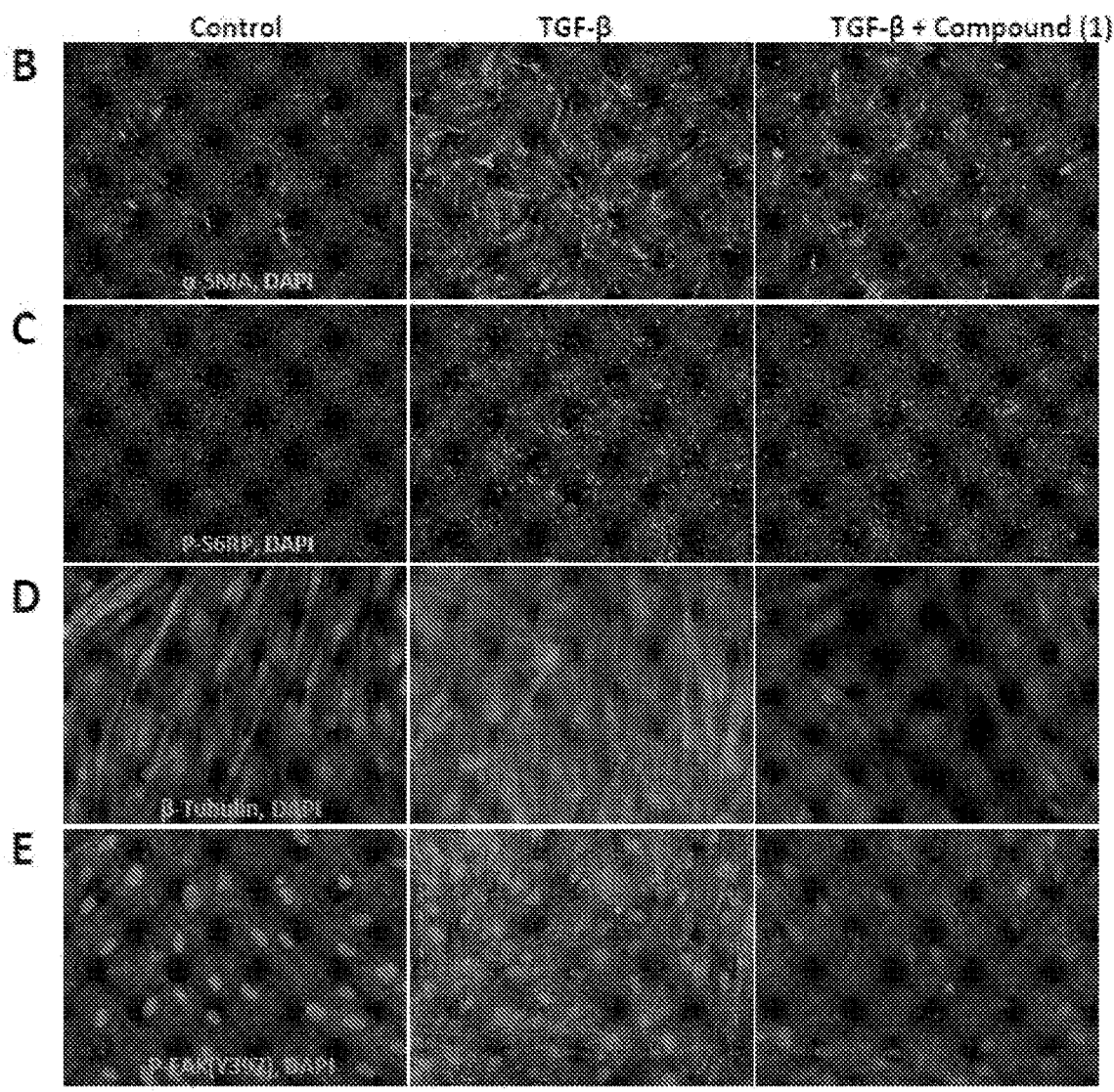
Figure 19F:
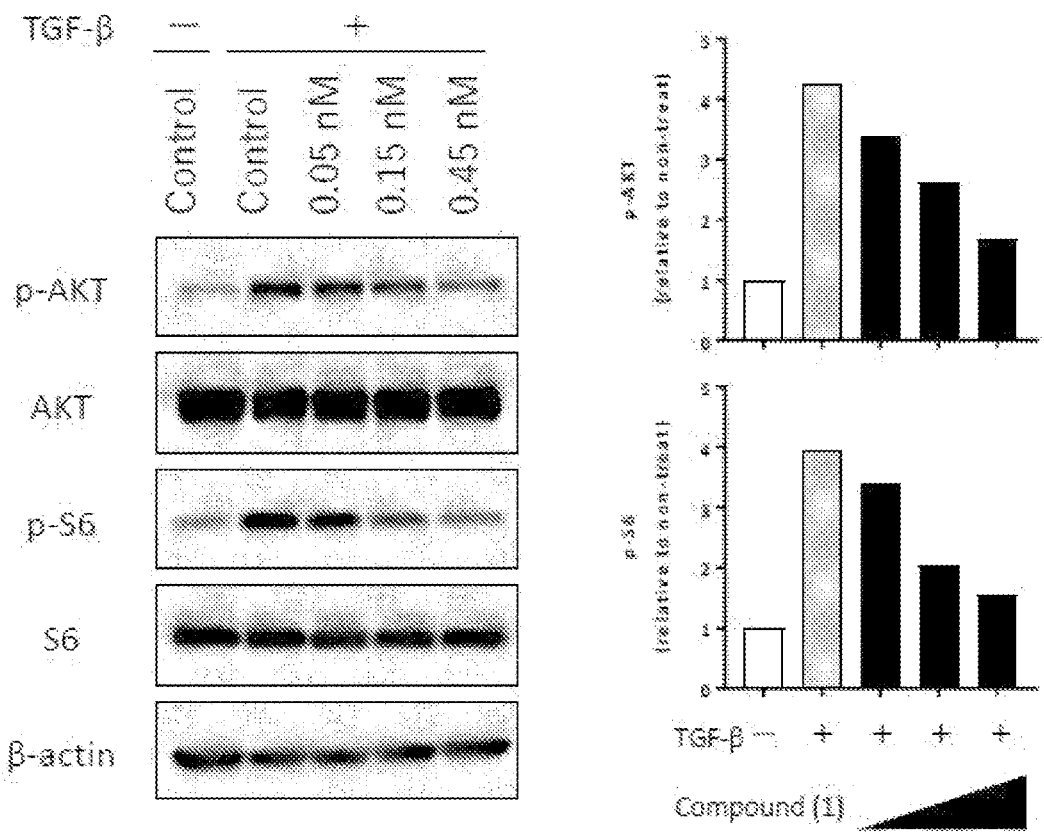
Figure 20A:
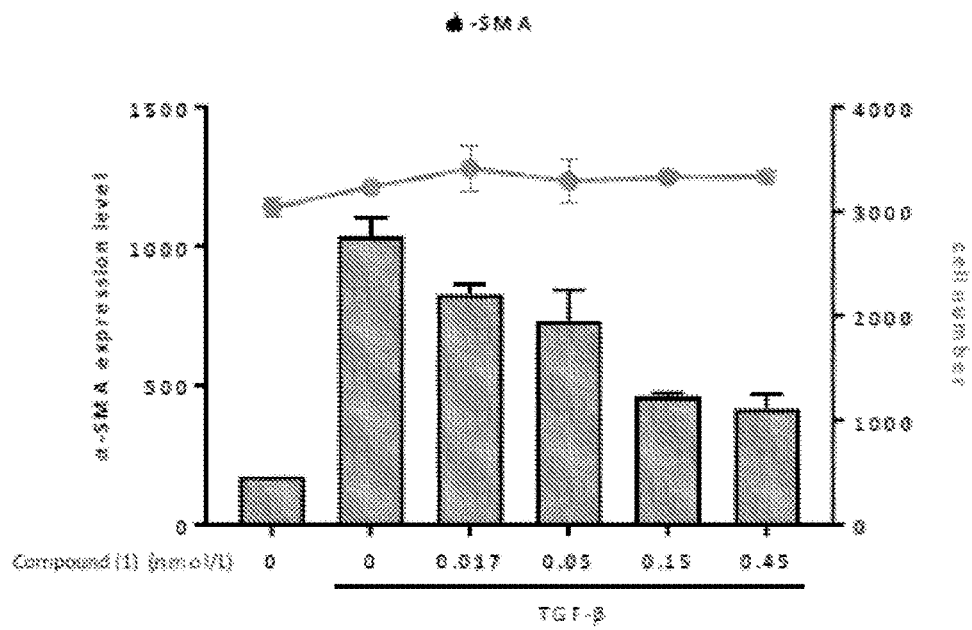
FIGS. 20A and 20B. Quantification of immunofluorescence images of BJ cells treated with TGF-β (1 ng/mL) and the indicated concentrations of Compound (1) for α-SMA (FIG. 20A), Phospho-S6-ribosomal protein (Ser235/236) (FIG. 20B).
Figure 20B:
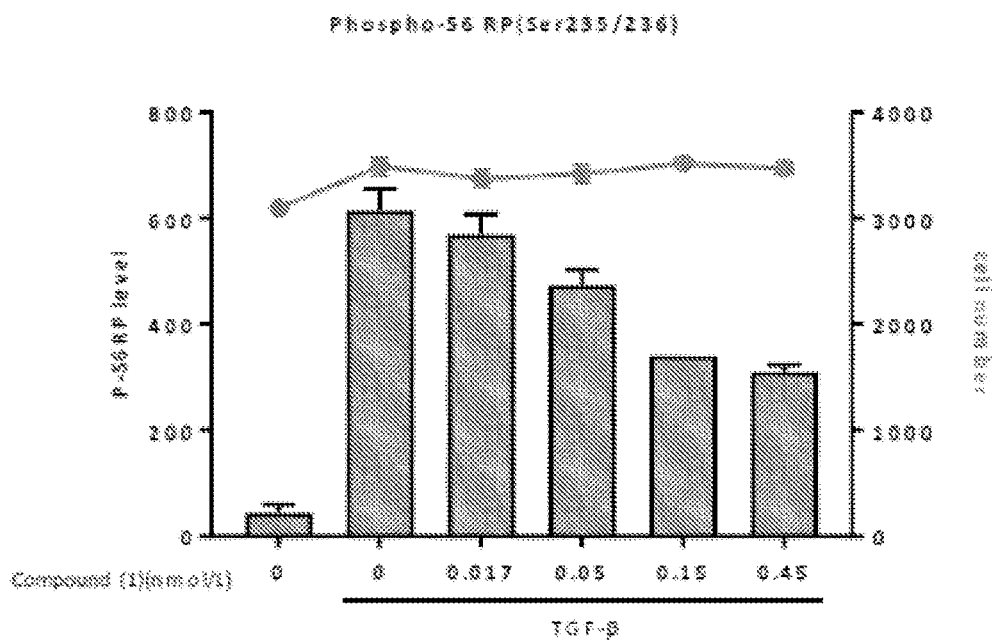
Figure 20C:
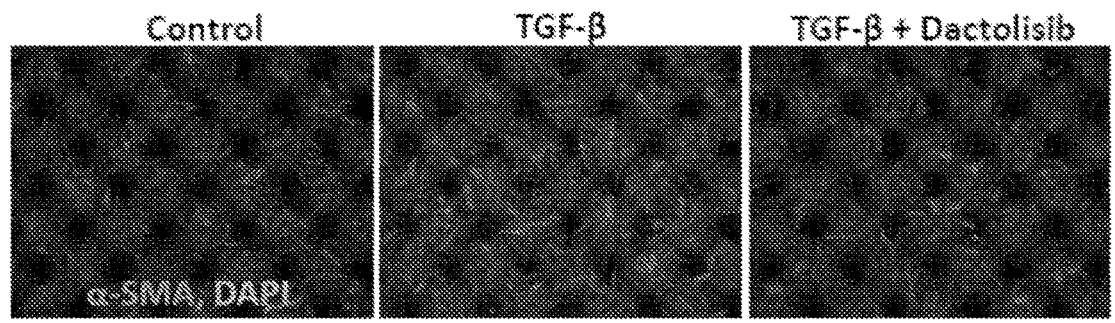
FIG. 20C. Immunofluorescence analysis of BJ cells treated with TGF-β in the absence or presence of dactolisib, a phosphatidylinositol 3 kinase inhibitor.

Pharmacological Test Example 25. Molecular Mechanisms of the α-SMA-Positive CAF Reduction Using an In Vitro Culture System The expression of α-SMA was induced in BJ normal human fibroblasts upon co-cultivation with FaDu cells, and the expression was attenuated by treatment with A83-01, a potent selective inhibitor of the TGF-β-receptor (FIG. 19A). These results suggested that TGF-β plays a major role as a mediator of α-SMA induction in this system. In addition, immunofluorescence analysis revealed that treatment with Compound (1) interfered with a-SMA induction by TGF-β in BJ cells without growth inhibitory activity (FIG. 19A, FIG. 20A).

Figures 19G, 19H:
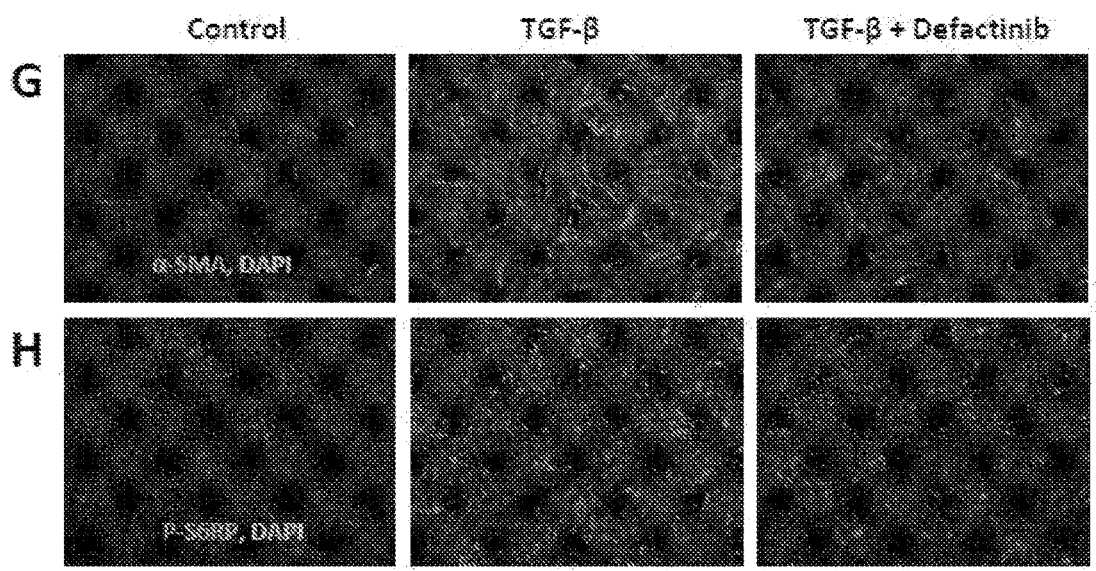
Figure 20D:
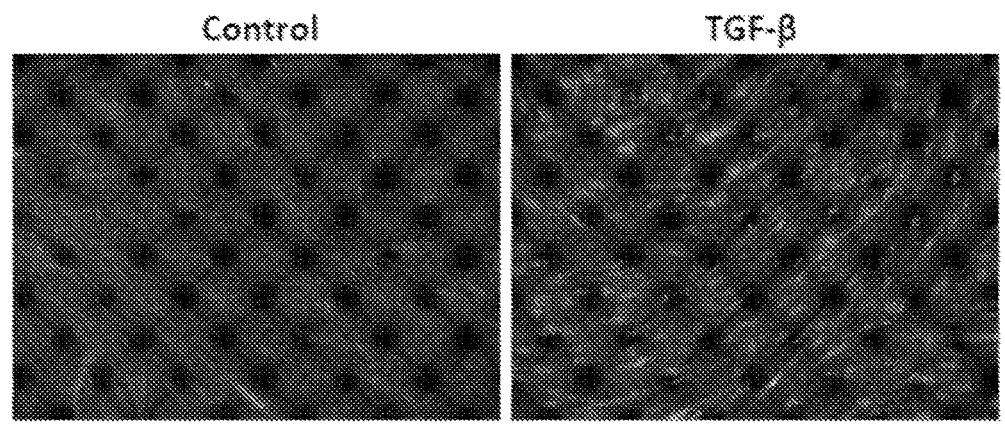
FIG. 20D. Immunofluorescence analysis of phosphorylated Smad2/3 in BJ cells pretreated with Compound (1) (72 hours) after 30 minutes of stimulation with TGF-β. Acetylated-α-tubulin was co-stained to confirm the activity of Compound (1).
Figure 20D:
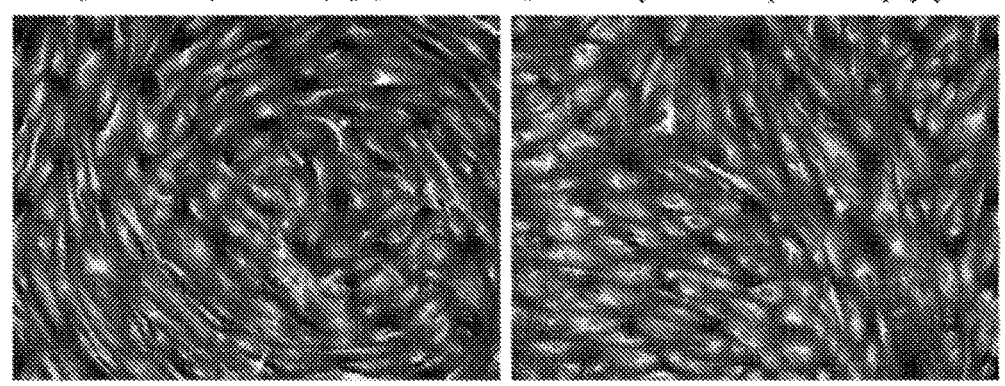
Figure 20E:
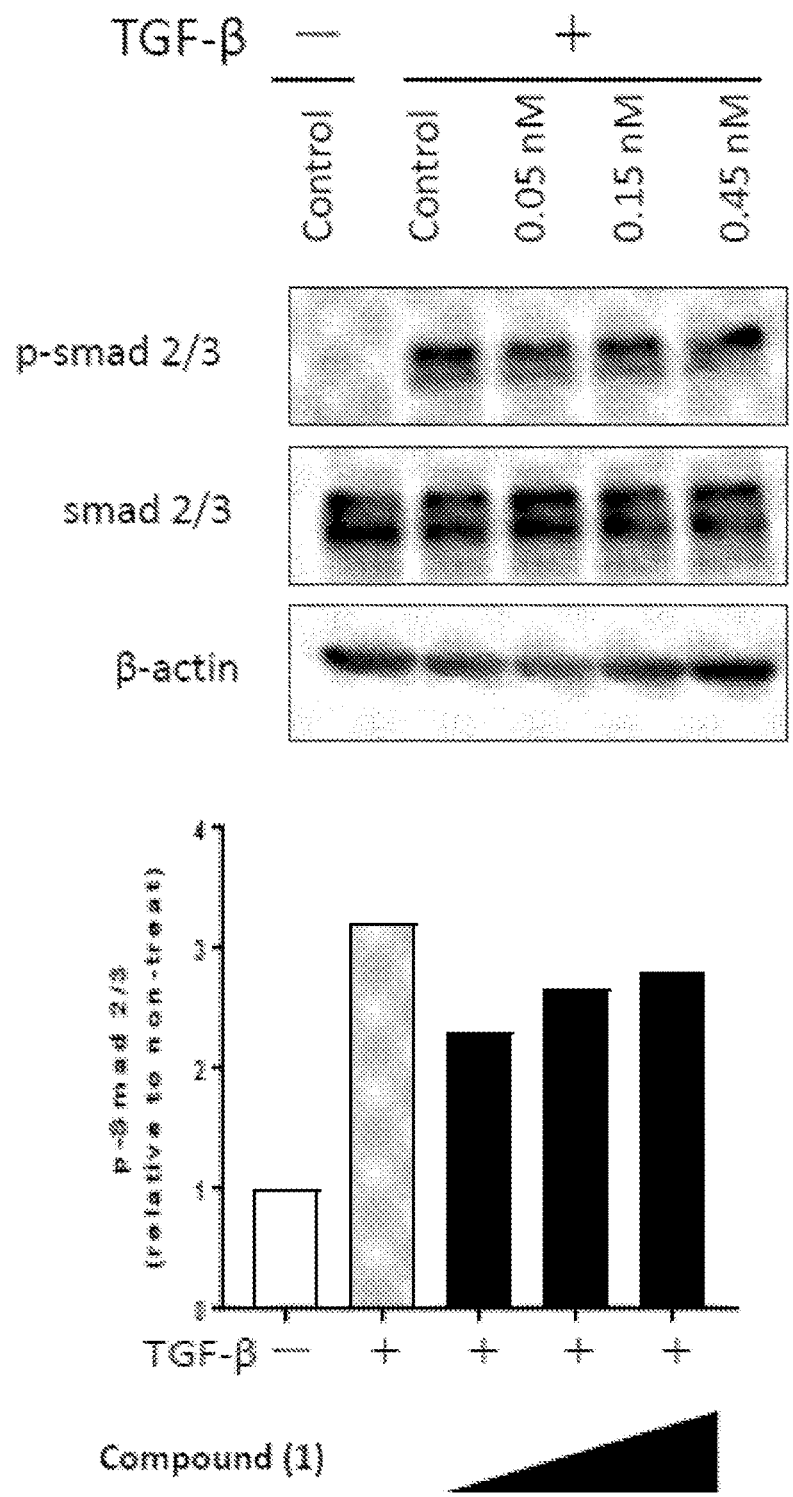
FIG. 20E. Western blot analysis of Smad2/3 in BJ cells treated with TGF-β and the indicated concentrations of Compound (1). The lens magnification used was ×4 (FIG. 20C) or ×40 (FIG. 20D).
Figure 21A:
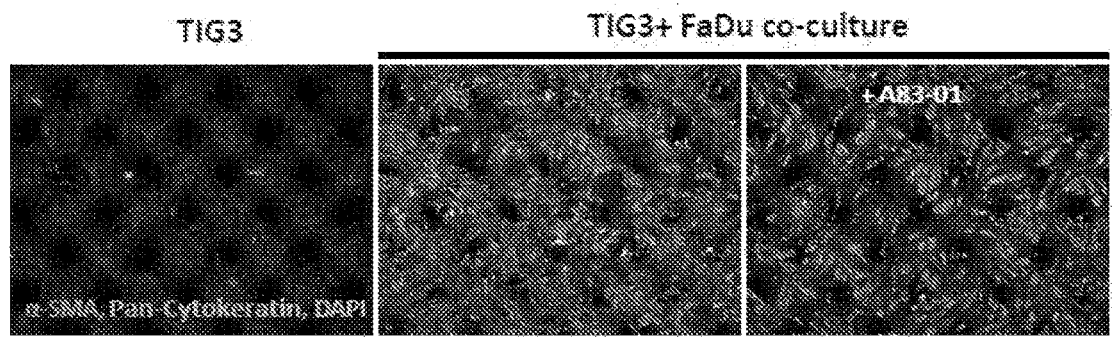
FIG. 21A. Immunofluorescence staining of α-SMA (red color) and pan-cytokeratin (green color) in TIG3 co-cultured with FaDu in the absence or presence of A83-01, an FAK inhibitor.
Figure 21B:
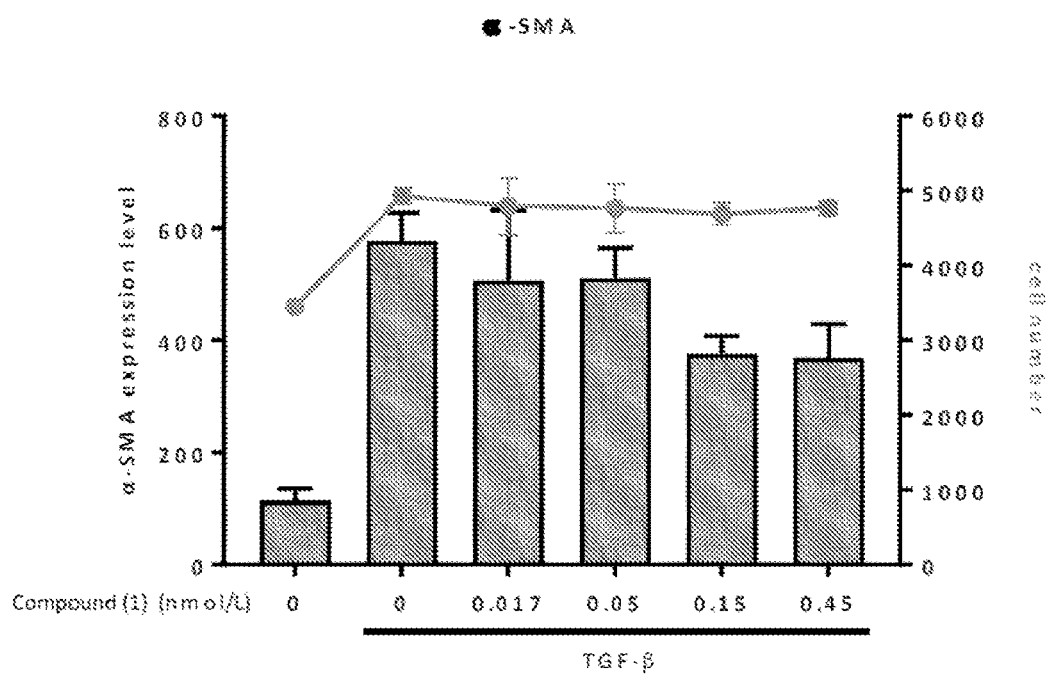
FIGS. 21B and 21C. Quantification of immunofluorescence images of TIG3 cells treated with TGF-β and the indicated concentrations of Compound (1) for α-SMA (FIG. 21B), Phospho-S6-ribosomal protein (Ser235/236) (FIG. 21C).
Figure 21C:
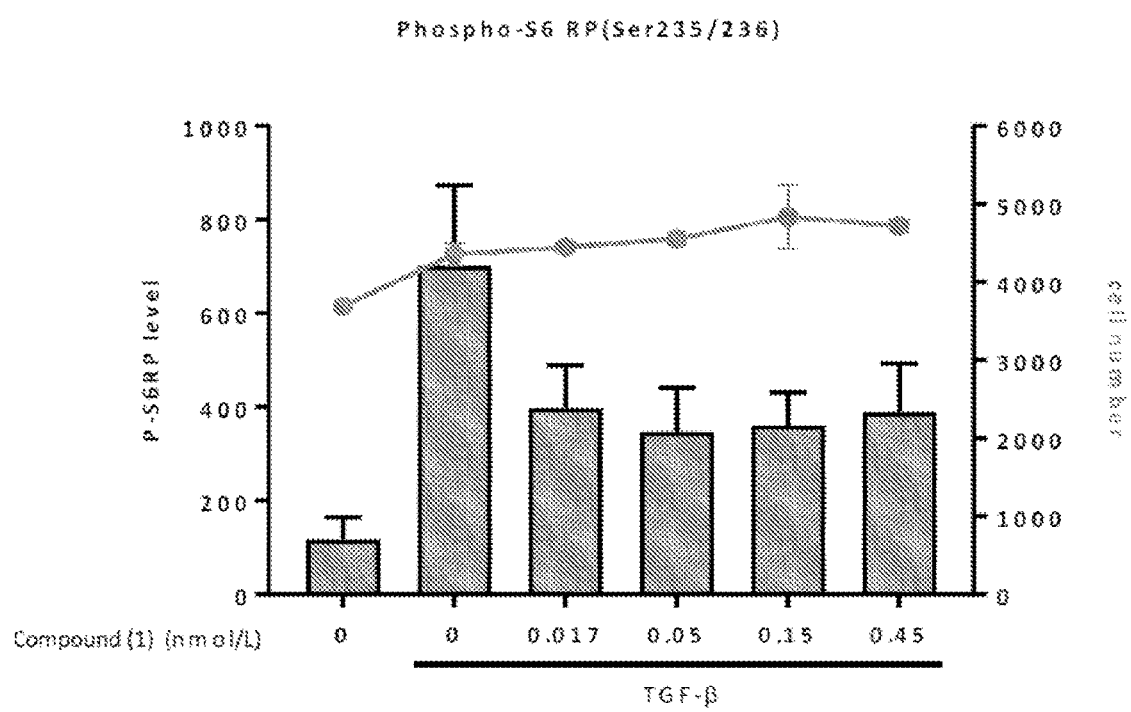
Figures 21D, 21E:
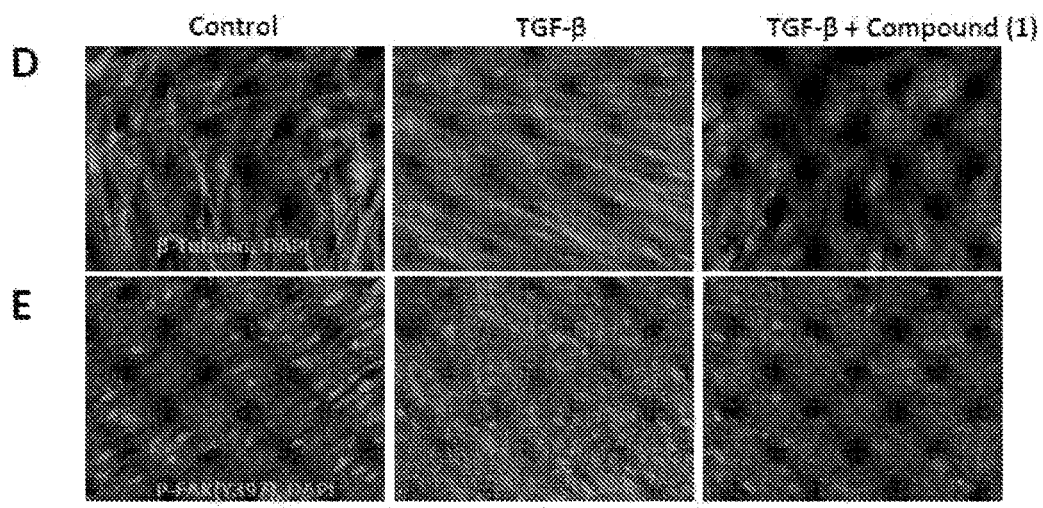
FIGS. 21D and 21E. Immunofluorescence analysis of TIG3 cells treated with TGF-β in the absence or presence of Compound (1) for β-tubulin (FIG. 21D), Phospho-FAK (Tyr397) (FIG. 21E).
Figure 21F:
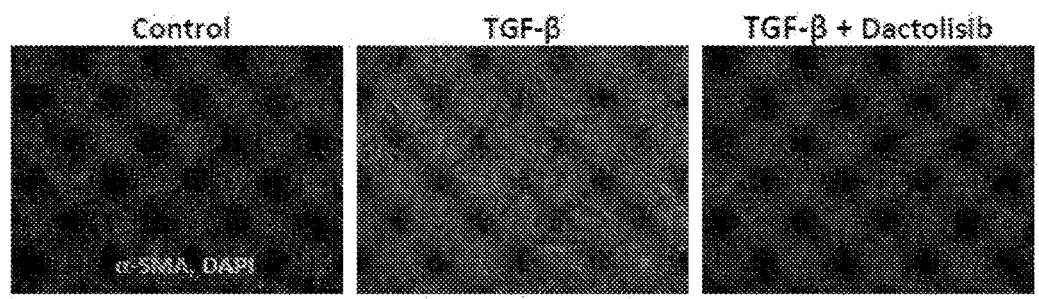
FIG. 21F Immunofluorescence analysis of TIG3 cells treated with TGF-β in the absence or presence of dactolisib 100 nmol/L for α-SMA.
Figures 21G, 21H:
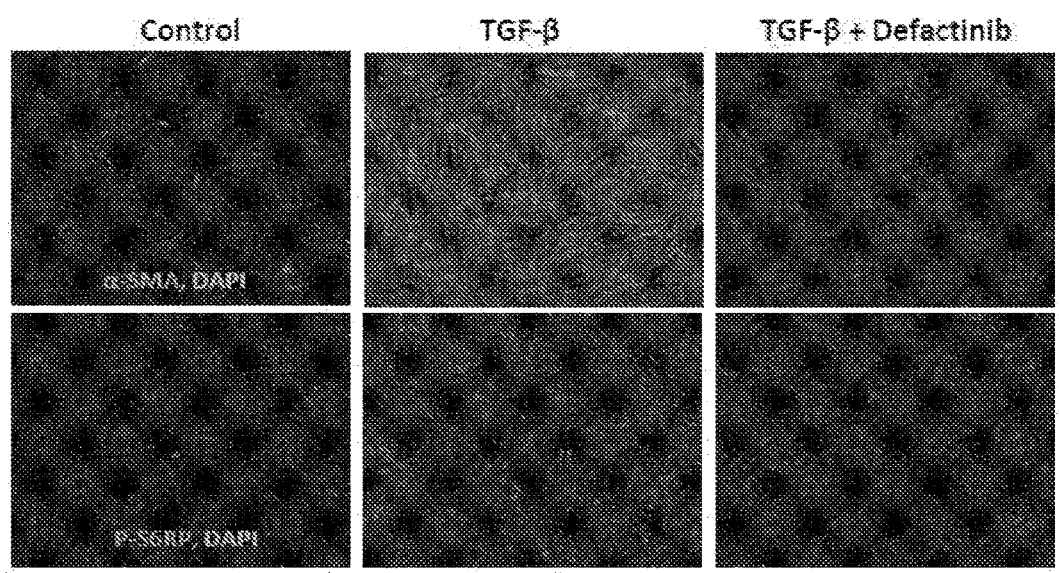
FIGS. 21G and 21H. Immunofluorescence analysis of TIG3 cells treated with TGF-β in the absence or presence of defactinib 3 μmol/L for α-SMA (FIG. 21G), Phospho-S6-ribosomal protein (Ser235/236) (FIG. 21H). The lens magnification was ×4 (FIGS. 21A, 21F-21H) or ×40 (FIGS. 21D and 21E).

Compound (1) did not significantly change the TGF-β-induced phosphorylation and nuclear localization of Smad2/3 (FIGS. 20D-20E), but it did reduce the activation of the PI3K/AKT/mTOR pathway, which plays essential roles in TGF-β-induced α-SMA expression (FIGS. 19C and 19F, FIGS. 20B-20C). Moreover, TGF-§ treatment enhanced P-tubulin expression and microtubule network formation, which were diminished by co-treatment with Compound (1) in BJ cells (FIG. 19D). Under the same experimental conditions, the enhanced formation of focal adhesions, which were detected as punctate structures with an antibody against phosphorylated FAK at tyrosine-397, after stimulation with TGF-β was decreased in BJ cells by treatment with Compound (1) (FIG. 19E). Many signalling complexes are assembled in focal adhesion sites, and those complexes dispatch several downstream signals, including those involved in the PI3K/AKT/mTOR pathway. See, e.g., Sulzmaier et. al. "FAK in cancer: mechanistic findings and clinical applications", *Nature Reviews Cancer* 2014, 14, 598-610. In fact, treatment with defactinib, an FAK inhibitor, clearly decreased the level of α-SMA expression as well as S6 ribosomal protein phosphorylation induced by TGF-β in BJ cells (FIGS. 19G-19H). All of the abovementioned phenomena were also observed in other normal human fibroblasts (TIG3 cells) (FIGS. 21A-21H).

Pharmacological Test Example 26. Bladder Carcinoma Cell Lines Growth Inhibition Assay In this assay, the growth inhibitory activity of Compound (1) in human bladder carcinoma cell lines RT4, RT112/84, and UM-UC-3 was measured. RT4 and RT112/84 cells were maintained in a RPMI-1640 (FUJIFILM Wako Pure Chemical Corporation, 189-02025) medium containing 10% fetal bovine serum (FBS: SIGMA Life Science, 172012-500ML), and penicillin and streptomycin (FUJIFILM Wako Pure Chemical Corporation, 168-23191) in a 5% $CO_2$ incubator (37° C.). UM-UC-3 cells were maintained in an E-MEM (FUJIFILM Wako Pure Chemical Corporation, 051-07615) medium containing 10% FBS, 1 mM Sodium Pyruvate (FUJIFILM Wako Pure Chemical Corporation, 190-14881), and penicillin and streptomycin in a 5% $CO_2$ incubator (37° C.). To each well of a 96 well plate (Corning, 3904), 90 μL of each cell suspension adjusted to a concentration of $5.55\times10^3$ cells/mL (RT4 or UM-UC-3) or $3.33\times10^4$ cells/mL (RT112/84) with the culture medium was added, and the cells were incubated overnight in a 5% $CO_2$ incubator (37° C.). On the next day, 10 μL of Compound (1) in three-fold dilution series suspended in the culture medium was added to each well, and the resultant was incubated for 3 days in a 5% $CO_2$ incubator (37° C.). Then, cell viability was determined by CellTiter-Glo® 2.0 Assay (Promega Corporation, G9243) with ARVO-X4 Multimode Plate Reader (Perkin-Elmer, Wellesley, Mass.). Value of the wells containing cells without adding the test compounds was defined as 100% and the value of the wells containing no cells was defined as 0%. The concentrations of the test compound necessary for inhibiting the cell growth by 50% (i.e., an $IC_{50}$ value) was calculated, and shown in Table 15.

TABLE 15

| Test compound | ($IC_{50}$ (nM)) | | |
|---|---|---|---|
| | RT4 | RT112/84 | UM-UC-3 |
| Compound (1) | 0.110 | 0.0497 | 0.512 |

Figure 22:
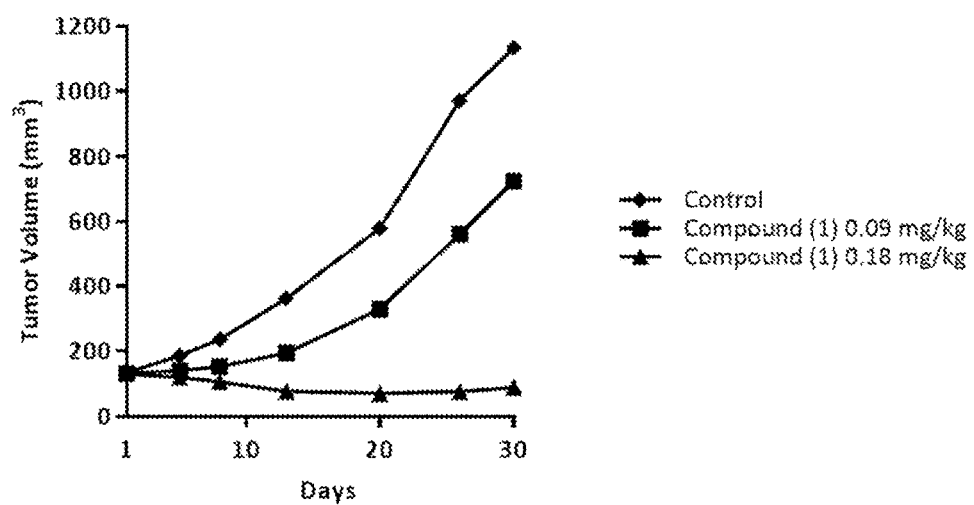
FIG. 22. Antitumor effect of Compound (1) in an HS-SY-II (human synovial sarcoma) xenograft model in mice as a monotherapy.

Pharmacological Test Example 27. Antitumor Effect in the HS-SY-II Xenograft Model in Mice as Monotherapy (FIG. 22)

A human synovial sarcoma cell line HS-SY-II, which had been cultured in a DMEM containing 10% FBS, and penicillin-streptomycin, was adjusted to a concentration of $1\times10^8$ cells/mL with 50% Geltrex (Thermo Fisher Scientific) in Hanks' Balanced Salt Solution to prepare a cell suspension. The cell suspension was inoculated in a volume of 100 μL into a subcutaneous part of a right flank of nude mice, 5 weeks of ages (CAnN.Cg-Foxn1nu/CrlCrlj, female, Charles River Laboratories Japan Inc.). Thirty days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume ($mm^3$)=Longest diameter (mm)× Shortest diameter (mm)×Shortest diameter (mm)/2

Relative tumor volume (RTV)=Tumor volume (day X)/Tumor volume (the first day)

Relative body weight (RBW)=Body weight (day X)/Body weight (the first day)

On the basis of the volumes of tumors obtained on Day 1, the mice were grouped such that averages of the tumor volumes were substantially equal among the groups. The experiment was conducted on groups each consisting of six mice. Compound (1) was dissolved in DMSO and a solution was stored in the freezer before use. Immediately before the administration, the stock solution was diluted with saline. The test compound in saline was intravenously once-weekly administered at 90 μg/kg or 180 μg/kg for 2 weeks (on Day 1 and Day 8). The tumor growth delay was observed in 90 μg/kg-treated group and the tumor regression was observed in 180 μg/kg-treated group.

Figure 23:
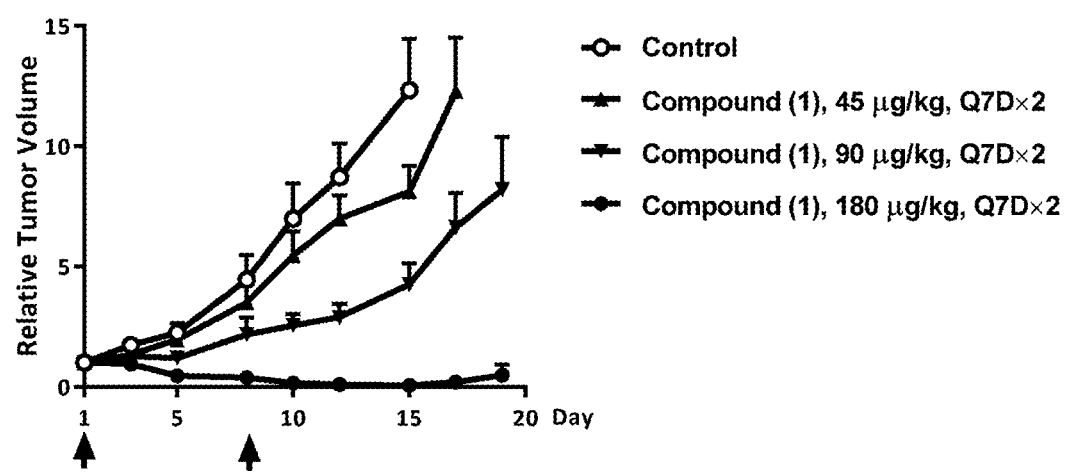
FIG. 23. Antitumor effect of Compound (1) in an HuTu 80 (human duodenal cell) xenograft model in mice as a monotherapy.

Pharmacological Test Example 28. Antitumor Effect in the HuTu 80 Xenograft Model in Mice as Monotherapy (FIG. 23)

A human duodenal cell line HuTu 80, which had been cultured in a EMEM containing 10% FBS, and penicillin-streptomycin, was adjusted to a concentration of $3\times10^7$ cells/mL in PBS to prepare a cell suspension. The cell suspension was inoculated in a volume of 100 μL into a subcutaneous part of a right flank of nude mice, 7 weeks of ages (CAnN.Cg-Foxn1nu/CrlCrlj, female, Charles River Laboratories Japan Inc.). Seven days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume ($mm^3$)=Longest diameter (mm)× Shortest diameter (mm)×Shortest diameter (mm)/2

Relative tumor volume (RTV)=Tumor volume (day X)/Tumor volume (the first day)

Relative body weight (RBW)=Body weight (day X)/Body weight (the first day)

On the basis of the volumes of tumors obtained on Day 1, the mice were grouped such that averages of the tumor volumes were substantially equal among the groups. The experiment was conducted on groups each consisting of six mice. Compound (1) was dissolved in DMSO and a solution was stored in the freezer before use. Immediately before the administration, the stock solution was diluted with saline. The test compound in saline was intravenously once-weekly administered at 45, 90, or 180 μg/kg for 2 weeks (on Day 1 and Day 8). The tumor growth delay was observed in 45 and 90 μg/kg-treated group and the tumor regression was observed in 180 µg/kg-treated group. Tumor regression (%) for Compound (1) is shown in Table 16.

TABLE 16

| Test compound | Dose (mg/kg) | Tumor Regression (%) |
|---|---|---|
| Compound (1) | 0.18 | 99 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (II):

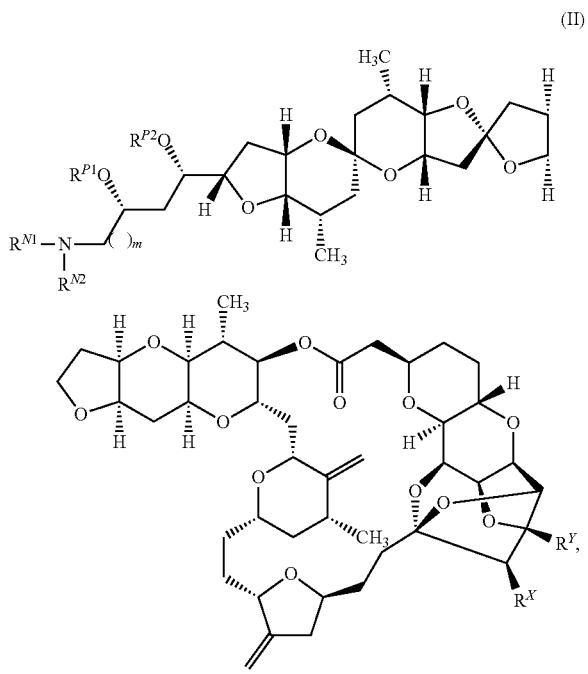

or a pharmaceutically acceptable salt or stereoisomer thereof, wherein:

$R^{N1}$ and $R^{N2}$ are independently hydrogen, optionally substituted alkyl, optionally substituted acyl, or a nitrogen protecting group, optionally wherein $R^{N1}$ and $R^{N2}$ are joined together with the intervening atoms to form optionally substituted heterocyclyl or optionally substituted heteroaryl;

$R^{P1}$ and $R^{P2}$ are independently hydrogen, optionally substituted alkyl, optionally substituted acyl, or an oxygen protecting group;

$R^X$ is hydrogen or —$OR^{Xa}$;

$R^Y$ is hydrogen or —$OR^{Ya}$;

$R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl; and m is 0 or 1.

2. The compound of claim 1, wherein the compound is of one of the following formulae:

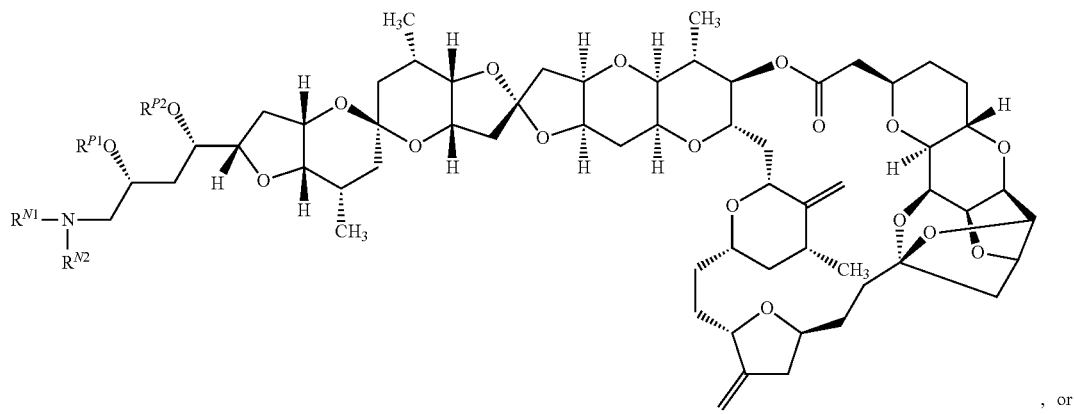

, or

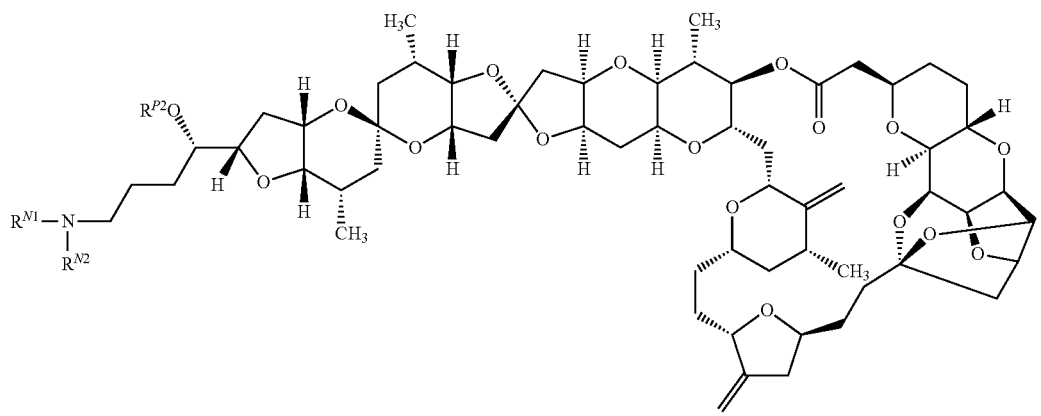

;

or a pharmaceutically acceptable salt or stereoisomer thereof.

3. A compound of Formula (IV):

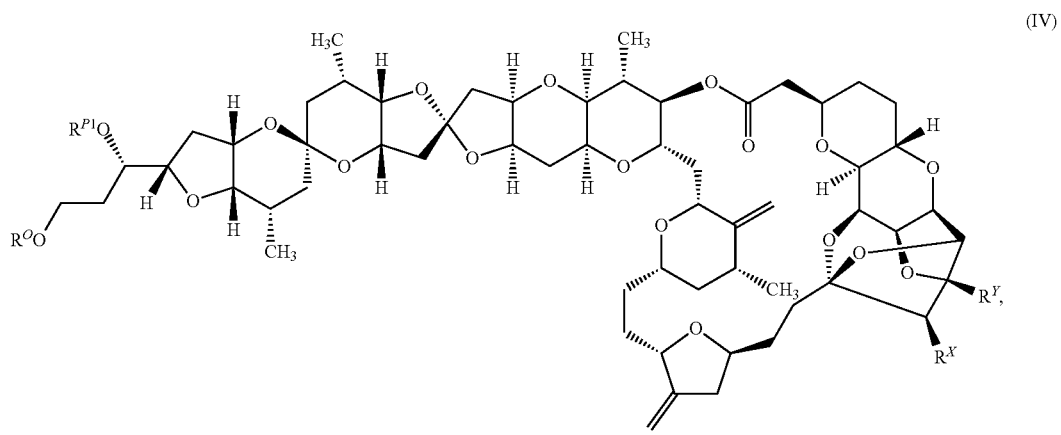

(IV)

or a pharmaceutically acceptable salt or stereoisomer thereof, wherein:
  $R^O$ is hydrogen, optionally substituted alkyl, optionally substituted acyl, or an oxygen protecting group;
  $R^{P1}$ is hydrogen, optionally substituted alkyl, optionally substituted acyl, or an oxygen protecting group;
  $R^X$ is hydrogen or —$OR^{Xa}$;
  $R^Y$ is hydrogen or —$OR^{Ya}$; and $R^{Xa}$ and $R^{Ya}$ are independently hydrogen, optionally substituted alkyl, optionally substituted acyl, or an oxygen protecting group, optionally wherein $R^{Xa}$ and $R^{Ya}$ are joined together with the intervening atoms to form optionally substituted heterocyclyl.

4. The compound of claim 3, wherein the compound is of the formula:

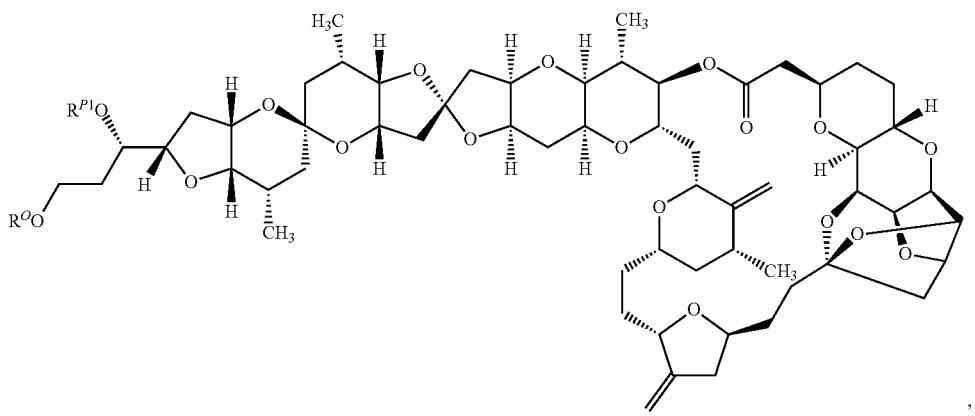

or a pharmaceutically acceptable salt or stereoisomer thereof.

5. The compound of claim 1, or a pharmaceutically acceptable salt or stereoisomer thereof, wherein m is 1.

6. The compound of claim 1, or a pharmaceutically acceptable salt or stereoisomer thereof, wherein m is 0.

7. The compound of claim 1, or a pharmaceutically acceptable salt or stereoisomer thereof, wherein both $R^{N1}$ and $R^{N2}$ are hydrogen.

8. The compound of claim 1, or a pharmaceutically acceptable salt or stereoisomer thereof, wherein both $R^{P1}$ and $R^{P2}$ are hydrogen.

9. The compound of claim 1, or a pharmaceutically acceptable salt or stereoisomer thereof, wherein $R^X$ and $R^Y$ are hydrogen.

10. The compound of claim 1, or a pharmaceutically acceptable salt or stereoisomer thereof, wherein $R^X$ and $R^Y$ are —OH.

11. The compound of claim 1, or a pharmaceutically acceptable salt or stereoisomer thereof, wherein $R^X$ is hydrogen; and $R^Y$ is —OH.

12. The compound of claim 1, wherein the compound is selected from the group consisting of:

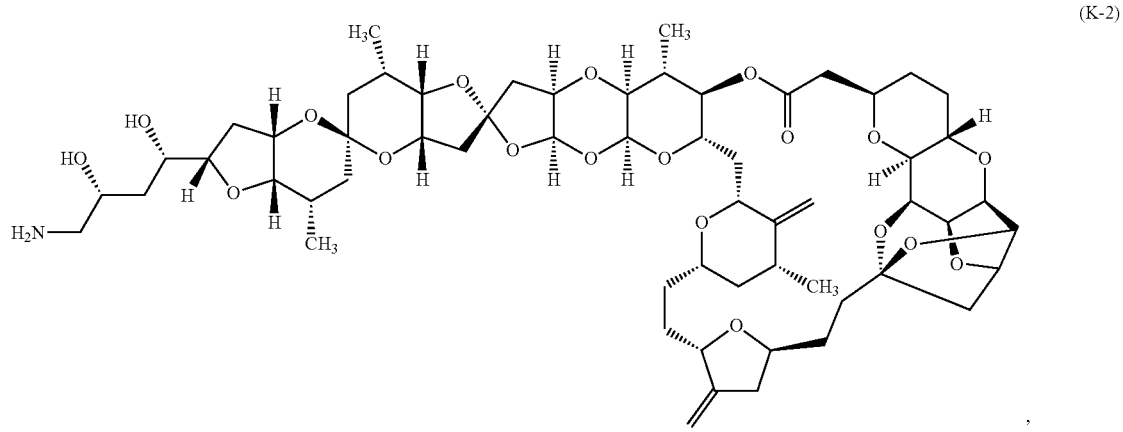

(K-2)

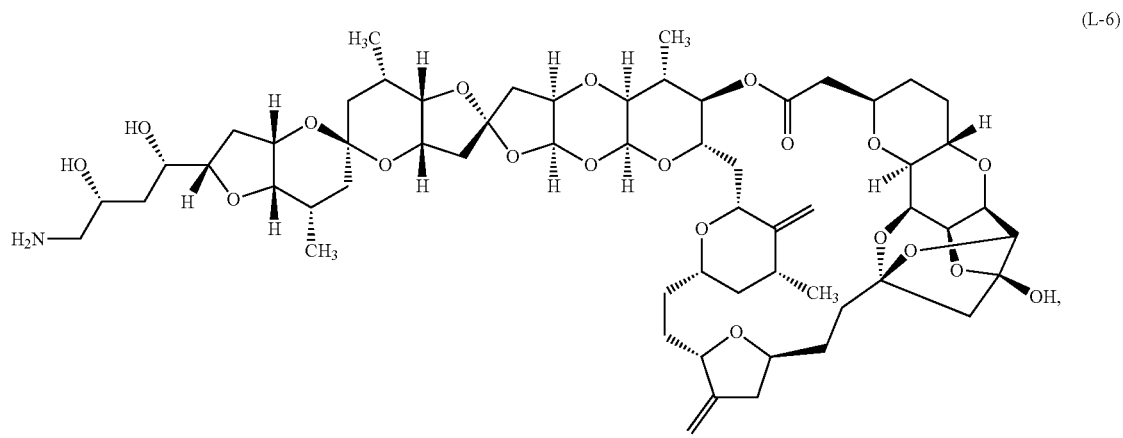

(L-6)

-continued
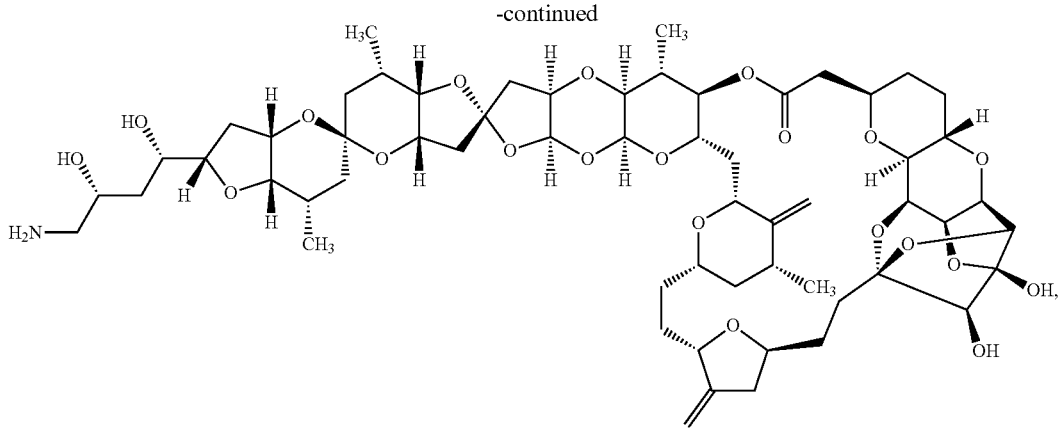
and pharmaceutically acceptable salts thereof.
13. The compound of claim 1, wherein the compound is selected from the group consisting of:
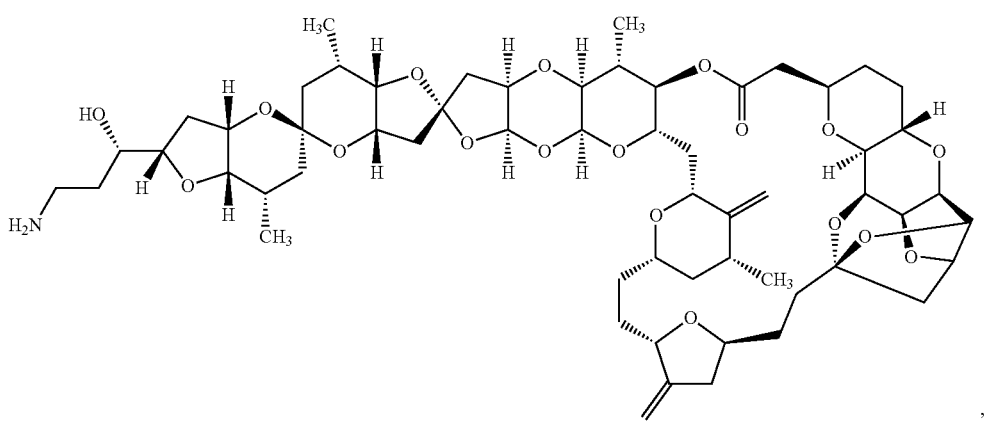
(N-1)
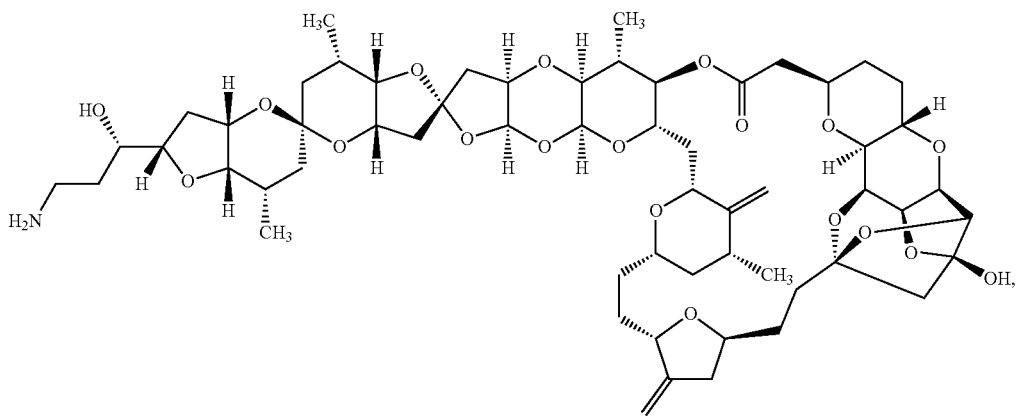

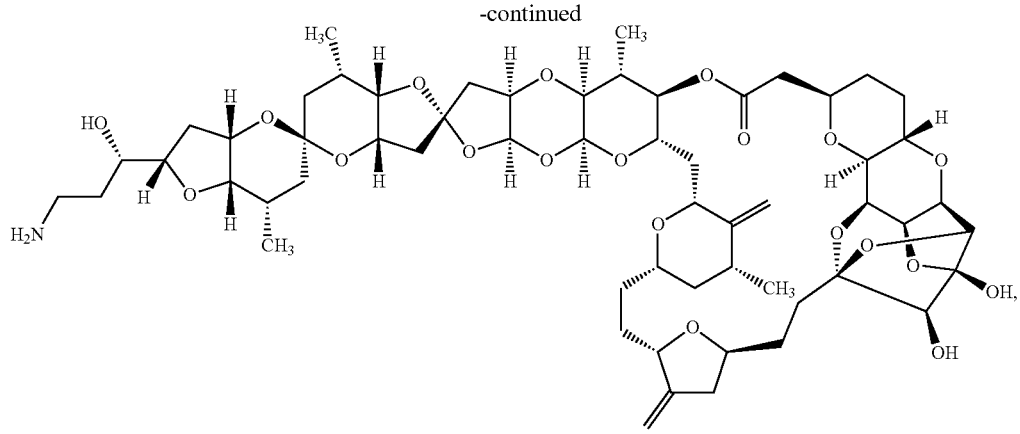
and pharmaceutically acceptable salts thereof.
14. The compound of claim 3, wherein the compound is selected from the group consisting of:
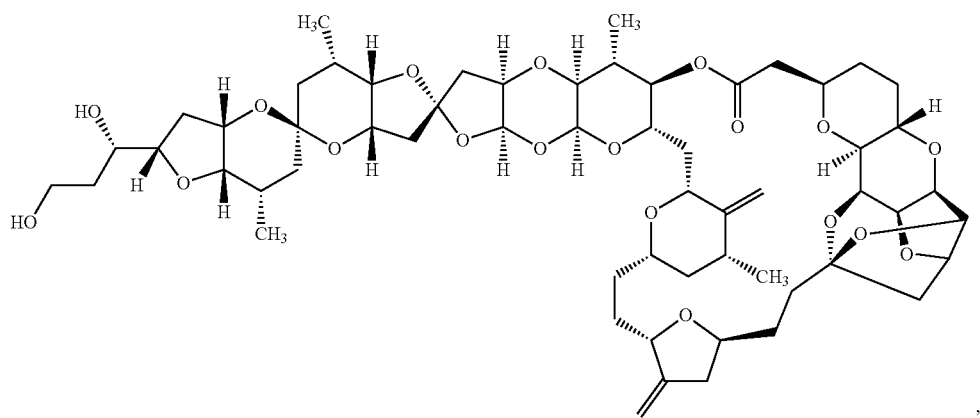
(M-3)
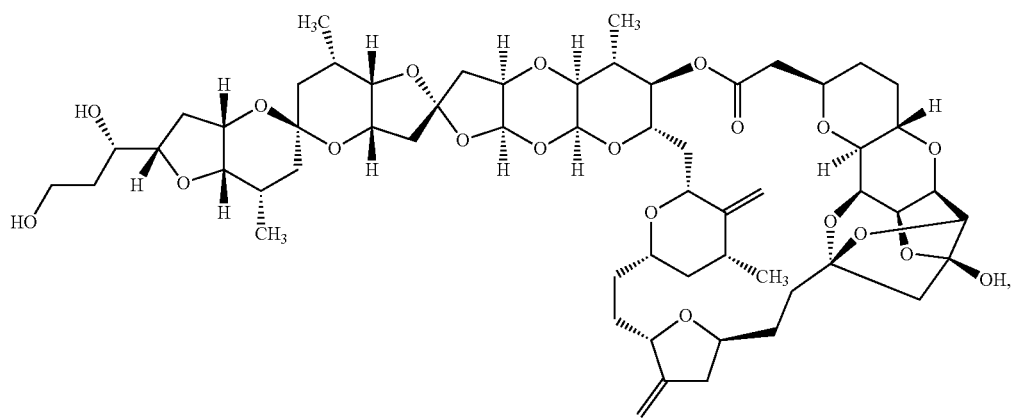

-continued

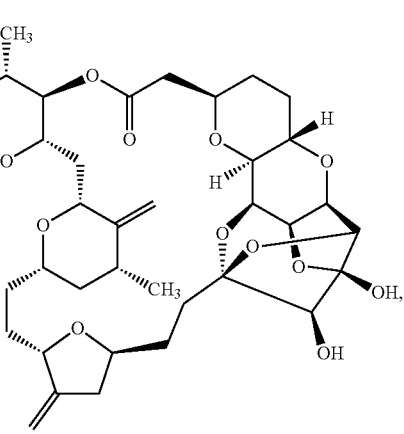

and pharmaceutically acceptable salts thereof.

15. A pharmaceutical composition comprising a compound of claim 1, or a pharmaceutically acceptable salt or stereoisomer thereof, and a pharmaceutically acceptable carrier.

16. A method for treating a proliferative disease in a subject comprising administering to the subject a compound of claim 1, or a pharmaceutically acceptable salt or stereoisomer thereof, or a pharmaceutical composition thereof.

17. The method of claim 16, wherein the proliferative disease is cancer or a tumor.

18. A method for inhibiting growth of tumor or cancer in a subject comprising administering to the subject a compound of claim 1, or a pharmaceutically acceptable salt or stereoisomer thereof, or a pharmaceutical composition thereof.

19. The compound of claim 1, wherein the compound is of Formula (II), or a pharmaceutically acceptable salt thereof.

20. The method of claim 17, wherein the cancer or tumor is characterized by angiogenesis, invasion, or metastasis.

21. The method of claim 17, wherein the cancer or tumor is breast cancer.

22. The method of claim 21, wherein the breast cancer is HER2-positive breast cancer.

23. The method of claim 21, wherein the breast cancer is HER2-negative breast cancer.

24. The method of claim 21, wherein the breast cancer is triple negative breast cancer.

25. The method of claim 17, wherein the cancer or tumor is lung cancer.

26. The method of claim 25, wherein the lung cancer is non-small cell lung cancer (NSCLC).

27. The method of claim 17, wherein the cancer or tumor is uterine cancer.

28. The method of claim 17, wherein the cancer or tumor is a sarcoma.

29. The method of claim 27, wherein the uterine cancer is uterine sarcoma.

30. The method of claim 17, wherein the cancer or tumor is prostate cancer.

31. The compound of claim 3, or a pharmaceutically acceptable salt or stereoisomer thereof, wherein $R^O$ is hydrogen.

32. The compound of claim 3, or a pharmaceutically acceptable salt or stereoisomer thereof, wherein $R^{P1}$ is hydrogen.

33. The compound of claim 3, or a pharmaceutically acceptable salt or stereoisomer thereof, wherein $R^X$ and $R^Y$ are hydrogen.

34. The compound of claim 3, or a pharmaceutically acceptable salt or stereoisomer thereof, wherein $R^X$ and $R^Y$ are —OH.

35. The compound of claim 3, or a pharmaceutically acceptable salt or stereoisomer thereof, wherein $R^X$ is hydrogen; and $R^Y$ is —OH.

36. The compound of claim 3, wherein the compound is of Formula (IV), or a pharmaceutically acceptable salt thereof.

37. A pharmaceutical composition comprising a compound of claim 3, or a pharmaceutically acceptable salt or stereoisomer thereof, and a pharmaceutically acceptable carrier.

38. A method for treating a proliferative disease in a subject comprising administering to the subject a compound of claim 3, or a pharmaceutically acceptable salt or stereoisomer thereof, or a pharmaceutical composition thereof.

39. The method of claim 38, wherein the proliferative disease is cancer or a tumor.

40. A method for inhibiting growth of tumor or cancer in a subject comprising administering to the subject a compound of claim 3, or a pharmaceutically acceptable salt or stereoisomer thereof, or a pharmaceutical composition thereof.

41. The method of claim 39, wherein the cancer or tumor is characterized by angiogenesis, invasion, or metastasis.

42. The method of claim 39, wherein the cancer or tumor is breast cancer.

43. The method of claim 42, wherein the breast cancer is HER2-positive breast cancer.

44. The method of claim 42, wherein the breast cancer is HER2-negative breast cancer.

45. The method of claim 42, wherein the breast cancer is triple negative breast cancer.

46. The method of claim 39, wherein the cancer or tumor is lung cancer.

47. The method of claim 46, wherein the lung cancer is non-small cell lung cancer (NSCLC).

48. The method of claim 39, wherein the cancer or tumor is uterine cancer.

49. The method of claim 39, wherein the cancer or tumor is a sarcoma.

50. The method of claim 48, wherein the uterine cancer is uterine sarcoma.

* * * * *

UNITED STATES PATENT AND TRADEMARK OFFICE
CERTIFICATE OF CORRECTION

PATENT NO. : 11,407,762 B2
APPLICATION NO. : 16/764245
DATED : August 9, 2022
INVENTOR(S) : Yoshito Kishi et al.

It is certified that error appears in the above-identified patent and that said Letters Patent is hereby corrected as shown below:

On the Title Page

At item (72), the place of residence of Inventor Kazunobu Kira, "Tsukuba (JP)" should be replaced with --Tsukuba-shi (JP)--.

At item (72), the place of residence of Inventor Ken Ito, "Tsukuba (JP)" should be replaced with --Tsukuba-shi (JP)--.

In the Claims

In Claim 1, at Column 184, Lines 12-38, the formula:

"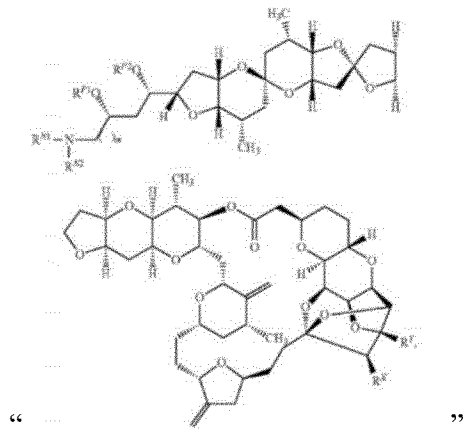"

Signed and Sealed this
Eighteenth Day of October, 2022

Katherine Kelly Vidal
*Director of the United States Patent and Trademark Office*

CERTIFICATE OF CORRECTION (continued)
U.S. Pat. No. 11,407,762 B2

Should be replaced with the formula:

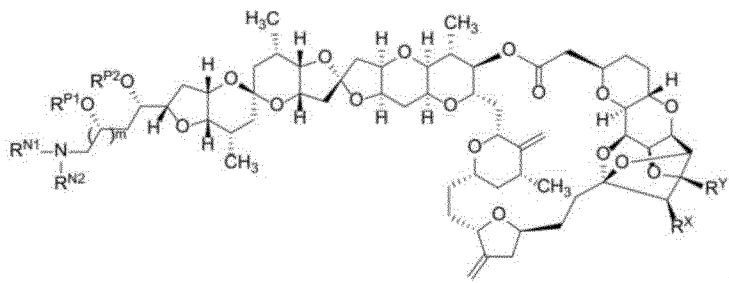

--   --.

In Claim 2, at Columns 185-186, Lines 21-40, the formula:

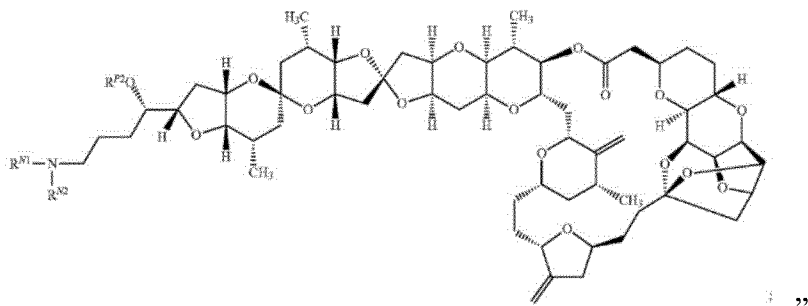

"   "

Should be replaced with the formula:

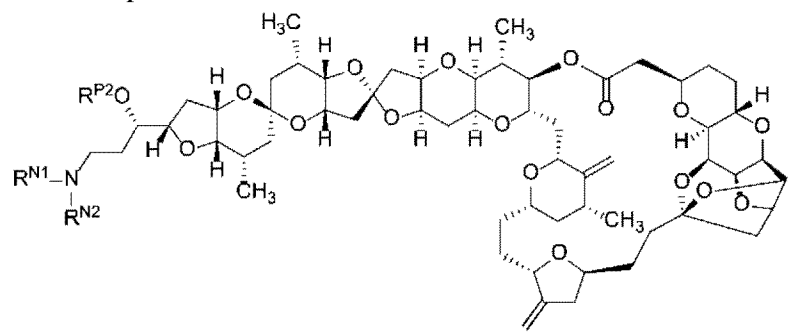

--   --.

In Claim 12, at Columns 187-188, Lines 31-50, the formula:

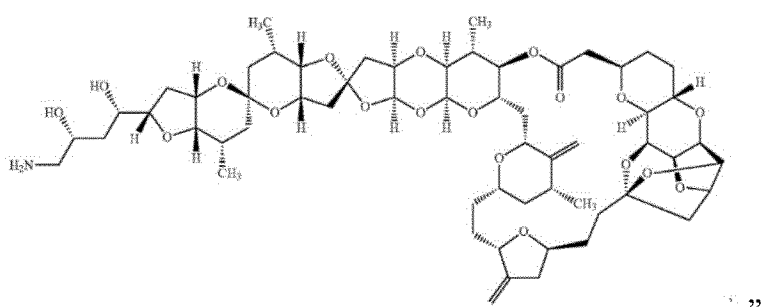

"   "

Should be replaced with the formula:
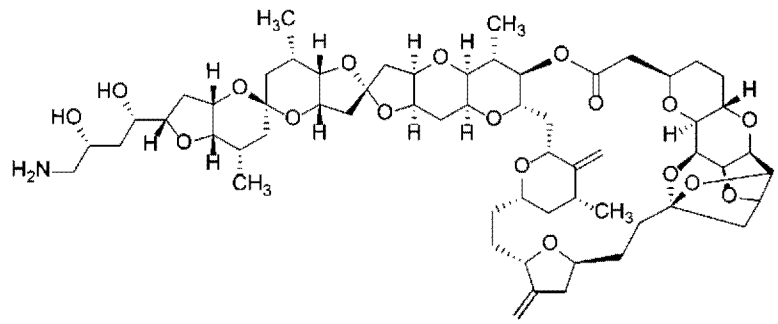
--.
In Claim 12, at Columns 187-188, Lines 51-67, the formula:
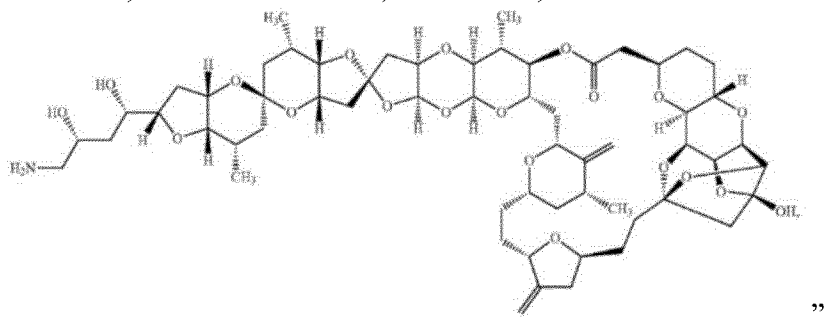
" "
Should be replaced with the formula:
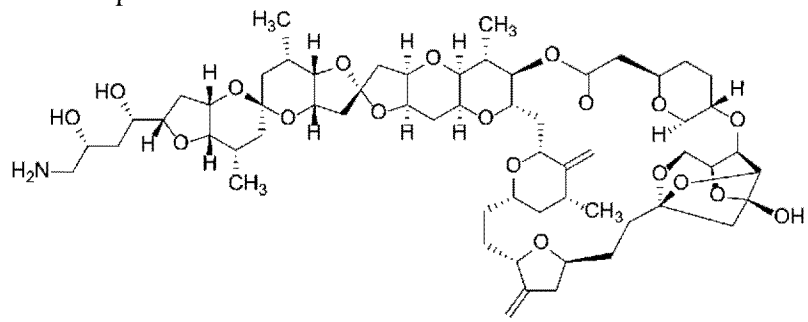
--.
In Claim 12, at Columns 189-190, Lines 2-19, the formula:
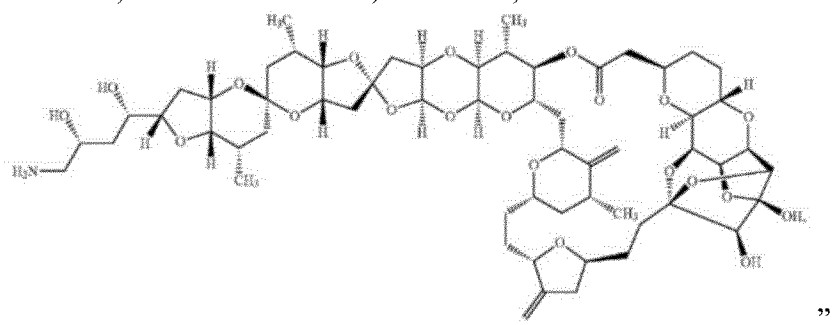
" "

Should be replaced with the formula:
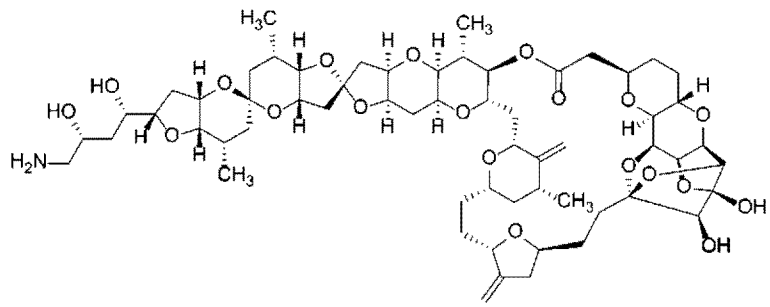
-- --.
In Claim 13, at Columns 189-190, Lines 24-40, the formula:
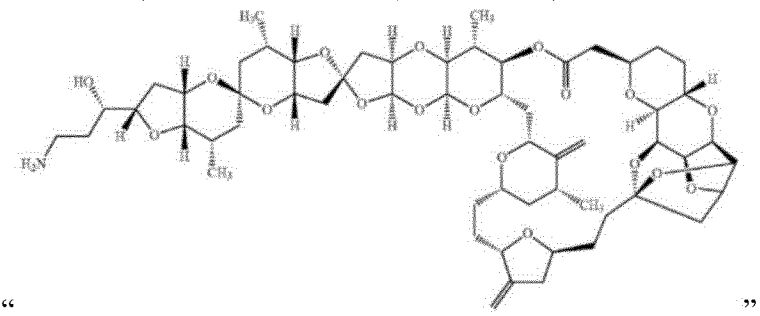
" "
Should be replaced with the formula:
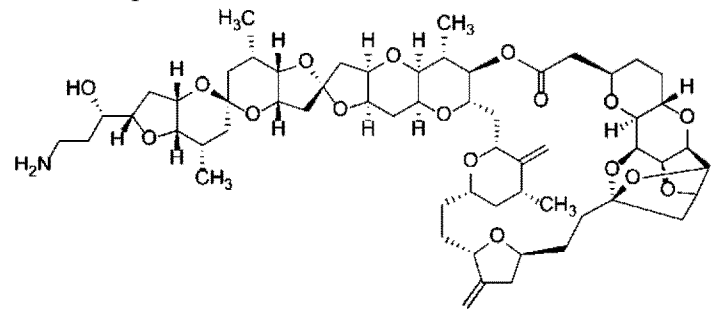
-- --.
In Claim 13, at Columns 189-190, Lines 51-65, the formula:
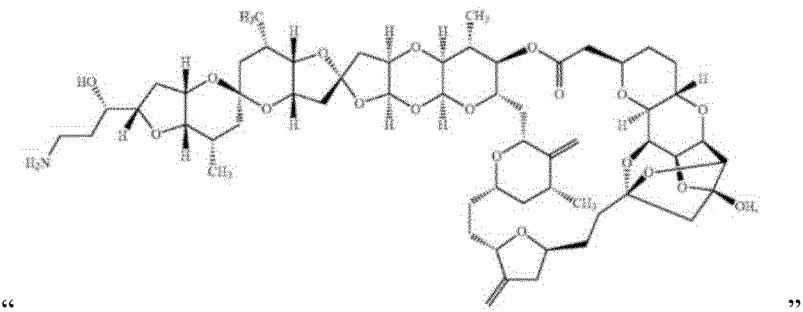
" "

CERTIFICATE OF CORRECTION (continued)
U.S. Pat. No. 11,407,762 B2

Should be replaced with the formula:

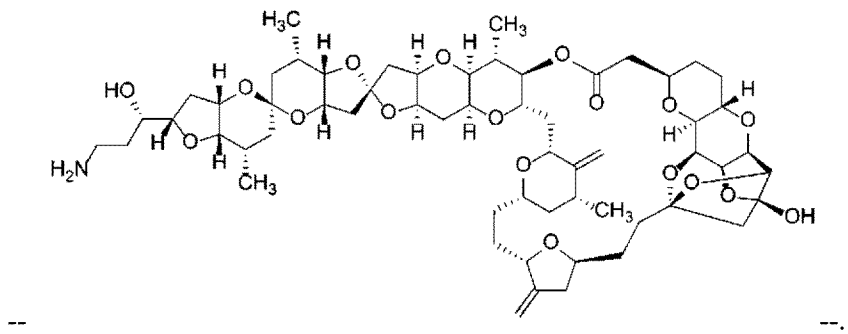

-- --.

In Claim 13, at Columns 191-192, Lines 2-19, the formula:

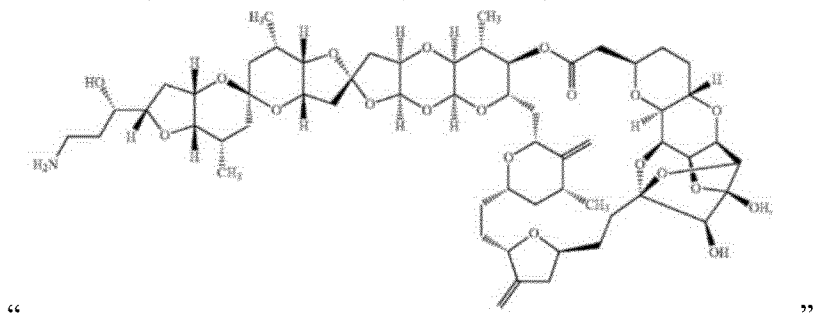

" "

Should be replaced with the formula:

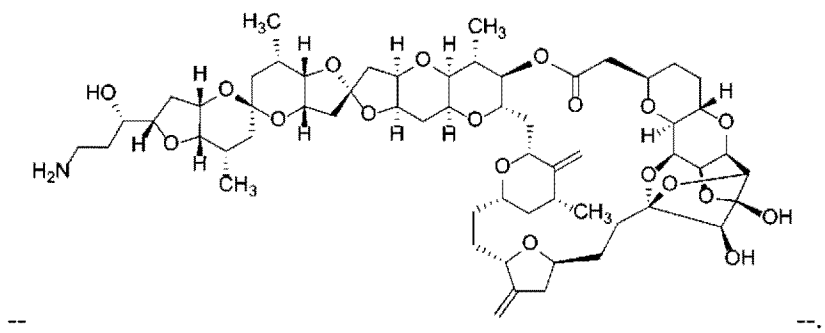

-- --.

In Claim 14, at Columns 191-192, Lines 23-40, the formula:

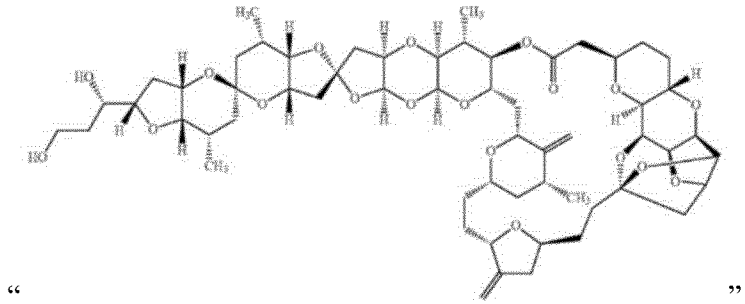

" "

Should be replaced with the formula:
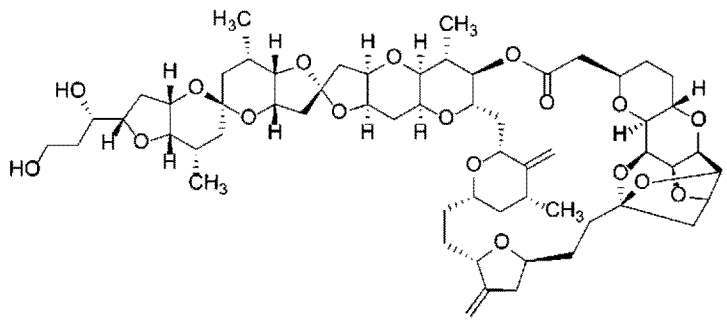
--.
In Claim 14, at Columns 191-192, Lines 51-65, the formula:
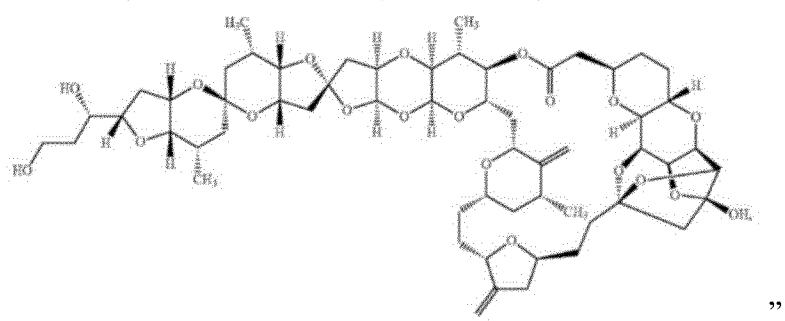
" "
Should be replaced with the formula:
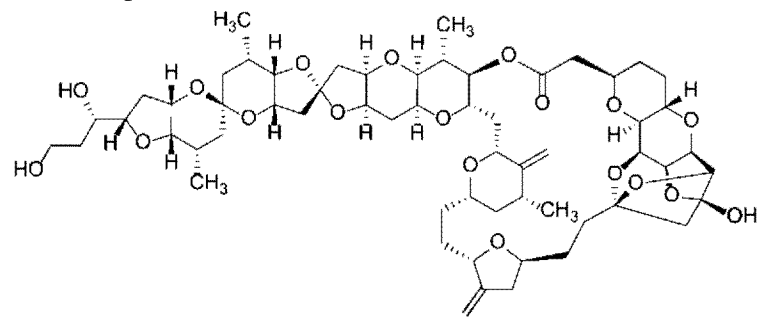
--.
In Claim 14, at Columns 193-194, Lines 2-19, the formula:
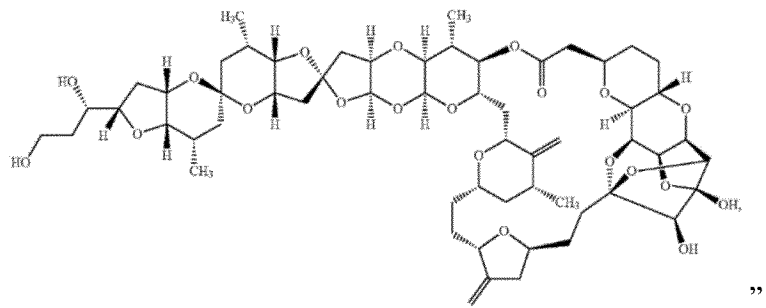
" "

CERTIFICATE OF CORRECTION (continued)
U.S. Pat. No. 11,407,762 B2

Should be replaced with the formula:

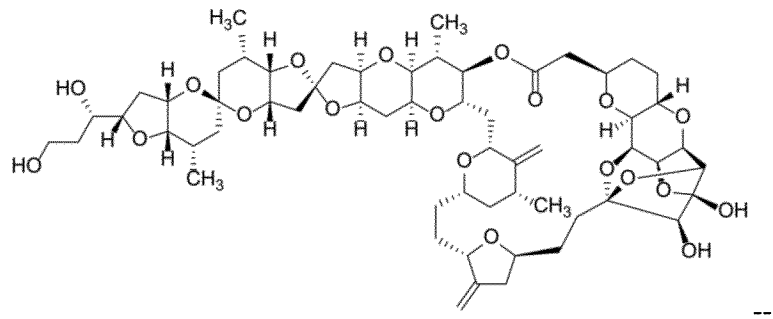

-- --.